US010822326B2

(12) United States Patent
Metcalf et al.

(10) Patent No.: US 10,822,326 B2
(45) Date of Patent: Nov. 3, 2020

(54) SUBSTITUTED HETEROARYL ALDEHYDE COMPOUNDS AND METHODS FOR THEIR USE IN INCREASING TISSUE OXYGENATION

(71) Applicant: Global Blood Therapeutics, Inc., South San Francisco, CA (US)

(72) Inventors: Brian Metcalf, South San Francisco, CA (US); Chihyuan Chuang, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/519,552

(22) Filed: Jul. 23, 2019

(65) Prior Publication Data
US 2020/0190058 A1 Jun. 18, 2020

Related U.S. Application Data

(63) Continuation of application No. 15/864,433, filed on Jan. 8, 2018, now Pat. No. 10,377,741, which is a continuation of application No. 15/391,669, filed on Dec. 27, 2016, now abandoned, which is a continuation of application No. 13/730,730, filed on Dec. 28, 2012, now Pat. No. 9,012,450.

(60) Provisional application No. 61/661,327, filed on Jun. 18, 2012, provisional application No. 61/581,063, filed on Dec. 28, 2011.

(51) Int. Cl.
| | |
|---|---|
| C07D 401/12 | (2006.01) |
| C07D 213/65 | (2006.01) |
| C07D 213/68 | (2006.01) |
| C07D 213/69 | (2006.01) |
| C07D 213/80 | (2006.01) |
| C07D 401/14 | (2006.01) |
| C07D 405/14 | (2006.01) |
| C07D 413/12 | (2006.01) |
| C07D 471/04 | (2006.01) |
| C07D 487/04 | (2006.01) |

(52) U.S. Cl.
CPC ......... *C07D 401/12* (2013.01); *C07D 213/65* (2013.01); *C07D 213/68* (2013.01); *C07D 213/69* (2013.01); *C07D 213/80* (2013.01); *C07D 401/14* (2013.01); *C07D 405/14* (2013.01); *C07D 413/12* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,266,582 A | 11/1993 | De Nanteuil et al. |
| 5,290,941 A | 3/1994 | Volante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 11/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greenwald et al. |
| 6,627,646 B2 | 9/2003 | Bakale |
| 6,630,496 B1 | 10/2003 | Seehra et al. |
| 7,160,910 B2 | 1/2007 | Safo et al. |

(Continued)

FOREIGN PATENT DOCUMENTS

| | | |
|---|---|---|
| CA | 2720096 | 10/2009 |
| CN | 101113148 | 1/2008 |

(Continued)

OTHER PUBLICATIONS

U.S. Appl. No. 61/581,053, filed Dec. 28, 2011, Metcalf et al.

(Continued)

*Primary Examiner* — Po-Chih Chen
(74) *Attorney, Agent, or Firm* — Sheppard Mullin Richter & Hampton LLP

(57) ABSTRACT

Provided are substituted heteroaryl aldehydes and derivatives thereof that act as allosteric modulators of hemoglobin, methods and intermediates for their preparation, pharmaceutical compositions comprising the modulators, and methods for their use in treating disorders mediate by hemoglobin and disorders that would benefit from increased tissue oxygenation.

4 Claims, No Drawings

(56) References Cited

U.S. PATENT DOCUMENTS

| | | |
|---|---|---|
| 7,411,083 B2 | 8/2008 | Gopalsamy et al. |
| 7,994,367 B2 | 8/2011 | Nakazawa |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,150,569 B2 | 10/2015 | Fukuda |
| 9,248,199 B2 | 2/2016 | Metcalf et al. |
| 9,422,279 B2 | 8/2016 | Metcalf et al. |
| 9,447,071 B2 | 9/2016 | Li et al. |
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |
| 10,017,491 B2 | 7/2018 | Metcalf et al. |
| 10,034,879 B2 | 7/2018 | Metcalf et al. |
| 10,137,118 B2 | 11/2018 | Li et al. |
| 10,450,269 B1 | 10/2019 | Xu et al. |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann |
| 2009/0163512 A1 | 6/2009 | Chen et al. |
| 2009/0312315 A1 | 12/2009 | Yamaguchi et al. |
| 2010/0048901 A1 | 2/2010 | Takahashi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2013/0273157 A1 | 10/2013 | Ishii et al. |
| 2014/0004184 A1 | 1/2014 | Ashraf et al. |
| 2014/0142149 A1 | 5/2014 | Zhang et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0225366 A1 | 8/2015 | Li |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0303099 A1 | 3/2016 | Dufu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0332984 A1 | 11/2016 | Metcalf et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0327484 A1 | 11/2017 | Li et al. |
| 2017/0355713 A1 | 12/2017 | Harris et al. |
| 2018/0125789 A1 | 5/2018 | Dalziel et al. |
| 2018/0186807 A1 | 7/2018 | Yee et al. |
| 2018/0201577 A1 | 7/2018 | Xu et al. |
| 2018/0354929 A1 | 12/2018 | Metcalf et al. |
| 2019/0010121 A1 | 1/2019 | Xu et al. |
| 2019/0010176 A1 | 1/2019 | Harris |
| 2019/0106404 A1 | 4/2019 | Li et al. |
| 2019/0111037 A1 | 4/2019 | Li et al. |
| 2019/0112287 A1 | 4/2019 | Metcalf et al. |
| 2019/0160060 A1 | 5/2019 | Metcalf et al. |
| 2019/0202782 A1 | 7/2019 | Xu et al. |
| 2019/0255031 A1 | 8/2019 | Li et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2217016 | 1/1900 |
| FR | 2909379 | 6/2008 |
| GB | 1409865 | 10/1975 |
| GB | 1593417 | 7/1981 |
| IL | 64573 | 4/1985 |
| JP | 57-145844 | 9/1982 |
| JP | 59029667 | 2/1984 |
| JP | 61-040236 | 2/1986 |
| JP | 63230687 | 9/1988 |

(56) References Cited

FOREIGN PATENT DOCUMENTS

| | | |
|---|---|---|
| JP | S-63258463 | 10/1988 |
| JP | 01190688 | 7/1989 |
| JP | 06-041118 | 2/1994 |
| JP | 07-025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006-342115 | 12/2006 |
| JP | 2009-203230 | 9/2009 |
| WO | WO-91/19697 | 12/1991 |
| WO | WO-92/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/41120 | 11/1997 |
| WO | WO-97/44306 | 11/1997 |
| WO | WO-98/08818 | 3/1998 |
| WO | WO 98/09967 | 3/1998 |
| WO | WO-98/21199 | 5/1998 |
| WO | WO-99/29694 | 6/1999 |
| WO | WO-99/43672 | 9/1999 |
| WO | WO-99/47529 | 9/1999 |
| WO | WO-99/48490 | 9/1999 |
| WO | WO-99/59978 | 11/1999 |
| WO | WO-99/62908 | 12/1999 |
| WO | WO-00/12121 | 3/2000 |
| WO | WO-00/26202 | 5/2000 |
| WO | WO-00/35858 | 6/2000 |
| WO | WO-00/40564 | 7/2000 |
| WO | WO-00/71123 A1 | 11/2000 |
| WO | WO-00/75145 | 12/2000 |
| WO | WO-00/78746 | 12/2000 |
| WO | WO-01/00612 | 1/2001 |
| WO | WO-01/19823 | 3/2001 |
| WO | WO-01/23383 | 4/2001 |
| WO | WO-01/32596 | 5/2001 |
| WO | WO-01/36375 | 5/2001 |
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO 02/40456 | 5/2002 |
| WO | WO-02/051849 | 7/2002 |
| WO | WO-02/053547 | 7/2002 |
| WO | WO-03/051366 | 6/2003 |
| WO | WO-03/053368 | 7/2003 |
| WO | WO-03/101959 | 12/2003 |
| WO | WO-2004/014899 | 2/2004 |
| WO | WO-2004/018430 | 3/2004 |
| WO | WO-2004/024705 | 3/2004 |
| WO | WO-2004/050030 | 6/2004 |
| WO | WO-2004/056727 | 7/2004 |
| WO | WO-2004/058790 | 7/2004 |
| WO | WO 2004/073675 | 9/2004 |
| WO | WO-2004/087075 | 10/2004 |
| WO | WO-2004/111031 | 12/2004 |
| WO | WO-2005/047249 | 5/2005 |
| WO | WO-2005/074513 | 8/2005 |
| WO | WO-2005/077932 | 8/2005 |
| WO | WO-2005/086951 | 9/2005 |
| WO | WO-2005/087766 | 9/2005 |
| WO | WO-2005/096337 | 10/2005 |
| WO | WO-2006/011469 | 2/2006 |
| WO | WO-2006/065204 | 6/2006 |
| WO | WO-2006/088173 | 8/2006 |
| WO | WO 2006/101318 | 9/2006 |
| WO | WO 2006/101321 | 9/2006 |
| WO | WO-2006/103463 | 10/2006 |
| WO | WO-2006/106711 | 10/2006 |
| WO | WO-2006/116764 | 11/2006 |
| WO | WO-2006/003923 | 12/2006 |
| WO | WO-2007/003962 | 1/2007 |
| WO | WO-2007/009389 | 1/2007 |
| WO | WO-2007/017267 | 2/2007 |
| WO | WO-2007/047204 | 4/2007 |
| WO | WO-2007/049675 | 5/2007 |
| WO | WO-2007/061923 | 5/2007 |
| WO | WO-2007/084914 | 7/2007 |
| WO | WO 2007/095495 | 8/2007 |
| WO | WO-2007/117180 | 10/2007 |
| WO | WO 2008/012495 | 1/2008 |
| WO | WO-2008/013414 | 1/2008 |
| WO | WO-2008/016132 | 2/2008 |
| WO | WO-2008/029200 | 3/2008 |
| WO | WO-2008/041118 | 4/2008 |
| WO | WO-2008/051532 | 5/2008 |
| WO | WO-2008/060391 | 5/2008 |
| WO | WO-2008/066145 | 6/2008 |
| WO | WO-2008/081096 | 7/2008 |
| WO | WO-2008/101682 | 8/2008 |
| WO | WO-2008/116620 | 10/2008 |
| WO | WO-2009/001214 | 12/2008 |
| WO | WO-2009/011850 | 1/2009 |
| WO | WO-2009/050183 | 4/2009 |
| WO | WO-2009/125606 | 10/2009 |
| WO | WO-2009/128537 | 10/2009 |
| WO | WO-2009/130560 | 10/2009 |
| WO | WO-2009/136889 | 11/2009 |
| WO | WO-2009/146555 | 12/2009 |
| WO | WO 2009/153191 | 12/2009 |
| WO | WO-2010/031589 | 3/2010 |
| WO | WO-2010/056631 | 5/2010 |
| WO | WO-2010/129055 | 11/2010 |
| WO | WO-2011/033045 | 3/2011 |
| WO | WO-2011/088201 | 7/2011 |
| WO | WO-2011/136459 | 11/2011 |
| WO | WO-2012/020060 | 2/2012 |
| WO | WO-2012/138981 | 10/2012 |
| WO | WO-2012/141228 | 10/2012 |
| WO | WO-2013/052803 | 4/2013 |
| WO | WO-2013/102142 | 7/2013 |
| WO | WO-2013/102145 | 7/2013 |
| WO | WO-2014/104384 | 7/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |
| WO | WO-2015/120133 | 8/2015 |
| WO | WO-2016/160755 | 10/2016 |
| WO | WO-2017/096230 | 6/2017 |

OTHER PUBLICATIONS

U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.
Abdulmalik et al., Sickle cell disease: current therapeutic approaches, Expert Opinion Ther. Patents, 2005, vol. 15(11), pp. 1497-1506.
Abraham et al., Vanillin, a Potential Agent for the Treatment of Sickle Cell Anemia, Blood, Mar. 2005, vol. 77 (6), pp. 1334-1341.
Adhikary, P.K., et al., "A new antisickling agent: In vitro studies of its effect on S/S erythrocytes and on hemoglobin S", Experientia. 1978, vol. 34, No. 6, pp. 804-806.
Appendix A provided with Israel office action dated Aug. 11, 2016 for IL 233329.
Arya R, et al. "Tucaresol increases oxygen affinity and reduces haemolysis in subjects with sickle cell anaemia," Br. J. Haematol., 93(4):817-21 (1996).
Ashizawa et al., Polymorphism and crystallization of the pharmaceutical drugs (Iyakuhin No Takeigensho To Shoseki No Kagaku)

(56) References Cited

OTHER PUBLICATIONS

Maruzen Planet Co., Ltd., Sep. 20, 2002, pp. 3-16 and pp. 273-278. (in Japanese with partial English translation).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
Bacsa et al., "Novel products from Baylis-Hillman reactions of salicylaldehydes", South African Journal of Chemistry (1998), 51(1), 47-54 CODEN: SAJCDG; ISSN: 0379-4350.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Ballet et al., Novel selective human melanocortin-3 receptor ligands: Use of the 4-amino-1,2,4,5-tetrahydro-2-benzazepin-3-one (Aba) scaffold, Bioorganic & Medicinal Chemistry Letters (2007), 17(9), 2492-2498 CODEN: BMCLES; ISSN: 0960-894X.
Barnes, et al., "Prospects for new drugs for chronic obstructive pulmonary disease." the Lancet, 2004, 364, 985-996.
Barnes. "COPD: is there light at the end of the tunnel?" Current Opinion in Pharmacology, 2004, 4:263-272.
Baxter et al., "Reductive aminations of carbonyl compounds with borohydride and borane reducing agents", Organic Reactions (Hoboken, NJ, United States) (2002), 59, No pp. given bin/mrwhome/107610747/HOME.
Beaumont et al., Design of ester prodrugs to enhance oral absorption of poorly permeable compounds: challenges to the discovery scientist. Curr. Drug Metab. 2003, 4:461-85.
Beddell, Sustituted benzaldehydes designed to increase the oxygen affinity of human haemoglobin and inhibit the sickling of sickle erythrocycles, Br. J. Pharmac., 82:397-407, 1984.
Beena et al., "Synthesis and antibacterial activity evaluation of metronidazole-triazole conjugates", Bioorganic & Medicinal Chemistry Letters, 2009, 19(5):1396-1398.
Behanna. Equity Research—Global Blood Therapeutics. Sep. 8, 2015. Retrieved from the Internet: URL:http://www.fintechsecurities.com/Websites/fintechsecurities/images/Research_Blog/Zacks/Sep2015/GBT150908.pdf.
Berge et al., "Pharmaceutical Salts", Journal of Pharmaceutical Science, 1977, 66:1-19.
Beringer et al., Remington's Pharmaceutical Sciences, Mack Pub., 21st Edition, 2005, pp. 1072-1076.
Bernstein. Crystals in Supramolecular Chemistry. ACA Transactions. 2004; 39:1-14.
Bernstein. Polymorphism in Molecular Crystals. Clarendon Press, Oxford. 2002. 115-118, 272.
Bode et al.,"Novel synthesis and x-ray crystal structure of a coumarin derivative", South African Journal of Chemistry (1992), 45(1), 25-7 CODEN: SAJCDG; ISSN:0379-4350.
Bonaventura, et al., "Molecular Controls of the Oxygenation and Redox Reactions of Hemoglobin." Antioxidants & Redox Signaling, 18(17), 2013, 2298-2313.
Bottino, et al. Study on the scope of tert-amino effect: new extensions of type 2 reactions to bridged biaryls. J. Phys. Org. Chem. 2012; 25(11):1033-1041.
Bradbury et al., "New nonpeptide angiotensin II receptor antagonists", Journal of Medicinal Chemistry, 1993, vol. 36, pp. 1245-1254.
Braga, et al. Making crystals from crystals: a green route to crystal engineering and polymorphism. Chem Commun (Camb). Aug. 7, 2005;(29):3635-45. Epub Jun. 15, 2005.
Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.
Brown et al., "1,2-Dihydroisoquinollnes. III, Dimerization", Tetrahedron (1966), 22(8), 2437-43 CODEN: TETRAB; ISSN;0040-4020.
Byrn, et al. Pharmaceutical solids: a strategic approach to regulatory considerations. Pharmaceutical Research. 1995; 12(7):945-954.
Caira. Crystalline Polymorphism of Organic Compounds. Topics in Current Chemistry, Springer, Berlin, DE. 1998; 198:163-208.
"Can Voxelotor Offer New Hope for Sickle Cell Disease?," Dec. 3, 2018, available at: https://www.ashclinicalnews.org/on-location/voxelotor-offers-new-hope-sickle-cell-disease/. 4 pages.
CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.
Chemical Abstract Registry No. 1142191-55-6, indexed in the Registry File on STN CA Online May 4, 2009.
Cheng, et al. Vilsmeier formylation of tert-anilines: dibenzo[b,f][1,5]diazocines and quinazolinium salts via the 't-amino effect'. J. Chem. Soc., Perkin Trans 1. 1998; 1257-1262.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-13][1,3]oxazin-6-yl)-(4-trifluoromethoxybenzyl)amine (6-Amino PA-824).," J. Med. Chem., Aug. 2011, vol. 54(16), pp. 5639-5659.
Ciganek, "The catalyzed a-hydroxyalkylation and a-aminoalkylation of activated olefins (the Morita-Baylis-Hillman reaction", Organic Reactions (Hoboken, NJ, United States) (1997), 51, No pp given CODEN:ORHNBA URL:http://www3.Interscience.wiley.com/cgi-bin/mnwhome/107610747/HOME.
CMU Pharmaceutical polymorphism, internet p. 1-3 (2002) printout Apr. 3, 2008.
Concise Encyclopedia Chemistry, NY: Walter de Gruyter, 1993, 872-873.
Congreve et al. Application of Fragment Screening by X-ray Crstallography to the Discovery of Aminopyridimes as Inhibitors of Beta-Secretase. J. Med. Chem. 50:1124-1132 (2007).
Cos et al., "Structure-Activity Relationship and Classification of Flavonoids as Inhibitors of Xanthine Oxidase and Superoxide Scavengers," J. Nat. Prod., (1998), 61:71-76.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN:1427163-92-5 & CN 102 952 062 A, Mar. 6, 2013, 2 pages.
Database Pubchem Compound Dec. 4, 2011 XP 003033770 (11 pages).
Database Registry, 2011, RN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Davidovich, et al. Detection of polymorphism by powder x-ray diffraction: interference by preferred orientation. Am. Pharm. Rev. 2004; 10, 12, 14, 16, 100.
Dean. Analytical Chemistry Handbook. University of Tennesse, Knoxville. McGraw-Hill, Inc. 1995; 10.24-10.26.
Deem. "Red Blood Cells and Hemoglobin in Hypoxic Pulmonary Vasoconstriction" Advances in experimental medicine and biology, (2006) 588, 217-231.
Desai et al. Preparation of N-[ro-(4-aryl-1-piperazinypethyl/propyl]-3-hydroxyphthalimidines. Indian Journal of Chemistry. 39:455-457 (2000).
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).
Ding et al., "Crystal structure of bis[μ2-2-(2-formylphenoxy)acetato-O,O]-bis[μ2-2-2-formylphynoxy)acetato-O,O]-octakis(n-

(56) References Cited

OTHER PUBLICATIONS butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.
Doelker, English translation of S.T.P, Pratiques (1999), 9(5), 399-409.
Doelker. English translation of Ann. Pharm. Fr., 2002, 60: 161-176.
Einfalt, et al. Methods of amorphization and investigation of the amorphous state. Acta Pharm. 2013; 63:305-334.
Elwahy, "Synthesis of new benzo-substituted macrocyclic containing quinoxaline subunits" Tetrahedron (2000), 56(6), 897-907 CODEN:TETRAB; ISSN:0040-4020.
Epsztajn et al., "Application of organolithium", Tetrahedron, Elsevier Science Publishers, Amsterdam, NL, 1991, vol. 47, No. 9, pp. 1697-1706.
European Search Report and Search Opinion dated Aug. 4, 2015 for EP Application No. 12862525.8. 9 pages.
European Search Report and Search Opinion dated Jul. 21, 2016 for EP Application No. 14769616.5. 8 pages.
European Search Report and Search Opinion dated May 28, 2015 for EP Application No. 12862096.0. 13 pages.
European Search Report and Search Opinion dated Nov. 16, 2016 for EP Application No. 16194019.2. 13 pages.
European Search Report and Search Opinion dated Sep. 26, 2016 for EP Application No. 14768759.4. 6 pages.
Experimental Chemistry (vol. 2)(Jikken Kagaku Koza, Zoku), Separation and refining, Maruzen Co.Ltd. Jan. 25, 1967, pp. 159-178 and pp. 186-187. (in Japanese with partial English translation).
Extended European Search Report and opinion dated Jul. 20, 2016 for EP Application No. 14768414.6. 10 pages.
Extended European Search Report and Search Opinion dated Jul. 18, 2016 for EP Application No. 14770695.6. 13 pages.
Extended European Search Report and Search Opinion dated Jul. 7, 2016 for EP Application No. 14768317.1. 7 pages.
Extended European Search Report and Search Opinion dated May 17, 2017 for EP Application No. 15746995.8. 8 pages.
Extended European Search Report and Search Opinion dated Nov. 23, 2015 for EP Application No. 12862525.8. 16 pages.
Gadaginamath, et al., "Synthesis and antibacterial activity of novel 1-butyl-2-phenoxyl2-phenylthlol2-aminomethyl-5-methoxyindole derivatives", Polish Journal of Chemistry (1997), 71(7), 923-928 CODEN: PJCHDQ; ISSN:0137-5083.
Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.
GBT Announces Positive Top-line Data from Part A of the Phase 3 Hope Study of Voxelotor in Sickle Cell Disease, Press Release dated Jun. 27, 2018. Available at http://ir.gbt.com/phoenix.zhtml?c=254105&p=irol-newsArticle&ID=2356168.
Ghate et al., "Synthesis of vanillin ethers from 4-(bromomethyl) counmarins as anti-inflammatory agents," European Journal of Medicinal Chemistry (2003), 38(3), 297-302 CODEN: EJMCA5; ISSN: 0223-5234.
Gibson et al., "Novel small molecule bradykinin B2 receptor antagonists", Journal of Medicinal Chemistry, 2009, vol. 52, pp. 4370-4379.
Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).
Goodman and Gilman's the Pharmacological Basis of Therapeutics (Tenth Edition 2001), McGraw Hill. Chapter I, pp. 3-29.
Grashey, "The nitro group as a 1,3-dipole in cycloadditions" Angewandfe Chemie (1962), 74, 155 CODEN: ANCEAD; ISSN: 0044-8249.
Gu, et al. Grouping solvents by statistical analysis of solvent property parameters: implication to polymorph screening. Int J Pharm. Sep. 28, 2004;283(1-2):117-25.
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.
Guillory (in Brittain ed.) Polymorphism in Pharmaceutical Solids. NY, Marcel Dekker, Inc. 1999; 1-2:183-226.
Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.
Hang, Song. "Pharmaceutical Separation Engineering" East China University of Technology Press. Aug. 31, 2011; 270-272. (in Chinese with English abstract).
Hanmantgad et al., "Synthesis and pharmacological properties of some r-(2-benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.
He et al., "Prodrugs of Phosphonates, Phosphinates, and Phosphates", Prodrugs: Challenges and rewards Part 2, edited by Stella et al., 2007, pp. 223-264.
Heimbach et al., "Enzyme-mediated precipitation of patent drugs from their phosphate prodrugs", International Journal of Pharmaceutics, 261, p. 81-92, 2003.
Heimbach et al., "Prodrugs: Challenges and Rewards Part I," New York, NY, Singer:AAPS Press, (2007), 5(Chapter 2.2.1):157-215 Overcoming Poor Aqueous Solubility of Drigs for Oral Delivery.
Heimgartner et al., "Stereoselective synthesis of swainsonines from pyridines", Tetrahedron, Elsevier Science Publishers, Amsterdam, NL, 2005, vol. 61, No. 3, pp. 643-655.
Hoffman, et al. 3-Hydroxy-3-methyglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).
Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.
Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.
International Preliminary Report on Patentability dated Jun. 5, 2018 for PCT/US2016/064723. (10 pages).
International Preliminary Report on Patentability for PCT/US2014/022846 dated Sep. 15, 2015. 7 pages.
International Preliminary Report on Patentability for PCT/US2014/022742 dated Sep. 15, 2015. 7 pages.
International Preliminary Report on Patentability for PCT/US2014/022733 dated Sep. 15, 2015. 11 pages.
International Preliminary Report on Patentability for PCT/US2014/022769 dated Sep. 15, 2015. 8 pages.
International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Aug. 4, 2017 for PCT Application No. PCT/US2017/032104. 10 pages.
International Search Report and Written Opinion dated Dec. 8, 2014 for PCT Application No. PCT/US2014/052575. 10 pages.
International Search Report and Written Opinion dated Jan. 22, 2018 for PCT Application No. PCT/US2017/056352. 12 pages.
International Search Report and Written Opinion dated Jul. 22, 2014 for PCT Application No. PCT/US2014/022846. 11 pages.
International Search Report and Written Opinion dated Jul. 30, 2014 for PCT Application No. PCT/US2014/029682. 16 pages.
International Search Report and Written Opinion dated Jul. 31, 2014 for PCT Application No. PCT/US2014/022789. 13 pages.
International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 11, 2015 for PCT Application No. PCT/US2015/014589. 5 pages.

(56) References Cited

OTHER PUBLICATIONS

International Search Report and Written Opinion dated May 20, 2013 for PCT Application No. PCT/US2012/072183. 11 pages.
International Search Report and Written Opinion dated May 3, 2017 for PCT Application No. PCT/US2016/064723. 15 pages.
International Search Report and Written Opinion dated Nov. 28, 2014 for PCT Application No. PCT/US2014/052576. 10 pages.
International Search Report and Written Opinion dated Oct. 31, 2014 for PCT Application No. PCT/US2014/013575. 10 pages.
Israel office action dated Aug. 11, 2016 for Israeli Patent Application No. 233329.
Ito et al., A medium-term rat liver bioassay for rapid in vivo detection of carcinogenic potential of chemicals,01D Cancer Science, 2005, 94, pp. 3-8.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Jarvest et al., "Discovery and optimisation of potent, selective, ethanolamine Inhibitors of bacterial phynylalanyl tRNA synthetase", Bioorganic & Medicinal Chemistry Letter (2005), 15(9), 2305-2309 CODEN: BMCLES; ISSN: 0960-894X.
Karche et al., "Electronic Effects in Migratory Groups [1,4]-versus [1,2]-Rearrangement in Rhodium Carbenoid Generated Bicyclic Oxonium Ylides", Journal of Organic Chemistry (2001), 66(19), 6323-6332 CODEN: JOCEAH; ISSN: 0022-3263.
Katritzky et al., "Synthesis of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journal/2003/Vargoglis/AV-622A/6ss.pdf.
Kaye et al., "DABCO-catalyzed reactions of salicylaidehydes with acrylate derivatives", Synthetic Communications (1996), 26(11), 2085-97 CODEN: SYNCAV; ISSN: 0039-7911.
Kaye et al., "Does the DABCO-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Keidan, et al. Effect of BW12C on oxygen affinity of hemogoblin in sickle-cell disease. The Lancet. 1986; 327(8485):831-834.
Kessar et al., "Synthesis of lsoindolobenzazepines via photocyclization of N-(2-formylphenelhyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., An Interesting Application of Photocyclisation in Apophdeadane Alkalid Synthesis. Tetrahedron Letters (1987), 28(44), 5323-5326. CODEN: TELEAY; ISSN: 0040-4039.
Kirk-Othermer Encyclopedia of Chemical Technology. 2002; 8:95-147.
Kise et al., "Electroreductive Intramolecular Coupling of Phthalimides with Aromatic Aldehydes: Application to the Synthesis of Lennoxamine". Journal of Organic Chemistry (2011), 76(23), 9658-9880 CODEN:JOCEAH; ISSN: 0022-3263.
Klis, et al. Halogen-lithium exchange versus deprotonation: synthesis of diboromic acids derived from aryl-benzyl ethers. Tetrahedron Letters, 48(7):1169-1173 (2007).
Kratochvil. Chapter 8 Solid Forms of Pharmaceutical Molecues. J. Sestak et al. (eds.), Glassy, Amorphous and Nano-Crystalline Materials. Hot Topics in Thermal Analysis and Calorimetry 8, 2011, pp. 129-140.
Krow,"The Baeyer-Villiger oxidation of ketones and aldehydes", Organic Reactions (Hoboken, NJ, United States) (1993), 43, No pp. given CODEN: ORHNBA URL: http://www3.interscience.wiley.com/cgi- bin/mrwhome/107610747/HOME.
Kucera, et al. Evaluation of Ceolus(TM) microcrystalline cellulose grades for the direct compression of enteric-coated pellets. Drug Development and Industrial Pharmacy. Mar. 1, 2012; 38(3):341-350.

Lakkannavar et al., "4-[2'-benzylideneanllino aryloxymethyl] coumarins E and Z isomers". Indian Journal of Heterocycilc Chemistry (1995), 4(4), 303-4 CODEN: IJCHEI; ISSN: 0971-1627.
Lehrer, et al. GBT440, a novel anti-polymerization agent, for the treatment of sickle cell disease. Global Blood Therapeutics. Apr. 1, 2016. (50 pages) Retrieved from the Internet: http://casicklecell.org/img/PresentationSlidesWebinar3.pdf.
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Liu et al., "Synthesis of Double-Armed Benzo-15-crown-5 and Their Complexation Thermodynamics with Akal Cations", Journal of Inclusion Phenomena and Macrocyclic Chemistry (2005), 52(3-4), 229-235 CODEN: JIPCF5; ISSN: 1388-3127.
Luan, et al. OPS-MODE model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.
Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.
Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL Farmaco, 1996, vol. 51, No. 8, 9, pp. 579-587.
Mantyla et al., Synthesis, in vitro evaluation and antileishmanial activity of water-soluble prodrugs of buparvaquone. J. Med. Chem. 2004, 47:188-195.
Marchetti et al., "Synthesis and biological evaluation of 5-substituted O4-alkylpyrimidines as CDK2 inhibitors," Org. Biomol. Chem, 2010, vol. 8, pp. 2397-2407.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
Mathur. "Microcrystalline Cellulose" in: "Handbook of Pharmaceutical Excipients, Second Edition", Jan. 1, 1994, the Pharmaceutical Press, London, pp. 84-87.
McKay et al., 7,11,15,28-Tetrakis[(2-formylphenoxy)methyl]-1,21,23,25-tetramethylresorcin[4]arene cavitand ethyl acetate ciathrate at 173 K, Acta Crystallographica, Section E: Structure Reports Online (2009), E65(4), 692-693 CODEN: ACSEBH; ISSN: 1600-5368 URL: http://journals.lucr.org/e/issues/2009/04/00fl22 33/fl2233.pdf.
McKay et al., "Microwave-assisted synthesis of a new series of resorcin[4]arena cavitand-capped porphyrin capsules", Organic & Biomolecular Chemistry (2009), 7(19), 3958-3968 CODEN: OBCRAK; ISSN: 1477-0520.
Merlino et al., "Development of second generation amidinohydrazones, thio- and semicarbazones as Trypanosoma cruzi-inhibitors bearing benzofuroxan and benzimidazole 1,3-dioxide core scaffolds", MedChemComm (2010), 1(3), 216-228 CODEN: MCCEAY; ISSN: 2040-2503.
Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.
Metcalf, et al., "Discovery of GBT440, an Orally Bioavailable R-State Stabilizer of Sickle Cell Hemoglobin," ACS Med. Chem. Lett., 2017, 8, 321-326.
Mitra et al., "Synthesis and biological evaluation of dibenz[b,f][1,5]oxazocine derivatives for agonist activity at x-opioid receptor", European Journal of Medicinal Chemistry (2011), 46(5), 1713-1720 CODEN: EJMCA5; ISSN: 0223-5234.

(56) References Cited

OTHER PUBLICATIONS

Mulwad et al., "Synthesis and anitmicrobial activity of [6'-methyl-4'-methoxy-2-oxo-2H-[1]-benzopyran)-2",4" dihydro-[1",2",4"}-triazol-3'-one and 3'phenylthiazolidin-4'-one-phenoxymethyl derivatives of dipyranoquinoline", Pharmaceutical Chemistry Journal Ahead of Print CODEN: PCJOAU; ISSN: 0091-150.

Muzaffar, et al., "Polymorphism and Drug Availability: a Review" J of Pharm. (Lahore), 1979, 1(1), 59-66.

Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.

Neelima et al., "A novel annelation reaction: synthesis of 6H-[1]benzopyrano[4,3-b]quinoiones "Chemistry & Industry (London, United Kingdom) (1986), (4), 141-2 CODEN: CHINAG; ISSN: 0009-3068.

New Introduction of Pharmacology (Sin Yakuzaigaku Soron)(revised 3rd Edition),Apr. 10, 1987, Nankodo Co., Ltd p. 111. (in Japanese with partial English translation).

New Pharmaceutical Preparation (Shin Seizaigaku), Nanzando Co.,Ltd., Apr. 25, 1984, p. 102-103 and pp. 232-233. (in Japanese with partial English translation).

Nnamani, et al., "Pyridyl derivatives of benzaldehyde as potential antisickling agents," Chem. Biodivers., (2008), 5(9):1762-1769.

Nogrady, Medicinal Chemistry a Biochemical Approach, Oxford University Press, New York, pp. 388-392 (1985).

Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.

Notice of Allowance dated Dec. 19, 2014 for U.S. Appl. No. 13/730,730. 11 pages.

Nyerges et al, "Synthesis of Indazole N-oxides via the 1.7-electrocyclization of azomethine ylides", Tetrahedron Letters (2001), 42(30), 5081-5083 CODEN: TELEAY; ISSN:0040-4039.

Nyerges et al, "Synthesis of Indazole N-oxides via the 1.7-electrocyclization of azomethine ylides", Tetrahedron Letters (2004), 60(44), 9937-9944 CODEN: TETRAB; ISSN:0040-4020.

OECD SIDS "SIDS Initial Assessment Report for 13th SIAM," Nov. 2001, pp. 1-95.

Office Action dated Aug. 29, 2014 for U.S. Appl. No. 13/730,730. 17 pages.

Office Action dated Dec. 3, 2013 for U.S. Appl. No. 13/730,674. 8 pages.

Office Action dated Jul. 6, 2015 for U.S. Appl. No. 13/815,874. 14 pages.

Office Action dated Jun. 12, 2015 for CN Application No. 201280070743.5. 13 pages.

Office Action dated Jun. 29, 2015 for U.S. Appl. No. 13/815,810. 19 pages.

Office Action dated Jun. 30, 2014 for U.S. Appl. No. 13/730,674. 9 pages.

Office Action dated Sep. 18, 2013 for U.S. Appl. No. 13/730,674. 10 pages.

Oh, et al. Solid-phase synthesis of 1,3-oxazolidine derivatives. Tetrahedron Letters. 2000; 41:5069-5072.

O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.

Otsuka, et al., "Effect of Polymorphic Forms of Bulk Powders on Pharmaceutical Properties of Carbamazepine Granules." Chem. Pharm. Bull., 47(6) 852-856 (1999).

Patani, et al. Bioisosterism: A Rational Approach in Drug Design. J. Chem Rev. 1996, 96(8), pp. 3147-3176.

Paul, et al. Hydroxyl directed C-arylation: synthesis of 3-hydroxyflavones and 2-phenyl-3-hydroxy pyran-4-ones under transition-metal free conditions. Org. Biomol. Chem., 2018, 16:444-451.

Perez et al., "Preparation of new 1,2-disubstituted ferrocenyl ammonlum salt", Polyhedron (2009), 28(14), 3115-3119 CODEN: PLYHE; ISSN:0277-5387.

Perkins et al., "Manganese(II), Iron(II), cobalt(II), and cooper(II)complexes of an extended inherently chiral tris-bipyricyl cage", Proceedings of the National Academy of Sciences of the United States of America (2006), 103(3), 532-537 CODEN: PNASA6; ISSN: 0027-8424.

Pharmacy—Foundation and Application—(Chozaigaku, Kiso to Ouyou), Nanzando Co.,Ltd., Sep. 20, 1977 p. 142-145. (in Japanese with partial English translation).

Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.

Prohens, et al. Polymorphism in pharmaceutical industry. The Pharmacist. Apr. 1, 2007; 373:58-68. (in Spanish with English abstract).

Pubchem CID 54009805 Create Date: Dec. 4, 2011 p. 1.

Pubchem CID 54883281 Create Date: Aug. 19, 2012 p. 1.

Reagan-Shaw, et al. Dose translation from animal to human studies revisited. The FASEB Journal. Mar. 2007; 22:659-661.

Remington's Pharmaceutical Sciences, 17th Edition, A. Gennaro editor, Easton Pennsylvania. Table of Contents. (1985).

Rodriguez-Spong, et al. General principles of pharmaceutical solid polymorphism: a supramolecular perspective. Adv Drug Deliv Rev. Feb. 23, 2004;56(3):241-74.

Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.

Rooseboom et al., Enzyme-catalyzed activation of anticancer prodrugs. Pharmacol. Rev. 2004, 56:53-102.

Ruchirawat et al., "A novel synthesis of aporhoeadanes", Tetrahedron Letters (1984), 25(32), 3485-8 CODEN: TELEAY; ISSN: 0040-4039.

Safo, et al. Structural basis for the potent antisickling effect of a novel class of five-membered heterocyclic aldehydic compounds. J Med Chem. Sep. 9, 2004;47(19):4665-76.

Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.

Sahm et al., "Synthesis of 2-arylbenzofurans" Justus Liebigs Annalen der Chemie (1974), (4), 523-38 CODEN: JLACBF; ISSN: 0075-4617.

Sainsbury et al., "1,2-Dihydroisoquinolines, IV. Acylation" Tetrahedron (1966), 22(8), 2445-52 CODEN: TETRAB; ISSN: 0040-4020.

Sarodnick et al., "Quinoxalines XV, Convenient Synthesis and Structural Study of Pyrazolo[1,5-a]quinoxalines", Journal of Organic Chemistry (2009), 74(3), 1282-1287 CODEN: JOCEAH; ISSN: 0022-3263.

Schudel, et al. Uber die Chemie des Vitamins E. Helvatica Chimica Acta. 1963; 66:636-649.

Seddon. Pseudopolymorph: A Polemic. The Quill Centre, The Queen's University of Belfast, United Kingdom. Jul. 26, 2004. 2 pages.

Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).

Shin, et al. Interpretation of Animal Dose and Human Equivalent Dose for Drug Development. The Journal of Korean Oriental Medicine. 2010; 31(3):1-7.

Siddiqui et al., "The Presence of Substitutents on the Aryl Moiety of the Aryl Phosphoramidate Derivative of d4T Enhances Anti-HIV Efficasy in Cell Culture-Activity Relationship," J. Med. Chem., (1999), 42:393-399.

(56) References Cited

OTHER PUBLICATIONS

Silva et al., "Advances in prodrug design," Mini Rev. Med. Chem., (2005), 5(10):893-914.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Singhal, et al., "Drug Polymorphism and Dosage Form Design: a Practical Perspective" Advanced Drug Delivery reviews 56, p. 335-347 (2004).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Srivastava et al., "Synthesis adn biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Syntesis and mass spectrometric study of aryloxymethylquinoxalines and benzo[b]furylquinoxalines" Tetrahedron (2004), 60(29), 6063-6078 CODEN: TETRAB; ISSN:0040-4020.
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley. Solubilizing excipients in oral and injectable formulations. Pharm Res. Feb. 2004;21(2):201-30.
Swann et al., "Rates of reductive elimination of substituted nitrophenois from the (indol-3-yl)methyl position of indolequinones", Journal of the Chemical Society, Perkin Transactions 2 (2001), (8), 1340-1345.
Table of Compounds, each of which can be found either in Table 1 of U.S. Pat. No. 9,018,210 or Table 1 of U.S. Pat. No. 9,012,450.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
Testa et al., Hydrolysis in Drug and Prodrug Metabolism, Jun. 2003, Wiley-VCH, Zurich, 419-534.
The Pharmacopoeia of Japan the Sixteen edition, 2011 pp. 64-68 2.58 X-ray powder diffraction measuring method p. 2070 (in Japanese with partial English translation).
Tome et al., "Product class 13: 1,2,3-triazoles", Science of Synthesis (2004), 13, 415-601 CODEN: SSCYJ9.
Tsuge, et al. Suppressive Effect of Vitamin B6-Sugar Derivatives on the Proliferation of Feline Mammary Tumor Cell, FRM. Vitamins (Japan), 2006; 80(11):537-542. (in Japanese with English Abstract).
U.S. Pharmacopia #23, National Formulary #18, 1995, 1843-1844.
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
vanRompaey et al., "A versatile synthesis of 2-substituted 4-amino-1,2,4,5-tetrahydro-2-benzazepine-3-ones", Tetrahedron (2003), 59(24), 4421-4432 CODEN: TETRAB; ISSN:0040-4020.
vanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes" Organometallics (2010), 29(2), 409-416.
Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Wang et al., "Studies of Benzothiophane Template as Potent Factor IXa (FIXa) Inhibitors in Thrombosis", Journal of Medicinal Chemistry (2010), 53, 1465-1472.
Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.
Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Wermuth, Camille G., "Molecular Variations Based on Isosteric Replacements", the Practice of Medicinal Chemistry, 1996, pp. 203-232.
Yan et al., "Synthesis, crystal structure and antibacterial activity of dibutylitin carboxylate", Huaxue Tongbao (2007), 70(4), 313-316 CODEN: HHTPAU; ISSN: 0441-3776.
Yan et al., "Synthesis, crystal structure and antibacterial activity of di-n-butyltin di-2(2-formylphenoxy)acetic ester", Yingyong Huaxue (2007), 24(6), 660-664.
Yang, et al. Structural requirement of chalcones for the inhibitory activity of interleukin-5. Bioorg Med Chem. Jan. 1, 2007;15(1):104-11. Epub Oct. 10, 2006.
Yoon et al., The Chirality Conversion Reagent for Amino Acids Based on Salicyl Aldehyde. Bull. Korean Chem. Soc., (2012), 33:1715-1718.
Zhang et al., "DFT study on Rull-catalyzed cyclization of terminal alkynals to cycloalkenes", International Journal of Quantum Chemistry (2009), 109(4), 679-687 CODEN: IJQCB2; ISSN:0020-7608.
Zhang, et al. A selective fluorescent chemosensor with 1, 2, 4-triazole as subunit for Cu (II) and its application in imaging Cu (II) in living cells. Dyes and Pigments. 2012; 92(3):1370-1375.
Zhang, et al. Current prodrug strategies for improving oral absorption of nucleoside analogues. Asian Journal of Pharmaceutical Sciences. Apr. 2014; 9(2):65-74.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.
Zwaagstra et al., "Synthesis and Structure-Activity Relationships of Carboxylated Chalcones: A Novel Series of Cys-LT1 (LTD4) Recaptor Antagonists", Journal of Medicinal Chemistry (1997), 40(7), 1075-1089 CODEN: JMCMAR; ISSN: 0022-2623.
CAS Registry No. 329222-79-9; STN Entry Date Mar. 28, 2001; Benzaldehyde, 2-[(4-chloro-3-methylphenoxy)methyl]-4-methoxy-.
CAS Registry No. 733030-49-4; STN Entry Date Aug. 26, 2004; Benzaldehyde, 5-bromo-2-(phenoxymethyl)-.
CAS Registry No. 886362-88-5; STN Entry Date Jun. 1, 2006; Benzaldehyde, 2,4-dichloro-6-[(4-fluorophenoxy)methyl]-.
Extended European Search Report and opinion dated Nov. 11, 2019 for EP Application No. 17796828.6. 7 pages.
FDA approves voxelotor for sickle cell disease. Dated Nov. 25, 2019. https://www.fda.gov/drugs/resources-information-approved-drugs/fda-approves-voxelotor-sickle-cell-disease. 2 pages.
Hebbel et al., "Sickle hemoglobin oxygen affinity-shifting strategies have unequal cerebrovascular risks," Am. J. Hematol., 93(3), 321-325 (2018).
Li, et al. Iron-Catalyzed Cascase Arene-Aldehyde/Cyclizations for the Highly Efficient Synthesis of Xanthenes and Its Analogous: Observation of a C—C Bond Cleavage in Indole-Based Triarylmethanes. J. Org. Chem., 2009, 74, 6797-6801.
Vichinsky et al., "A Phase 3 Randomized Trial of Voxelotor in Sickle Cell Disease," N. Engl. J. Med, 2019; 381(6), 509-519.

SUBSTITUTED HETEROARYL ALDEHYDE COMPOUNDS AND METHODS FOR THEIR USE IN INCREASING TISSUE OXYGENATION

REFERENCES TO RELATED APPLICATIONS

This application is a continuation of U.S. patent application Ser. No. 15/864,433, filed Jan. 8, 2018, now U.S. Pat. No. 10,377,741, which is a continuation of U.S. patent application Ser. No. 15/391,669, filed Dec. 27, 2016, which is a continuation of U.S. patent application Ser. No. 14/662,145, filed Mar. 18, 2015, which is a continuation of U.S. patent application Ser. No. 13/730,730, filed Dec. 28, 2012, now U.S. Pat. No. 9,012,450, which claims benefit under 35 U.S.C. § 119(e) to U.S. Provisional Patent Application Nos. 61/661,327, filed Jun. 18, 2012, and 61/581,063, filed Dec. 28, 2011, the disclosures of each of which are hereby incorporated by reference in their entireties for all purposes.

FIELD OF THE INVENTION

The present invention generally relates to substituted heteroaryl aldehydes and derivatives thereof that act as allosteric modulators of hemoglobin, methods and intermediates for their preparation, pharmaceutical compositions comprising the modulators, and methods for their use in treating disorders mediate by hemoglobin and disorders that would benefit from increased tissue oxygenation.

BACKGROUND OF THE INVENTION

Hemoglobin (Hb) is a tetrameric protein in red blood cells that transports up to four oxygen molecules from the lungs to various tissues and organs throughout the body. Hemoglobin binds and releases oxygen through conformational changes, and is in the tense (T) state when it is unbound to oxygen and in the relaxed (R) state when it is bound to oxygen. The equilibrium between the two conformational states is under allosteric regulation. Natural compounds such as 2,3-bisphosphoglycerate (2,3-BPG), protons, and carbon dioxide stabilize hemoglobin in its de-oxygenated T state, while oxygen stabilizes hemoglobin in its oxygenated R state. Other relaxed R states have also been found, however their role in allosteric regulation has not been fully elucidated.

Sickle cell disease is a prevalent disease particularly among those of African and Mediterranean descent. Sickle hemoglobin (HbS) contain, a point mutation where glutamic acid is replaced with valine, allowing the T state to become susceptible to polymerization to give the HbS containing red blood cell, their characteristic sickle shape. The sickled cell, are also mom rigid than normal red blood cells, and their lack of flexibility can lead to blockage of blood vessels. Certain synthetic aldehydes have been found to shift the equilibrium from the polymer forming T state to the non-polymer forming R state (Nnamani et al. Chemistry & Biodiversity Vol. 5, 2008 pp. 1762-1769) by acting as allosteric modulators to stabilize the R stale through formation of a Schiff base with an amino group on hemoglobin.

U.S. Pat. No. 7,160,910 discloses 2-furfuraldehydes and related compounds that are also allosteric modulators of hemoglobin. One particular compound 5-hydroxymethyl-2-furfuraldehyde (5HMF) was found to be a potent hemoglobin modulator both in vitro and in vivo. Transgenic mice producing human HbS that were treated with 5HMF were found to have significantly improved survival times when exposed to extreme hypoxia (5% oxygen). Under these hypoxic conditions, the 5HMF heated mice were also found to have reduced amounts of hypoxia-induced sickled red blood cells as compared to the non-treated mice.

A need exists for therapeutics that can shift the equilibrium between the deoxygenated and oxygenated states of Hb to treat disorders that are mediated by Hb or by abnormal Hb such as HbS. A need also exists for therapeutics to treat disorders that would benefit from having Hb in the R state with on increased affinity for oxygen. Such therapeutics would have applications ranging, for example, from sensitizing hypoxic tumor cells that are resistant to standard radiotherapy or chemotherapy due to the low levels of oxygen in the cell, to treating pulmonary and hypertensive disorders, and to promoting wound healing.

BRIEF SUMMARY OF THE INVENTION

The present invention provides, in one aspect, allosteric modulators of hemoglobin. In another aspect, provided are pharmaceutical compositions comprising the allosteric modulators disclosed herein. In other aspects, provided are methods for treating disorders mediated by hemoglobin and methods for increasing tissue oxygenation for treating disorders that would benefit from increased oxygenation, such methods comprising administering the allosteric modulators disclosed herein to a subject in need thereof. In still other aspects, provided are methods for preparing the allosteric modulators disclosed herein. These and other embodiments of the invention are more folly described in the description that follows.

DETAILED DESCRIPTION OF THE INVENTION

I. Definitions

As used herein, the below terms have the following meanings unless specified otherwise.

The abbreviations used herein are conventional, unless otherwise defined: aq=aqueous; Boc=t-butylcarboxy, (Boc)$_2$O=di-tert-butyl dicarbonate, ° C.=degrees celcius, mCPBA=m-chloroperoxybenzoic acid, DCM=dichloromethane (CH$_2$Cl$_2$), DIBAL=diisobutylaluminum hydride, DIEA=diisopropylethyl amine; DMF=dimethyl formamide, EtOAc=ethyl acetate, EtOH=ethanol, g=gram, H$_2$=hydrogen; H$_2$O=water, HBr=hydrogen bromide; HCl=hydrogen chloride, HPLC=high pressure liquid chromatography, h=hour, LAH=lithium aluminum hydride (LiAlH$_4$); MeCN=acetonitrile; LRMS=Low Resolution Mass Spectrum MS=Mass Spectrum, m/z=mass to charge ratio, MHz=Mega Hertz, MeOH=methanol, μM=micromolar, μL=microliter, mg=milligram, mM=millimolar, mmol=millimole, mL=milliliter, min=minute, M=molar. Na$_2$CO$_3$=sodium carbonate, ng=nanogram, N=Normal, NMR=nuclear magnetic resonance, Pd/C=palladium on carbon, rp=reverse phase, sat=saturated, rt=room temperature, SEM=(2-(trimethylsilyl)ethoxy)methyl, TEA=triethylamine, THF=tetrahydrofuran, TFA=trifluoroacetic acid, TLC=thin layer chromatography, and TMS=trimethylsilyl.

It is noted hero that as used in this specification and the appended claims, the singular forms "a," "an," and "the" include plural reference unless the context clearly dictates otherwise.

"Alkoxy" refers to —(O)alkyl) where alkyl as defined herein. Representative examples of alkoxy groups include methoxy, ethoxy, t-butoxy, and the like.

"Alkyl," by itself or as part of another substituent, means, unless otherwise stated, a straight or branched drain, folly saturated aliphatic hydrocarbon radical having the number of carbon atom, designated. For example, "$C_{1-8}$alkyl" refer, to a hydrocarbon radial straight or branched, containing from 1 to 8 carbon atom, that is derived by the removal of one hydrogen atom from a single carbon atom of a parent alkane. Alkyl include, branched chain isomer, of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" refers to a linear monovalent hydrocarbon radical or a branched monovalent hydrocarbon radical having the number of carbon atoms indicated in the prefix and containing at least one double bond, but no more than three double bonds. For example, $C_{2-8}$alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, $C_{2-8}$alkynyl is meant to include ethynyl, propynyl and the like.

The term "allosteric modulators" refers to compounds that bind to hemoglobin to modulate its affinity for oxygen. In one group of embodiments, the allosteric modulators act to stabilize or destabilize a particular hemoglobin conformation. In one group of embodiments, the modulators stabilize the relaxed R state. In other embodiments, the modulators destabilize the tense T state. In one group of embodiments, the allosteric modulators can destabilize one conformation while stabilizing another. In some such embodiments, the modulators stabilize a relaxed R state and destabilize the tense T state. The modulators, in addition to modulating the affinity of hemoglobin for oxygen, may also confer additional properties to hemoglobin such as increasing its solubility. The present disclosure is not intended to be limited to the mechanism by which the allosteric modulators interact with and regulate hemoglobin. In one group of embodiments, the allosteric modulators inhibit the polymerization of HbS and the sickling of red blood cells. In one group of embodiments, the binding of the allosteric modulators provided herein to hemoglobin can occur through covalent or non-covalent interactions. In one embodiment, the allosteric modulators react through its aldehyde substituent with an amine group on a hemoglobin amino acid side chain to form a Schiff base.

"Amino" refers to a monovalent radical —$NH_2$.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of aryl groups include phenyl, 1-naphthyl, 2-naphthyl and 4-biphenyl.

"Bond" when used as an element in a Markush group means that the corresponding group does not exist, and the groups of both sides are directly linked.

"Cycloalkyl" refers to a saturated or partially saturated cyclic group of from 3 to 14 carbon atoms and no ring heteroatoms and having a single ring or multiple rings including fused, bridged, and spiro ring systems. The term "cycloalkyl" includes cycloalkenyl groups, a partially saturated cycloalkyl ring having at least one site of >C=C< ring unsaturation. Examples of cycloalkyl groups include, for instance, adamantyl, cyclopropyl, cyclobutyl, cyclopentyl, cyclooctyl, and cyclohexenyl. "$C_{u'-v'}$cycloalkyl" refers to cycloalkyl groups having u' to v' carbon atoms as ring members. "$C_{u'-v'}$cycloalkenyl" refers to cycloalkenyl groups having u' to v' carbon atoms as ring members.

The term "hemoglobin" as used herein refers to any hemoglobin protein, including normal hemoglobin (Hb) and sickle hemoglobin (HbS).

"Heteroaryl" refers to a cyclic or polycyclic radical having at least one aromatic ring and from one to five ring heteroatom selected from N, O, and S, and optionally one or more oxo (=O) substituents attached to one or more carbon ring atoms, and wherein the nitrogen and sulfur ring atoms are optionally oxidized. A heteroaryl group can be attached to the remainder of the molecule through a heteroatom or through a carbon atom and can contain 5 to 10 carbon atoms. Heteroaryl groups include polycyclic aromatic ring(s) fused to non-aromatic cycloalkyl or heterocycloalkyl groups, and where the point of attachment to the remainder of the molecule can be through any suitable ring atom of any ring. In a polycyclic heteroaryl group, the ring heteroatom(s) can be in either an aromatic or non-aromatic ring or both. The term "aromatic ring" include any ring having at least one planar resonance structure where 2n+2 pi electrons are delocalized about the ring. Examples of heteroaryl groups include, but are not limited to, imidazopyridinyl groups, pyrrolopyridinyl groups, pyrazolopyridinyl groups, triazolopyridinyl groups, pyrazolopyrazinyl groups, pyridinyl groups, pyrazinyl groups, oxazolyl groups, imidazolyl groups, triazolyl groups, tetrazolyl groups, pyrazolyl groups, quinolinyl groups, isoquinolinyl groups, indazolyl groups, benzooxazolyl groups, naphthyridinyl groups, and quinoxalinyl groups. Other non-limiting examples of heteroaryl groups include xanthine, hypoxanthine, 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl, 6-quinolyl 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. "Bicyclic heteroaryl" refers to a heteroaryl radical that contains two rings.

The term "heterocycloalkyl" refers to a cycloalkyl group containing at least one ring heteroatom and optionally one or more oxo substituents. As used heroin, the term "heteroatom" is meant to include oxygen (O), nitrogen (N), and sulfur (S), wherein the heteroatoms are optionally oxidized, and the nitrogen atom(s) are optionally quaternized. Each heterocycle can be attached at any available ring carbon or heteroatom. Each heterocycle may have one or more rings. When multiple rings are present, they can be fused together. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, piperidine, morpholine, piperazine, isoxazoline, pyrazoline, imidazoline, pyrrolidine, and the like.

"Halo" or "halogen" by themselves or as part of another substituent, mean, unless otherwise stated, a fluorine, chlorine, bromine, or iodine atom. Additionally, terms such as "haloalkyl", ore meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "halo$C_{1-8}$alkyl" is meant to include difluoromethyl, trifluoromethyl, 2,2,2-trifluoroethyl, 4-chlorobutyl, 3-bromopropyl, and the like. The term "haloalkenyl", and "haloalkynyl" refers to alkenyl and alkynyl radicals having one or more halogen atoms. Additionally, term "haloalkoxy" refers to an alkoxy radical substituted with one or more halogen atoms. In one group of embodiments, the haloakyl, haloalkenyl, haloalkynyl, and haloalkoxy groups have from one to 5 or from one to 3 halo atoms. Examples of haloalkoxy groups include difluoromethoxy and trifluoromethoxy. In one group of embodiments, the halo atoms of the haloalkenyl and haloalkynyl groups are attached to the aliphatic portions of these groups.

The terms "optional" or "optionally" as used throughout the specification means that the subsequently described event or circumstance may but need not occur, and that the description includes instances where the event or circumstance occurs and instances m which it does not. For example, "heteroaryl group optionally substituted with an alkyl group means that the alkyl may but need not be present, and the description includes situations where the heteroaryl group is substituted with an alkyl group and situations where the heteroaryl group is not substituted with the alkyl group.

"Oxo" refers to the divalent atom =O.

In each of the above embodiments designating a number of atoms e.g. "$C_{1-8}$" is meant to include all possible embodiments that have one fewer atom. Non-limiting examples include $C_{1-4}$, $C_{1-5}$, $C_{1-6}$, $C_{1-7}$, $C_{2-8}$, $C_{2-7}$, $C_{3-8}$, $C_{3-7}$ and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or mote of the symptoms of the condition or disorder being treated. The therapeutically effective amount will vary depending on the compound, the disorder or condition and its severity and the age, weight, etc., of the mammal to be treated.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TBS"), trityl and substituted trityl groups, allyloxycarbonyl, 9-fluorenylmethyloxycarbonyl ("FMOC"), nitroveratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "aldehyde protecting group" refers to any known protecting group used to mask the aldehyde functionality. Aldehyde protecting groups include acetals and hemiacetals. The acetals and hemiacetals can be prepared from $C_{1-8}$ alcohols or $C_{2-8}$ diols. In one group of embodiments, the aldehyde protecting group is a five or six membered cyclic acetal formed from condensation of the aldehyde with ethylene or propylene glycol. In another group of embodiments the aldehyde protecting group is an imine or hydroxyimine. The aldehyde protecting groups of the present disclosure also include prodrug groups that convert the aldehyde to a prodrug, where the aldehyde is formed in vivo as the active agent under physiological conditions upon administration of the prodrug. The prodrug group can also serve to increase the bioavailability of the aldehyde. In one group of embodiments, the prodrug group is hydrolyzed in vivo to the aldehyde. In one group of embodiments, the aldehyde protecting group is a thiazolidine or N-acetylthiazolidine prodrug group. In one group of embodiments, the aldehyde protecting group is a thiazolidine prodrug group disclosed in U.S. Pat. No. 6,355,661. In one group of embodiments the modulators provided herein are condensed with L-cysteine or a L-cysteine derivative to form the corresponding thiazolidine protected aldehyde prodrug. In one group of embodiments, the thiazolidine has the formula

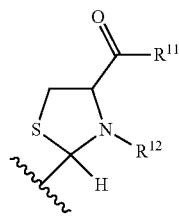

wherein $R^{11}$ is selected from the group consisting of OH, alkoxy, substituted alkoxy, cycloalkoxy, substituted cycloalkoxy, aryloxy, substituted aryloxy, heteroaryloxy, substituted heteroaryloxy, $N(R^{13})_2$ where $R^{13}$ is independently H, alkyl, substituted alkyl, alkenyl, substitute alkenyl, aryl, substituted aryl, heteroaryl, and substituted heteroaryl; $R^{12}$ is H or -L-$R^{14}$, where L is carbonyl or sulfonyl; $R^{14}$ is selected from the group consisting of alkyl, substituted alkyl, aryl, substituted aryl, heteroaryl, and substituted heteroaryl; the wavy line signifies the point of attachment to the phenyl ring of the allosteric modulators disclosed herein; and the term "substituted" refers to substitution by one or more substituents selected from the group consisting of COOH, CHO, oxyacyl, acyloxy, cycloacyloxy, phenol, phenoxy, pyridinyl, pyrrolidinyl, amino, amido, hydroxy, alkoxy, cycloalkoxy, F, Cl, Br, $NO_2$, cyano, sulfuryl, and the like. In one group of embodiments, provided are modulators having a thiazolidine protecting group where $R^{11}$ is alkoxy and $R^{12}$ is H, or where $R^{11}$ is OH and $R^{12}$ is —C(O)alkyl, or where $R^{11}$ is NH(heteroaryl) and $R^{12}$ is —C(O)alkyl.

The term "sickle cell disease" refers to diseases mediated by sickle hemoglobin (HbS) that results from a single point mutation in the hemoglobin (Hb). Sickle coll diseases includes sickle cell anemia, sickle-hemoglobin C disease (HbSC), sickle beta-plus-thalassaemia (HbS/$\beta^4$) and sickle beta-zero-thalassaemia (HbS/$\beta^0$).

The "subject" is defined herein to include animals such as mammals, including, but not limited to, primates (e.g., humans), cows, sheep, goats, horses, dogs, cats, rabbits, rate, mice and the like. In preferred embodiments, the subject is a human.

"Tautomer" refers to alternate forms of a molecule that differ in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring mom arrangements are possible.

The terms "treat", "treating", "treatment" and grammatical variations thereof as used herein, includes partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the invention may be applied preventively, prophylactically, palliatively or remedially.

The symbol > when used in connection with a substituent signifies that the substituent is a divalent substituent attached to two different atoms through a single atom on the substituent The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

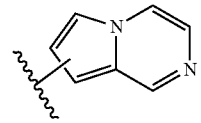

is intended to include, as the point of attachment, any of the six substitutable carbon atoms.

Compounds that have the same molecular formula but differ in the nature or sequence of bonding of their atoms or the arrangement of their atoms in space are termed "isomers". Isomers that differ in the arrangement of their atoms in space are termed "stereoisomers" "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that ore non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The compounds of the present invention may also contain unnatural proportions of atomic isotopes at one or more of the atoms that constitute such compounds. For example, the compounds may be radiolabeled with isotopes, such as for example deuterium ($^2$H), tritium ($^3$H), iodine-125 ($^{125}$I) or carbon-14 ($^{14}$C). All isotopic variations of the compounds of the present invention, whether radioactive or not, are intended to be encompassed within the scope of the present invention.

Unless indicated otherwise, the nomenclature of substituents that are not explicitly defined herein are arrived at by naming the terminal portion of the functionality followed by the adjacent functionality toward the point of attachment. For example, the substituent "alkoxyalkyl" refers to an akyl group that is substituted with alkoxy and "hydoxyalkyl" refers to an akyl group that is substituted with hydroxy. For both of these substituents, the point of attachment is at the alkyl group.

It is understood that the definitions and formulas provided herein are not intended to include impermissible substitution patterns (e.g., methyl substituted with 5 fluoro groups). Such impermissible substitution patterns are well known to the skilled artisan.

II. Hemoglobin Modulators

In one group of embodiments, provided is a compound of Formula (I):

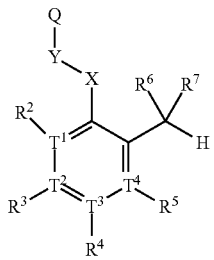

(I)

or a tautomer or pharmaceutically acceptable salt thereof, wherein Q is selected from the group consisting of aryl, heteroaryl, and heterocycloalkyl, each optionally substituted with one to three $R^a$;

Y is O or $CR^{1a}R^{1b}$, where $R^{1a}$ is H or halo and $R^{1b}$ is selected from the group consisting of H, halo, and OH;

X is selected from the group consisting of O, >CH(CH$_2$)$_n$R$^8$, and C(R$^9$)$_2$ where n is 0 or 1, $R^8$ is OH, and $R^9$ is independently H or halo; or Y-xtaken together is —NHC(O)— or —C(O)NH—;

$R^2$, $R^3$, $R^4$, and $R^5$ are independently absent or selected from the group consisting of hydrogen, halo, $R^b$, $OR^d$, O(CH$_2$)$_x$OR$^d$, O(CH$_2$)$_z$NR$^d$R$^d$, OC(O)R$^e$, SR$^d$, CN, NO$_2$, CO$_2$R$^d$, CONR$^d$R$^d$, C(O)R$^d$, OC(O)NR$^d$R$^d$, NR$^d$C(O)R$^e$, NR$^d$C(O)$_2$R$^e$, NR$^d$C(O)NR$^d$R$^d$, S(O)R$^e$, S(O)$_2$R$^e$, NR$^d$S(O)$_2$R$^e$, S(O)$_2$NR$^d$R$^d$, and N$_3$ where z is 0, 1, 2, or 3; or $R^5$ is —(CH$_2$)$_p$R$^{5a}$ where p is 0 or 1 and $R^{5a}$ is OH;

$R^6$ and $R^7$ together form oxo or an aldehyde protecting group, or $R^6$ together with $R^{1b}$, $R^8$, or $R^5$ forms a cyclic ether where one of $R^{1b}$, $R^8$, or $R^{5a}$ is O, $R^6$ is a bond, and R is selected from the group consisting of OH, C$_{1-8}$alkoxy, and haloC$_{1-8}$alkoxy;

$T^1$, $T^2$, $T^3$, and $T^4$ are independently C or N provided that at least one of $T^1$, $T^2$, $T^3$, and $T^4$ is N and at least one of $T^1$, $T^2$, $T^1$, and $T^4$ is C;

each $R^a$ is independently selected from the group consisting of halo, $R^b$, $OR^d$, O(CH$_2$)$_u$OR$^d$, O(CH$_2$)$_u$NR$^d$R$^d$, O(CH$_2$)$_u$NR$^d$C(O)R$^e$, O(CH$_2$)$_u$NR$^d$C(O)$_2$R$^e$, O(CH$_2$)$_u$NR$^d$S(O)$_2$R$^e$, NH$_2$, —(CH$_2$)$_k$OC(O)R$^e$, —(CH$_2$)$_k$SR$^d$, CN, NO$_2$, —(CH$_2$)$_k$CO$_2$(C$_{1-8}$alkyl)OH, —(CH$_2$)$_k$CO$_2$(C$_{1-8}$alkyl)(heteroaryl)C(O)(C$_{1-8}$alkyl), —(CH$_2$)$_k$CO$_2$R$^d$, —(CH$_2$)$_k$CONR$^d$R$^d$, —(CH$_2$)$_k$NR$^d$C(O)R$^e$, —(CH$_2$)$_k$NR$^d$C(O)$_2$R$^e$, —(CH$_2$)$_k$C(O)R$^d$, —(CH$_2$)$_k$OC(O)NR$^d$R$^d$, —NR$^d$(CH$_2$)$_u$OR$^d$, —NR$^d$(CH$_2$)$_u$NR$^d$R$^d$, —NR$^d$(CH$_2$)$_u$NR$^d$C(O)R$^e$, —NR$^d$(CH$_2$)$_u$NR$^d$C(O)$_2$R$^e$, —NR$^d$(CH$_2$)$_u$NR$^d$S(O)$_2$R$^e$, —(CH$_2$)$_k$NR$^d$C(O)R$^e$, —(CH$_2$)$_k$NR$^d$C(O)$_2$R$^d$, —(CH$_2$)$_k$NR$^d$C(O)NR$^d$R$^d$, —(CH$_2$)$_k$S(O)R$^e$, —(CH$_2$)$_k$S(O)$_2$R$^e$, —(CH$_2$)$_k$NR$^d$S(O)$_2$R$^e$, —C(O)(CH$_2$)$_k$NR$^d$S(O)$_2$R$^e$, —(CH$_2$)$_k$C(O)NR$^d$S(O)$_2$R$^e$, —(CH$_2$)$_k$S(O)$_2$NR$^d$R$^d$, N$_3$, —(CH$_2$)$_k$aryl optionally substituted with one to three $R^c$, —NR$^d$(CH$_2$)$_k$aryl optionally substituted with one to three $R^c$, —(CH$_2$)$_k$heteroaryl optionally substituted with one to three $R^c$, —NR$^d$(CH$_2$)$_k$heteroaryl optionally substituted with one to three $R^c$, —(CH$_2$)$_k$heterocycloalkyl optionally substituted with one to three $R^c$, and —NR$^d$(CH$_2$)$_k$heterocycloalkyl optionally substituted with one to three $R^c$ where k is 0, 1, 2, 3, 4, 5, or 6 and u is 1, 2, 3, 4, 5, or 6;

$R^b$ is independently selected from the group consisting of C$_{1-8}$alkyl, C$_{2-8}$alkenyl, and C$_{2-8}$alkynyl, each optionally independently substituted with one to three halo, $OR^d$, or $NR^dR^d$;

each $R^c$ is independently selected from the group consisting of halo, C$_{1-8}$alkyl, haloC$_{1-8}$alkyl, C$_{2-8}$alkenyl, haloC$_{2-8}$alkenyl, C$_{2-8}$alkynyl, haloC$_{2-8}$alkynyl, (CH$_2$)$_m$OR$^f$, OC(O)R$^g$, SR$^f$, CN, NO$_2$, (CH$_2$)$_m$CO$_2$R$^f$, CONR$^f$R$^f$, C(O)R$^f$, OC(O)NR$^f$R$^f$, (CH$_2$)$_m$NR$^f$R$^f$, NR$^f$C(O)R$^g$, NR$^f$C(O)$_2$R$^g$, NR$^f$C(O)NR$^f$R$^f$, S(O)R$^g$, S(O)$_2$R$^g$, NR$^f$S(O)$_2$R$^g$, S(O)$_2$NR$^f$R$^f$, N$_3$, (R$^f$)$_m$SiC$_{1-8}$alkyl, heteroaryl optionally substituted with one to three $R^h$, cycloalkyl optionally substituted with one to three $R^h$, and heterocycloalkyl optionally substituted with one to three $R^h$ where m is selected from the group consisting of 0, 1, 2, 3, 4, 5, and 6;

each $R^h$ is independently selected from the group consisting of halo, C$_{1-8}$alkyl, haloC$_{1-8}$alkyl, OR$^j$, OC(O)R, SR$^j$, NO$_2$, CO$_2$R$^j$, CONR$^j$R$^j$, C(O)R$^j$, OC(O)NR$^j$R$^j$, NR$^j$R$^j$, NR$^j$C(O)R$^t$, NR$^j$C(O)$_2$R$^t$, NR$^j$C(O)NR$^j$R$^j$, S(O)R$^t$, S(O)$_2$R$^t$, NR$^j$(O)$_2$R$^t$, and S(O)$_2$NR$^j$R$^j$; $R^d$, $R^f$, and $R^j$ are each independently selected from the group consisting of hydrogen, C$_{1-8}$alkyl, haloC$_{1-8}$alkyl, C$_{2-8}$alkenyl, haloC$_{2-8}$alkenyl, C$_{2-8}$alkynyl, and haloC$_{2-8}$ alkynyl; and $R^e$, $R^g$, and $R^t$ are each independently selected from the group consisting of C$_{1-8}$alkyl, haloC$_{1-8}$alkyl, C$_{2-8}$alkenyl, haloC$_{2-8}$alkenyl, C$_{2-8}$ alkynyl, and haloC$_{2-8}$alkynyl.

In one group of embodiments, X and Y are not both O.

In one group of embodiments, when X is O, $R^{1b}$ is not OH.

In one group of embodiments, when Y is O, and n is 0, $R^8$ is not OH.

In one group of embodiments, z is 0. In another group of embodiments, z is 1. In yet another group of embodiments, z is 2. In still another group of embodiments, z is 3.

In one group of embodiments, when $R^6$ and $R^7$ together are oxo, Y is $CH_2$, X is O or $CH_2$, and $R^5$ is H, halo, OH, CHO, or $OCH_3$, then Q is V or W.

In one group of embodiments, the compound is not

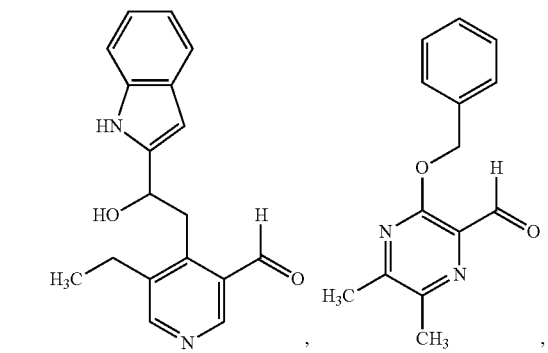

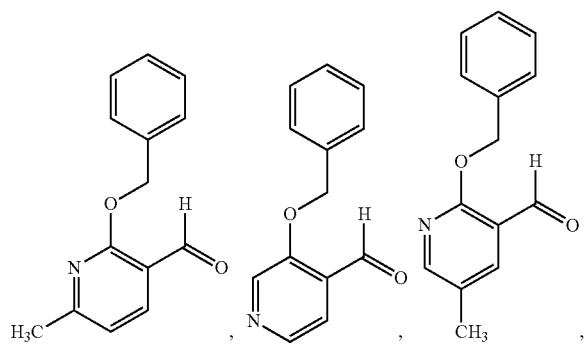

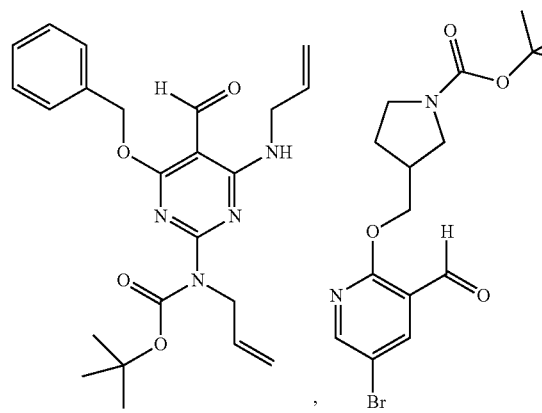

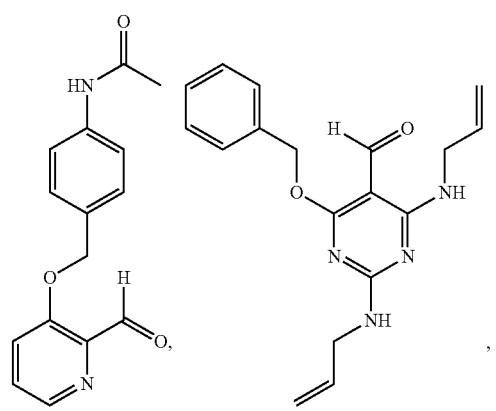

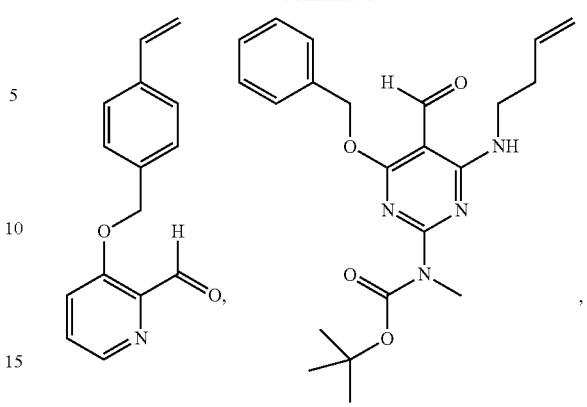

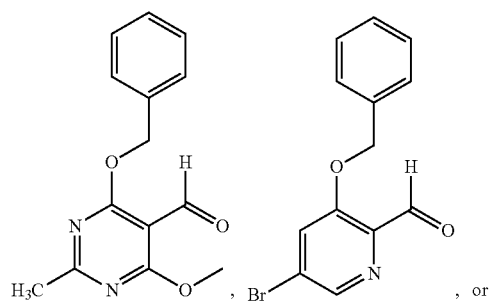

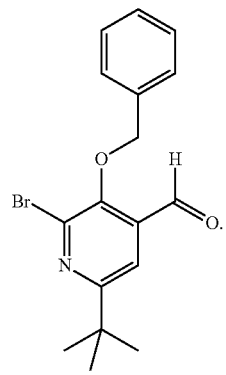

, or

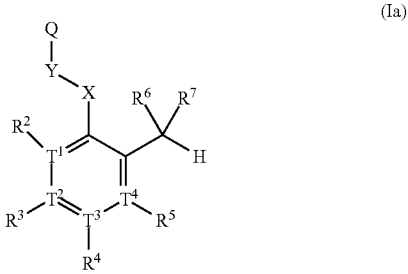

In one group of embodiments, provided is a compound of Formula (Ia):

$$\text{(Ia)}$$

or a tautomer or pharmaceutically acceptable salt thereof, wherein Q is selected from the group consisting of aryl, heteroaryl, and heterocycloalkyl, each optionally substituted with one to three $R^a$;

Y is O or $CR^{1a}R^{1b}$, where $R^{1a}$ is H or halo and $R^{1b}$ is selected from the group consisting of H, halo, and OH;

X is selected from the group consisting of O, >CH(CH$_2$)$_n$R$^8$, and C(R$^9$)$_2$ where n is 0 or 1, R$^8$ is OH, and R$^9$ is independently H or halo; or Y—X taken together is —NHC(O)— or —C(O)NH—;

R$^2$, R$^3$, R$^4$, and R$^5$ are independently absent or selected from the group consisting of hydrogen, halo, R$^b$, OR$^d$, OC(O)R$^e$, SR$^d$, CN, NO$_2$, CO$_2$R$^d$, CONR$^d$R$^d$, C(O)R$^d$, OC(O)NR$^d$R$^d$, NR$^d$R$^d$, NR$^d$C(O)R$^e$, NR$^d$C(O)NR$^d$R$^d$, S(O)R$^e$, S(O)$_2$R$^e$, NR$^d$S(O)$_2$R$^e$, S(O)$_2$NR$^d$R$^d$, and N$_3$; or R$^5$ is —(CH$_2$)$_p$R$^{5a}$ where p is 0 or 1 and R$^{5e}$ is OH;

R$^6$ and R$^7$ together form oxo or an aldehyde protecting group, or R$^6$ together with R$^{1b}$, R$^8$, or R$^5$ forms a cyclic ether where one of R$^{1b}$, R$^8$, or R$^{5a}$ is O, R$^6$ is a bond, and R$^7$ is selected from the group consisting of OH, C$_{1-8}$alkoxy, and haloC$_{1-8}$alkoxy:

T$^1$, T$^2$, T$^3$, and T$^4$ are independently C or N provided that at least one of T$^1$, T$^2$, T$^3$, and T$^4$ is N and at least one of T$^1$, T$^2$, T$^3$, and T$^4$ is C;

each R$^a$ is independently selected from the group consisting of halo, R$^b$, OR$^d$, OC(O)R$^e$, SR$^d$, CN, NO$_2$, CO$_2$R$^d$, CONR$^d$R$^d$, C(O)R$^d$, OC(O)NR$^d$R$^d$, NR$^d$C(O)R$^e$, NR$^d$C(O)$_2$R$^d$, NR$^d$C(O)NR$^d$R$^d$, S(O)R$^e$, S(O)$_2$R$^e$, NR$^d$S(O)$_2$R$^e$, S(O)$_2$NR$^d$R$^d$, N$_3$, aryl optionally substituted with one to three R$^c$, heteroaryl optionally substituted with one to three R$^c$, and heterocycloalkyl optionally substituted with one to three R$^e$;

each R$^b$ is independently selected from the group consisting of C$_{1-8}$alkyl, C$_{2-5}$alkenyl, and C$_{2-8}$alkynyl, each optionally independently substituted with one to three halo, OR$^d$, or NR$^d$R$^d$;

each R$^c$ is independently selected from the group consisting of halo, C$_{1-8}$alkyl, haloC$_{1-8}$alkyl, C$_{2-8}$alkenyl, haloC$_{2-8}$alkenyl, C$_{2-8}$alkynyl, haloC$_{2-8}$alkynyl, (CH$_2$)$_m$OR$^f$, OC(O)R$^g$, SR$^f$, CN, NO$_2$, CO$_2$R$^f$, CONR$^f$R$^f$, C(O)R$^f$, OC(O)NR$^f$R$^f$, (CH$_2$)$_m$NR$^f$R$^f$, NR$^f$C(O)R$^g$, NR$^f$C(O)$_2$R$^g$, NR$^f$C(O)NR$^f$R$^f$, S(O)R$^g$, S(O)$_2$R$^g$, NR$^f$S(O)$_2$R$^g$, S(O)$_2$NR$^f$R$^f$, and N$_3$ where m is selected from the group consisting of 0, 1, 2, 3, 4, 5, and 6;

each R$^d$ and R$^f$ is independently selected from the group consisting of hydrogen, C$_{1-8}$alkyl, haloC$_{1-8}$alkyl, C$_{2-8}$alkenyl, haloC$_{2-8}$alkenyl, C$_{2-8}$alkynyl, and haloC$_{2-8}$alkynyl; and each R$^e$ and R$^g$ is independently selected from the group consisting of C$_{1-8}$alkyl, haloC$_{1-8}$alkyl, C$_{2-8}$alkenyl, haloC$_{2-8}$alkenyl, C$_{2-8}$alkynyl, and haloC$_{2-8}$alkynyl;

provided that X and Y are not both O;
provided that when X is O, R$^{1b}$ is not OH;
provided that when Y is O, and n is 0, R$^8$ is not OH.

In one group of embodiments, the compound is not:

-continued

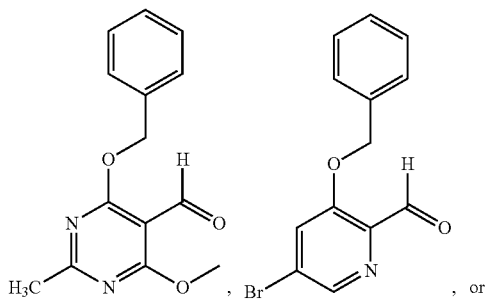, or

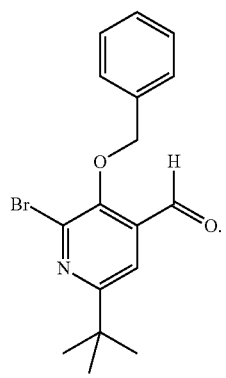

In one group of embodiments, provided is a compound having Formula (Ia)

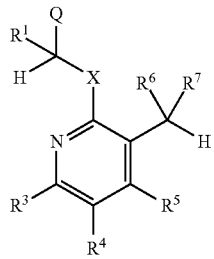

(Ia)

or a tautomer or pharmaceutically acceptable salt thereof.

In one group of embodiments, provided is a compound having Formula (Ib):

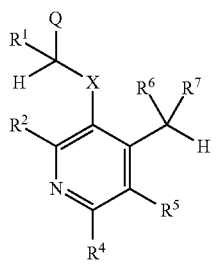

(Ib)

or a tautomer or pharmaceutically acceptable salt thereof.

In one group of embodiments, provided is a compound having Formula (Ic):

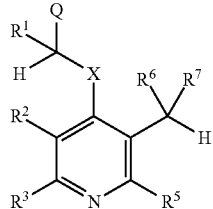

(Ic)

or a tautomer or pharmaceutically acceptable salt thereof.

In one group of embodiments, provided is a compound having Formula (Id):

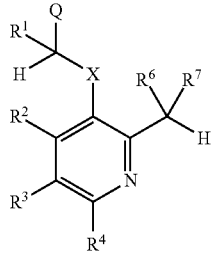

(Id)

or a tautomer or pharmaceutically acceptable salt thereof.

In one group of embodiments, at least two of $T^1$, $T^2$, $T^3$, and $T^4$ are N.

In one group of embodiments, provided is a compound having Formula (Ie), (If), (Ig), or (Ih):

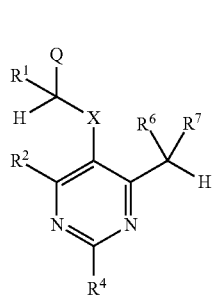

(Ie)

or a tautomer or pharmaceutically acceptable salt thereof.

In one group of embodiments, provided is a compound having Formula (If):

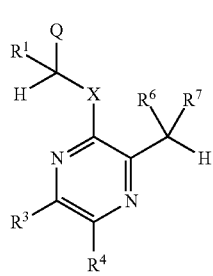

(If)

or a tautomer or pharmaceutically acceptable salt thereof.

In one group of embodiments, provided is a compound having Formula (Ig):

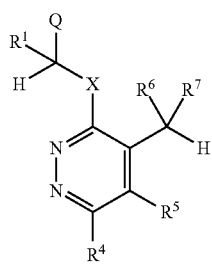

(Ig)

or a tautomer or pharmaceutically acceptable salt thereof.

In one group of embodiments, provided is a compound having Formula (h):

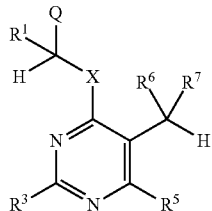

(Ih)

or a tautomer or pharmaceutically acceptable salt thereof.

In one group of embodiments, $R^6$ and $R^7$ together form oxo.

In one group of embodiments, $R^6$ and $R^7$ together form a thiazolidine.

In one group of embodiments, $R^6$ together with $R^{1b}$, $R^8$, or $R^5$ forms a cyclic ether where one of $R^{1b}$, $R^8$, or $R^{5a}$ is O, $R^6$ is a bond, and $R^7$ is selected from the group consisting of OH, $C_{1-8}$alkoxy, and haloC$_{1-8}$alkoxy.

In one group of embodiments, provided is a compound having Formula (Ii):

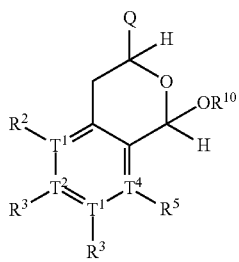

(Ii)

or a tautomer or pharmaceutically acceptable salt thereof, wherein $R^{10}$ is selected from the group consisting of H, $C_{1-8}$alkyl, and haloC$_{1-8}$alkyl.

In one group of embodiments, provided is a compound having Formula (Ij):

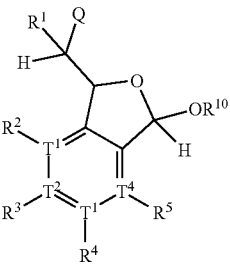

(Ij)

or a tautomer or pharmaceutically acceptable salt thereof, wherein $R^{10}$ is selected from the group consisting of H, $C_{1-8}$alkyl, and haloC$_{1-8}$alkyl.

In one group of embodiments, provided is a compound having Formula (Ik):

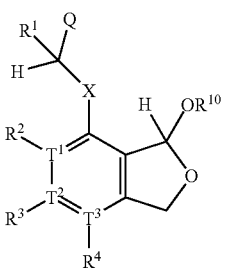

(Ik)

or a tautomer or pharmaceutically acceptable salt thereof, wherein $R^{10}$ is selected from the group consisting of H, $C_{1-8}$alkyl, and haloC$_{1-8}$alkyl.

In one group of embodiments, provided is a compound having Formula (Il):

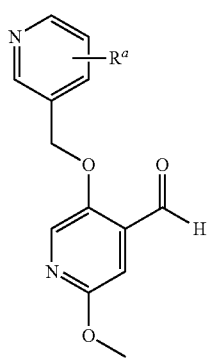

(Il)

or a tautomer or pharmaceutically acceptable salt thereof.

In one group of embodiments, provided is a compound having Formula (Im):

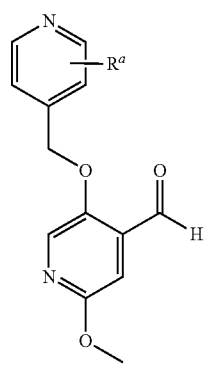

(Im)

or a tautomer or pharmaceutically acceptable salt thereof.

In one group embodiments, at least one $R^a$ is heteroaryl optionally substituted with one to three $R^c$.

In one group of embodiments at least one $R^a$ is heteroaryl attached to Q at the ring atom adjacent to ring atom bearing Y.

In one group of embodiments at least one $R^a$ is heteroaryl substituted with at least one $C_{1-8}$alkyl. In one group of embodiments at least one $R^a$ heteroaryl is substituted with at least one methyl.

In one group of embodiments at least one $R^a$ is pyrazolyl substituted with at least one $C_{1-8}$alkyl. In one group of embodiments at least one $R^a$ is pyrazoyl substituted with at least one $C_{1-8}$alkyl. In one group of embodiments, at least one $R^a$ is pyrazol-5-yl. In one group of embodiments, at least one $R^a$ is 4-methyl-pyrazol-5-yl.

In one group of embodiments, Q is a heteroaryl or heterocycloalkyl group optionally substituted with one to three $R^a$.

In one group of embodiments, Q is a bicyclic heteroaryl or heterocycloalkyl group optionally substituted with one to three $R^a$.

In one group of embodiments, Q is a bicyclic heteroaryl group optionally substituted with one to three $R^a$.

In one group of embodiments, Q is a bicyclic heteroaryl group substituted with one to three $R^a$. In one group of embodiments, Q is isoquinolin-4-yl optionally substituted with one to three $R^a$ wherein at least one $R^a$ is heteroaryl optionally substituted with one to three $R^c$. In one group of embodiments at least one $R^a$ is heteroaryl attached to said Q at the ring atom adjacent to ring atom bearing Y. In one group of embodiments at least one $R^a$ is heteroaryl substituted with at least one $C_{1-8}$alkyl. In one group of embodiments at least one $R^a$ heteroaryl is substituted with at least one methyl. In one group of embodiments at least one $R^a$ is pyrazolyl substituted with at least one $C_{1-8}$alkyl. In one group of embodiments at least one $R^a$ is pyrazoyl substituted with at least one methyl. In one group of embodiments, $R^a$ is pyrazol-5-yl. In one group of embodiments, $R^a$ is 4-methyl-pyrazol-5-yl.

In one group of embodiments, Q is selected from the group consisting of

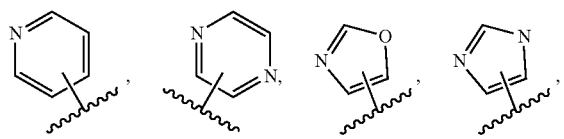

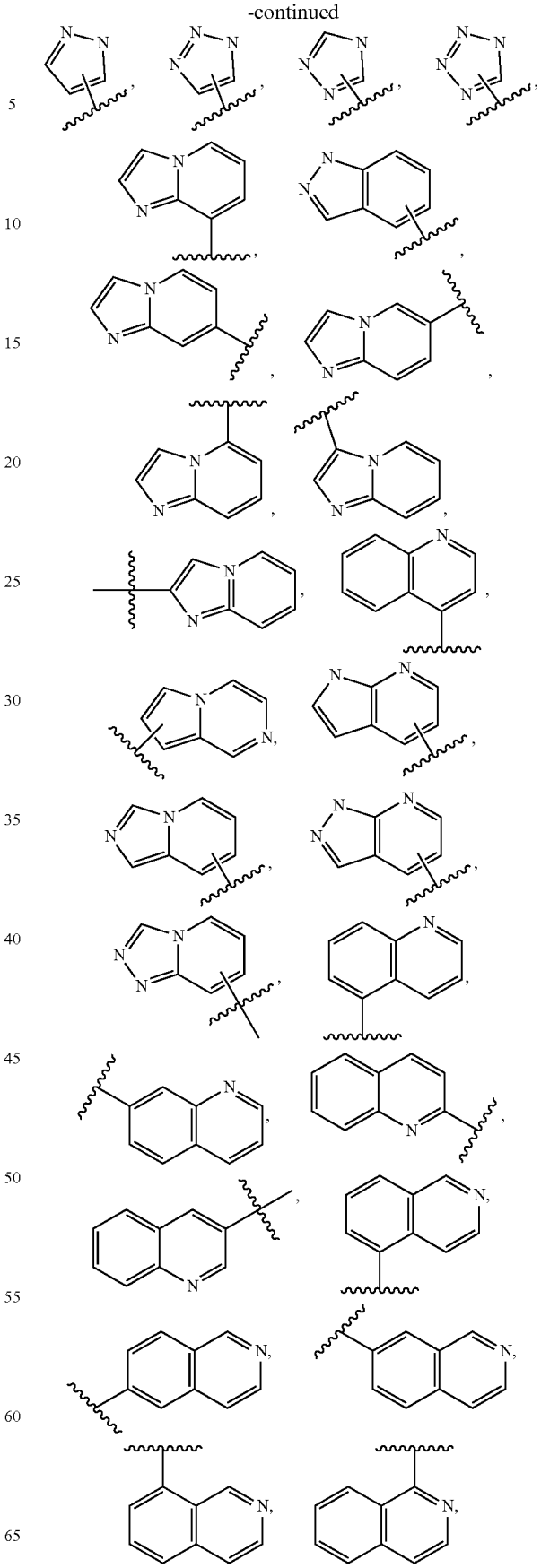

-continued

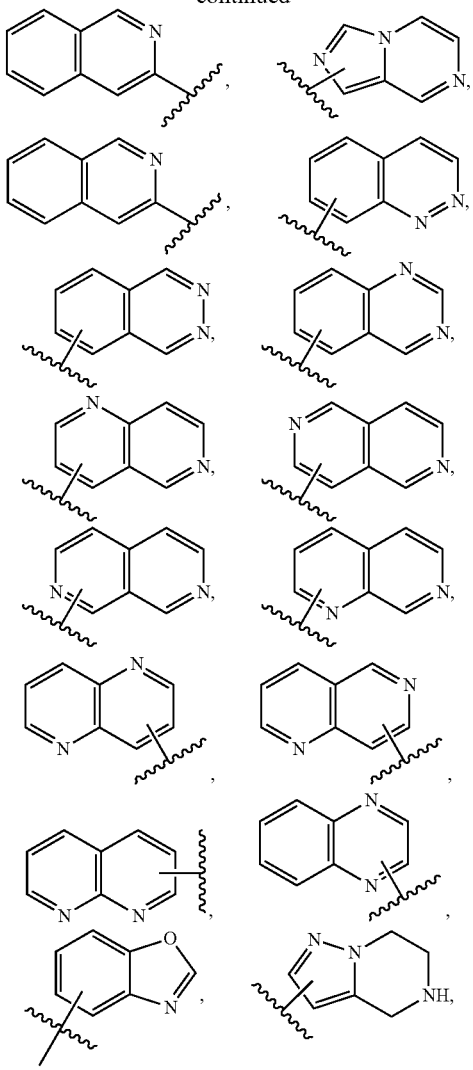

and naphthalene containing two to four ring nitrogen atoms, each optionally substituted with one to three $R^a$ and wherein the wavy line signifies the point of attachment to Y.

In one group of embodiments, Q is selected from the group consisting of

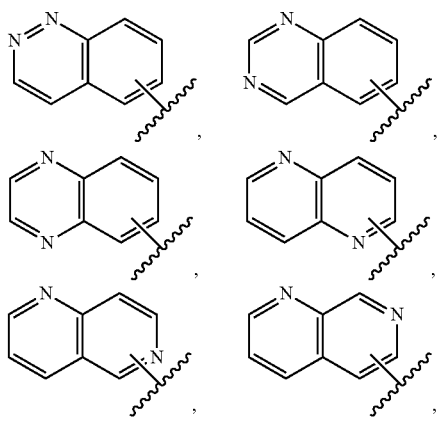

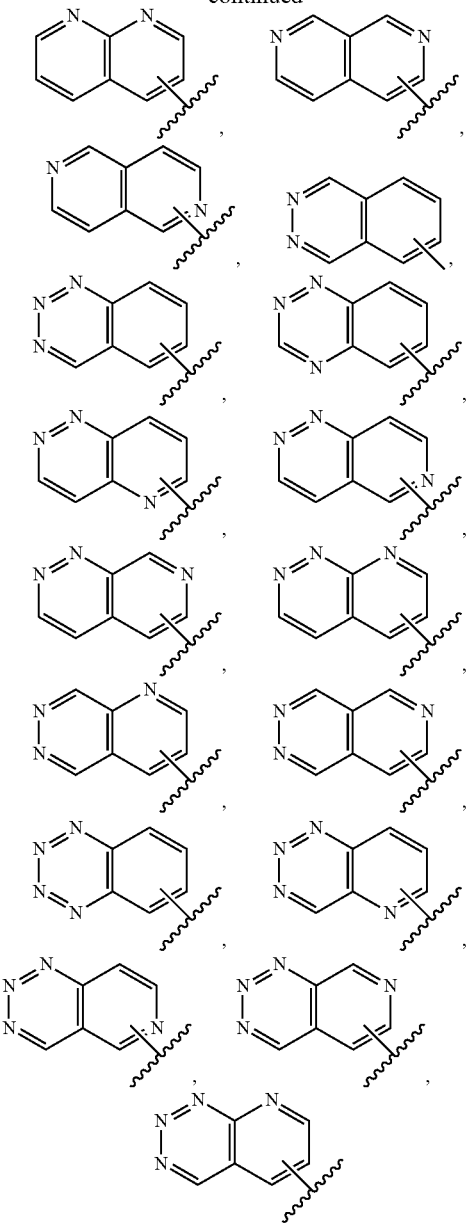

wherein Q is optionally substituted with one to three $R^a$.

In one group of embodiments, Q is selected from the group consisting of

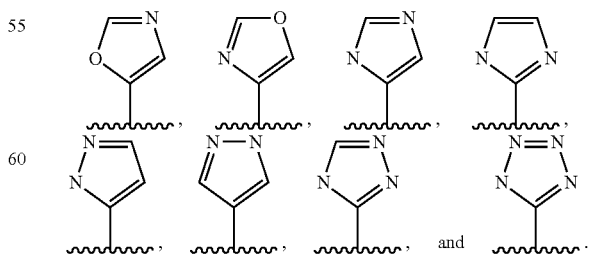

In one group of embodiments, Q is substituted with $CONR^dR^d$, $NR^dR^d$, or heteroaryl optionally substituted with one to three $R^c$. In one group of embodiments, Q is substituted with heteroaryl having one to two nitrogen ring atoms.

In one group of embodiments, Q is not unsubstituted pyridin-2-yl, unsubstituted pyridin-3-yl, or unsubstituted pyridine-4-yl. In one group of embodiments, Q is pyridin-2-yl, pyridin-3-yl, or pyridine-4-yl, each of which is substituted with one to three $R^c$.

In one group of embodiments, Q is pyridin-2-yl, pyridin-3-yl, or pyridine-4-yl, said Q is optionally substituted with CN or $CONR^dR^d$.

In one group of embodiments, Q is pyridin-2-yl, pyridin-3-yl, or pyridine-4-yl, said Q is optionally substituted with one to three $R^a$ wherein at least one $R^a$ is heteroaryl optionally substituted with one to three $R^a$. In one group of embodiments at least one $R^a$ is heteroaryl attached to said Q at the ring atom adjacent to ring atom bearing Y. In one group of embodiments at least one $R^a$ is heteroaryl substituted with at least one $C_{1-8}$alkyl. In one group of embodiments at least one $R^a$ heteroaryl is substituted with at least one methyl. In one group of embodiments at least one $R^a$ is pyrazolyl substituted with at least one $C_{1-8}$alkyl. In one group of embodiments at least one $R^a$ is pyrazoyl substituted with at least one methyl. In one group of embodiments, $R^a$ is pyrazol-5-yl. In one group of embodiments, $R^a$ is 4-methyl-pyrazol-5-yl.

In one group of embodiments, Q is substituted with at least one $R^a$ selected from the group consisting of —$(CH_2)_k$H, —$(CH_2)_kNH_2$, —$(CH_2)_kNH(C_{1-8}$alkyl), —$(CH_2)_kN(C_{1-8}$alkyl)($C_{1-8}$alkyl), —$(CH_2)_kNHC(O)C_{1-8}$alkyl), —$(CH_2)_kN(C_{1-8}$alkyl)$C(O)(C_{1-8}$alkyl), —$(CH_2)_kNHC(O)_2(C_{1-8}$alkyl), —$(CH_2)_kN(C_{1-8}$alkyl)$C(O)_2(C_{1-8}$alkyl), —$(CH_2)_kNHS(O)_2(C_{1-8}$alkyl), —$(CH_2)_kN(C_{1-8}$alkyl)$S(O)_2(C_{1-8}$alkyl), and —$(CH_2)_k$heterocycloalkyl optionally substituted with one to three $R^e$ where k is selected from the group consisting of 0, 1, 2, 3, 4, 5, and 6. In some embodiments the heterocycloalkyl group is morpholino or piperazinyl optionally substituted with alkyl, —$C(O)C_{1-8}$alkyl, —$C(O)^2C_{1-8}$alkyl, or —$S(O)_2C_{1-8}$alkyl.

In one group of embodiments, Q is substituted with at least one $R^a$ selected from the group consisting of —$NR^d(CH_2)_kOH$, —$NR^d(CH_2)_kNH_2$, —$NR^d(CH_2)_kNH(C_{1-8}$alkyl), —$NR^d(CH_2)_kN(C_{1-8}$alkyl)($C_{1-8}$alkyl), —$NR^d(CH_2)_kNHC(O)(C_{1-8}$alkyl), —$NR^d(CH_2)_kN(C_{1-8}$alkyl)$C(O)C_{1-8}$alkyl), —$NR^d(CH_2)_kNHC(O)_2(C_{1-8}$alkyl), —$NR^d(CH_2)_kN(C_{1-8}$alkyl)$C(O)_2(C_{1-8}$alkyl), —$NR^d(CH_2)_kNHS(O)_2(C_{1-8}$alkyl), —$NR^d(CH_2)_kN(C_{1-4}$alkyl)$S(O)_2(C_{1-8}$alkyl), and —$NR^d(CH_2)_k$heterocycloalkyl optionally substituted with one to three $R^e$ where k is selected from the group consisting of 0, 1, 2, 3, 4, 5, and 6. In some embodiments, $R^d$ is H or $C_{1-8}$alkyl. In some embodiments the heterocycloalkyl group is morpholino or piperazinyl optionally substituted with alkyl, —$C(O)C_{1-8}$alkyl, —$C(O)_2C_{1-8}$alkyl, or —$S(O)_2C_{1-8}$alkyl.

In one group of embodiments, Q is substituted with at least one $R^a$ selected from the group consisting of $C(CH_2)_kOH$, $O(CH_2)_kNH_2$, $O(CH_2)_kNH(C_{1-8}$alkyl), $O(CH_2)_kN(C_{1-8}$alkyl($C_{1-8}$alkyl), $O(CH_2)_kNHC(O)(C_{1-8}$alkyl), $O(CH_2)_kN(C_{1-8}$alkyl)$C(O)(C_{1-8}$alkyl), $O(CH_2)_kNHC(O)_2(C_{1-8}$alkyl), $O(CH_2)_kN(C_{1-8}$alkyl)$C(O)_2(C_{1-8}$alkyl), $O(CH_2)_kNHS(O)_2(C_{1-8}$alkyl), $O(CH_2)_kN(C_{1-8}$alkyl)$S(O)_2(C_{1-8}$alkyl), and $O(CH_2)_k$heterocycloalkyl optionally substituted with one to three $R^e$ where k is selected from the group consisting of 0, 1, 2, 3, 4, 5, and 6. In some embodiments the heterocycloalkyl group is morpholino or piperazinyl optionally substituted with alkyl, —$C(O)C_{1-8}$alkyl, —$C(O)_2C_{1-8}$alkyl, or —$S(O)_2C_{1-8}$alkyl.

In one group of embodiments, $T^1$ is C and $R^2$ is H.

In one group of embodiments, $T^3$ is C and $R^j$ is H.
In one group of embodiments, $T^4$ is C and $R^5$ is H.
In one group of embodiments, $T^3$ is C and $R^4$ is $C_{1-8}$alkoxy.

In one group of embodiments, $R^2$, $R^3$, $R^5$ when present are H and $R^4$ is $C_{1-8}$ alkoxy.

In one group of embodiments, $R^4$ is methoxy.

In one group of embodiments, $R^4$ is haloalkoxy. In one group of embodiments, $R^4$ is $OCHF_2$. In one group of embodiments, $R^4$ is $OCF_3$.

In one group of embodiments, $R^2$, $R^3$, $R^4$, and $R^5$ when present are H.

In one group of embodiments, one of $R^2$, $R^3$, $R^4$, and $R^5$ is selected from the group consisting of —$O(CH_2)_zOH$, —$O(CH_2)_zNH_2$, —$O(CH_2)_zNH(C_{1-8}$alkyl), and —$O(CH_2)_zN(C_{1-8}$alkyl)($C_{1-8}$alkyl) where z is selected from the group consisting of 0, 1, 2, 3, 4, 5, and 6.

In one group of embodiments, X is O.
In one group of embodiments, $CH_2$.
In one group of embodiments, X is $C(R^9)_2$ and at least one of $R^9$ is F.
In one group of embodiments, Y is $CH_2$.
In one group of embodiments, Y is $CR^{1a}R^{1b}$ and at least one of $R^{1a}$ or $R^{1b}$ is F.

In one group of embodiments, the compound is not:

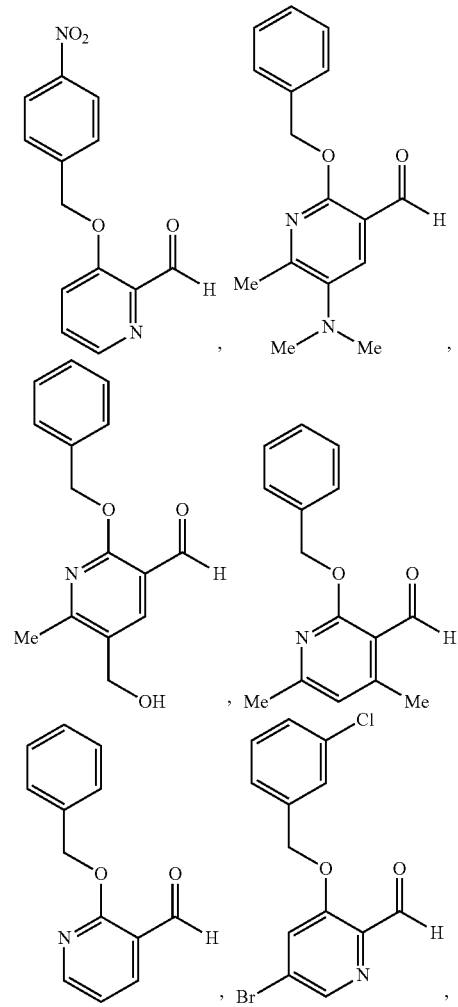

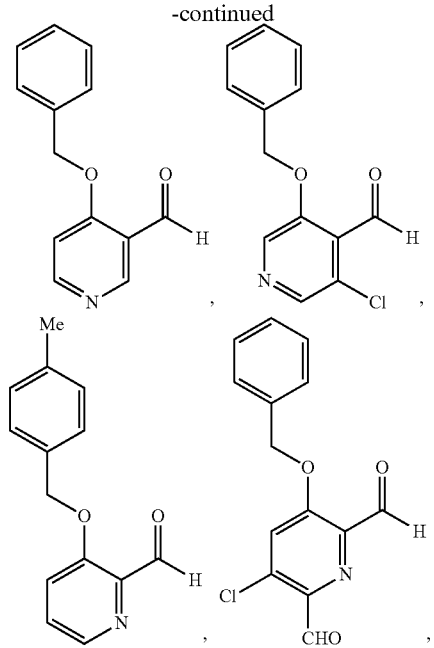
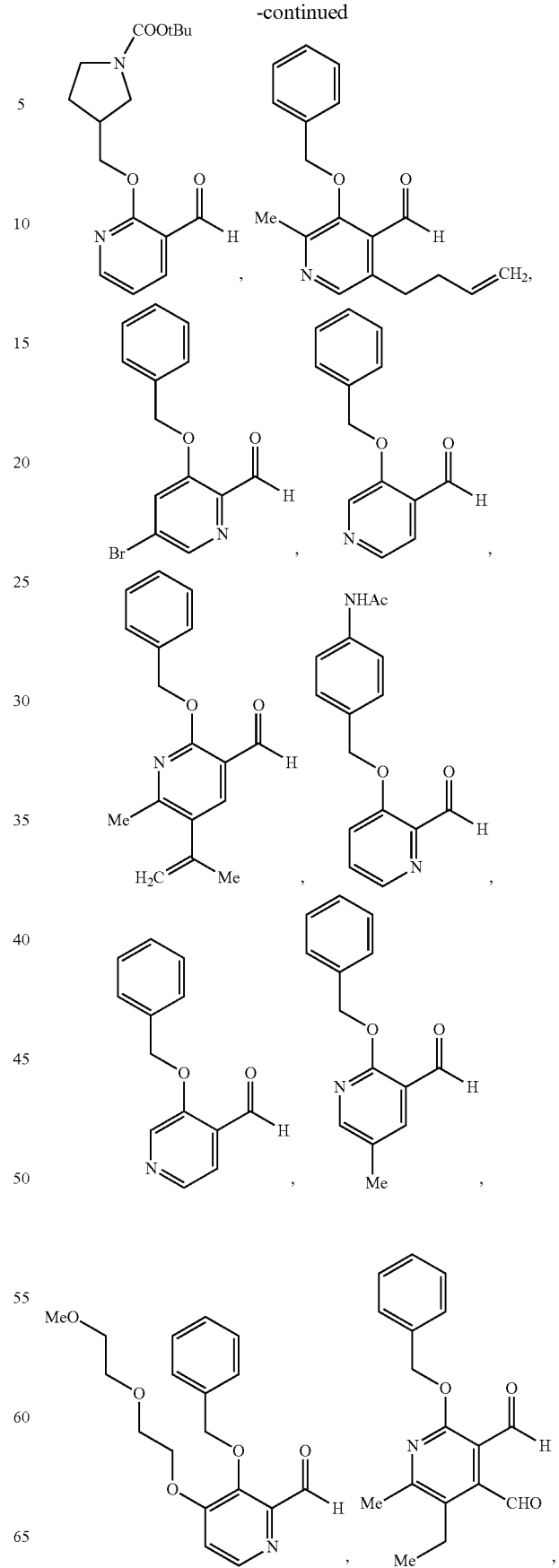

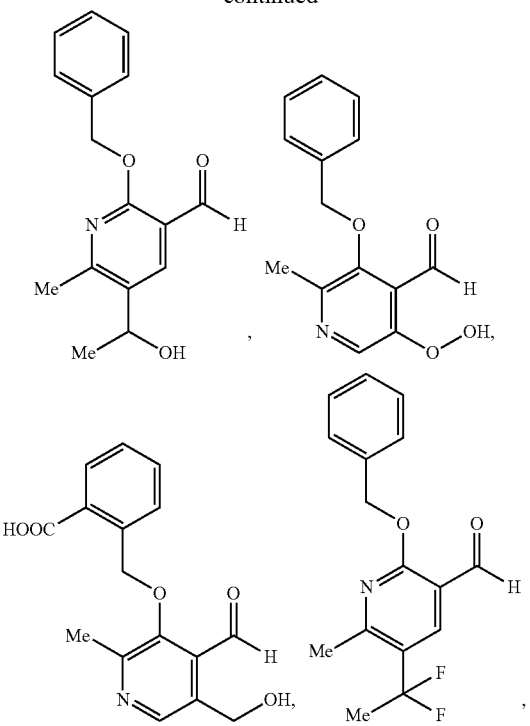

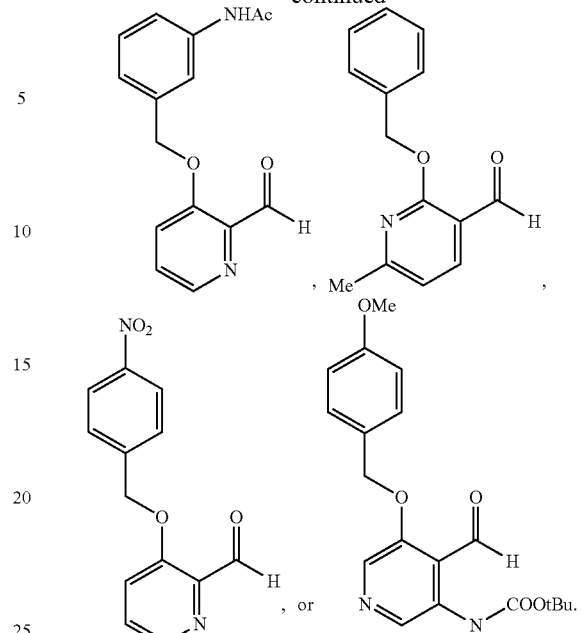

In another group of embodiments, the invention provides compounds of Formula (Ib):

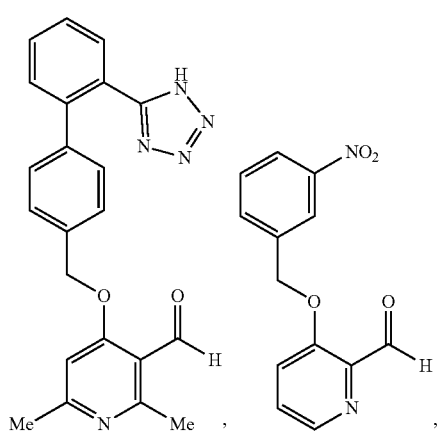

(Ib)

or a tautomer or pharmaceutically acceptable salt thereof, wherein:

Q is selected from the group consisting of aryl, heteroaryl, and heterocycloalkyl, each optionally substituted with one to three Ra;

Y is O or $CH_2$;

X is O or $CH_2$;

$R^2$ and $R^3$ are independently absent or selected from the group consisting of hydrogen, halo, $R^b$, $OR^d$, $O(CH_2)_zOR^d$, $O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2 R^e$, $S(O)NR^dR^d$, and $N_3$ where z is 0, 1, 2, or 3;

$R^4$ is absent or selected from the group consisting of hydrogen, $R^b$, $OR^d$, $O(CH_2)_zOR^d$, where z is 0, 1, 2, or 3;

$R^5$ is absent or selected from the group consisting of hydrogen, halo, $R^b$, and $OR^d$;

$R^6$ and $R^7$ together form oxo or an aldehyde protecting group;

$T^1$, $T^2$, $T^3$, and $T^4$ are independently C or N provided that at least one of $T^1$, $T^2$, $T^3$, and $T^4$ is N and at least one of $T^1$, $T^2$, $T^3$, and $T^4$ is C;

each $R^a$ is independently selected from the group consisting of halo, oxo, $R^b$, $OR^d$, $O(CH_2)_uOR^d$, $O(CH_2)_uNR^dR^d$, $O(CH_2)_uNR^dC(O)R^e$, $O(CH_2)_uNR^dC(O)_2R^e$, $O(CH_2)_uNR^dS(O)_2R^e$, $NH_2$, —$(CH_2)_kOC(O)R^e$, —$(CH_2)_kSR^d$, CN, $NO_2$, —$(CH_2)_kCO_2(C_{1-8}alkyl)OH$, —$(CH_2)_k(CO_2(C_{1-8}$ alkyl)(heteroaryl)C(O)(C_{1-8}alkyl)$, —$(CH_2)_kCO_2R^d$, —$(CH_2)_kCONR^dR^d$, —$(CH_2)_kNR^dC(O)R^e$, —$(CH_2)_kNR^dC(O)_2R^e$, —$(CH_2)_kC(O)R^d$, —$(CH_2)_kOC(O)NR^dR^d$, —$NR^d(CH_2)_uOR^d$, —$NR^d(CH_2)_uNR^dR^d$, —$NR^d(CH_2)_uNR^dC(O)R^e$, —$NR^d(CH_2)_uNR^dC(O)_2R^e$, —$NR^d(CH_2)_uNR^dS(O)_2R^e$, —$(CH_2)_kNR^dC(O)_2R^e$, —$(CH_2)_kNR^dC(O)_2R^d$, —$(CH_2)_kNR^dC(O)NR^dR^d$, —$(CH_2)_kS(O)R^e$, —$(CH_2)_kS(O)_2R^e$, —$(CH_2)_kNR^dS(O)_2R^e$, —$C(O)(CH_2)_kNR^dS(O)_2R^e$, —$(CH_2)_kC(O)NR^dS(O)_2R^e$, —$(CH_2)_kS(O)_2NR^dR^d$, $N_3$, —$(CH_2)_k$aryl optionally substituted with one to three $R^c$, —$NR^d(CH_2)_k$aryl optionally substituted with one to three $R^c$, —$(CH_2)_k$heteroaryl optionally substituted with one to three $R^c$, —$NR^d(CH_2)_k$heteroaryl optionally substituted with one to three $R^c$, —$(CH_2)_k$heterocycloalkyl optionally substituted with one to three $R^c$, and —$NR^d(CH_2)_k$heterocycloalkyl optionally substituted with one to three $R^c$ where k is 0, 1, 2, 3, 4, 5, or 6 and u is 1, 2, 3, 4, 5, or 6;

each $R^b$ is independently selected from the group consisting of $C_{1-8}$alkyl, $C_{2-8}$alkenyl, and $C_{2-8}$ alkynyl, each optionally independently substituted with one to three halo, $OR^d$, or $NR^dR^d$;

each $R^c$ is independently selected from the group consisting of halo, $C_{1-8}$alkyl, halo$C_{1-8}$alkyl, $C_{2-8}$alkenyl, halo$C_{2-8}$alkenyl, $C_{2-8}$alkynyl, halo$C_{2-8}$alkynyl, $(CH_2)_mOR^f$, $OC(O)R^g$, $SR^f$, CN, $NO_2$, $(CH_2)_mCO_2R^f$, $CONR^fR^f$, $C(O)R^f$, $OC(O)NR^fR^f$, $(CH_2)_mNR^fR^f$, $NR^fC(O)R^g$, $NR^fC(O)_2R^g$, $NR^fC(O)NR^fR^f$, $S(O)R^g$, $S(O)_2R^g$, $NR^fS(O)_2R^g$, $S(O)_2NR^fR^f$, $N_3$, $(R^f)_mSiC_{1-8}$alkyl, heteroaryl optionally substituted with one to three $R^h$, cycloalkyl optionally substituted with one to three $R^h$, and heterocycloalkyl optionally substituted with one to three $R^h$ where m is selected from the group consisting of 0, 1, 2, 3, 4, 5, and 6;

each $R^h$ is independently selected from the group consisting of halo, $C_{1-8}$alkyl, halo$C_{1-8}$alkyl, $OR^j$, $OC(O)R$, $SR^j$, $NO_2$, $CO_2R^j$, $CONR^jR^j$, $C(O)R^j$, $OC(O)NR^jR^j$, $NR^jR^j$, $NR^j$-$C(O)R^t$, $NR^jC(O)_2R^t$, $NR^jC(O)NR^jR^j$, $S(O)R^t$, $S(O)_2R^t$, $NR^jS(O)_2R^t$, and $S(O)_2NR^jR^j$;

$R^d$, $R^f$, and $R^j$ are each independently selected from the group consisting of hydrogen, $C_{1-8}$ alkyl, halo$C_{1-8}$alkyl, $C_{2-8}$ alkenyl, halo$C_{2-8}$alkenyl, $C_{2-8}$ alkynyl, and halo$C_{2-8}$ alkynyl; and $R^e$, $R^g$, and $R^t$ are each independently selected from the group consisting of $C_{1-8}$ alkyl, halo$C_{1-8}$alkyl, $C_{2-8}$ alkenyl, halo$C_{2-8}$alkenyl, $C_{2-8}$alkynyl, and halo$C_{1-8}$alkynyl;

provided that X and Y are not both O;
provided that when Q is phenyl and $R^4$ is $C_{1-4}$alkyl or $C_{2-8}$alkenyl, Q is substituted with at least one $R^a$;
provided that when $R^5$ is halo, Q is substituted with at least 1 $R^a$;
provided that when $R^5$ is $R^b$, Q is not phenyl; and
provided that when $R^2$, $R^3$, $R^4$, and $R^5$ are H and Q is phenyl, Q is substituted with at least one $R^a$ selected from 4-carboxy, 3-carboxy, and ($C_{1-8}$ alkyl 3-carboxylate).

In one group of embodiments, the invention provides compounds of Formula Ib wherein $R^2$ and $R^3$ are independently absent or selected from the group consisting of hydrogen, $R^b$, $OR^d$, $O(CH_2)_zOR^d$, $O(CH_2)_zNR^dR^d$, $OC(O)R^e$, $CO_2R^d$, $CONR^dR^d$, and $C(O)R^d$, where z is 1, 2, or 3.

In one group of embodiments, the invention provides compounds of Formula Ib wherein at least one z is 0. In another group of embodiments, at least one z is 1. In yet another group of embodiments, at least one z is 2. In still another group of embodiments, at least one z is 3. In another group of embodiments, no z is 0.

In one group of embodiments, the invention provides compounds of Formula Ib wherein $T^2$ is N; $T^1$, $T^3$ and $T^4$ are C; $R^2$ and $R^3$ are H; $R^3$ is absent; and $R^4$ is $C_{1-8}$alkoxy.

In one group of embodiments, the invention provides compounds of Formula Ib wherein $T^2$ is N; $T^1$, $T^3$, and $T^4$ are C; $R^2$ and $R^3$ are H; $R^3$ is absent; and $R^3$ is selected from hydroxy and $C_{1-8}$alkoxy.

In one group of embodiments, the invention provides compounds of Formula Ib wherein $T^4$ is N; $T^1$, $T^2$, and $T^3$ are C; $R^2$ and $R^3$ are H; $R^5$ is absent; and $R^4$ is selected from $C_{1-8}$ alkyl and $C_{1-8}$alkoxy.

In one group of embodiments, the invention provides compounds of Formula Ib wherein $T^1$ is N; $T^2$, $T^3$, and $T^4$ are C; $R^3$, $R^4$, and $R^3$ are H; and $R^2$ is absent.

In one group of embodiments, the invention provides compounds of Formula Ib wherein $T^2$ is N; $T^1$, $T^3$, and $T^4$ are C; $R^2$, $R^4$, and $R^5$ are H; and $R^3$ is absent.

In one group of embodiments, the invention provides compounds of Formula Ib wherein $T^3$ is N; $T^1$, $T^2$, and $T^4$ are C; $R^2$, $R^3$, and $R^3$ are H; and $R^4$ is absent.

In one group of embodiments, the invention provides compounds of Formula Ib wherein $T^4$ is N; $T^1$, $T^2$, and $T^3$ are C; $R^2$, $R^3$, and $R^4$ are H; and $R^5$ is absent.

In one group of embodiments, the invention provides compounds of Formula Ib wherein Q is selected from an imidazopyridinyl group, a pyrrolopyridinyl group, a pyrazolopyridinyl group, a triazolopyridinyl group, a pyrazolopyrazinyl group, a pyridinyl group, a pyrazinyl group, an oxazolyl group, an imidazolyl group, a triazolyl group, a tetrazolyl group, a pyrazolyl group, a quinolinyl group, an isoquinolinyl group, an indazolyl group, a benzooxazolyl group, a naphthyridinyl group, and a quinoxalinyl group; and wherein Q is optionally substituted with one to three $R^a$.

In another group of embodiments, the invention provides compounds of Formula Ic:

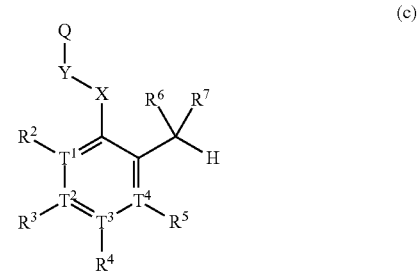

(c)

or a tautomer or pharmaceutically acceptable salt thereof, wherein:
Y is $CH_2$;
X is O or $CH_2$;
$T^1$, $T^2$, $T^3$, and $T^4$ are C or N, provided that no more than one of $T^1$, $T^2$, $T^3$, and $T^4$ is N;
Q is selected from the group consisting of
i) heteroaryl optionally substituted with one to three $R^a$;
wherein
$R^2$, $R^3$, $R^4$, and $R^5$, are independently absent or selected from the group consisting of hydrogen, halo, $R^b$, $OR^d$, $O(CH_2)_zOR^d$, $O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$ where z is 0, 1, 2, or 3;
ii) aryl substituted with one to three —$(CH_2)_kCO_2R^d$; wherein $R^2$ and $R^5$ are independently absent or selected from the group consisting of hydrogen, halo, $OR^d$, $O(CH_2)_zOR^d$, $O(CH_2)_zNR^dR^d$, $OC(O)R^e$, $SR^d$, $CN$, $NO_2$, $CO_2R^d$, $CONR^dR^d$, $C(O)R^d$, $OC(O)NR^dR^d$, $NR^dR^d$, $NR^dC(O)R^c$, $NR^dC(O)_2R^c$, $NR^dC(O)NR^dR^d$, $S(O)R^e$, $S(O)_2R^e$, $NR^dS(O)_2R^c$, $S(O)_2NR^dR^d$, and N, where z is 0, 1, 2, or 3;

$R^3$ and $R^4$ are independently absent or selected from the group consisting of hydrogen, halo, $R^b$, $OR^d$, $OR^0$, $O(CH_2)_zOR^d$, $O(CH_2)_zNR^dR^d$, $OC(O)R^e$, $SR^d$, $CN$, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$ where z is 0, 1, 2, or 3;

iii) unsubstituted aryl, wherein $R^2$, $R^3$, and $R^4$, are independently absent or selected from the group consisting of hydrogen, halo, $R^b$, $OR^d$, $O(CH_2)_zOR^d$, $O(CH_2)_zNR^dR^d$, $OC(O)R^e$, $SR^d$, $CN$, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$ where z is 0, 1, 2, or 3; and $R^5$ is absent or is $OR^d$; and iv) heterocycloalkyl, optionally substituted with one to three $R^a$; wherein $R^2$, $R^3$, $R^4$, and $R^5$, are independently absent or selected from the group consisting of hydrogen, $R^b$ $OR^d$, $O(CH_2)_zOR^d$, $O(CH_2)_zNR^dR^d$, $OC(O)R^e$, $SR^d$, $CN$, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$ where z is 0, 1, 2, or 3;

$R^6$ and $R^7$ together form oxo or an aldehyde protecting group;

each $R^a$ is independently selected from the group consisting of halo, oxo, $R^b$, $OR^d$, $O(CH_2)_uOR^d$, $O(CH_2)_uNR^dR^d$, $O(CH_2)_uNR^dC(O)R^e$, $O(CH_2)_uNR^dC(O)_2R^e$, $O(CH_2)_uNR^dS(O)_2R^e$, $NH_2$, —$(CH_2)_kOC(O)R^e$, —$(CH_2)_kSR^d$, $CN$, $NO_2$, —$(CH_2)_kCO_2(C_{1-8}alkyl)OH$, —$(CH_2)_kCO_2(C_{1-8}alkyl)$(heteroaryl)$C(O)(C_{1-8}alkyl)$, —$(CH_2)_kCO_2R^d$, —$(CH_2)_kCONR^dR^d$, —$(CH_2)_kNR^dC(O)R^e$, —$(CH_2)_kNR^dC(O)_2R^e$, —$(CH_2)_kC(O)R^d$, —$(CH_2)_kOC(O)NR^dR^d$, —$NR^d(CH_2)_uOR^d$, —$NR^d(CH_2)_uNR^dR^d$, —$NR^d(CH_2)_uNR^dC(O)R^e$, —$NR^d(CH_2)_uNR^dC(O)R^e$, —$NR^d(CH_2)_uNR^dS(O)_2R^e$, —$(CH_2)_kNR^dC(O)R^e$, —$(CH_2)_kNR^dC(O)_2R^e$, —$(CH_2)_kNR^dC(O)NR^dR^d$, —$(CH_2)_kS(O)R^e$, —$(CH_2)_kS(O)_2R^e$, —$(CH_2)_kNR^dS(O)R^e$, —$C(O)(CH_2)_kNR^dS(O)_2R^e$, —$(CH_2)_k$ $C(O)NR^dS(O)_2R^e$, —$(CH_2)_kS(O)_2NR^dR^d$, $N_3$, —$(CH_2)_k$ aryl optionally substituted with one to three $R^c$, —$NR^d(CH_2)_k$aryl optionally substituted with one to three $R^c$, —$(CH_2)_k$heteroaryl optionally substituted with one to three $R^c$, —$NR^d(CH_2)_k$heteroaryl optionally substituted with one to three $R^c$, —$(CH_2)_k$heterocycloalkyl optionally substituted with one to three $R^c$, and —$NR^d(CH_2)_k$heterocycloalkyl optionally substituted with one to three $R^c$ where k is 0, 1, 2, 3, 4, 5, or 6 and u is 1, 2, 3, 4, 5, or 6;

each $R^b$ is independently selected from the group consisting of $C_{1-8}$alkyl, $C_{2-8}$alkenyl, and $C_{2-8}$alkynyl, each optionally independently substituted with one to three halo, $OR^d$, or $NR^dR^d$;

each $R^c$ is independently selected from the group consisting of halo, $C_{1-8}$alkyl, halo$C_{1-8}$alkyl, $C_{2-8}$alkenyl, halo$C_{2-8}$ alkenyl, $C_{2-8}$alkynyl, halo$C_{2-8}$alkynyl, $(CH_2)_mOR^f$, $OC(O)$ $R^g$, $SR^f$, $CN$, $NO_2$, $(CH_2)_mCO_2R^f$, $CONR^fR^f$, $C(O)R^f$, $OC(O)NR^fR^f$, $(CH_2)_mNR^fR^f$, $NR^fC(O)R^g$, $NR^fC(O)_2R^g$, $NR^fC(O)NR^fR^f$, $S(O)R^g$, $S(O)_2R^g$, $NR^fS(O)_2R^g$, $S(O)_2$ $NR^fR^f$, $N_3$, $(R^f)_mSiC_{1-8}$alkyl, heteroaryl optionally substituted with one to three $R^h$, cycloalkyl optionally substituted with one to three $R^h$, and heterocycloalkyl optionally substituted with one to three $R^h$ where m is selected front the group consisting of 0, 1, 2, 3, 4, 5, and 6;

each $R^h$ is independently selected from the group consisting of halo, $C_{1-8}$alkyl, halo$C_{1-8}$alkyl, $OR^j$, $OC(O)R$, $SR^j$, $NO_2$, $CO_2R^j$, $CONR^jR^j$, $C(O)R^j$, $OC(O)NR^jR^j$, $NR^jR^j$, $NR^jC(O)R^t$, $NR^jC(O)_2R^t$, $NR^jC(O)NR^jR^j$, $S(O)$ $R^t$, $S(O)_2R^t$, $NR^jS(O)_2R^t$, and $S(O)_2$, $NR^jR^j$;

$R^d$, $R^f$, and $R^j$ are each independently selected from the group consisting of hydrogen, $C_{1-8}$ alkyl, halo$C_{1-8}$ alkyl, $C_{2-8}$ alkenyl, halo$C_{2-8}$alkenyl, $C_{2-8}$alkynyl, and halo$C_{2-8}$alkynyl; and $R^e$, $R^g$ and $R^t$ are each independently selected from the group consisting of $C_{1-8}$alkyl, halo$C_{1-8}$alkyl, $C_{2-8}$alkenyl, halo$C_{2-8}$alkenyl, $C_{2-8}$alkynyl, and halo$C_{2-8}$alkynyl.

In one group of embodiments, the invention provides compounds of Formula Ic, wherein $R^6$ and $R^7$ together form oxo.

In one group of embodiments, the invention provides compounds of Formula Ic, wherein $R^2$ and $R^3$ are independently absent or selected from the group consisting of hydrogen, $R^b$, $OR^d$, $O(CH_2)_zOR^d$, $O(CH_2)_zNR^dR^d$, $OC(O)$ $R^e$, $CO_2R^d$, $CONR^dR^d$, and $C(O)R^d$, where z is 1, 2, or 3.

In one group of embodiments, the invention provides compounds of Formula Ic, wherein $T^2$ is N; $R^2$ and $R^5$ are H; $R^3$ is absent; and $R^4$ is $C_{1-8}$alkoxy, halo$C_{1-8}$alkoxy, and $O(CH_2)_2C_{1-8}$alkyl.

In one group of embodiments, the invention provides compounds of Formula Ic, wherein $T^2$ is N; $R^2$ and $R^4$ are H; $R^3$ is absent; and $R^5$ is selected from hydroxy and $C_{1-8}$alkoxy.

In one group of embodiments, the invention provides compounds of Formula Ic, wherein $T^4$ is N; $R^2$ and $R^3$ are H; $R^5$ is absent; and $R^4$ is selected from $C_{1-8}$alkyl and $C_{1-8}$alkoxy.

In one group of embodiments, the invention provides compounds of Formula Ic, wherein $T^1$ is N; $R^3$, $R^4$, and $R^5$ are H; and $R^2$ is absent.

In one group of embodiments, the invention provides compounds of Formula Ic, wherein $T^2$ is N; $R^2$, $R^4$, and $R^5$ are H; and $R^3$ is absent.

In one group of embodiments, the invention provides compounds of Formula Ic, wherein $T^3$ is N; $R^2$, $R^3$, and $R^5$ are H; and $R^4$ is absent.

In one group of embodiments, the invention provides compounds of Formula Ic, wherein $T^4$ is N; $R^2$, $R^3$, and $R^4$ are H; and $R^5$ is absent.

In one group of embodiments, the invention provides compounds of Formula Ic, or another group of embodiments of Formula Ic that is disclosed herein, wherein Q is selected from the group consisting of an imidazopyridinyl group, a pyrrolopyridinyl group, a pyrazolopyridinyl group, a triazolopyridinyl group, a pyrazolopyrazinyl group, a pyridinyl group, a pyrazinyl group, an oxazolyl group, an imidazolyl group, a triazolyl group, a tetrazolyl group, a pyrazolyl group, a quinolinyl group, an isoquinolinyl group, an indazolyl group, a benzooxazolyl group, a naphthyridinyl group, and a quinoxalinyl group; and wherein Q is optionally substituted with one to three $R^a$.

In one group of embodiments, the invention provides compounds of Formula Ic, or another group of embodiments of Formula Ic that is disclosed herein, wherein Q is selected from the group consisting of:

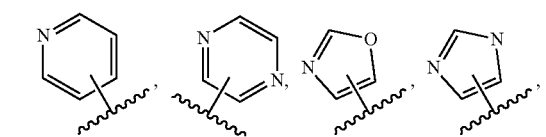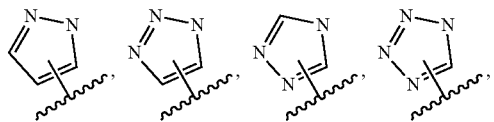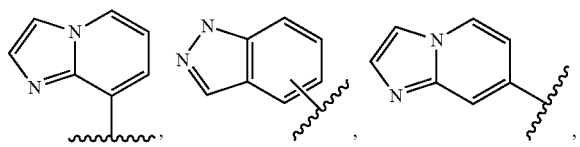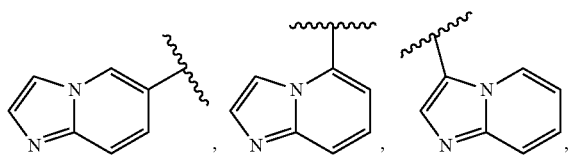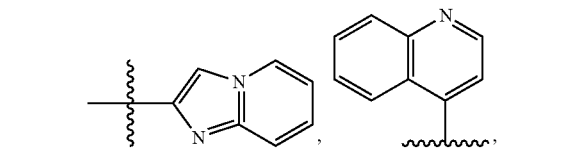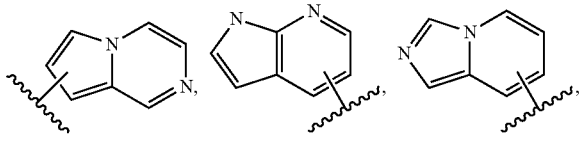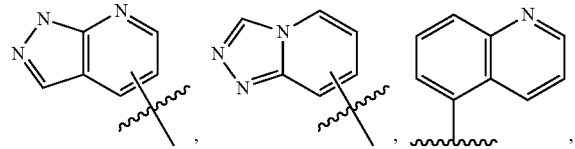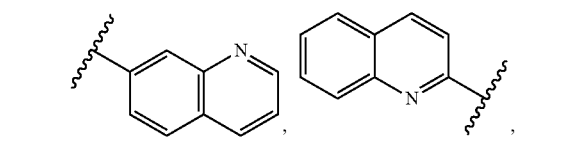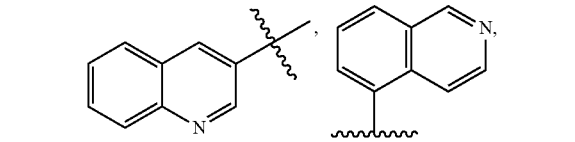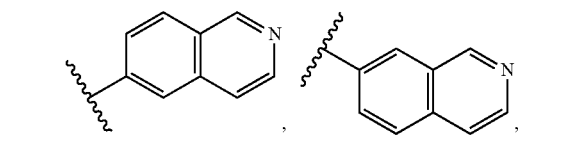

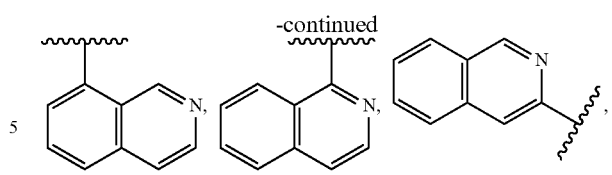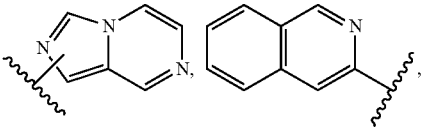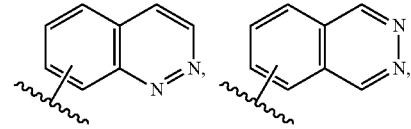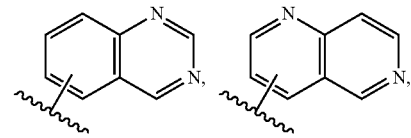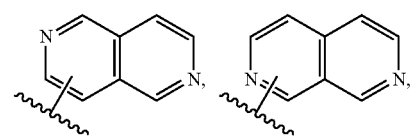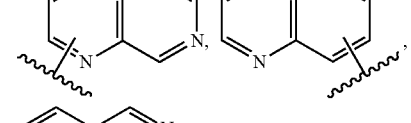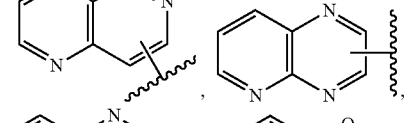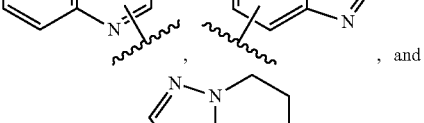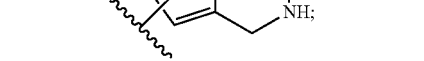

and wherein Q is optionally substituted with one to three $R^a$.

In one group of embodiments, the invention provides compounds of Formula Ic wherein at least one z is 0. In another group of embodiments, at least one z is K In yet another group of embodiments, at least one z is 2. In still another group of embodiments, at least one z is 3. In another group of embodiments, no z is 0.

In certain embodiments, the compounds of Formula I, Ib and Ic. or tautomers or pharmaceutically acceptable salts thereof, are selected from Table 1 below.

TABLE 1

| Compound | Structure | Name |
|---|---|---|
| 1 | 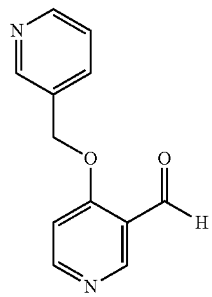 [SMILES: O=Cc1cnccc1OCc1cccnc1] | 4-(pyridin-3-ylmethoxy)nicotinaldehyde |
| 2 | 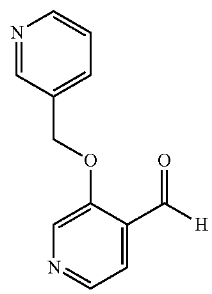 [SMILES: O=Cc1ccncc1OCc1cccnc1] | 3-(pyridin-3-ylmethoxy)isonicotinaldehyde |
| 3 | 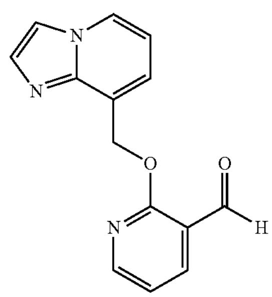 [SMILES: O=Cc1cccnc1OCc1cccn2ccnc12] | 2-(imidazo[1,2-a]pyridin-8-ylmethoxy)nicotinaldehyde |
| 4 | 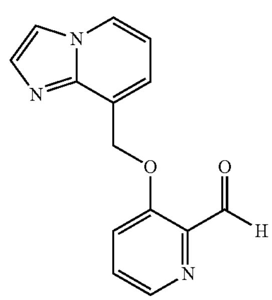 [SMILES: O=Cc1ncccc1OCc1cccn2ccnc12] | 3-(imidazo[1,2-a]pyridin-8-ylmethoxy)picolinaldehyde |
| 5 | 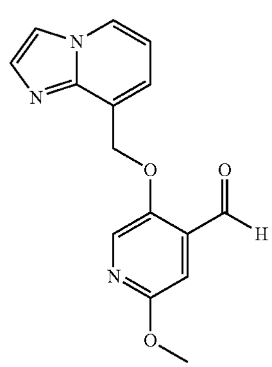 [SMILES: COc1cc(C=O)c(OCc2cccn3ccnc23)cn1] | 5-(imidazo[1,2-a]pyridin-8-ylmethoxy)-2-methoxyisonicotinaldehyde |

TABLE 1-continued

| Compound | Structure | Name |
|---|---|---|
| 6 | 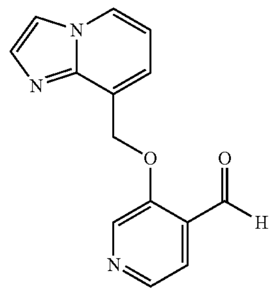 [SMILES: O=Cc1ccncc1OCc1cccn2ccnc12] | 3-(imidazo[1,2-a]pyridin-8-ylmethoxy)isonicotinaldehyde |
| 7 | 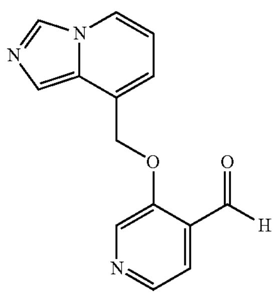 [SMILES: O=Cc1ccncc1OCc1cccn2cncc12] | 3-(imidazo[1,5-a]pyridin-8-ylmethoxy)isonicotinaldehyde |
| 8 | 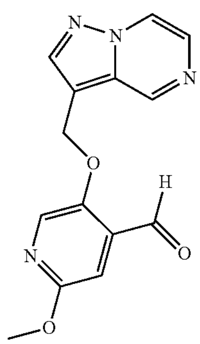 [SMILES: COc1cc(C=O)c(OCc2cnn3ccncc23)cn1] | 2-methoxy-5-(pyrazolo[1,5-a]pyrazin-3-ylmethoxy)isonicotinaldehyde |
| 9 | 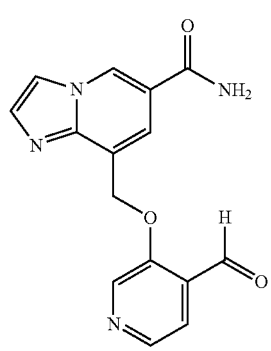 [SMILES: NC(=O)c1cc(COc2cnccc2C=O)c2nccn2c1] | 8-((3-formylpyridin-2-yloxy)methyl)imidazo[1,2-a]pyridine-6-carboxamide |

TABLE 1-continued

| Compound | Structure | Name |
|---|---|---|
| 10 | 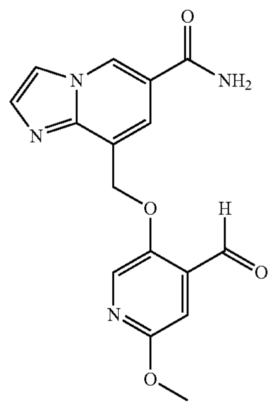 [SMILES: COc1cc(C=O)c(OCc2cc(C(N)=O)cn3ccnc23)cn1] | 8-((4-formyl-6-methoxypyridin-3-yloxy)methyl)imidazo[1,2-a]pyridine-6-carboxamide |
| 11 | 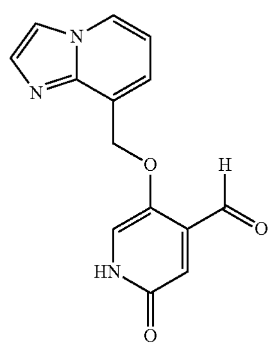 [SMILES: O=Cc1cc(=O)[nH]cc1OCc1cccn2ccnc12] | 5-(imidazo[1,2-a]pyridin-8-ylmethoxy)-2-oxo-1,2-dihydropyridine-4-carbaldehyde |
| 12 | 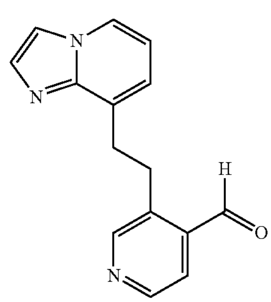 [SMILES: O=Cc1ccncc1CCc1cccn2ccnc12] | 2-(2-(imidazo[1,2-a]pyridin-8-yl)ethyl)nicotinaldehyde |
| 13 | 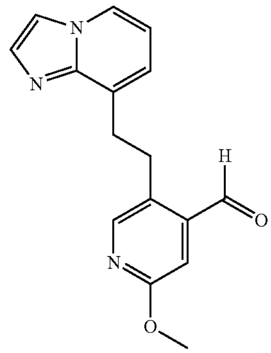 [SMILES: COc1cc(C=O)c(CCc2cccn3ccnc23)cn1] | 5-(2-(imidazo[1,2-a]pyridin-8-yl)ethyl)-2-methoxyisonicotinaldehyde |

TABLE 1-continued

| Compound | Structure | Name |
|---|---|---|
| 14 | 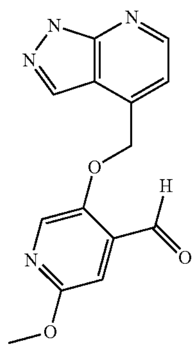 [SMILES: COc1cc(C=O)c(OCc2ccnc3[nH]ncc23)cn1] | 5-((1H-pyrazolo[3,4-b]pyridin-4-yl)methoxy)-2-methoxyisonicotinaldehyde |
| 15 | 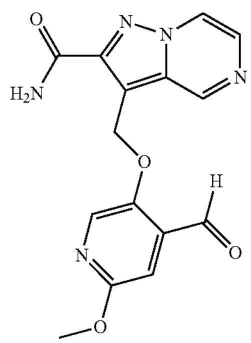 [SMILES: COc1cc(C=O)c(OCc2c(C(N)=O)nn3ccncc23)cn1] | 3-((4-formyl-6-methoxypyridin-3-yloxy)methyl)pyrazolo[1,5-a]pyrazine-2-carboxamide |
| 16 | 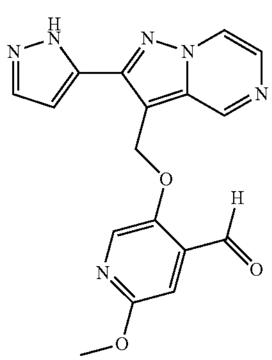 [SMILES: COc1cc(C=O)c(OCc2c(-c3ccn[nH]3)nn3ccncc23)cn1] | 5-((2-(1H-pyrazol-5-yl)pyrazolo[1,5-a]pyrazin-3-yl)methoxy)-2-methoxyisonicotinaldehyde |
| 17 | 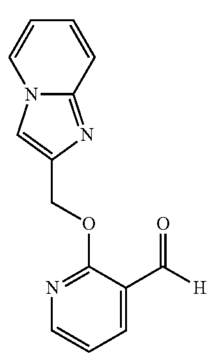 [SMILES: O=Cc1cccnc1OCc1cn2ccccc2n1] | 2-(imidazo[1,2-a]pyridin-2-ylmethoxy)nicotinaldehyde |

TABLE 1-continued

| Compound | Structure | Name |
|---|---|---|
| 18 | 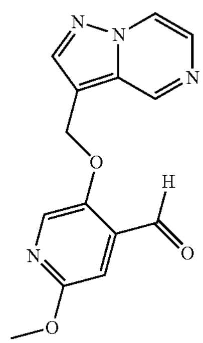 [SMILES: COc1cc(C=O)c(OCc2cnn3ccncc23)cn1] | 2-methoxy-5-((4,5,6,7-tetrahydropyrazolo[1,5-a]pyrazin-3-yl)methoxy)isonicotinaldehyde |
| 19 | 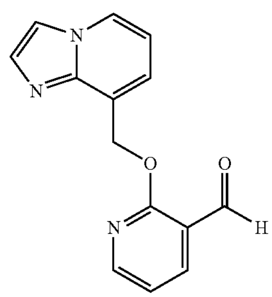 [SMILES: O=Cc1cccnc1OCc1cccn2ccnc12] | 2-(imidazo[1,2-a]pyridin-8-ylmethoxy)nicotinaldehyde |
| 20 | 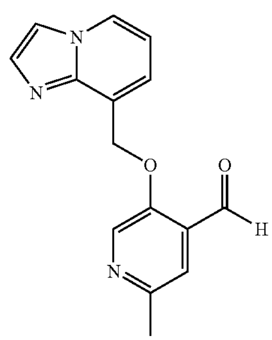 [SMILES: Cc1cc(C=O)c(OCc2cccn3ccnc23)cn1] | 5-(imidazo[1,2-a]pyridin-8-ylmethoxy)-2-methylisonicotinaldehyde |
| 21 | 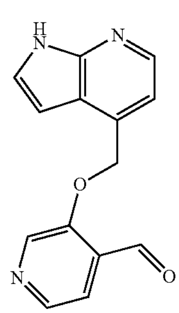 [SMILES: O=Cc1ccncc1OCc1ccnc2[nH]ccc12] | 3-((1H-pyrrolo[2,3-b]pyridin-4-yl)methoxy)isonicotinaldehyde |

TABLE 1-continued

| Compound | Structure | Name |
|---|---|---|
| 22 | 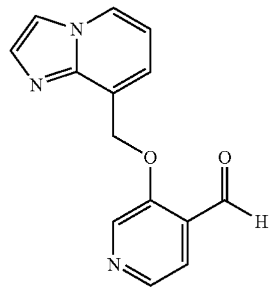 [SMILES: O=Cc1ccncc1OCc1cccn2ccnc12] | 3-(imidazo[1,2-a]pyridin-8-ylmethoxy)isonicotinaldehyde |
| 23 | 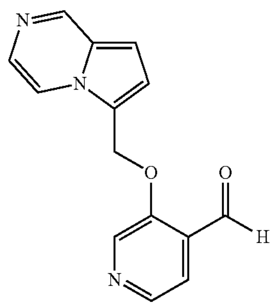 [SMILES: O=Cc1ccncc1OCc1ccc2cnccn12] | 3-(pyrrolo[1,2-a]pyrazin-6-ylmethoxy)isonicotinaldehyde |
| 24 | 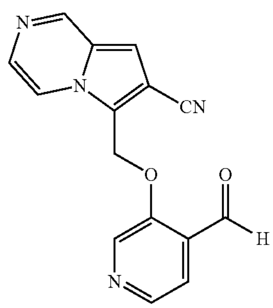 [SMILES: N#Cc1cc2cnccn2c1COc1cnccc1C=O] | 6-((4-formylpyridin-3-yloxy)mehtyl)pyrrolo[1,2-a]pyrazine-7-carbonitrile |
| 25 | 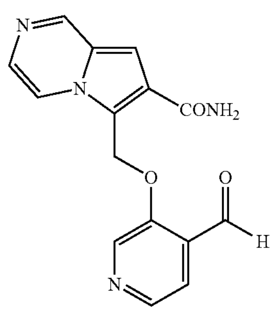 [SMILES: NC(=O)c1cc2cnccn2c1COc1cnccc1C=O] | 6-((4-fornylpyridin-3-yloxy)methyl)pyrrolo[1,2-a]pyrazine-7-carboxamide |
| 26 | 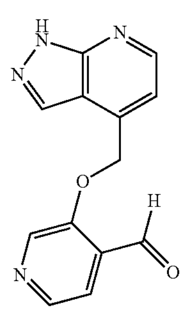 [SMILES: O=Cc1ccncc1OCc1ccnc2[nH]ncc12] | 3-((1H-pyrazolo[3,4-b]pyridin-4-yl)methoxy)isonicotinaldehyde |

TABLE 1-continued

| Compound | Structure | Name |
|---|---|---|
| 27 | 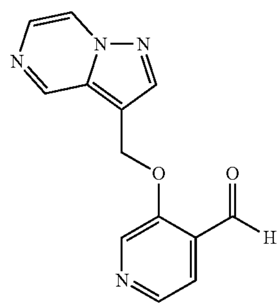 [SMILES: O=Cc1ccncc1OCc1cnn2ccncc12] | 3-(pyrazolo[1,5-a]pyrazin-3-ylmethoxy)isonicotinaldehyde |
| 28 | 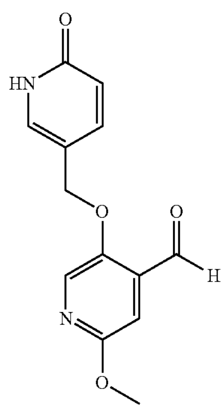 | 2-methoxy-5-((6-oxo-1,6-dihydropyridin-3-yl)methoxy)isonicotinaldehyde |
| 29 | 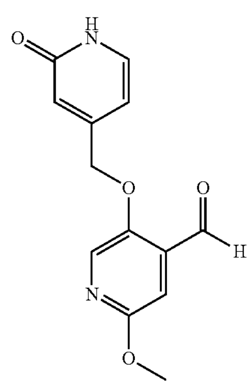 [SMILES: COc1cc(C=O)c(OCc2cc[nH]c(=O)c2)cn1] | 2-methoxy-5-((2-oxo-1,2-dihydropyridin-4-yl)methoxy)isonicotinaldehyde |
| 30 | 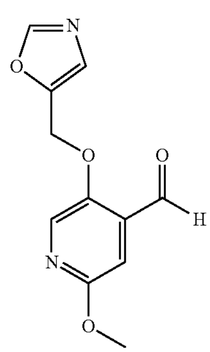 [SMILES: COc1cc(C=O)c(OCc2cnco2)cn1] | 2-methoxy-5-(oxazol-5-ylmethoxy)isonicotinaldehyde |

TABLE 1-continued

| Compound | Structure | Name |
|---|---|---|
| 31 | 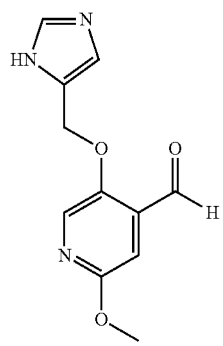 [SMILES: COc1cc(C=O)c(OCc2cnc[nH]2)cn1] | 5-((1H-imidazol-5-yl)methoxy)-2-methoxyisonicotinaldehyde |
| 32 | 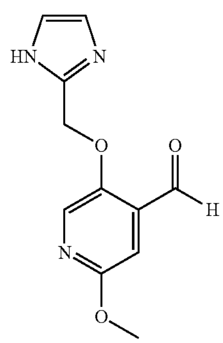 [SMILES: COc1cc(C=O)c(OCc2ncc[nH]2)cn1] | 5-((1H-imidazol-2-yl)methoxy)-2-methoxyisonicotinaldehyde |
| 33 | 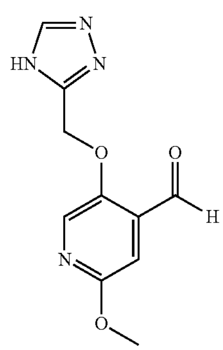 [SMILES: COc1cc(C=O)c(OCc2nnc[nH]2)cn1] | 5-((4H-1,2,4-triazol-3-yl)methoxy)-2-methoxyisonicotinaldehyde |
| 34 | 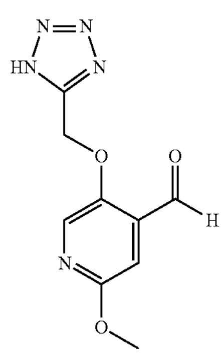 [SMILES: COc1cc(C=O)c(OCc2nnn[nH]2)cn1] | 5-((1H-tetrazol-5-yl)methoxy)-2-methoxyisonicotinaldehyde |

TABLE 1-continued

| Compound | Structure | Name |
|---|---|---|
| 35 | 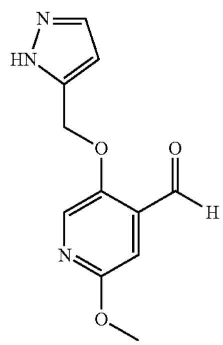 [SMILES: COc1cc(C=O)c(OCc2ccn[nH]2)cn1] | 5-((1H-pyrazol-5-yl)methoxy)-2-methoxyisonicotinaldehyde |
| 36 | 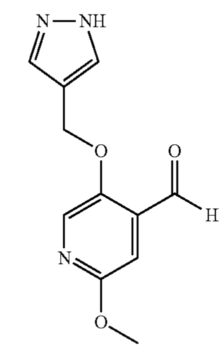 [SMILES: COc1cc(C=O)c(OCc2cn[nH]c2)cn1] | 5-((1H-pyrazol-4-yl)methoxy)-2-methoxyisonicotinaldehyde |
| 37 | 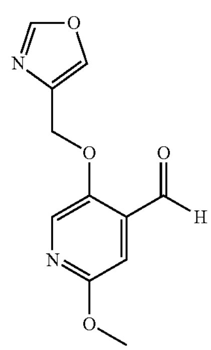 [SMILES: COc1cc(C=O)c(OCc2cocn2)cn1] | 2-methoxy-5-(oxazol-4-ylmethxoy)isonicotinaldehyde |
| 38 | 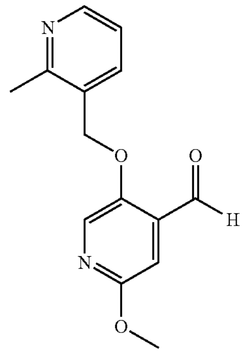 [SMILES: COc1cc(C=O)c(OCc2cccnc2C)cn1] | 2-methoxy-5-((2-methylpyridin-3-yl)methoxy)isonicotinaldehyde |

TABLE 1-continued

| Compound | Structure | Name |
|---|---|---|
| 39 | 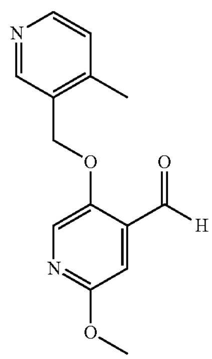 [SMILES: COc1cc(C=O)c(OCc2cnccc2C)cn1] | 2-methoxy-5-((4-methylpyridin-3-yl)methoxy)isonicotinaldehyde |
| 40 | 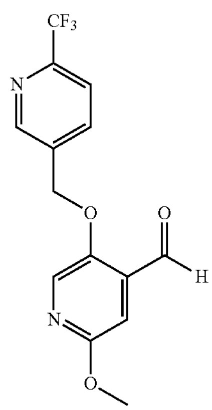 [SMILES: COc1cc(C=O)c(OCc2ccc(C(F)(F)F)nc2)cn1] | 2-methoxy-5-((6-(trifluoromethyl)pyridin-3-yl)methoxy)isonicotinaldehyde |
| 41 | 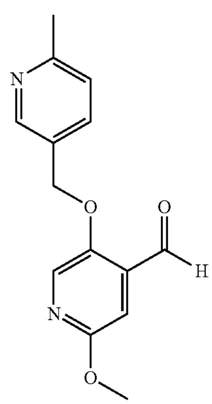 [SMILES: COc1cc(C=O)c(OCc2ccc(C)nc2)cn1] | 2-methoxy-5-((6-methylpyridin-3-yl)methoxy)isonicotinaldehyde |
| 42 | 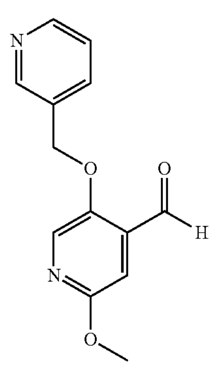 [SMILES: COc1cc(C=O)c(OCc2cccnc2)cn1] | 2-methoxy-5-(pyridin-3-ylmethoxy)isonicotinaldehyde |

TABLE 1-continued

| Compound | Structure | Name |
|---|---|---|
| 43 | 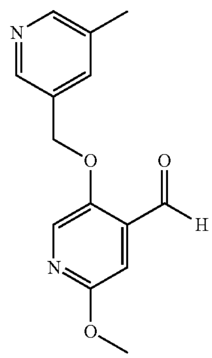 [SMILES: COc1cc(C=O)c(OCc2cncc(C)c2)cn1] | 2-methoxy-5-((5-methylpyridin-3-yl)methoxy)isonicotinaldehyde |
| 44 | 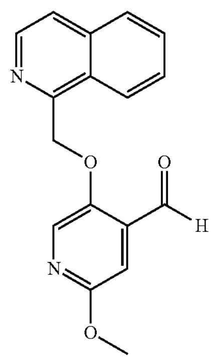 [SMILES: COc1cc(C=O)c(OCc2nccc3ccccc23)cn1] | 5-(isoquinolin-1-ylmethoxy)-2-methoxyisonicotinaldehyde |
| 45 | 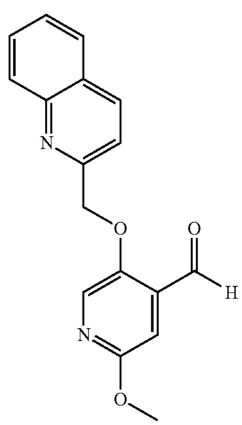 [SMILES: COc1cc(C=O)c(OCc2ccc3ccccc3n2)cn1] | 2-methoxy-5-(quinolin-2-ylmethoxy)isonicotinaldehyde |
| 46 | 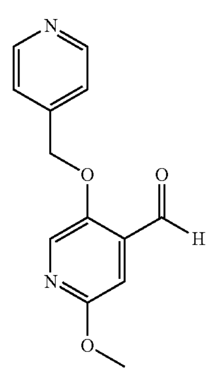 [SMILES: COc1cc(C=O)c(OCc2ccncc2)cn1] | 2-methoxy-5-(pyridin-4-ylmethoxy)isonicotinaldehyde |

TABLE 1-continued

| Compound | Structure | Name |
|---|---|---|
| 47 | 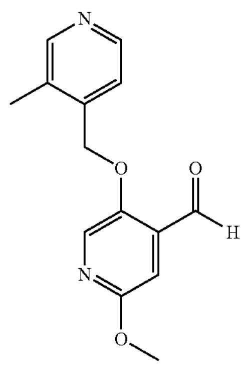 [SMILES: COc1cc(C=O)c(OCc2ccncc2C)cn1] | 2-methoxy-5-((3-methylpyridin-4-yl)methoxy)isonicotinaldehyde |
| 48 | 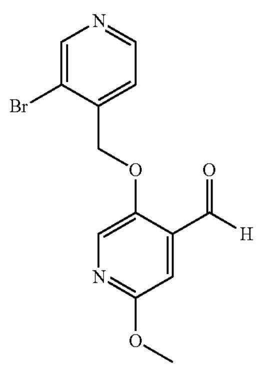 [SMILES: COc1cc(C=O)c(OCc2ccncc2Br)cn1] | 5-((3-bromopyridin-4-yl)methoxy)-2-methoxyisonicotinaldehyde |
| 49 | 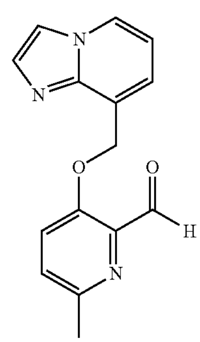 [SMILES: Cc1ccc(OCc2cccn3ccnc23)c(C=O)n1] | 3-(imidazo[1,2-a]pyridin-8-ylmethoxy)-6-methylpicolinaldehyde |
| 50 | 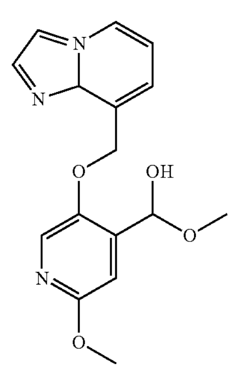 | (5-(imidazo[1,2-a]pyridin-5-ylmethoxy)-2-methoxypyridin-4-yl)(methoxy)methanol |

TABLE 1-continued

| Compound | Structure | Name |
|---|---|---|
| 51 | 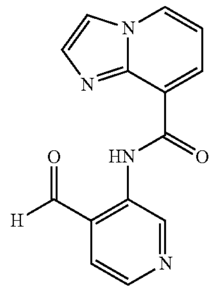 [SMILES: O=Cc1ccncc1NC(=O)c1cccn2ccnc12] | N-(4-formylpyridin-3-yl)imidazo[1,2-a]pyridine-8-carboxamide |
| 52 | 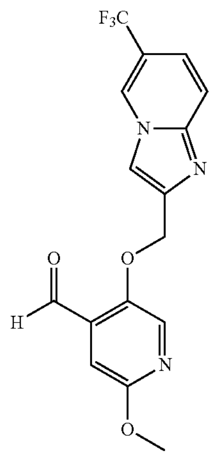 [SMILES: COc1cc(C=O)c(OCc2cn3cc(C(F)(F)F)ccc3n2)cn1] | 2-methoxy-5-((6-(trifluoromethyl)imidazo[1,2-a]pyridin-2-yl)methoxy)isonicotinaldehyde |
| 53 | 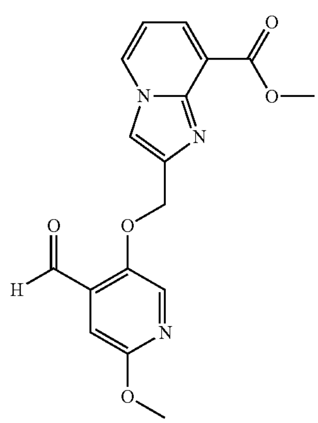 [SMILES: COC(=O)c1cccn2cc(COc3cnc(OC)cc3C=O)nc12] | methyl 2-((4-formyl-6-methoxypyridin-3-yloxy)methyl)imidazo[1,2-a]pyridine-8-carboxylate |
| 54 | 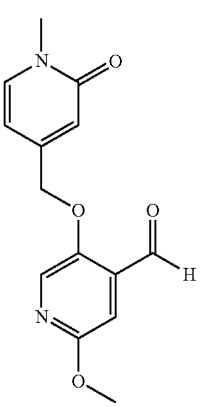 [SMILES: COc1cc(C=O)c(OCc2ccn(C)c(=O)c2)cn1] | 2-methoxy-5-((1-methyl-2-oxo-1,2-dihydropyridin-4-yl)methoxy)isonicotinaldehyde |

TABLE 1-continued

| Compound | Structure | Name |
|---|---|---|
| 55 | 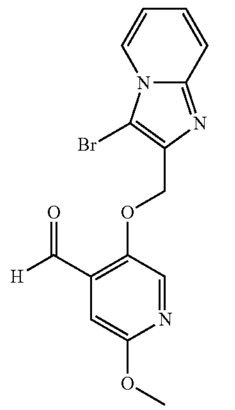 [SMILES: COc1cc(C=O)c(OCc2nc3ccccn3c2Br)cn1] | 5-((3-bromoimidazo[1,2-a]pyridin-2-yl)methoxy)-2-methoxyisonicotinaldehyde |
| 56 | 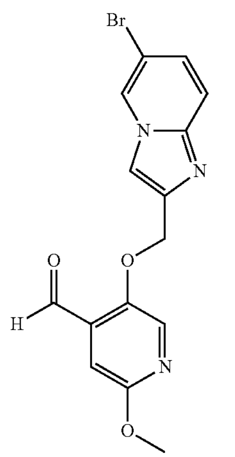 [SMILES: COc1cc(C=O)c(OCc2cn3cc(Br)ccc3n2)cn1] | 5-((6-bromoimidazo[1,2-a]pyridin-2-yl)methoxy)-2-methoxyisonicotinaldehyde |
| 57 | 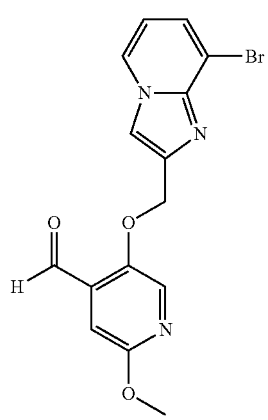 [SMILES: COc1cc(C=O)c(OCc2cn3cccc(Br)c3n2)cn1] | 5-((8-bromoimidazo[1,2-a]pyridin-2-yl)methoxy)-2-methoxyisonicotinaldehyde |

TABLE 1-continued
| Compound | Structure | Name |
| --- | --- | --- |
| 58 | 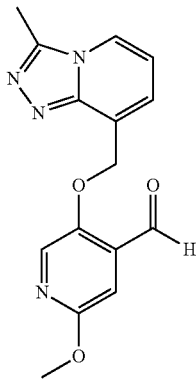 [SMILES: COc1cc(C=O)c(OCc2cccn3c(C)nnc23)cn1] | 2-methoxy-5-((3-methyl-[1,2,4]triazolo[4,3-a]pyridin-8-yl)methoxy)isonicotinaldehyde |
| 59 | 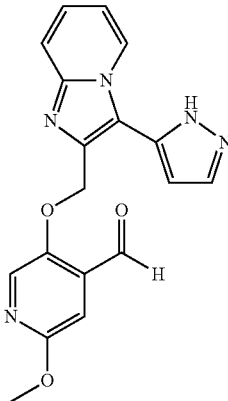 | 5-((3-(1H-pyrazol-5-yl)imidazo[1,2-a]pyridin-2-yl)methoxy)-2-methoxyisonicotinaldehyde |
| 60 | 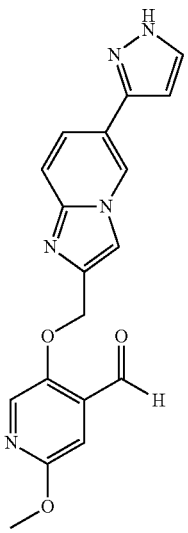 [SMILES: COc1cc(C=O)c(OCc2cn3cc(-c4cc[nH]n4)ccc3n2)cn1] | 5-((6-(1H-pyrazol-3-yl)imidazo[1,2-a]pyridin-2-yl)methoxy)-2-methoxyisonicotinaldehyde |

TABLE 1-continued
| Compound | Structure | Name |
|---|---|---|
| 61 | 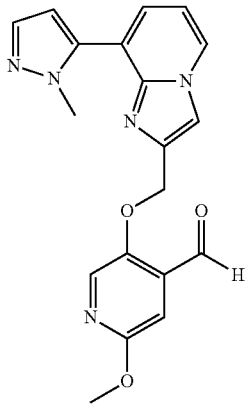 [SMILES: COc1cc(C=O)c(OCc2cn3cccc(-c4ccnn4C)c3n2)cn1] | 2-methoxy-5-((8-(1-methyl-1H-pyrazol-5-yl)imidazo[1,2-a]pyridin-2-yl)methoxy)isonicotinaldehyde |
| 62 | 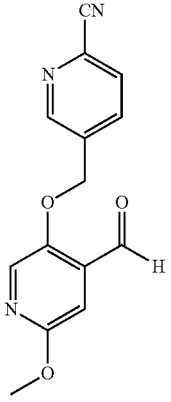 [SMILES: COc1cc(C=O)c(OCc2ccc(C#N)nc2)cn1] | 5-((4-formyl-6-methoxypyridin-3-yloxy)methyl)picolinonitrile |
| 63 | 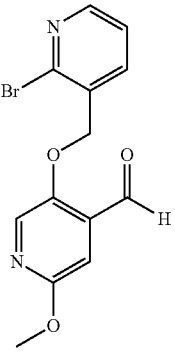 | 5-((2-bromopyridin-3-yl)methoxy)-2-methoxyisonicotinaldehyde |
| 64 | 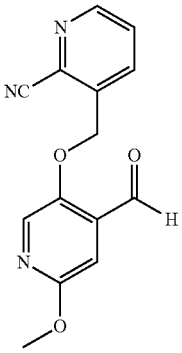 [SMILES: COc1cc(C=O)c(OCc2cccnc2Br)cn1] | 3-((4-formyl-6-methoxypyridin-3-yloxy)methyl)picolinonitrile |

TABLE 1-continued

| Compound | Structure | Name |
|---|---|---|
| 65 | 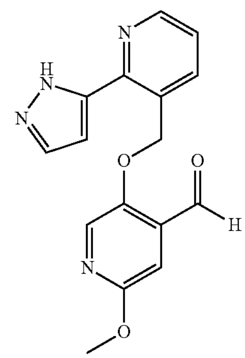 [SMILES: COc1cc(C=O)c(OCc2cccnc2-c2ccn[nH]2)cn1] | 5-((2-(1H-pyrazol-5-yl)pyridin-3-yl)methoxy)-2-methoxyisonicotinaldehyde |
| 66 | 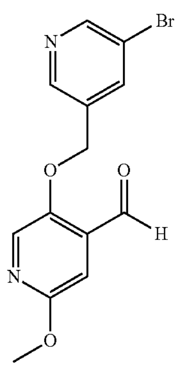 [SMILES: COc1cc(C=O)c(OCc2cncc(Br)c2)cn1] | 5-((5-bromopyridin-3-yl)methoxy)-2-methoxyisonicotinaldehyde |
| 67 | 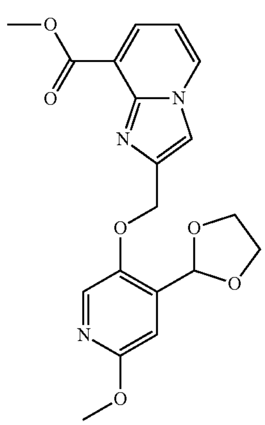 [SMILES: COC(=O)c1cccn2cc(COc3cnc(OC)cc3C3OCCO3)nc12] | methyl 2-((4-(1,3-dioxolan-2-yl)-6-methoxypyridin-3-yloxy)methyl)imidazo[1,2-a]pyridine-8-carboxylate |
| 68 | 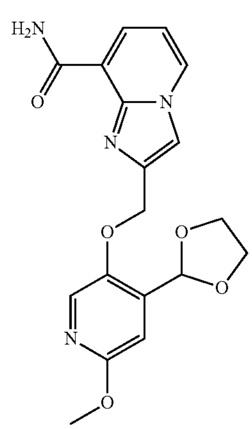 [SMILES: COc1cc(C2OCCO2)c(OCc2cn3cccc(C(N)=O)c3n2)cn1] | 2-((4-(1,3-dioxolan-2-yl)-6-methoxypyridin-3-yloxy)methyl)imidazo[1,2-a]pyridine-8-carboxamide |

TABLE 1-continued

| Compound | Structure | Name |
|---|---|---|
| 69 | 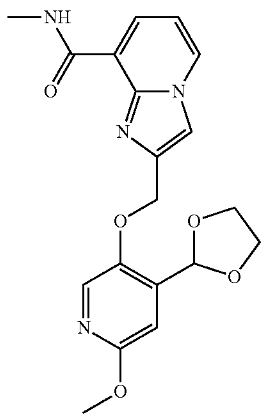 [SMILES: CNC(=O)c1cccn2cc(COc3cnc(OC)cc3C3OCCO3)nc12] | 2-((4-(1,3-dioxolan-2-yl)-6-methoxypyridin-3-yloxy)methyl)-N-methylimidazo[1,2-a]pyridine-8-carboxamide |
| 70 | 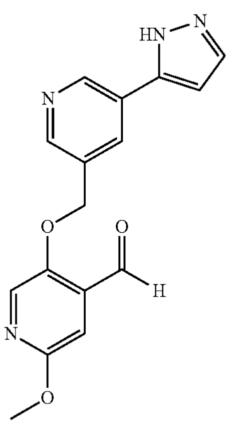 [SMILES: COc1cc(C=O)c(OCc2cncc(-c3ccn[nH]3)c2)cn1] | 5-((5-(1H-pyrazol-5-yl)pyridin-3-yl)methoxy)-2-methoxyisonicotinaldehyde |
| 71 | 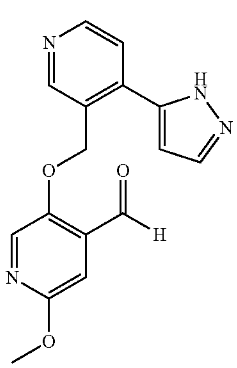 [SMILES: COc1cc(C=O)c(OCc2cnccc2-c2ccn[nH]2)cn1] | 5-((4-(1H-pyrazol-5-yl)pyridin-3-yl)methoxy)-2-methoxyisonicotinaldehyde |

TABLE 1-continued

| Compound | Structure | Name |
|---|---|---|
| 72 | 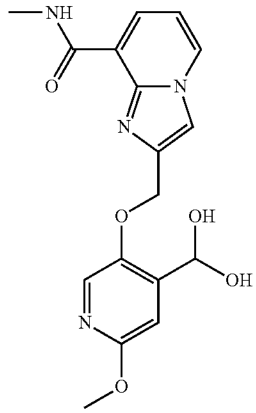 [SMILES: CNC(=O)c1cccn2cc(COc3cnc(OC)cc3C(O)O)nc12] | 2-((4-(dihydroxymethyl)-6-methoxypyridin-3-yloxy)methyl)-N-methylimidazo[1,2-a]pyridine-8-carboxamide |
| 73 | 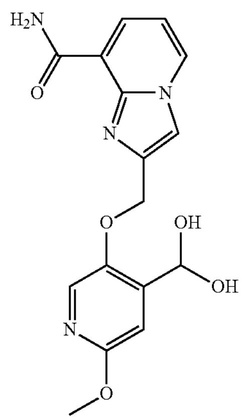 [SMILES: COc1cc(C(O)O)c(OCc2cn3cccc(C(N)=O)c3n2)cn1] | 2-((4-(dihydroxymethyl)-6-methoxypyriidn-3-yloxy)methyl)imidazo[1,2-a]pyridine-8-carboxamide |
| 74 | 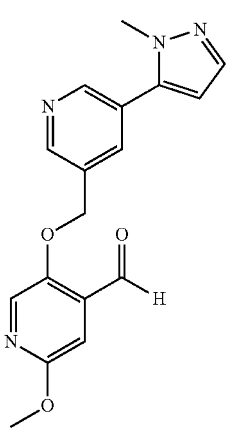 [SMILES: COc1cc(C=O)c(OCc2cncc(-c3ccnn3C)c2)cn1] | 2-methoxy-5-((5-(1-methyl-1H-pyrazol-5-yl)pyridin-3-yl)methoxy)isonicotinaldehyde |

TABLE 1-continued

| Compound | Structure | Name |
|---|---|---|
| 75 | 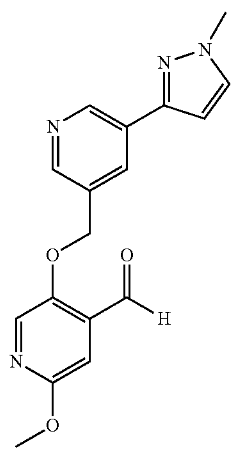 [SMILES: COc1cc(C=O)c(OCc2cncc(-c3ccn(C)n3)c2)cn1] | 2-methoxy-5-((5-(1-methyl-1H-pyrazol-3-yl)pyridin-3-yl)methoxy)isonicotinaldehyde |
| 76 | 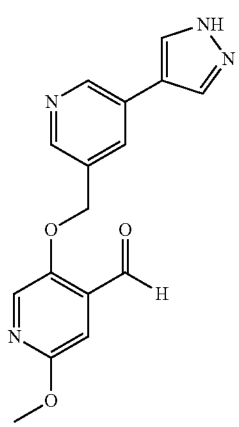 [SMILES: COc1cc(C=O)c(OCc2cncc(-c3cn[nH]c3)c2)cn1] | 5-((5-(1H-pyrazol-4-yl)pyridin-3-yl)methoxy)-2-methoxyisonicotinaldehyde |
| 77 | 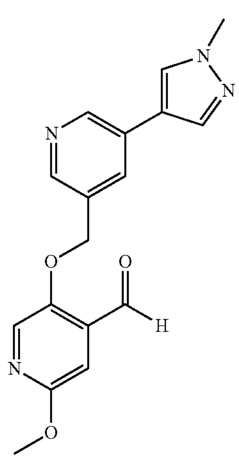 [SMILES: COc1cc(C=O)c(OCc2cncc(-c3cnn(C)c3)c2)cn1] | 2-methoxy-5-((5-(1-methyl-1H-pyrazol-4-yl)pyridin-3-yl)methoxy)isonicotinaldehyde |

TABLE 1-continued

| Compound | Structure | Name |
|---|---|---|
| 78 | 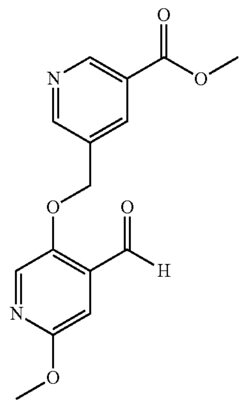 [SMILES: COC(=O)c1cncc(COc2cnc(OC)cc2C=O)c1] | methyl 5-((4-formyl-6-methoxypyridin-3-yloxy)methyl)nicotinate |
| 79 | 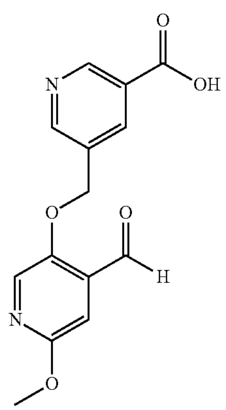 [SMILES: COc1cc(C=O)c(OCc2cncc(C(=O)O)c2)cn1] | 5-((4-formyl-6-methoxypyridin-3-yloxy)methyl)nicotinic acid |
| 80 | 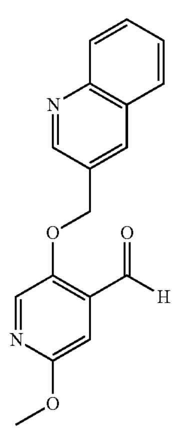 | 2-methoxy-5-(quinolin-3-ylmethoxy)isonicotinaldehyde |

TABLE 1-continued

| Compound | Structure | Name |
|---|---|---|
| 81 | 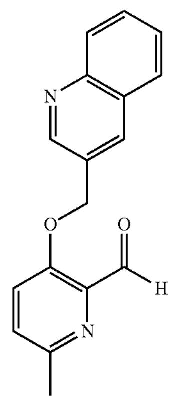 | 6-methyl-3-(quinolin-3-ylmethoxy)picolinaldehyde |
| 82 | 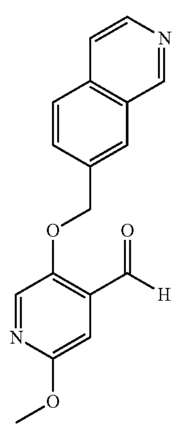 [SMILES: COc1cc(C=O)c(OCc2ccc3ccncc3c2)cn1] | 5-(isoquinolin-7-ylmethoxy)-2-methoxyisonicotinaldehyde |
| 83 | 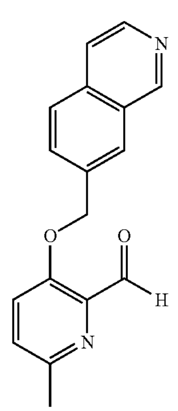 [SMILES: Cc1ccc(OCc2ccc3ccncc3c2)c(C=O)n1] | 3-(isoquinolin-7-ylmethoxy)-6-methylpicolinaldehyde |

TABLE 1-continued
| Compound | Structure | Name |
|---|---|---|
| 84 | 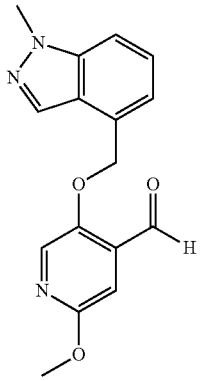 [SMILES: COc1cc(C=O)c(OCc2cccc3c2cnn3C)cn1] | 2-methoxy-5-((1-methyl-1H-indazol-4-yl)methoxy)isonicotinaldehyde |
| 85 | 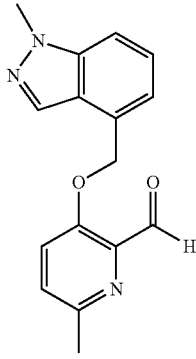 [SMILES: Cc1ccc(OCc2cccc3c2cnn3C)c(C=O)n1] | 6-methyl-3-((1-methyl-1H-indazol-4-yl)methoxy)picolinaldehyde |
| 86 | 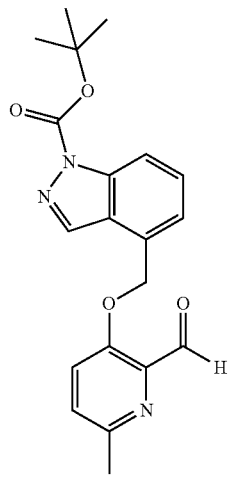 [SMILES: Cc1ccc(OCc2cccc3c2cnn3C(=O)OC(C)(C)C)c(C=O)n1] | tert-butyl 4-((2-formyl-6-methylpyridin-3-yloxy)methyl)-1H-indazole-1-carboxylate |

TABLE 1-continued

| Compound | Structure | Name |
|---|---|---|
| 87 | 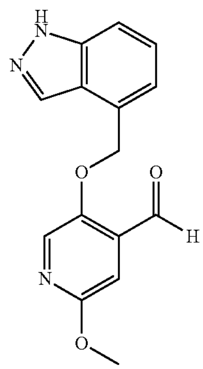 [SMILES: COc1cc(C=O)c(OCc2cccc3[nH]ncc23)cn1] | 5-((1H-indazol-4-yl)methoxy)-2-methoxyisonicotinaldehyde |
| 88 | 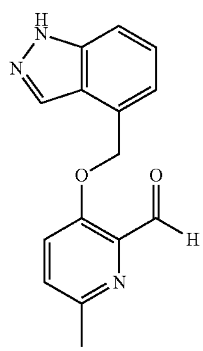 [SMILES: Cc1ccc(OCc2cccc3[nH]ncc23)c(C=O)n1] | 3-((1H-indazol-4-yl)methoxy-6-methylpicolinaldehyde |
| 89 | 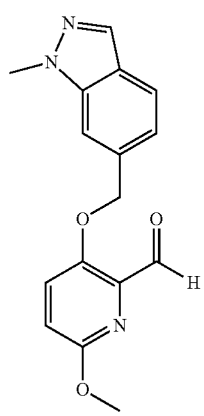 [SMILES: COc1ccc(OCc2ccc3cnn(C)c3c2)c(C=O)n1] | 6-methoxy-3-((1-methyl-1H-indazol-6-yl)methoxy)picolinaldehyde |
| 90 | 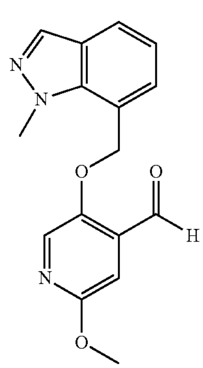 [SMILES: COc1cc(C=O)c(OCc2cccc3cnn(C)c23)cn1] | 2-methoxy-5-((1-methyl-1H-indazol-7-yl)methoxy)isonicotinaldehyde |

TABLE 1-continued

| Compound | Structure | Name |
|---|---|---|
| 91 | 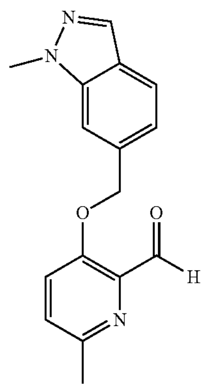 [SMILES: Cc1ccc(OCc2ccc3cnn(C)c3c2)c(C=O)n1] | 6-methyl-3-((1-methyl-1H-indazol-6-yl)methoxy)picolinaldehyde |
| 92 | 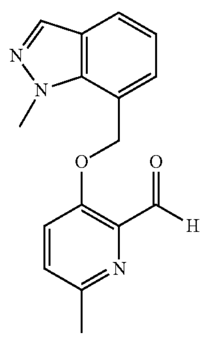 [SMILES: Cc1ccc(OCc2cccc3cnn(C)c23)c(C=O)n1] | 6-methyl-3-((1-methyl-1H-indazol-7-yl)methoxy)picolinaldehyde |
| 93 | 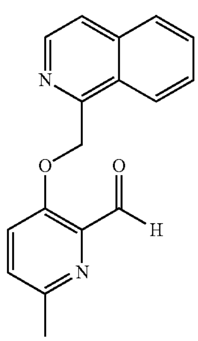 [SMILES: Cc1ccc(OCc2nccc3ccccc23)c(C=O)n1] | 3-(isoquinolin-1-ylmethoxy)-6-methylpicolinaldehyde |
| 94 | 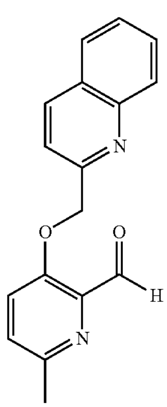 [SMILES: Cc1ccc(OCc2ccc3ccccc3n2)c(C=O)n1] | 6-methyl-3-(quinolin-2-ylmethoxy)picolinaldehyde |

TABLE 1-continued

| Compound | Structure | Name |
|---|---|---|
| 95 | 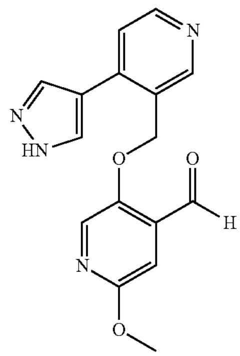 [SMILES: COc1cc(C=O)c(OCc2cnccc2-c2cn[nH]c2)cn1] | 5-((4-(1H-pyrazol-4-yl)pyridin-3-yl)methoxy)-2-methoxyisonicotinaldehyde |
| 96 | 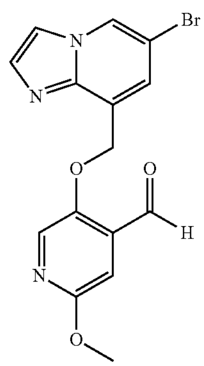 [SMILES: COc1cc(C=O)c(OCc2cc(Br)cn3ccnc23)cn1] | 5-((6-bromoimidazo[1,2-a]pyridin-8-yl)methoxy)-2-methoxyisonicotinaldehyde |
| 97 | 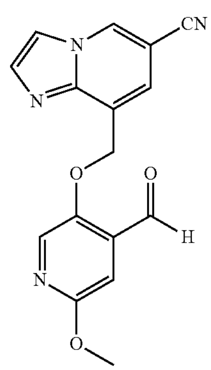 [SMILES: COc1cc(C=O)c(OCc2cc(C#N)cn3ccnc23)cn1] | 8-((4-formyl-6-methoxypyridin-3-yloxy)methyl)imidazo[1,2-a]pyridine-6-carbonitrile |
| 98 | 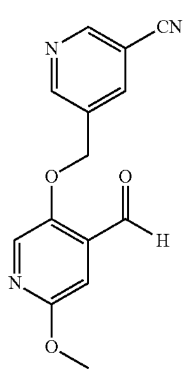 [SMILES: COc1cc(C=O)c(OCc2cncc(C#N)c2)cn1] | 5-((4-formoyl-6-methoxypyridin-3-yloxy)methyl)nicotinonitrile |

TABLE 1-continued
| Compound | Structure | Name |
|---|---|---|
| 99 | 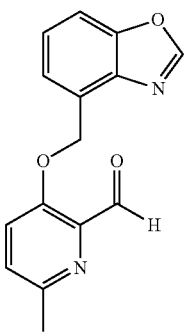 [SMILES: Cc1ccc(OCc2cccc3ocnc23)c(C=O)n1] | 3-(benzo[d]oxazol-4-ylmethoxy)-6-methylpicolinaldehyde |
| 100 | 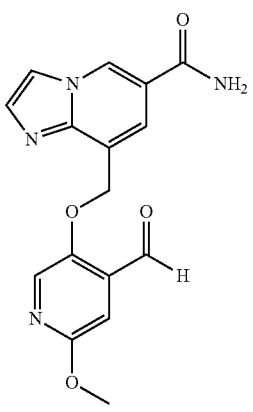 [SMILES: COc1cc(C=O)c(OCc2cc(C(N)=O)cn3ccnc23)cn1] | 8-((4-formyl-6-methoxypyridin-3-yloxy)methyl)imidazo[1,2-a]pyridine-6-carboxamide |
| 101 | 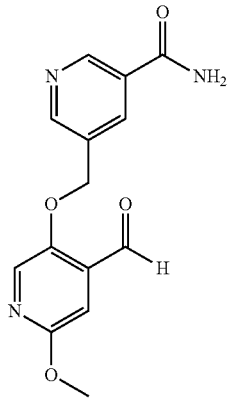 [SMILES: COc1cc(C=O)c(OCc2cncc(C(N)=O)c2)cn1] | 5-((4-formyl-6-methoxypyridin-3-yloxy)methyl)nicotinamide |
| 102 | 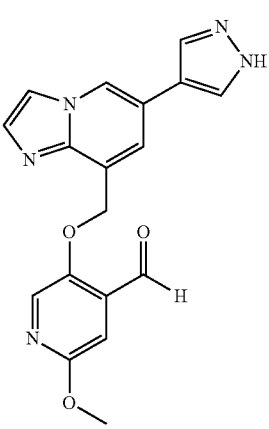 [SMILES: COc1cc(C=O)c(OCc2cc(-c3cn[nH]c3)cn3ccnc23)cn1] | 5-((6-(1H-pyrazol-4-yl)imidazo[1,2-a]pyridin-8-yl)methoxy)-2-methoxyisonicotinaldehyde |

TABLE 1-continued

| Compound | Structure | Name |
|---|---|---|
| 103 | 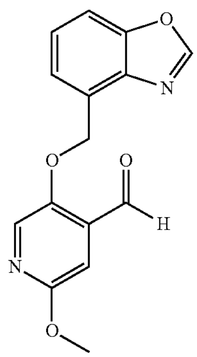 [SMILES: COc1cc(C=O)c(OCc2cccc3ocnc23)cn1] | 5-(benzo[d]oxazol-4-ylmethoxy)-2-methoxyisonicotinaldehyde |
| 104 | 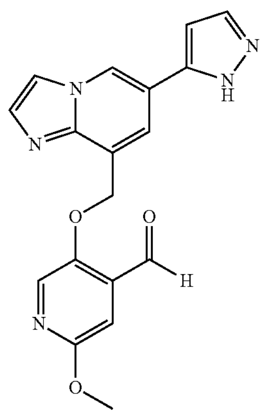 [SMILES: COc1cc(C=O)c(OCc2cc(-c3ccn[nH]3)cn3ccnc23)cn1] | 5-((6-(1H-pyrazol-5-yl)imidazo[1,2-a]pyridin-8-yl)methoxy)-2-methoxyisonicotinaldehyde |
| 105 | 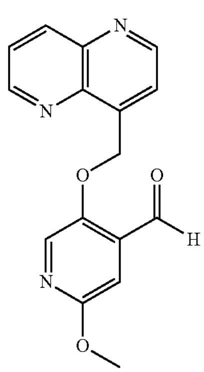 [SMILES: COc1cc(C=O)c(OCc2ccnc3cccnc23)cn1] | 5-((1,5-naphthyridin-4-yl)methoxy)-2-methoxyisonicotinaldehyde |
| 106 | 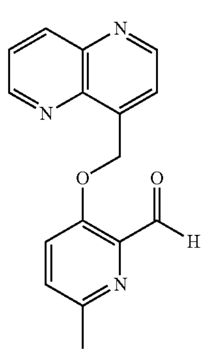 [SMILES: Cc1ccc(OCc2ccnc3cccnc23)c(C=O)n1] | 3-((1,5-naphthyridin-4-yl)methoxy)-6-methylpicolinaldehyde |

TABLE 1-continued

| Compound | Structure | Name |
|---|---|---|
| 107 | 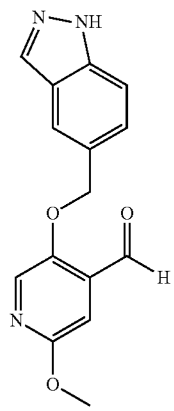 [SMILES: COc1cc(C=O)c(OCc2ccc3[nH]ncc3c2)cn1] | 5-((1H-indazol-5-yl)methoxy)-2-methoxyisonicotinaldehyde |
| 108 | 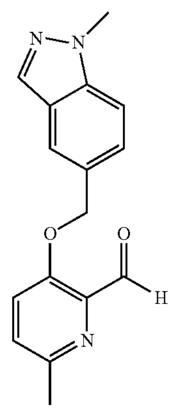 [SMILES: Cc1ccc(OCc2ccc3c(cnn3C)c2)c(C=O)n1] | 6-methyl-3-((1-methyl-1H-indazol-5-yl)methoxy)picolinaldehyde |
| 109 | 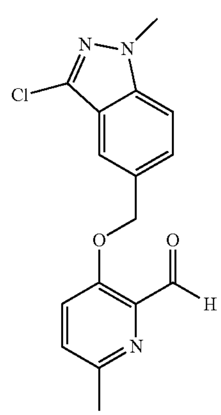 [SMILES: Cc1ccc(OCc2ccc3c(c2)c(Cl)nn3C)c(C=O)n1] | 3-((3-chloro-1-methyl-1H-indazol-5-yl)methoxy)-6-methylpicolinaldehyde |

TABLE 1-continued

| Compound | Structure | Name |
|---|---|---|
| 110 | 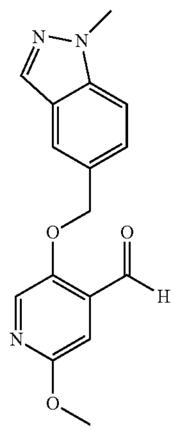 [SMILES: COc1cc(C=O)c(OCc2ccc3c(cnn3C)c2)cn1] | 2-methoxy-5-((1-methyl-1H-indazol-5-yl)methoxy)isonicotinaldehyde |
| 111 | 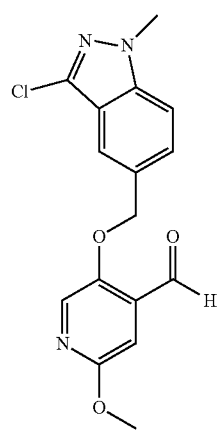 [SMILES: COc1cc(C=O)c(OCc2ccc3c(c2)c(Cl)nn3C)cn1] | 5-((3-chloro-1-methyl-1H-indazol-5-yl)methoxy)-2-methoxyisonicotinaldehyde |
| 112 | 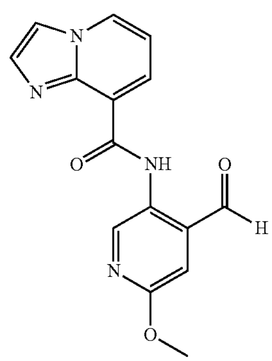 [SMILES: COc1cc(C=O)c(NC(=O)c2cccn3ccnc23)cn1] | N-(4-formyl-6-methoxypyridin-3-yl)imidazo[1,2-a]pyridine-8-carboxamide |
| 113 | 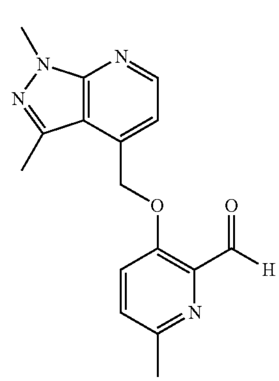 [SMILES: Cc1ccc(OCc2ccnc3c2c(C)nn3C)c(C=O)n1] | 3-((1,3-dimethyl-1H-pyrazolo[3,4-b]pyridin-4-yl)methoxy)-6-methylpicolinaldehyde |

TABLE 1-continued

| Compound | Structure | Name |
|---|---|---|
| 114 | 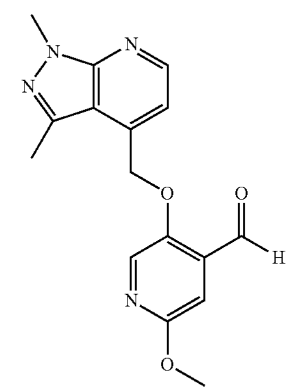 [SMILES: COc1cc(C=O)c(OCc2ccnc3c2c(C)nn3C)cn1] | 5-((1,3-dimethyl-1H-pyrazolo[3,4-b]pyridin-4-yl)methoxy)-2-methoxyisonicotinaldehyde |
| 115 | 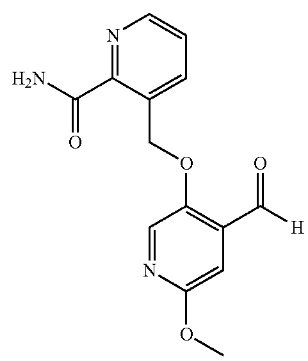 [SMILES: COc1cc(C=O)c(OCc2cccnc2C(N)=O)cn1] | 3-((4-formyl-6-methoxypyridin-3-yloxy)methyl)picolinamide |
| 116 | 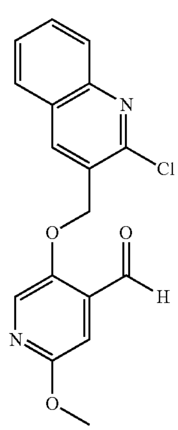 [SMILES: COc1cc(C=O)c(OCc2cc3ccccc3nc2Cl)cn1] | 5-((2-chloroquinolin-3-yl)methoxy)-2-methoxyisonicotinaldehyde |

TABLE 1-continued

| Compound | Structure | Name |
|---|---|---|
| 117 | 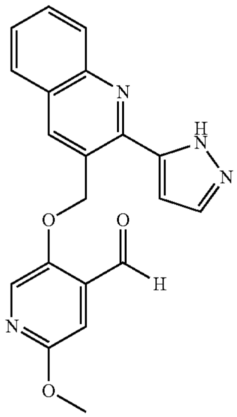 [SMILES: COc1cc(C=O)c(OCc2cc3ccccc3nc2-c2ccn[nH]2)cn1] | 5-((2-(1H-pyrazol-5-yl)quinolin-3-yl)methoxy)-2-methoxyisonicotinaldehyde |
| 118 | 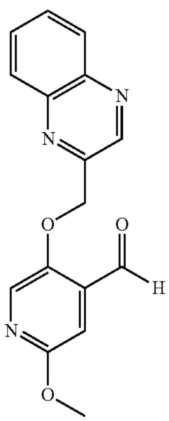 [SMILES: COc1cc(C=O)c(OCc2cnc3ccccc3n2)cn1] | 2-methoxy-5-(quinoxalin-2-ylmethoxy)isonictoinaldehyde |
| 119 | 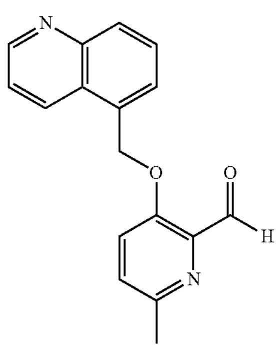 [SMILES: Cc1ccc(OCc2cccc3ncccc23)c(C=O)n1] | 6-methyl-3-(quinolin-5-ylmethoxy)picolinaldehyde |
| 120 | 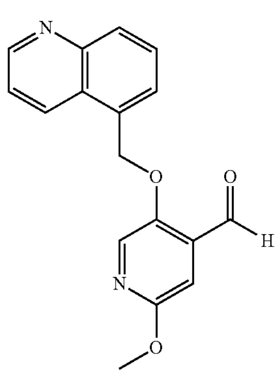 [SMILES: COc1cc(C=O)c(OCc2cccc3ncccc23)cn1] | 2-methoxy-5-(quinolin-5-ylmethoxy)isonicotinaldehyde |

TABLE 1-continued

| Compound | Structure | Name |
|---|---|---|
| 121 | 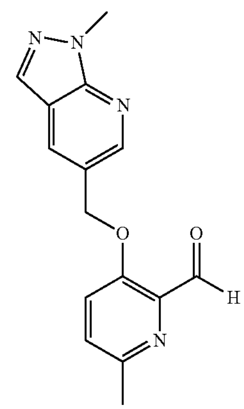 [SMILES: Cc1ccc(OCc2cnc3c(cnn3C)c2)c(C=O)n1] | 6-methyl-3-((1-methyl-1H-pyrazolo[3,4-b]pyridin-5-yl)methoxy)picolinaldehyde |
| 122 | 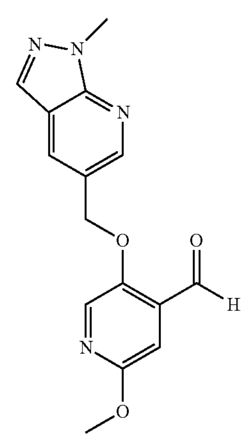 [SMILES: COc1cc(C=O)c(OCc2cnc3c(cnn3C)c2)cn1] | 2-methoxy-5-((1-methyl-1H-pyrazolo[3,4-b]pyridin-5-yl)methoxy)isonicotinaldehyde |
| 123 | 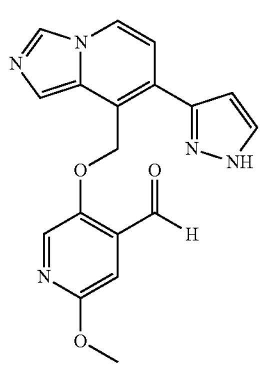 [SMILES: COc1cc(C=O)c(OCc2c(-c3cc[nH]n3)ccn3cncc23)cn1] | 5-((7-(1H-pyrazol-3-yl)imidazo[1,5-a]pyridin-8-yl)methoxy)-2-methoxyisonicotinaldehyde |

TABLE 1-continued

| Compound | Structure | Name |
|---|---|---|
| 124 | 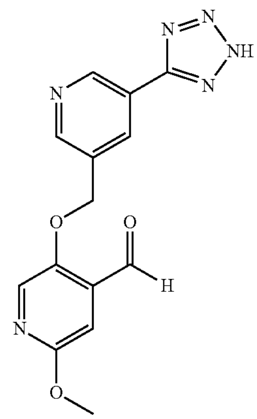 [SMILES: COc1cc(C=O)c(OCc2cncc(-c3nn[nH]n3)c2)cn1] | 5-((5-(2H-tetrazol-5-yl)pyridin-3-yl)methoxy)-2-methoxyisonicotinaldehyde |
| 125 | 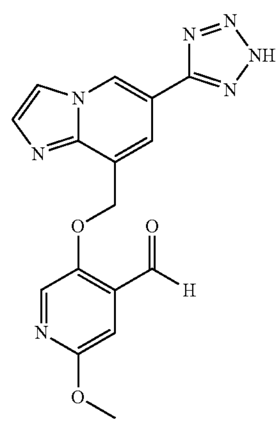 [SMILES: COc1cc(C=O)c(OCc2cc(-c3nn[nH]n3)cn3ccnc23)cn1] | 5-((6-(2H-tetrazol-5-yl)imidazo[1,2-a]pyridin-8-yl)methoxy)-2-methoxyisonicotinaldehyde |
| 126 | 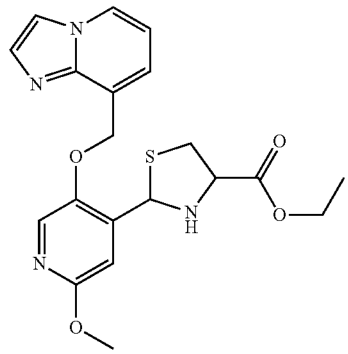 [SMILES: CCOC(=O)C1CSC(c2cc(OC)ncc2OCc2cccn3ccnc23)N1] | ethyl 2-(5-(imidazo[1,2-a]pyridin-8-ylmethoxy)-2-methoxypyriidn-4-yl)thiazolidine-4-carboxylate |
| 127 | 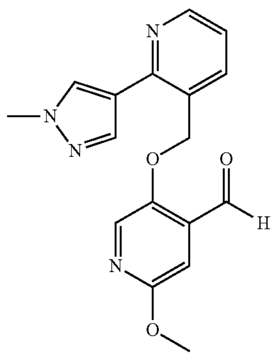 [SMILES: COc1cc(C=O)c(OCc2cccnc2-c2cnn(C)c2)cn1] | 2-methoxy-5-((2-(1-methyl-1H-pyrazol-4-yl)pyridin-3-yl)methoxy)isonicotinaldehye |

TABLE 1-continued

| Compound | Structure | Name |
|---|---|---|
| 128 | 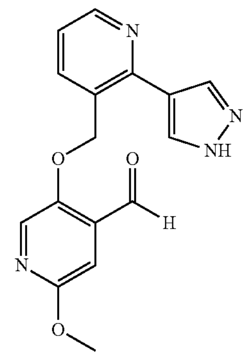 [SMILES: COc1cc(C=O)c(OCc2cccnc2-c2cn[nH]c2)cn1] | 5-((2-(1H-pyrazol-4-yl)pyridin-3-yl)methoxy)-2-methoxyisonicotinaldehyde |
| 129 | 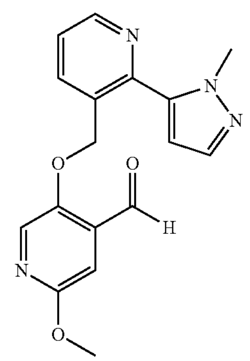 [SMILES: COc1cc(C=O)c(OCc2cccnc2-c2ccnn2C)cn1] | 2-methoxy-5-((2-(1-methyl-1H-pyrazol-5-yl)pyridin-3-yl)methoxy)isonicotinaldehyde |
| 130 | 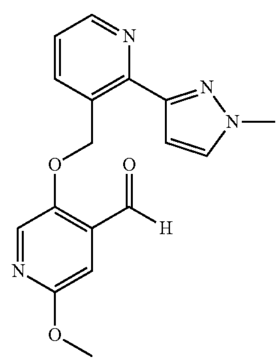 [SMILES: COc1cc(C=O)c(OCc2cccnc2-c2ccn(C)n2)cn1] | 2-methoxy-5-((2-(1-methyl-1H-pyrazol-3-yl)pyridin-3-yl)methoxy)isonicotinaldehyde |
| 131 | 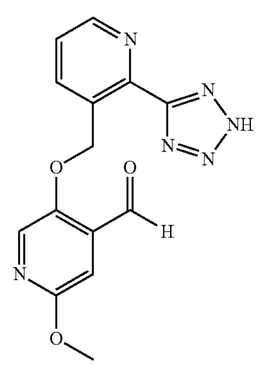 [SMILES: COc1cc(C=O)c(OCc2cccnc2-c2nn[nH]n2)cn1] | 5-((2-(2H-tetrazol-5-yl)pyridin-3-yl)methoxy)-2-methoxyisonicotinaldehyde |

TABLE 1-continued

| Compound | Structure | Name |
|---|---|---|
| 132 | 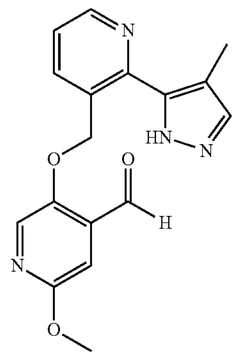 [SMILES: COc1cc(C=O)c(OCc2cccnc2-c2[nH]ncc2C)cn1] | 2-methoxy-5-((2-(4-methyl-1H-pyrazol-5-yl)pyridin-3-yl)methoxy)isonicotinaldehyde |
| 133 | 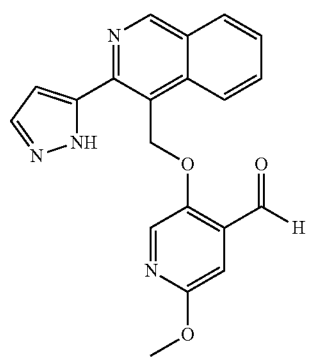 [SMILES: COc1cc(C=O)c(OCc2c(-c3ccn[nH]3)ncc3ccccc23)cn1] | 5-((3-(1H-pyrazol-5-yl)isoquinolin-4-yl)methoxy)-2-methoxyisonicotinaldehyde |
| 134 | 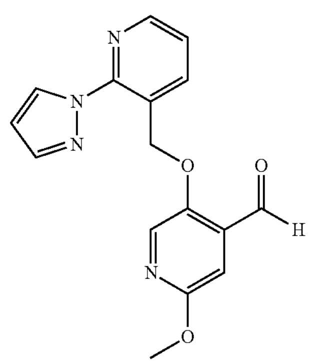 [SMILES: COc1cc(C=O)c(OCc2cccnc2-n2cccn2)cn1] | 5-((2-(1H-pyrazol-1-yl)pyridin-3-yl)methoxy)-2-methoxyisonicotinaldehyde |
| 135 | 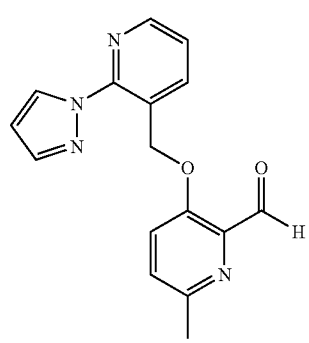 [SMILES: Cc1ccc(OCc2cccnc2-n2cccn2)c(C=O)n1] | 3-((2-(1H-pyrazol-1-yl)pyridin-3-yl)methoxy)-6-methylpicolinaldehyde |

TABLE 1-continued

| Compound | Structure | Name |
|---|---|---|
| 136 | 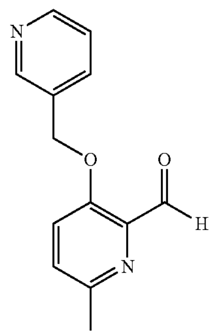 [SMILES: Cc1ccc(OCc2cccnc2)c(C=O)n1] | 6-methyl-3-(pyridin-3-ylmethoxy)picolinaldehyde |
| 137 | 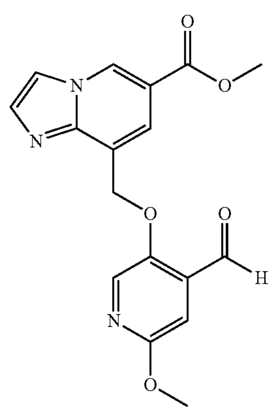 [SMILES: COC(=O)c1cc(COc2cnc(OC)cc2C=O)c2nccn2c1] | methyl 8-(((4-formyl-6-methoxypyridin-3-yl)oxy)methyl)imidazo[1,2-a]pyridine-6-carboxylate |
| 138 | 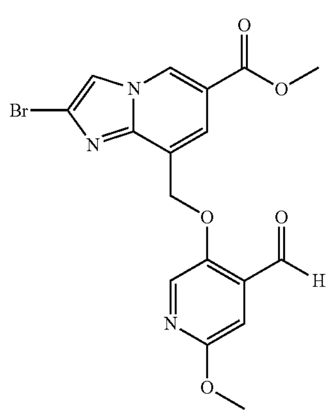 [SMILES: COC(=O)c1cc(COc2cnc(OC)cc2C=O)c2nc(Br)cn2c1] | methyl 2-bromo-8-(((4-formyl-6-methoxypyridin-3-yl)oxy)methyl)imidazo[1,2-a]pyridine-6-carboxylate |
| 139 | 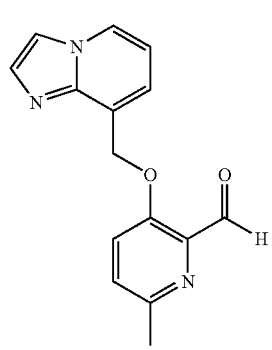 [SMILES: Cc1ccc(OCc2cccn3ccnc23)c(C=O)n1] | 3-(imidazo[1,5-a]pyridin-8-ylmethoxy)-6-methylpicolinaldehyde |

TABLE 1-continued
| Compound | Structure | Name |
|---|---|---|
| 140 | 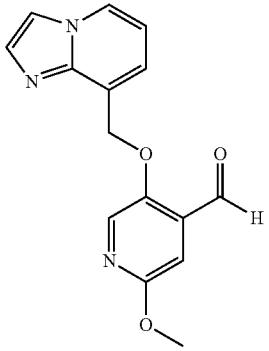 [SMILES: COc1cc(C=O)c(OCc2cccn3ccnc23)cn1] | 5-(imidazo[1,5-a]pyridin-8-ylmethoxy)-2-methoxyisonicotinaldehyde |
| 141 | 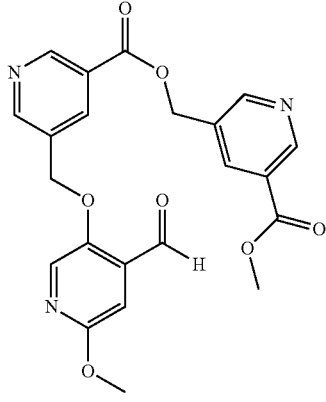 [SMILES: COC(=O)c1cncc(COC(=O)c2cncc(COc3cnc(OC)cc3C=O)c2)c1] | (5-(methoxycarbonyl)pyridin-3-yl)methyl 5-(((4-formyl-6-methoxypyridin-3-yl)oxy)methyl)nicotinate |
| 142 | 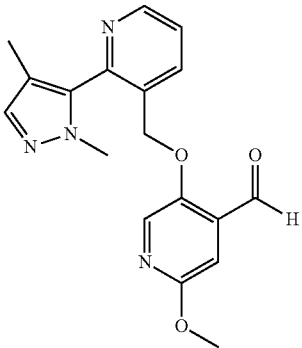 [SMILES: COc1cc(C=O)c(OCc2cccnc2-c2c(C)cnn2C)cn1] | 5-((2-(1,4-dimethyl-1H-pyrazol-5-yl)pyridin-3-yl)methoxy)-2-methoxyisonicotinaldehyde/ |
| 143 | 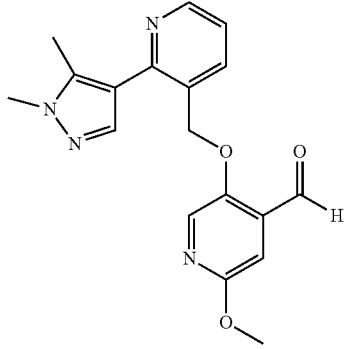 [SMILES: COc1cc(C=O)c(OCc2cccnc2-c2cnn(C)c2C)cn1] | 5-((2-(1,5-dimethyl-1H-pyrazol-4-yl)pyridin-3-yl)methoxy)-2-methoxyisonicotinaldehyde |

TABLE 1-continued

| Compound | Structure | Name |
|---|---|---|
| 144 | 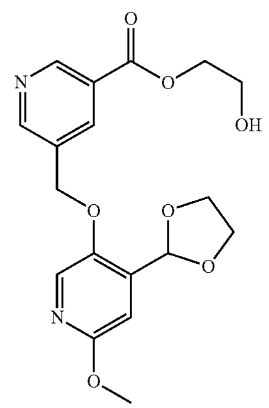 [SMILES: COc1cc(C2OCCO2)c(OCc2cncc(C(=O)OCCO)c2)cn1] | 2-hydroxyethyl 5-(((4-(1,3-dioxolan-2-yl)-6-methoxypyridin-3-yl)oxy)methyl)nicotinate |
| 145 | 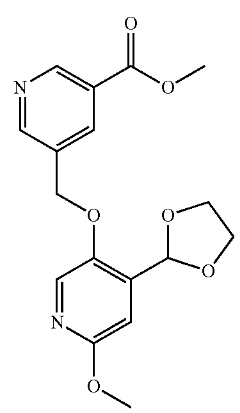 [SMILES: COC(=O)c1cncc(COc2cnc(OC)cc2C2OCCO2)c1] | methyl 5-(((4-(1,3-dioxolan-2-yl)-6-methoxypyridin-3-yl)oxy)methyl)nicotinate |
| 146 | 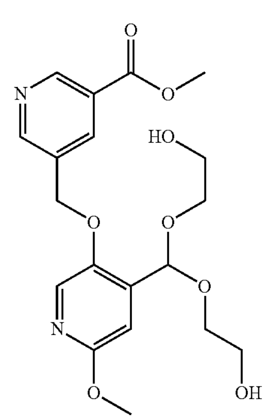 [SMILES: COC(=O)c1cncc(COc2cnc(OC)cc2C(OCCO)OCCO)c1] | methyl 5-(((4-(bis(2-hydroxyethoxy)methyl)-6-methoxypyridin-3-yl)oxy)methyl)nicotinate |

TABLE 1-continued

| Compound | Structure | Name |
|---|---|---|
| 147 | 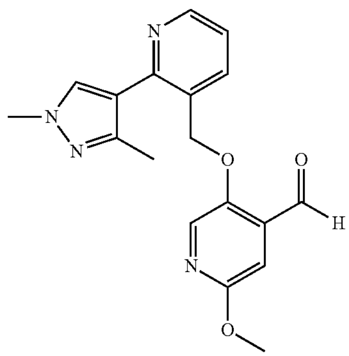 [SMILES: COc1cc(C=O)c(OCc2cccnc2-c2cn(C)nc2C)cn1] | 5-((2-(1,3-dimethyl-1H-pyrazol-4-yl)pyridin-3-yl)methoxy)-2-methoxyisonicotinaldehyde |
| 148 | 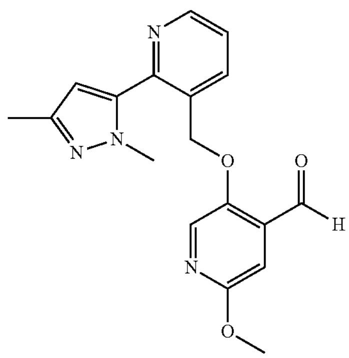 [SMILES: COc1cc(C=O)c(OCc2cccnc2-c2cc(C)nn2C)cn1] | 5-((2-(1,3-dimethyl-1H-pyrazol-5-yl)pyridin-3-yl)methoxy)-2-methoxyisonicotinaldehyde |
| 149 | 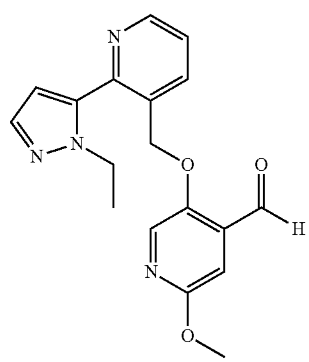 [SMILES: CCn1nccc1-c1ncccc1COc1cnc(OC)cc1C=O] | 5-((2-(1-ethyl-1H-pyrazol-5-yl)pyridin-3-yl)methoxy)-2-methoxyisonicotinaldehyde |
| 150 | 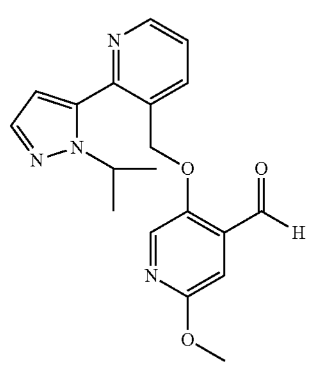 [SMILES: COc1cc(C=O)c(OCc2cccnc2-c2ccnn2C(C)C)cn1] | 5-((2-(1-isopropyl-1H-pyrazol-5-yl)pyridin-3-yl)methoxy)-2-methoxyisonicotinaldehyde |

TABLE 1-continued

| Compound | Structure | Name |
| --- | --- | --- |
| 151 | 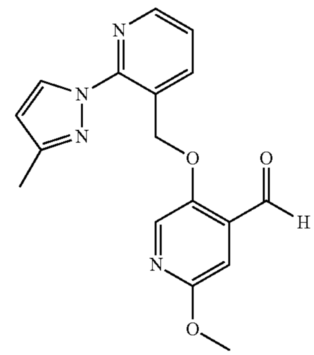 [SMILES: COc1cc(C=O)c(OCc2cccnc2-n2ccc(C)n2)cn1] | 2-methoxy-5-((2-(3-methyl-1H-pyrazol-1-yl)pyridin-3-yl)methoxy)isonicotinaldehyde |
| 152 | 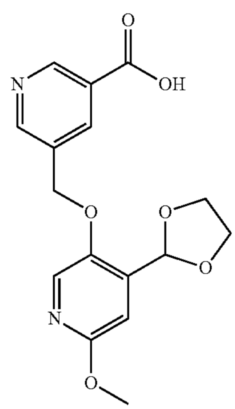 [SMILES: COc1cc(C2OCCO2)c(OCc2cncc(C(=O)O)c2)cn1] | 5-(((4-(1,3-dioxolan-2-yl)-6-methoxypyridin-3-yl)oxy)methyl)nicotinic acid |
| 153 | 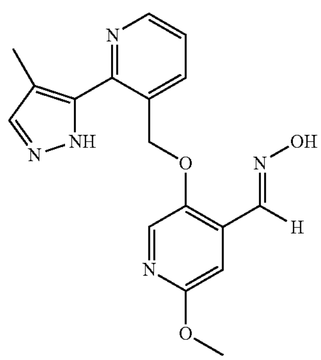 [SMILES: COc1cc(/C=N/O)c(OCc2cccnc2-c2[nH]ncc2C)cn1] | (E)-2-methoxy-5-((2-(4-methyl-1H-pyrazol-5-yl)pyridin-3-yl)methoxy)isonicotinaldehyde oxime |
| 154 | 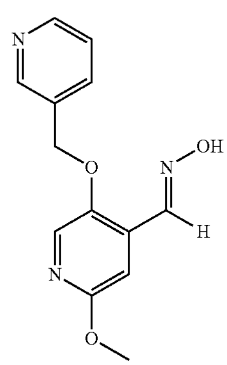 [SMILES: COc1cc(/C=N/O)c(OCc2cccnc2)cn1] | (E)-2-methoxy-5-(pyridin-3-ylmethoxy)isonicotinaldehyde oxime |

TABLE 1-continued

| Compound | Structure | Name |
|---|---|---|
| 155 | 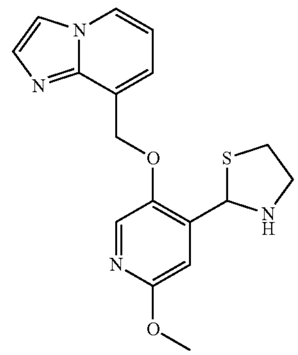 [SMILES: COc1cc(C2NCCS2)c(OCc2cccn3ccnc23)cn1] | 2-(5-(imidazo[1,2-a]pyridin-8-ylmethoxy)-2-methoxypyridin-4-yl)thiazolidine |
| 156 | 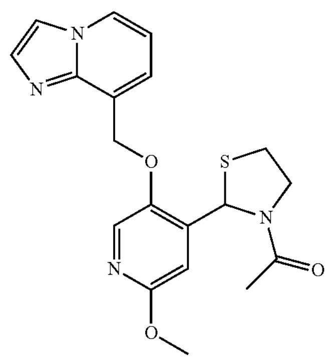 [SMILES: COc1cc(C2SCCN2C(C)=O)c(OCc2cccn3ccnc23)cn1] | 1-(2-(5-(imidazo[1,2-a]pyridin-8-ylmethoxy)-2-methoxypyridin-4-yl)thiazolidin-3-yl)ethanone |
| 157 | 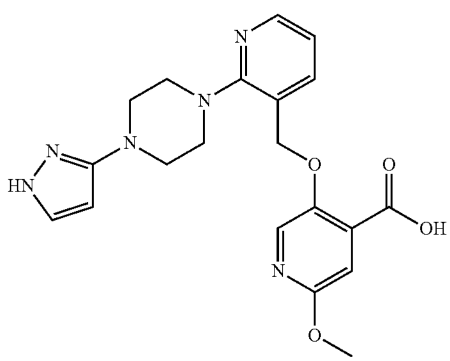 [SMILES: COc1cc(C(=O)O)c(OCc2cccnc2N2CCN(c3cc[nH]n3)CC2)cn1] | 5-((2-(4-(1H-pyrazol-3-yl)piperazin-1-yl)pyridin-3-yl)methoxy)-2-methoxyisonicotinaldehyde |
| 158 | 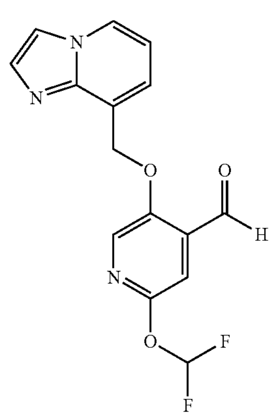 [SMILES: O=Cc1cc(OC(F)F)ncc1OCc1cccn2ccnc12] | 2-(difluoromethoxy)-5-(imidazo[1,2-a]pyridin-8-ylmethoxy)isonicotinaldehyde |

TABLE 1-continued

| Compound | Structure | Name |
|---|---|---|
| 159 | 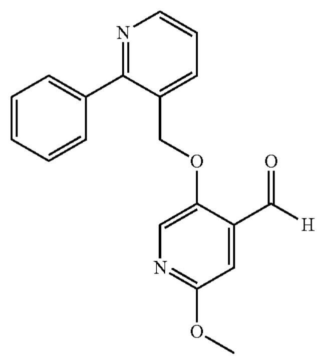 [SMILES: COc1cc(C=O)c(OCc2cccnc2-c2ccccc2)cn1] | 2-methoxy-5-((2-phenylpyridin-3-yl)methoxy)isonicotinaldehyde |
| 160 | 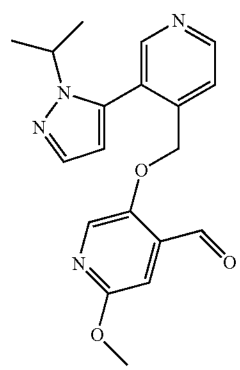 [SMILES: COc1cc(C=O)c(OCc2ccncc2-c2ccnn2C(C)C)cn1] | 5-((3-(1-isopropyl-1H-pyrazol-5-yl)pyridin-4-yl)methoxy)-2-methoxyisonicotinaldehyde |
| 161 | 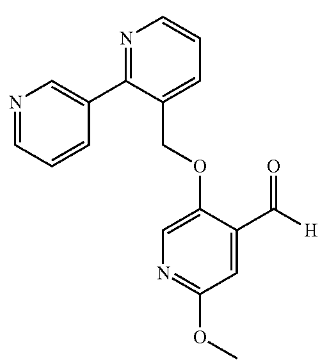 [SMILES: COc1cc(C=O)c(OCc2cccnc2-c2cccnc2)cn1] | 5-([2,3'-bipyridin]-3-ylmethoxy)-2-methoxyisonicotinaldehyde |
| 162 | 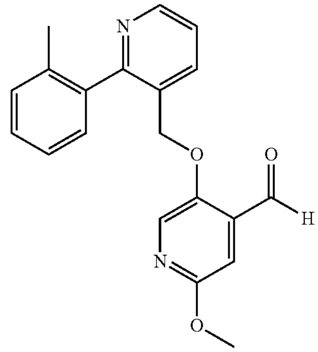 [SMILES: COc1cc(C=O)c(OCc2cccnc2-c2ccccc2C)cn1] | 2-methoxy-5-((2-(o-tolyl)pyridin-3-yl)methoxy)isonicotinaldehyde |

TABLE 1-continued

| Compound | Structure | Name |
|---|---|---|
| 163 | 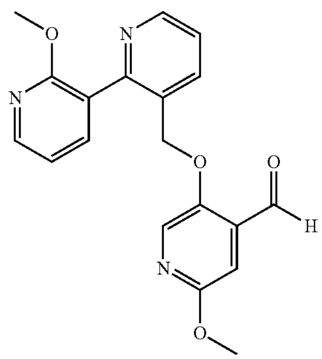 [SMILES: COc1cc(C=O)c(OCc2cccnc2-c2cccnc2OC)cn1] | 2-methoxy-5-(((2'-methoxy-[2,3'-bipyridin]-3-yl)methoxy)isonicotinaldehyde |
| 164 | 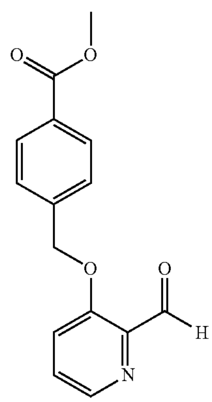 [SMILES: COC(=O)c1ccc(COc2cccnc2C=O)cc1] | methyl 4-(((2-formylpyridin-3-yl)oxy)methyl)benzoate |
| 165 | 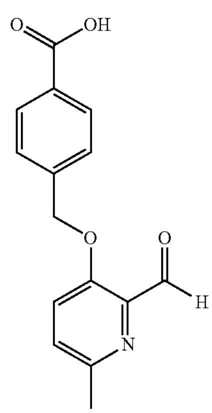 [SMILES: Cc1ccc(OCc2ccc(C(=O)O)cc2)c(C=O)n1] | 4-(((2-formyl-6-methylpyridin-3-yl)oxy)methyl)benzoic acid |
| 166 | 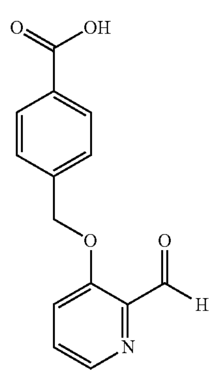 [SMILES: O=Cc1ncccc1OCc1ccc(C(=O)O)cc1] | 4-(((2-formylpyridin-3-yl)oxy)methyl)benzoic acid |

TABLE 1-continued

| Compound | Structure | Name |
|---|---|---|
| 167 | 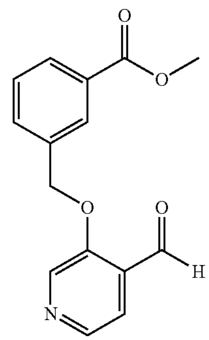 [SMILES: COC(=O)c1cccc(COc2cnccc2C=O)c1] | methyl 3-(((4-formylpyridin-3-yl)oxy)methyl)benzoate |
| 168 | 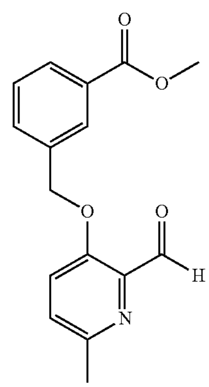 [SMILES: COC(=O)c1cccc(COc2ccc(C)nc2C=O)c1] | methyl 3-(((2-formyl-6-methylpyridin-3-yl)oxy)methyl)benzoate |
| 169 | 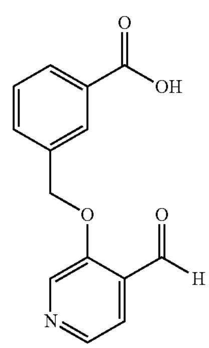 [SMILES: O=Cc1ccncc1OCc1cccc(C(=O)O)c1] | 3-(((4-formylpyridin-3-yl)oxy)methyl)benzoic acid |
| 170 | 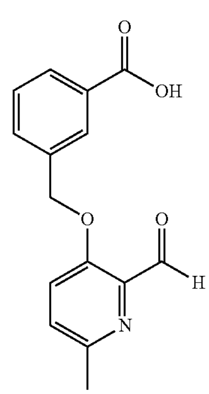 [SMILES: Cc1ccc(OCc2cccc(C(=O)O)c2)c(C=O)n1] | 3-(((2-formyl-6-methylpyridin-3-yl)oxy)methyl)benzoic acid |

TABLE 1-continued

| Compound | Structure | Name |
|---|---|---|
| 171 | 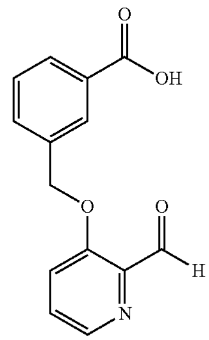 [SMILES: O=Cc1ncccc1OCc1cccc(C(=O)O)c1] | 3-(((2-formylpyridin-3-yl)oxy)methyl)benzoic acid |
| 172 | 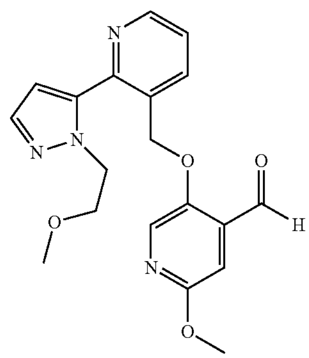 [SMILES: COCCn1nccc1-c1ncccc1COc1cnc(OC)cc1C=O] | 2-methoxy-5-((2-(1-(2-methoxyethyl)-1H-pyrazol-5-yl)pyridin-3-yl)methoxy)isonicotinaldehyde |
| 173 | 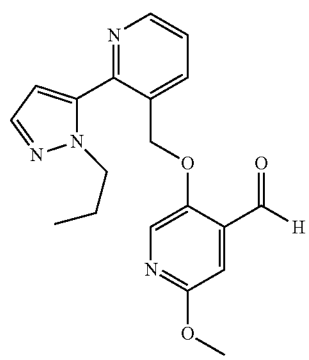 [SMILES: CCCn1nccc1-c1ncccc1COc1cnc(OC)cc1C=O] | 2-methoxy-5-((2-(1-propyl-1H-pyrazol-5-yl)pyridin-3-yl)methoxy)isonicotinaldehyde |
| 174 | 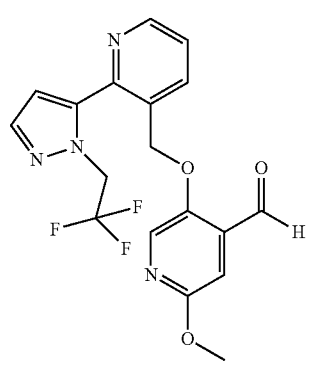 [SMILES: COc1cc(C=O)c(OCc2cccnc2-c2ccnn2CC(F)(F)F)cn1] | 2-methoxy-5-((2-(1-(2,2,2-trifluoroethyl)-1H-pyrazol-5-yl)pyridin-3-yl)methoxy)isonicotinaldehyde |

TABLE 1-continued

| Compound | Structure | Name |
|---|---|---|
| 175 | 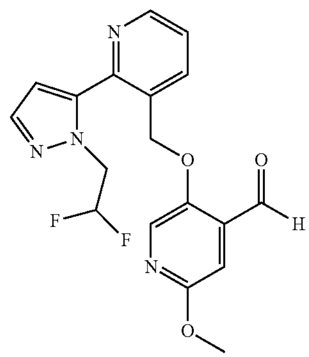 [SMILES: COc1cc(C=O)c(OCc2cccnc2-c2ccnn2CC(F)F)cn1] | 5-((2-(1-(2,2-difluoroethyl)-1H-pyrazol-5-yl)pyridin-3-yl)methoxy)-2-methoxyisonicotinaldehyde |
| 176 | 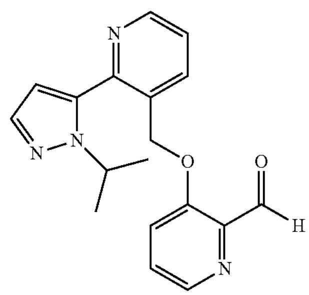 [SMILES: CC(C)n1nccc1-c1ncccc1COc1cccnc1C=O] | 3-((2-(1-isopropyl-1H-pyrazol-5-yl)pyridin-3-yl)methoxy)picolinaldehyde |
| 177 | 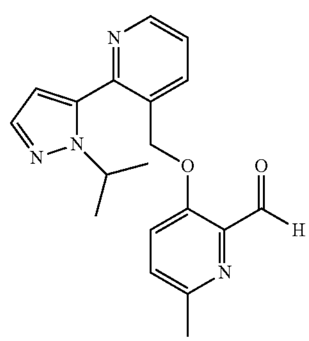 [SMILES: Cc1ccc(OCc2cccnc2-c2ccnn2C(C)C)c(C=O)n1] | 3-((2-(1-isopropyl-1H-pyrazol-5-yl)pyridin-3-yl)methoxy)-6-methylpicolinaldehyde |
| 178 | 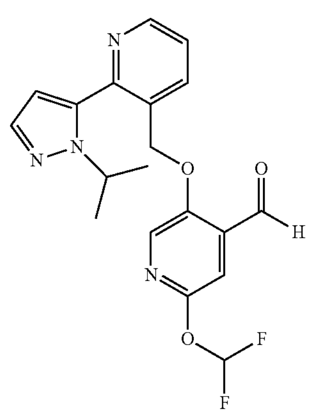 [SMILES: CC(C)n1nccc1-c1ncccc1COc1cnc(OC(F)F)cc1C=O] | 2-(difluoromethoxy)-5-((2-(1-isopropyl-1H-pyrazol-5-yl)pyridin-3-yl)methoxy)isonicotinaldehyde |

TABLE 1-continued
| Compound | Structure | Name |
|---|---|---|
| 179 | 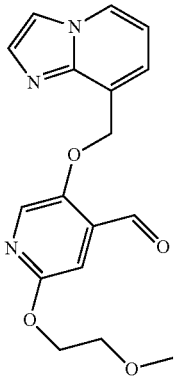 [SMILES: COCCOc1cc(C=O)c(OCc2cccn3ccnc23)cn1] | 5-(imidazo[1,2-a]pyridin-8-ylmethoxy)-2-(2-methoxyethoxy)isonicotinaldehyde |
| 180 | 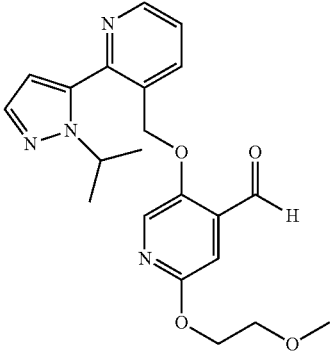 [SMILES: COCCOc1cc(C=O)c(OCc2cccnc2-c2ccnn2C(C)C)cn1] | 5-((2-(1-isopropyl-1H-pyrazol-5-yl)pyridin-3-yl)methoxy)-2-(2-methoxyethoxy)isonicotinaldehyde |
| 181 | 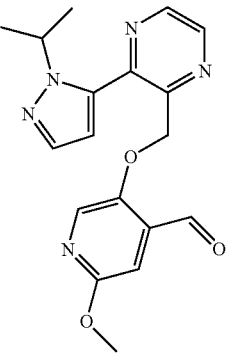 [SMILES: COc1cc(C=O)c(OCc2nccnc2-c2ccnn2C(C)C)cn1] | 5-((3-(1-isopropyl-1H-pyrazol-5-yl)pyrazin-2-yl)methoxy)-2-methoxyisonicotinaldehyde |
| 182 | 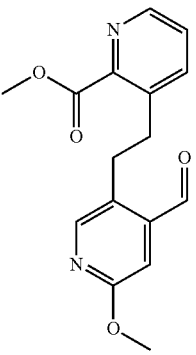 [SMILES: COC(=O)c1ncccc1CCc1cnc(OC)cc1C=O] | 3-((4-formyl-6-methoxypyridin-3-yloxy)methyl)picolinate |

TABLE 1-continued

| Compound | Structure | Name |
|---|---|---|
| 183 | 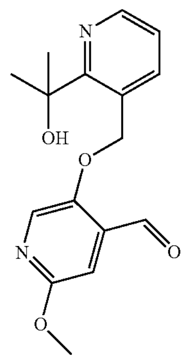 [SMILES: COc1cc(C=O)c(OCc2cccnc2C(C)(C)O)cn1] | 5-((2-(2-hydroxypropan-2-yl)pyridin-3-yl)methoxy)-2-methoxyisonicotinaldehyde |
| 184 | 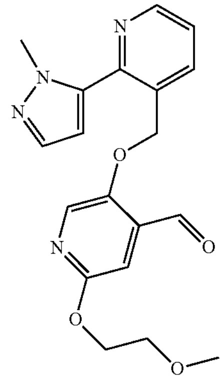 [SMILES: COCCOc1cc(C=O)c(OCc2cccnc2-c2ccnn2C)cn1] | 2-(2-methoxyethoxy)-5-((2-(1-methyl-1H-pyrazol-5-yl)pyridin-3-yl)methoxy)isonicotinaldehyde |
| 185 | 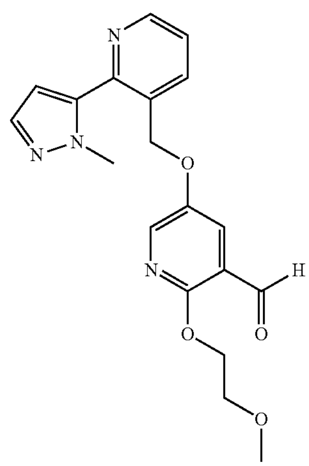 [SMILES: COCCOc1ncc(OCc2cccnc2-c2ccnn2C)cc1C=O] | 2-(2-methoxyethoxy)-5-((2-(1-methyl-1H-pyrazol-5-yl)pyridin-3-yl)methoxy)nicotinaldehyde |
| 186 | 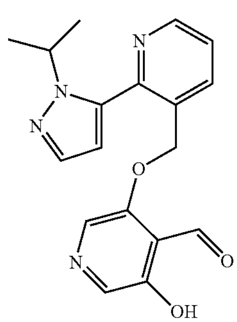 [SMILES: CC(C)n1nccc1-c1ncccc1COc1cncc(O)c1C=O] | 3-hydroxy-5-((2-(1-isopropyl-1H-pyrazol-5-yl)pyridin-3-yl)methoxy)isonicotinaldehyde |

TABLE 1-continued

| Compound | Structure | Name |
|---|---|---|
| 187 | 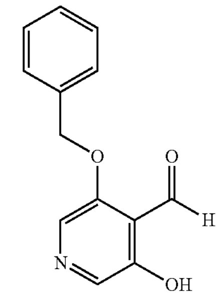 [SMILES: O=Cc1c(O)cncc1OCc1ccccc1] | 3-(benzyloxy)-5-hydroxyisonicotinaldehyde |
| 188 | 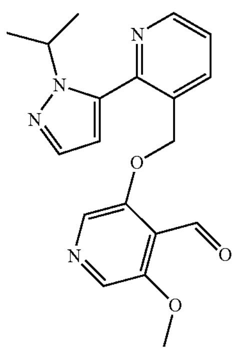 [SMILES: COc1cncc(OCc2cccnc2-c2ccnn2C(C)C)c1C=O] | 3-((2-(1-isopropyl-1H-pyrazol-5-yl)pyridin-3-yl)methoxy)-5-methoxyisonicotinaldehyde |
| 189 | 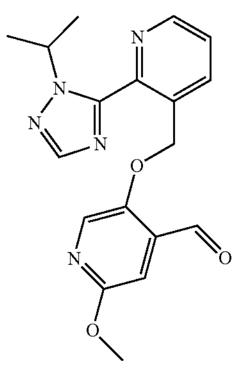 [SMILES: COc1cc(C=O)c(OCc2cccnc2-c2ncnn2C(C)C)cn1] | 5-((2-(2-isopropyl-2H-1,2,4-triazol-3-yl)pyridin-3-yl)methoxy)-2-methoxyisonicotinaldehyde |
| 190 | 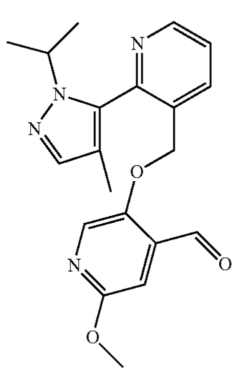 [SMILES: COc1cc(C=O)c(OCc2cccnc2-c2c(C)cnn2C(C)C)cn1] | 5-((2-(1-isopropyl-4-methyl-1H-pyrazol-5-yl)pyridin-3-yl)methoxy)-2-methoxyisonicotinaldehyde |

TABLE 1-continued

| Compound | Structure | Name |
|---|---|---|
| 191 | 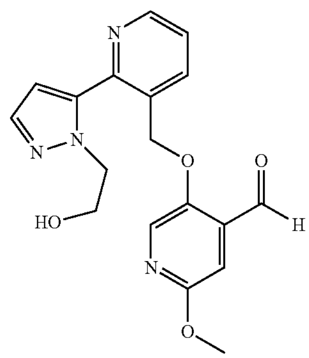 [SMILES: COc1cc(C=O)c(OCc2cccnc2-c2ccnn2CCO)cn1] | 5-((2-(1-(2-hydroxyethyl)-1H-pyrazol-5-yl)pyridin-3-yl)methoxy)-2-methoxyisonicotinaldehyde |
| 192 | 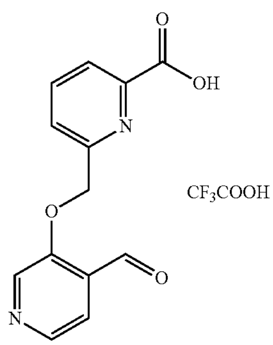 [SMILES: O=Cc1ccncc1OCc1cccc(C(=O)O)n1 ; "CF3COOH"] | 2,2,2-trifluoroacetic acid:6-(((4-formylpyridin-3-yl)oxy)methyl)picolinic acid (1:1) |
| 193 | 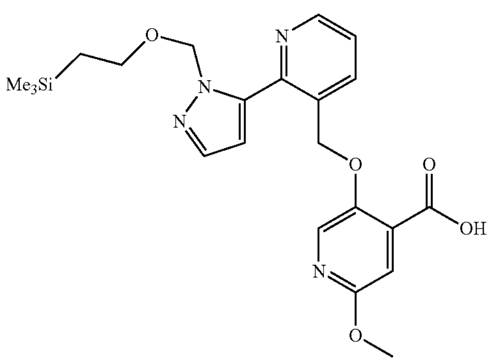 [SMILES: COc1cc(C(=O)O)c(OCc2cccnc2-c2ccnn2COCC[Si](C)(C)C)cn1] | 2-methoxy-5-((2-(1-((2-(trimethylsilyl)ethoxy)methyl)-1H-pyrazol-5-yl)pyridin-3-yl)methoxy)isonicotinaldehyde |
| 194 | 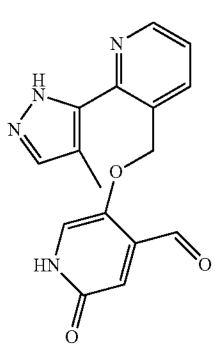 [SMILES: Cc1cn[nH]c1-c1ncccc1COc1c[nH]c(=O)cc1C=O] | 5-((2-(4-methyl-1H-pyrazol-5-yl)pyridin-3-yl)methoxy)-2-oxo-1,2-dihydropyridine-4-carbaldehyde |

TABLE 1-continued

| Compound | Structure | Name |
|---|---|---|
| 195 | 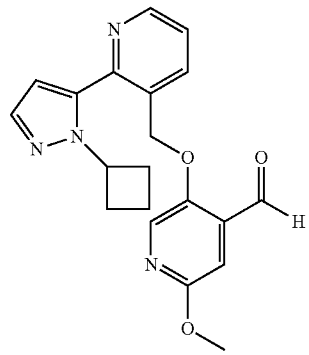 [SMILES: COc1cc(C=O)c(OCc2cccnc2-c2ccnn2C2CCC2)cn1] | 5-((2-(1-cyclobutyl-1H-pyrazol-5-yl)pyridin-3-yl)methoxy)-2-methoxyisonicotinaldehyde |
| 196 | 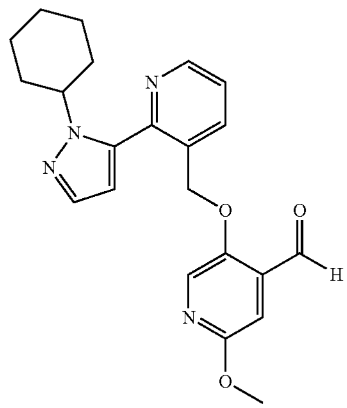 [SMILES: COc1cc(C=O)c(OCc2cccnc2-c2ccnn2C2CCCCC2)cn1] | 5-((2-(1-cyclohexyl-1H-pyrazol-5-yl)pyridin-3-yl)methoxy)-2-methoxyisonicotinaldehyde |
| 197 | 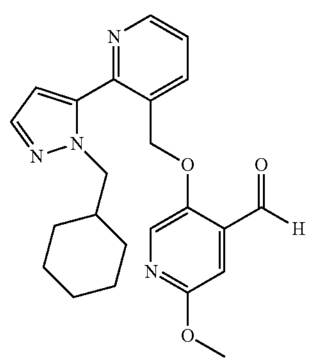 [SMILES: COc1cc(C=O)c(OCc2cccnc2-c2ccnn2CC2CCCCC2)cn1] | 5-((2-(1-(cyclohexylmethyl)-1H-pyrazol-5-yl)pyridin-3-yl)methoxy)-2-methoxyisonicotinaldehyde |
| 198 | 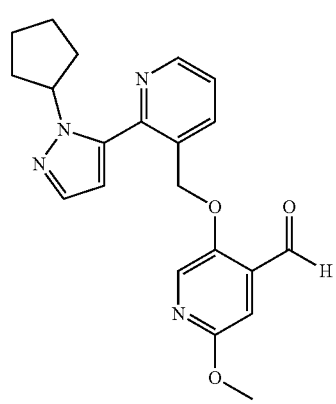 [SMILES: COc1cc(C=O)c(OCc2cccnc2-c2ccnn2C2CCCC2)cn1] | 5-((2-(1-cyclopentyl-1H-pyrazol-5-yl)pyridin-3-yl)methoxy)-2-methoxyisonicotinaldehyde |

TABLE 1-continued

| Compound | Structure | Name |
|---|---|---|
| 199 | 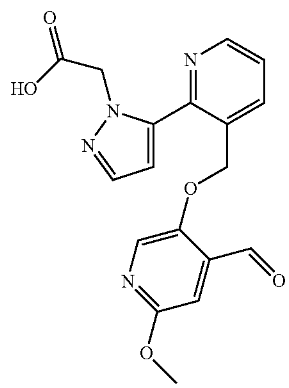 [SMILES: COc1cc(C=O)c(OCc2cccnc2-c2ccnn2CC(=O)O)cn1] | 2-(5-(3-((4-formyl-6-methoxypyridin-3-yloxy)methyl)pyridin-2-yl)-1H-pyrazol-1-yl)acetic acid |
| 200 | 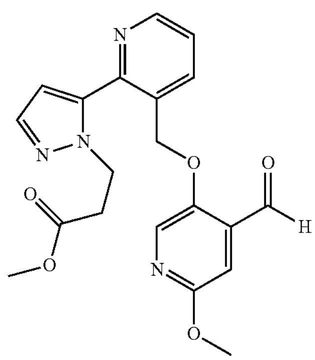 [SMILES: COC(=O)CCn1nccc1-c1ncccc1COc1cnc(OC)cc1C=O] | methyl 3-(5-(3-(((4-formyl-6-methoxypyridin-3-yl)oxy)methyl)pyridin-2-yl)-1H-pyrazol-1-yl)propanoate |
| 201 | 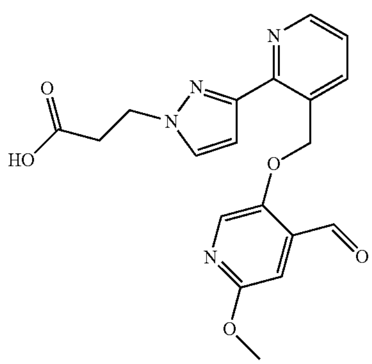 [SMILES: COc1cc(C=O)c(OCc2cccnc2-c2ccn(CCC(=O)O)n2)cn1] | 3-(3-(3-((4-formyl-6-methoxypyridin-3-yloxy)methyl)pyridin-2-yl)-1H-pyrazol-1-yl)propanoic acid |
| 202 | 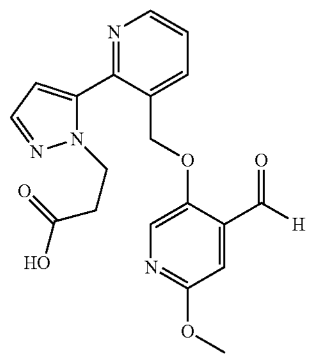 [SMILES: COc1cc(C=O)c(OCc2cccnc2-c2ccnn2CCC(=O)O)cn1] | 3-(5-(3-(((4-formyl-6-methoxypyridin-3-yl)oxy)methyl)pyridin-2-yl)-1H-pyrazol-1-yl)propanoic acid |

TABLE 1-continued

| Compound | Structure | Name |
|---|---|---|
| 203 | 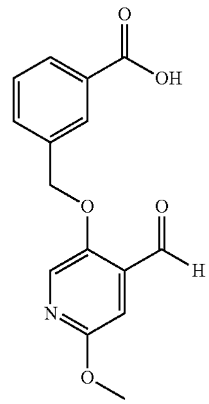 [SMILES: COc1cc(C=O)c(OCc2cccc(C(=O)O)c2)cn1] | 3-(((4-formyl-6-methoxypyridin-3-yl)oxy)methyl)benzoic acid |
| 204 | 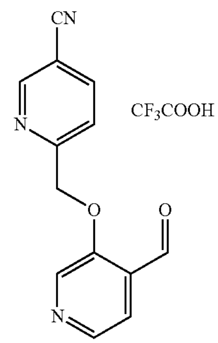 [SMILES: N#Cc1ccc(COc2cnccc2C=O)nc1 ; "CF3COOH"] | 6-(((4-formylpyridin-3-yl)oxy)methyl)nicotinonitrile 2,2,2-trifluoroacetate |
| 205 | 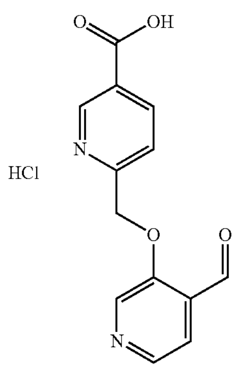 [SMILES: Cl ; O=Cc1ccncc1OCc1ccc(C(=O)O)cn1] | 6-(((4-formylpyridin-3-yl)oxy)methyl)nicotinic acid hydrochloride |
| 206 | 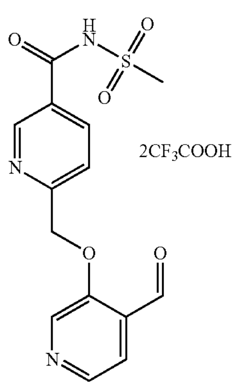 [SMILES: CS(=O)(=O)NC(=O)c1ccc(COc2cnccc2C=O)nc1] | 2,2,2-trifluoroacetic acid:6-(((4-formylpyridin-3-yl)oxy)methyl)-N-(methylsulfonyl)nicotinamide (2:1) |

TABLE 1-continued

| Compound | Structure | Name |
|---|---|---|
| 207 | 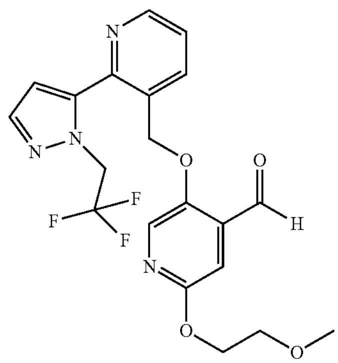 [SMILES: COCCOc1cc(C=O)c(OCc2cccnc2-c2ccnn2CC(F)(F)F)cn1] | 2-(2-methoxyethoxy)-5-((2-(1-(2,2,2-trifluoroethyl)-1H-pyrazol-5-yl)pyridin-3-yl)methoxy)isonicotinaldehyde |
| 208 | 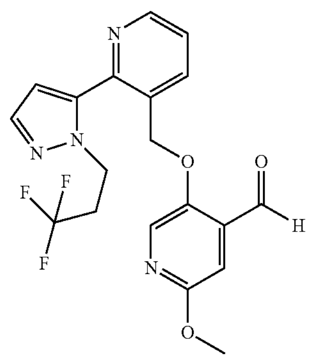 [SMILES: COc1cc(C=O)c(OCc2cccnc2-c2ccnn2CCC(F)(F)F)cn1] | 2-methoxy-5-((2-(1-(3,3,3-trifluoropropyl)-1H-pyrazol-5-yl)pyridin-3-yl)methoxy)isonicotinaldehyde |
| 209 | 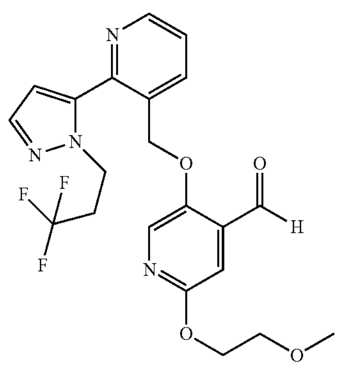 [SMILES: COCCOc1cc(C=O)c(OCc2cccnc2-c2ccnn2CCC(F)(F)F)cn1] | 2-(2-methoxyethoxy)-5-((2-(1-(3,3,3-trifluoropropyl)-1H-pyrazol-5-yl)pyridin-3-yl)methoxy)isonicotinaldehyde |
| 210 | 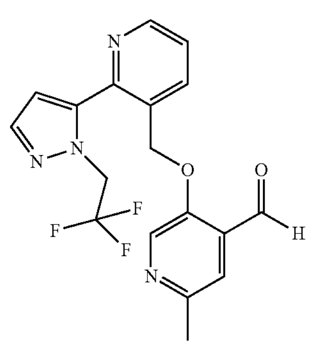 [SMILES: Cc1cc(C=O)c(OCc2cccnc2-c2ccnn2CC(F)(F)F)cn1] | 2-methyl-5-((2-(1-(2,2,2-trifluoroethyl)-1H-pyrazol-5-yl)pyridin-3-yl)methoxy)isonicotinaldehyde |

TABLE 1-continued

| Compound | Structure | Name |
|---|---|---|
| 211 | 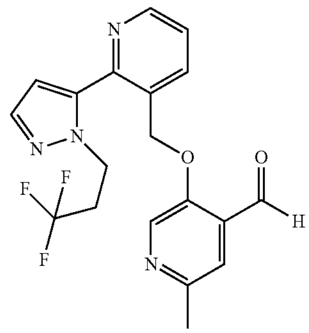 [SMILES: Cc1cc(C=O)c(OCc2cccnc2-c2ccnn2CCC(F)(F)F)cn1] | 2-methyl-5-((2-(1-(3,3,3-trifluoropropyl)-1H-pyrazol-5-yl)pyridin-3-yl)methoxy)isonicotinaldehyde |
| 212 | 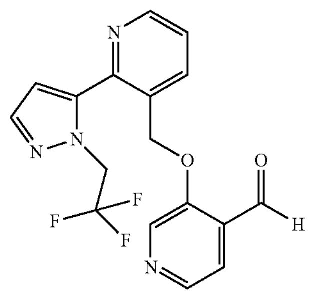 [SMILES: O=Cc1ccncc1OCc1cccnc1-c1ccnn1CC(F)(F)F] | 3-((2-(1-(2,2,2-trifluoroethyl)-1H-pyrazol-5-yl)pyridin-3-yl)methoxy)isonicotinaldehyde |
| 213 | 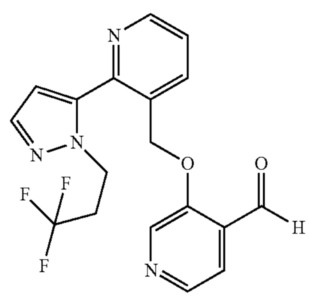 [SMILES: O=Cc1ccncc1OCc1cccnc1-c1ccnn1CCC(F)(F)F] | 3-((2-(1-(3,3,3-trifluoropropyl)-1H-pyrazol-5-yl)pyridin-3-yl)methoxy)isonicotinaldehyde |
| 214 | 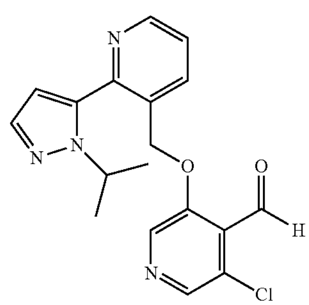 [SMILES: CC(C)n1nccc1-c1ncccc1COc1cncc(Cl)c1C=O] | 3-chloro-5-((2-(1-isopropyl-1H-pyrazol-5-yl)pyridin-3-yl)methoxy)isonicotinaldehyde |
| 215 | 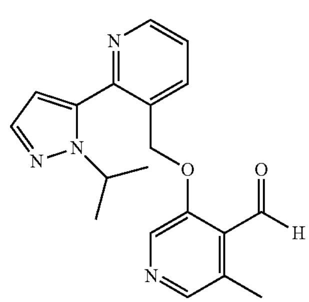 [SMILES: Cc1cncc(OCc2cccnc2-c2ccnn2C(C)C)c1C=O] | 3-((2-(1-isopropyl-1H-pyrazol-5-yl)pyridin-3-yl)methoxy)-5-methylisonicotinaldehyde |

TABLE 1-continued

| Compound | Structure | Name |
|---|---|---|
| 216 | 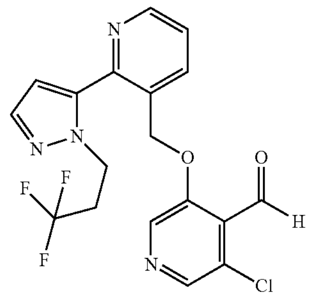 [SMILES: O=Cc1c(Cl)cncc1OCc1cccnc1-c1ccnn1CCC(F)(F)F] | 3-chloro-5-((2-(1-(3,3,3-trifluoropropyl)-1H-pyrazol-5-yl)pyridin-3-yl)methoxy)isonicotinaldehyde |
| 217 | 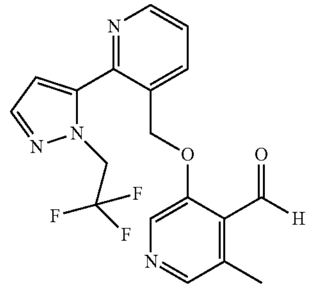 [SMILES: Cc1cncc(OCc2cccnc2-c2ccnn2CC(F)(F)F)c1C=O] | 3-methyl-5-((2-(1-(2,2,2-trifluoroethyl)-1H-pyrazol-5-yl)pyridin-3-yl)methoxy)isonicotinaldehyde |

In one group of embodiments, the compound is selected from 5-hydroxy-2-(2-methoxyethoxy)isonicotinaldehyde (Compound 218), 5-hydroxy-2-(2-methoxyethoxy)nicotinaldehyde (Compound 219), 5-((2-(1-isopropyl-1H-pyrazol-5-yl)pyridin-3-yl)methoxy)-2-oxo-1,2-dihydropyridine-4-carbaldehyde (Compound 220), 5-((2-(4-methyl-1H-pyrazol-5-yl)pyridin-3-yl)methoxy)-2-oxo-1,2-dihydropyridine-4-carbaldehyde (Compound 221), or a tautomer or pharmaceutically acceptable salt thereof.

In one group of embodiments, the compound is selected from:
5-(imidazo[1,2-a]pyridin-8-ylmethoxy)-2-methoxyisonicotinaldehyde,
2-methoxy-5-((5-methylpyridin-3-yl)methoxy)isonicotinaldehyde,
5-(isoquinolin-1-ylmethoxy)-2-methoxyisonicotinaldehyde,
2-methoxy-5-(quinolin-2-ylmethoxy)isonicotinaldehyde,
2-methoxy-5-(pyridin-4-ylmethoxy)isonicotinaldehyde,
3-(imidazo[1,2-a]pyridin-8-ylmethoxy)-6-methylpicolinaldehyde,
methyl 2-((4-formyl-6-methoxypyridin-3-yloxy)methyl)imidazo[1,2-a]pyridine-8-carboxylate,
2-methoxy-5-((3-methyl-[1,2,4]triazolo[4,3-a]pyridin-8-yl)methoxy)isonicotinaldehyde,
5-((2-bromopyridin-3-yl)methoxy)-2-methoxyisonicotinaldehyde,
5-((2-(1H-pyrazol-5-yl)pyridin-3-yl)methoxy)-2-methoxyisonicotinaldehyde,
5-((5-bromopyridin-3-yl)methoxy)-2-methoxyisonicotinaldehyde,
2-methoxy-5-((5-(1-methyl-1H-pyrazol-5-yl)pyridin-3-yl)methoxy)isonicotinaldehyde,
5-((4-formyl-6-methoxypyridin-3-yloxy)methyl)nicotinic acid,
2-methoxy-5-(quinolin-3-ylmethoxy)isonicotinaldehyde,
2-methoxy-5-((1-methyl-1H-indazol-4-yl)methoxy)isonicotinaldehyde,
tert-butyl 4-((2-formyl-6-methylpyridin-3-yloxy)methyl)-1H-indazole-1-carboxylate,
6-methyl-3-((1-methyl-1H-indazol-6-yl)methoxy)picolinaldehyde,
6-methyl-3-((1-methyl-1H-indazol-7-yl)methoxy)picolinaldehyde,
3-(isoquinolin-1-ylmethoxy)-6-methylpicolinaldehyde,
5-(benzo[d]oxazol-4-ylmethoxy)-2-methoxyisonicotinaldehyde,
3-((1,5-naphthyridin-4-yl)methoxy)-6-methylpicolinaldehyde,
6-methyl-3-((1-methyl-1H-indazol-5-yl)methoxy)picolinaldehyde,
6-methyl-3-(quinolin-5-ylmethoxy)picolinaldehyde,
2-methoxy-5-(quinolin-5-ylmethoxy)isonicotinaldehyde,
2-methoxy-5-((2-(1-methyl-1H-pyrazol-5-yl)pyridin-3-yl)methoxy)isonicotinaldehyde,
2-methoxy-5-((2-(1-methyl-1H-pyrazol-3-yl)pyridin-3-yl)methoxy)isonicotinaldehyde,
5-((2-(2H-tetrazol-5-yl)pyridin-3-yl)methoxy)-2-methoxyisonicotinaldehyde,
2-methoxy-5-((2-(4-methyl-1H-pyrazol-5-yl)pyridin-3-yl)methoxy)isonicotinaldehyde,
5-((3-(1H-pyrazol-5-yl)isoquinolin-4-yl)methoxy)-2-methoxyisonicotinaldehyde,
5-((2-(1H-pyrazol-1-yl)pyridin-3-yl)methoxy)-2-methoxyisonicotinaldehyde,
5-(imidazo[1,5-a]pyridin-8-ylmethoxy)-2-methoxyisonicotinaldehyde,
5-((2-(1,5-dimethyl-1H-pyrazol-4-yl)pyridin-3-yl)methoxy)-2-methoxyisonicotinaldehyde,
5-((2-(1-ethyl-1H-pyrazol-5-yl)pyridin-3-yl)methoxy)-2-methoxyisonicotinaldehyde,
5-((2-(1-isopropyl-1H-pyrazol-5-yl)pyridin-3-yl)methoxy)-2-methoxyisonicotinaldehyde,
2-(difluoromethoxy)-5-(imidazo[1,2-a]pyridin-8-ylmethoxy)isonicotinaldehyde, 2-methoxy-5-((2-phenylpyridin-3-yl)methoxy)isonicotinaldehyde,
5-((3-(1-isopropyl-1H-pyrazol-5-yl)pyridin-4-yl)methoxy)-2-methoxyisonicotinaldehyde,
5-([2,3'-bipyridin]-3-ylmethoxy)-2-methoxyisonicotinaldehyde,
2-methoxy-5-((2-(o-tolyl)pyridin-3-yl)methoxy)isonicotinaldehyde,
2-methoxy-5-((2'-methoxy-[2,3'-bipyridin]-3-yl)methoxy)isonicotinaldehyde,
4-(((2-formyl-6-methylpyridin-3-yl)oxy)methyl)benzoic acid,
4-(((2-formylpyridin-3-yl)oxy)methyl)benzoic acid,
methyl 3-(((4-formylpyridin-3-yl)oxy)methyl)benzoate,
methyl 3-(((2-formyl-6-methylpyridin-3-yl)oxy)methyl)benzoate,
3-(((4-formylpyridin-3-yl)oxy)methyl)benzoic acid,
3-(((2-formyl-6-methylpyridin-3-yl)oxy)methyl)benzoic acid,
3-(((2-formylpyridin-3-yl)oxy)methyl)benzoic acid,
2-methoxy-5-((2-(1-(2-methoxyethyl)-1H-pyrazol-5-yl)pyridin-3-yl)methoxy)isonicotinaldehyde,
2-methoxy-5-((2-(1-propyl-1H-pyrazol-5-yl)pyridin-3-yl)methoxy)isonicotinaldehyde,
2-methoxy-5-((2-(1-(2,2,2-trifluoroethyl)-1H-pyrazol-5-yl)pyridin-3-yl)methoxy)isonicotinaldehyde,
5-((2-(1-(2,2-difluoroethyl)-1H-pyrazol-5-yl)pyridin-3-yl)methoxy)-2-methoxyisonicotinaldehyde,
3-((2-(1-isopropyl-1H-pyrazol-5-yl)pyridin-3-yl)methoxy)picolinaldehyde,
3-((2-(1-isopropyl-1H-pyrazol-5-yl)pyridin-3-yl)methoxy)-6-methylpicolinaldehyde,
2-(difluoromethoxy)-5-((2-(1-isopropyl-1H-pyrazol-5-yl)pyridin-3-yl)methoxy)isonicotinaldehyde,
5-(imidazo[1,2-a]pyridin-8-ylmethoxy)-2-(2-methoxyethoxy)isonicotinaldehyde,
5-((2-(1-isopropyl-1H-pyrazol-5-yl)pyridin-3-yl)methoxy)-2-(2-methoxyethoxy)isonicotinaldehyde,
5-((3-(1-isopropyl-1H-pyrazol-5-yl)pyrazin-2-yl)methoxy)-2-methoxyisonicotinaldehyde,
3-((4-formyl-6-methoxypyridin-3-yloxy)methyl)picolinate,
5-((2-(2-hydroxypropan-2-yl)pyridin-3-yl)methoxy)-2-methoxyisonicotinaldehyde,
2-(2-methoxyethoxy)-5-((2-(1-methyl-1H-pyrazol-5-yl)pyridin-3-yl)methoxy)isonicotinaldehyde,
2-(2-methoxyethoxy)-5-((2-(1-methyl-1H-pyrazol-5-yl)pyridin-3-yl)methoxy)nicotinaldehyde,
3-hydroxy-5-((2-(1-isopropyl-1H-pyrazol-5-yl)pyridin-3-yl)methoxy)isonicotinaldehyde,
3-(benzyloxy)-5-hydroxyisonicotinaldehyde,
3-((2-(1-isopropyl-1H-pyrazol-5-yl)pyridin-3-yl)methoxy)-5-methoxyisonicotinaldehyde,
5-((2-(2-isopropyl-2H-1,2,4-triazol-3-yl)pyridin-3-yl)methoxy)-2-methoxyisonicotinaldehyde,
5-((2-(1-isopropyl-4-methyl-1H-pyrazol-5-yl)pyridin-3-yl)methoxy)-2-methoxyisonicotinaldehyde,
5-((2-(1-(2-hydroxyethyl)-1H-pyrazol)-5-yl)pyridin-3-yl)methoxy)-2-methoxyisonicotinaldehyde, 6-(((4-formylpyridin-3-yl)oxy)methyl)picolinic acid,
2,2,2-trifluoroacetic acid: 6-(((4-formylpyridin-3-yl)oxy)methyl)picolinic acid (1:1),
2-methoxy-5-((2-(1-((2-(trimethylsilyl)ethoxy)methyl)-1H-pyrazol-5-yl)pyridin-3-yl)methoxy)isonicotinaldehyde,
5-((2-(4-methyl-1H-pyrazol-5-yl)pyridin-3-yl)methoxy)-2-oxo-1,2-dihydropyridine-4-carbaldehyde,
5-((2-(1-cyclobutyl-1H-pyrazol-5-yl)pyridin-3-yl)methoxy)-2-methoxyisonicotinaldehyde,
5-((2-(1-cyclohexyl-1H-pyrazol-5-yl)pyridin-3-yl)methoxy)-2-methoxyisonicotinaldehyde,
5-((2-(1-(cyclohexylmethyl)-1H-pyrazol-5-yl)pyridin-3-yl)methoxy)-2-methoxyisonicotinaldehyde,
5-((2-(1-cyclopentyl-1H-pyrazol-5-yl)pyridin-3-yl)methoxy)-2-methoxyisonicotinaldehyde,
2-(5-(3-((4-formyl-6-methoxypyridin-3-yloxy)methyl)pyridin-2-yl)-1H-pyrazol-1-yl)acetic acid, methyl 3-(5-(3-(((4-formyl-6-methoxypyridin-3-yl)oxy)methyl)pyridin-2-yl)-1H-pyrazol-1-yl)propanoate,
3-(3-(3-((4-formyl-6-methoxypyridin-3-yloxy)methyl)pyridin-2-yl)-1H-pyrazol-1-yl)propanoic acid,
3-(S-(3-(((4-formyl-6-methoxypyridin-3-yl)oxy)methyl)pyridin-2-yl)-1H-pyrazol-1-yl)propanoic add,
3-(((4-formyl-6-methoxypyridin-3-yl)oxy)methyl)benzoic acid,
6-(((4-formylpyridin-3-yl)oxy)methyl)nicotinonitrile 2,2,2-trifluoracetate,
6-(((4-formylpyridin-3-yl)oxy)methyl)nicotinic acid,
6-(((4-formylpyridin-3-yl)oxy)methyl)nicotinic acid hydrochloride,
6-(((4-formylpyridin-3-yl)oxy)methyl)-N-(methylsulfonyl)nicotinamide,
2,2,2-trifluoroacetic acid: 6-(((4-formylpyridin-3-yl)oxy)methyl)-N-(methylsulfonyl)nicotinamide (2:1), 2-(2-methoxyethoxy)-5-((2-(1-(2,2,2-trifluoroethyl)-1H-pyrazol-5-yl)pyridin-3-yl)methoxy)isonicotinaldehyde,
2-methoxy-5-((2-(1-(3,3,3-trifluoropropyl)-1H-pyrazol-5-yl)pyridin-3-yl)methoxy)isonicotinaldehyde,
2-(2-methoxyethoxy)-5-((2-(1-(3,3,3-trifluoropropyl)-1H-pyrazol-5-yl)pyridin-3-yl)methoxy)isonicotinaldehyde,
2-methyl-5-((2-(1-(2,2,2-trifluoroethyl)-1H-pyrazol-5-yl)pyridin-3-yl)methoxy)isonicotinaldehyde,
2-methyl-5-((2-(1-(3,3,3-trifluoropropyl)-1H-pyrazol-5-yl)pyridin-3-yl)methoxy)isonicotinaldehyde,
3-((2-(1-(2,2,2-trifluoroethyl)-1H-pyrazol-5-yl)pyridin-3-yl)methoxy)isonicotinaldehyde,
3-((2-(1-(3,3,3-trifluoropropyl)-1H-pyrazol-5-yl)pyridin-3-yl)methoxy)isonicotinaldehyde,
3-chloro-5-((2-(1-isopropyl-1H-pyrazol-5-yl)pyridin-3-yl)methoxy)isonicotinaldehyde,
3-((2-(1-isopropyl-1H-pyrazol-5-yl)pyridin-3-yl)methoxy)-5-methylisonicotinaldehyde,
3-chloro-5-((2-(1-(3,3,3-trifluoropropyl)-1H-pyrazol-5-yl)pyridin-3-yl)methoxy)isonicotinaldehyde, and
3-methyl-5-((2-(1-(2,2,2-trifluoroethyl)-1H-pyrazol-5-yl)pyridin-3-yl)methoxy)isonicotinaldehyde,
or a tautomer or pharmaceutically acceptable salt thereof.

In one group of embodiments, provided is a pharmaceutical composition comprising a compound of any of the above embodiments or a tautomer or pharmaceutically acceptable salt thereof.

In one group of embodiments, provided is a compound in any of the Examples or Tables. In another group of embodiments, provided are any combinations of subembodiments as disclosed herein including any combination of elements disclosed herein including the a selection of any single elements.

The compounds of the present invention may be prepared by known organic synthesis techniques, including the methods described in more detail in the Examples.

In one group of embodiments, provided is an intermediate compound used in the preparation of the compounds disclosed herein.

In one group of embodiments, provided are methods for preparing the compounds disclosed herein.

For example, Scheme I shows a synthetic route for the synthesis of the compounds of Formula (I) where X is O and Y is CH$_2$. Phenol 1.1 is contacted with intermediate 1.2 in the presence of base under ether forming conditions to give ether 1.3, where Lg represents a leaving group such as a halogen leaving group. Conversely, when X is O and Y is CH$_2$, the compounds of Formula (I) can be prepared using the appropriate starting materials where the OH moiety of intermediate 1.1 is replaced with a leaving group and the Lg group of intermediate 1.2 is replaced with an OH group.

Scheme III shows an example of a synthetic route for the synthesis of the compounds of Formula (I) where R$^6$ together with R$^{1b}$ form a cyclic ether. Compound 3.1, is reacted with diethylphosphite and a base such as sodium methoxide to give intermediate 3.2, that is then condensed with aldehyde 3.3 to give alkene 3.4. Treatment of the alkene with H$_2$ under hydrogenation conditions gives lactone 3.4, which is then reduced with a suitable reducing agent such as LiBHEt$_3$ to give cyclic hemiacetal 3.5.

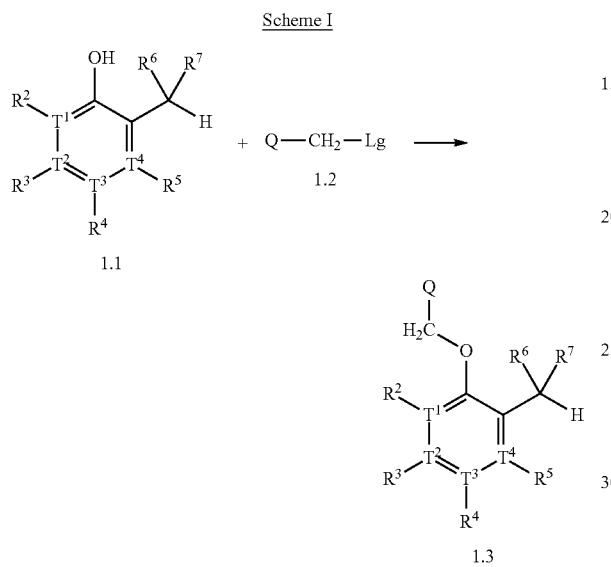

Scheme I

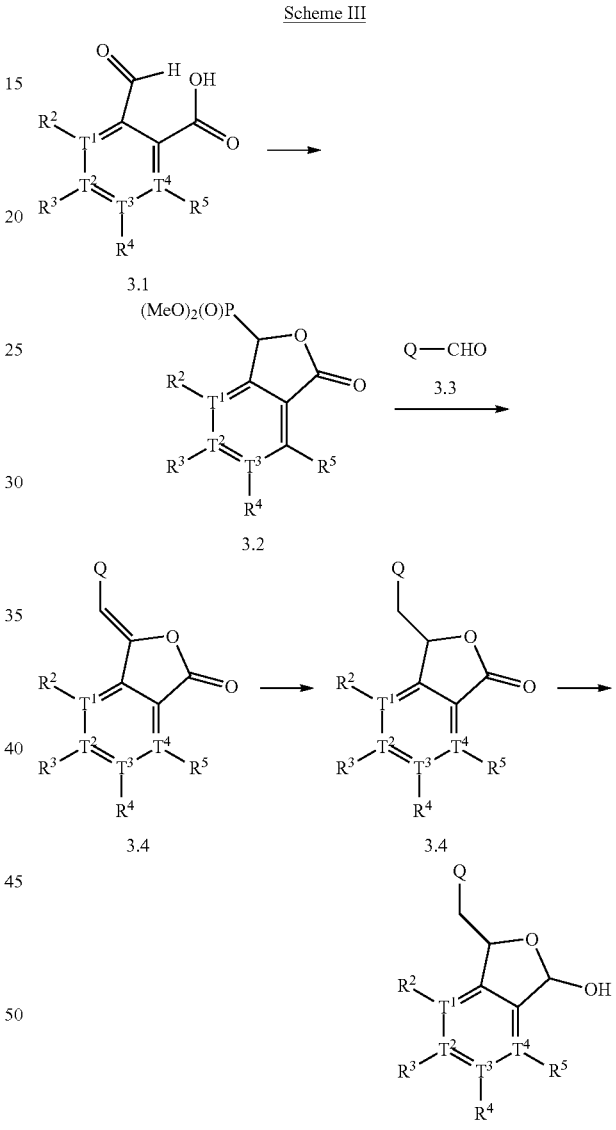

Scheme III

Scheme II shows an example of a synthetic route for the synthesis of the compounds of Formula (I) where X and Y are CH$_2$. Alkene 2.1 is contacted with alkene 2.2 under metathesis forming conditions in the presence of an appropriate transition metal catalyst. Suitable catalysts include ruthenium catalysts such as Grubbs' catalyst. Product 2.3 is then hydrogenated to give compound 2.4.

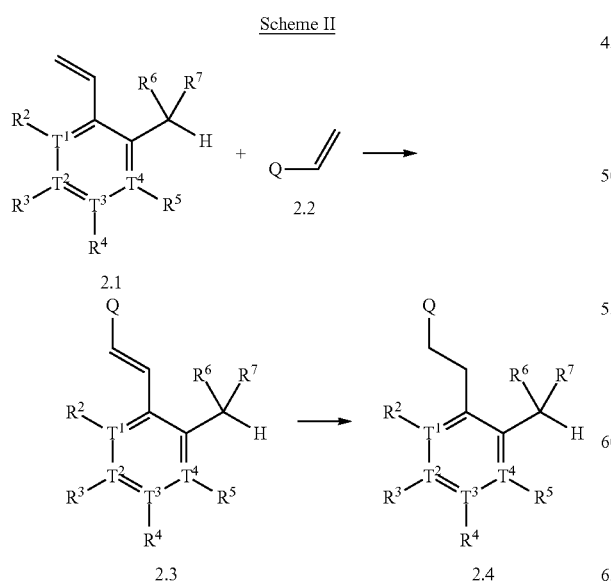

Scheme II

Scheme IV shows an example of synthesis of the compounds of Formula (I) where Q is pyridine-3-yl and R$^a$ heteroaryl. Acid 4.1 is reduced to alcohol 4.2 using known methods such as by forming the anhydride (e.g. treatment with triethylamine and i-butyl chloroformate) followed by reduction with NaBH$_4$. Alcohol 4.2 is converted to chloride 4.3 such as by treatment with thionyl chloride. Coupling of the halide with alcohol 4.4 under ether forming conditions gives the precursor 4.5 that can be functionalized with a variety to heteroaryl R$^a$ groups. For example, 4.5 can be coupled with pyrazole 4.6 under known organometallic coupling conditions (e.g. Pd(PPh₃)₄) to give 4.7, where PG is a nitrogen protecting group such as a silyl protecting group that can be removed to give the product 4.8.

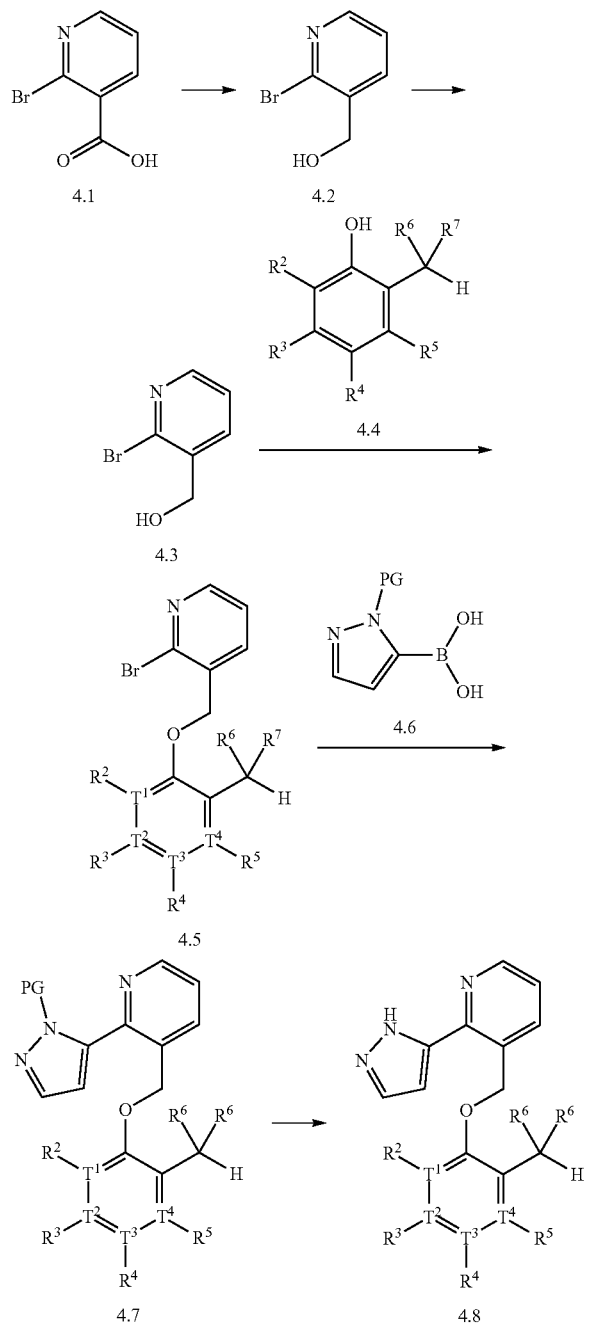

One skilled in the art will recognize that in certain embodiments it may be advantageous to use a protecting group strategy. The protecting group can be removed using methods known to those skilled in the art.

The compounds of the present invention may generally be utilized as the free base. Alternatively, the compounds of this invention may be used in the form of acid addition salts.

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

III. Compositions and Methods of Administration

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which docs not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use wilt generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution, in addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of of the indicated disease.

The pharmaceutical composition may additionally contain one or more other pharmacologically active agents in addition to a compound of this invention.

Dosage forms containing effective amounts of the modulators are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

IV. Methods

In one group of embodiments, provided is a method for increasing tissue oxygenation, the method comprising administering to a subject in need thereof a therapeutically effective amount of a compound of any of the above embodiments or a tautomer or pharmaceutically acceptable salt thereof.

In one group of embodiments, provided is a method for treating a condition associated with oxygen deficiency, the method comprising administering to a subject in need thereof a therapeutically effective amount of a compound of any of the above embodiments or a tautomer or pharmaceutically acceptable salt thereof.

In one group of embodiments, provided is a method for treating sickle cell disease, cancer, a pulmonary disorder, stroke, high altitude sickness, an ulcer, a pressure sore, Alzheimer's disease, acute respiratory disease syndrome, and a wound, the method comprising administering to a subject in need thereof a therapeutically effective amount of a compound of any of the above embodiments or a tautomer or pharmaceutically acceptable salt thereof.

In one group of embodiments, provided is a method for increasing tissue oxygenation or for treating a condition associated with oxygen deficiency, said method comprising administering to a subject in need thereof a therapeutically effective amount of a compound Formula (II):

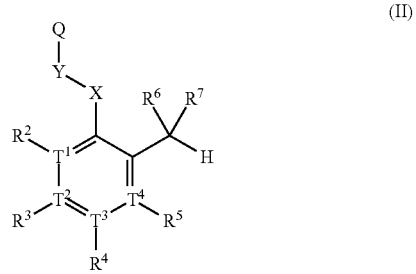

(II)

or a tautomer or pharmaceutically acceptable salt thereof,
wherein Q is selected from the group consisting of aryl, heteroaryl, and heterocycloalkyl, each optionally substituted with one to three $R^a$;

Y is O or $CR^{1a}R^{1b}$, where $R^{1a}$ is H or halo and $R^{1b}$ is selected from the group consisting of H, halo, and OH;

X is selected from the group consisting of O, >CH(CH$_2$)$_n$R$^8$, and C(R$^9$)$_2$ where n is 0 or 1, $R^8$ is OH, and $R^9$ is independently H or halo; or Y—X taken together is —NHC(O)— or —C(O)NH—;

$R^2$, $R^3$, $R^4$, and $R^5$ are independently absent or selected from the group consisting of hydrogen, halo, $R^b$, $OR^d$, $O(CH_2)_2OR^d$, $O(CH_2)_zNR^dR^d$, $OC(O)R^e$, $SR^d$, CN, NO$_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_aR^e$, $NR^dS(O)_2R^e$, $S(O)_2NR^dR^d$, and N$_3$ where z is 0, 1, 2, or 3; or $R^5$ is —(CH$_2$)$_pR^{5a}$ where p is 0 or 1 and $R^{5a}$ is OH;

$R^6$ and $R^7$ together form oxo or an aldehyde protecting group, or $R^6$ together with $R^{1b}$, $R^8$, or $R^5$ forms a cyclic ether where one of $R^{1b}$, $R^8$, or $R^{5a}$ is O, $R^6$ is a bond, and $R^7$ is selected from the group consisting of OH, C$_{1-8}$alkoxy, and haloC$_{1-8}$alkoxy;

$T^1$, $T^2$, $T^3$, and $T^4$ are independently C or N provided that at least one of $T^1$, $T^2$, $T^3$, and $T^4$ is N and at least one of $T^1$, $T^2$, $T^3$, and $T^4$ is C;

each $R^8$ is independently selected from the group consisting of halo, $R^b$, $OR^b$, $O(CH_2)_uOR^d$, $O(CH_2)_uNR^dR^d$, $O(CH_2)_uNR^dC(O)R^c$, $O(CH_2)_uNR^dC(O)_2R^e$, $O(CH_2)_uNR^dS(O)R^e$, NH$_2$, —(CH$_2$)$_kOC(O)R^c$, —(CH$_2$)$_kSR^d$, CN, NO$_2$, —(CH$_2$)$_kCO_2$(C$_{1-8}$alkyl)OH, —(CH$_2$)$_kCO_2$(C$_{1-8}$ alkyl)(heteroaryl)C(O)(C$_{1-8}$alkyl), —(CH$_2$)$_kCO_2R^d$, —(CH$_2$)$_kCONR^dR^d$, —(CH$_2$)$_kNR^dC(O)R^e$, —(CH$_2$)$_kNR^dC(O)_2R^e$, —(CH$_2$)$_kC(O)R^d$, —(CH$_2$)$_kOC(O)NR^dR^d$, —NR$^d$(CH$_2$)$_uOR^d$, —NR$^d$(CH$_2$)$_uNR^dR^d$, —NR$^d$(CH$_2$)$_uNR^dC(O)R^e$, —NR$^d$(CH$_2$)$_uNR^dC(O)_2R^e$, —NR$^d$(CH$_2$)$_uNR^dS(O)_2R^e$, —(CH$_2$)$_kNR^dC(O)R^e$, —(CH$_2$)$_kNR^dC(O)_2R^d$, —(CH$_2$)$_kNR^dC(O)NR^dR^d$, —(CH$_2$)$_kS(O)R^e$, —(CH$_2$)$_kS(O)_2R^e$, —(CH$_2$)$_kNR^dS(O)_2R^e$, —C(O)CH$_2$)$_kNR^dS(O)R^e$, —(CH$_2$)$_kC(O)NR^dS(O)_2R^e$, —(CH$_2$)$_kS(O)_2NR^dR^d$, N$_3$, —(CH$_2$)$_k$aryl optionally substituted with one to three $R^c$, —NR$^d$(CH$_2$)$_k$aryl optionally substituted with one to three $R^c$, —(CH$_2$)$_k$heteroaryl optionally substituted with one to three $R^c$, —NR$^d$(CH$_2$)$_k$heteroaryl optionally substituted with one to three $R^c$, —(CH$_2$)$_k$heterocycloalkyl optionally substituted with one to three $R^c$, and —NR$^d$(CH$_2$)$_k$heterocycloalkyl optionally substituted with one to three $R^c$ where k is 0, 1, 2, 3, 4, 5, or 6 and u is 1, 2, 3, 4, 5, or 6;

each $R^b$ is independently selected from the group consisting of C$_{1-8}$alkyl, C$_{2-8}$alkenyl, and C$_{2-8}$alkynyl, each optionally independently substituted with one to three halo, $OR^d$, or $NR^dR^d$;

each $R^c$ is independently selected from the group consisting of halo, C$_{1-8}$alkyl, haloC$_{1-8}$ alkyl, C$_{2-8}$alkenyl, haloC$_{2-8}$alkenyl, C$_{2-8}$alkynyl, haloC$_{2-8}$alkynyl, (CH$_2$)$_mOR^f$, OC(O)

R$^8$, SR$^f$, CN, NO$_2$, (CH$_2$)$_m$CO$_2$R$^f$, CONR$^j$R$^f$, C(O)R$^f$, OC(O)NR$^j$R$^f$, (CH$_2$)$_m$NR$^j$R$^f$, NR$^j$C(O)R$^g$, NR$^j$C(O)$_2$R$^g$, NR$^j$C(O)NR$^j$R$^f$, S(O)R$^g$, S(O)$_2$R$^g$, NR$^g$S(O)$_2$R$^g$, S(O)$_2$NR$^j$R$^f$, N$_3$, (R$^f$)$_m$SiC$_{1-8}$alkyl, heteroaryl optionally substituted with one to three R$^h$, cycloalkyl optionally substituted with one to three R$^h$, and heterocycloalkyl optionally substituted with one to three R$^h$ where m is selected from the group consisting of 0, 1, 2, 3, 4, 5, and 6;

each R$^h$ is independently selected from the group consisting of halo, C$_{1-8}$alkyl, haloC$_{1-8}$ alkyl, OR$^j$, OC(O)R, SR$^j$, NO$_2$, CO$_2$R$^j$, CONR$^j$R$^j$, C(O)R$^j$, OC(O)NR$^j$R$^j$, NR$^j$R$^j$, NR$^j$C(O)R$^t$, NR$^j$C(O)$_2$R$^t$, NR$^j$C(O)NR$^j$R$^j$, S(O)R$^t$, S(O)$_2$R$^t$, NR$^j$S(O)$_2$R$^t$, and S(O)$_2$NR$^j$R$^j$;

R$^d$, R$^f$, and R$^j$ are each independently selected from the group consisting of hydrogen, C$_{1-8}$ alkyl, haloC$_{1-8}$alkyl, C$_{1-8}$ alkenyl, haloC$_{2-8}$alkenyl, C$_{2-8}$alkynyl, and haloC$_{2-8}$alkynyl; and R$^e$, R$^g$, and R$^t$ are each independently selected from the group consisting of C$_{1-8}$alkyl, haloC$_{1-8}$alkyl, C$_{2-8}$ alkenyl, haloC$_{2-8}$alkenyl, C$_{2-8}$alkynyl, and haloC$_{2-8}$alkynyl;

provided that X and Y are not both O;

provided that when X is O, R$^{1b}$ is not OH; and provided that when Y is O, and n is 0, R$^8$ is not OH.

In one group of embodiments, provided is a method of any of the groups of embodiments disclosed herein, wherein at least one z is 0. In another group of embodiments, at least one z is 1. In yet another group of embodiments, at least one z is 2. In still another group of embodiments, at least one z is 3. In another group of embodiments, no z is 0.

V. Examples

The following examples are offered to illustrate, but not to limit, the claimed invention.

PREPARATIVE EXAMPLES

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods known in the art.

Example 1. Preparation of 3-(pyridin-3-ylmethoxy)isonicotinaldehyde

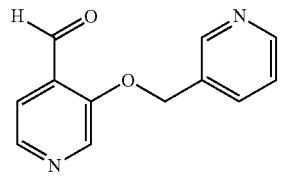 [SMILES: O=Cc1ccncc1OCc1cccnc1]

Step 1:

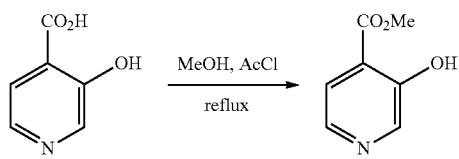 [SMILES: O=C(O)c1ccncc1O ; COC(=O)c1ccncc1O]

Acetyl chloride (20 mL) was added dropwise to methanol (200 mL) at 0° C. After the addition, the reaction mixture was stirred at this temp for 15 min and then 4.0 g of the acid was added. The reaction mixture was heated at reflux for 12 h. Methanol was removed to give a residue, which was then carefully neutralized with aq. sat. NaHCO$_3$ and then extracted with EtOAc (3×). The organic layers were combined, dried and evaporated to give the ester as a yellow solid, which was used in the next step without further purification.

Step 2:

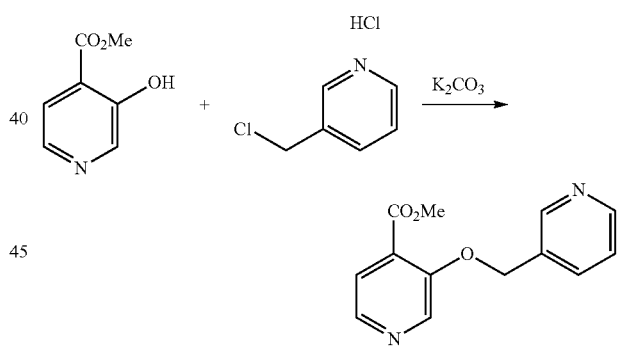

A mixture of chloride (300 mg, 1.5 mmol, 1.0 eq), hydroxypyridine (230 mg, 1.5 mmol, 1.0 eq) and potassium carbonate (621 mg, 4.5 mmol, 3.0 eq) were taken in DMF (10 mL) and the reaction mixture was heated at 80° C. for 4 h. Solvent was removed and the crude was purified by column chromatography (Hexane/EtOAc to EtOAc/MeOH) to provide the coupled product.

Step 3:

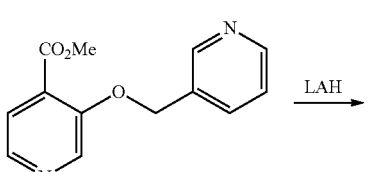

To an ice cold solution of ester (1.5 mmol, 1.0 eq) in THF (15 mL) was slowly added LAH solution (1.5 mL, 2M solution in THF) and the reaction mixture was stirred at this temp for 30 min. Then excess ethyl acetate was added slowly to quench excess LAH. Then water (1 mL), 15% NaOH (1 mL) and water (3 mL) were added and stirred at rt for 30 min. The clear solution was filtered and the solid was washed with ethyl acetate (3×). The organic layers were combined, dried and evaporated to give the crude alcohol, which was used in the next step without further purification.

Step 4:

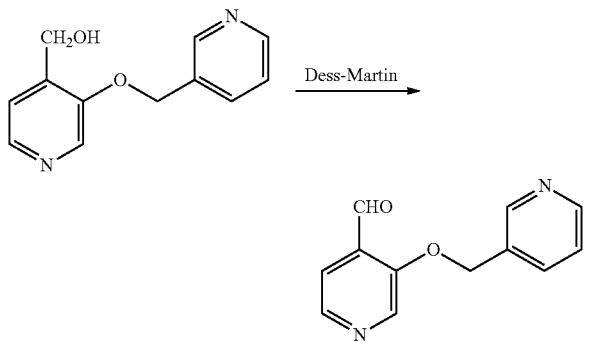

To a solution of the above alcohol (1.5 mmol, 1.0 eq) in DCM (15 mL) was added Dess-Martin reagent (2.25 mmol, 454 mg, 1.5 eq) and the reaction mixture was stirred at rt for 1 h. Solution was diluted with 25 mL DCM and then a 1:1 mixture of sat. NaHCO$_3$ and sat. Na$_2$S$_2$O$_3$ was added and stirred for 30 min to get two clear layers. Aqueous layer was separated and washed with DCM (3×). Organic layer was dried and evaporated to give a crude product, which was purified by column chromatography (EtOAc/MeOH). NMR (400 MHz, CDCl$_3$): δ 5.35 (s, 2H), 7.49 (m, 1H), 7.60 (d, 1H), 8.02 (m, 1H), 8.25 (m, 1H), 8.38 (s, 1H), 8.53 (m, 1H), 8.70 (m, lH) 10.58 (s, lH); MS: exact mass calculated for C$_{12}$H$_{10}$N$_2$O$_2$, 214.07; m/z found, 215 [M+H]$^+$.

Example 2. Preparation of 3-(imidazo[1,2-a]pyridin-8-ylmethoxy)isonicotinaldehyde

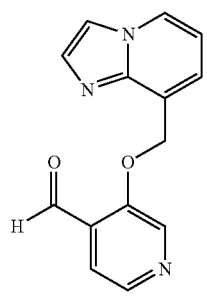 [SMILES: O=Cc1ccncc1OCc1cccn2ccnc12]

Step 1:

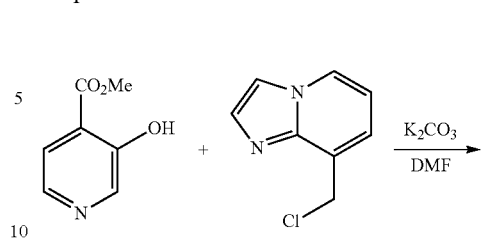

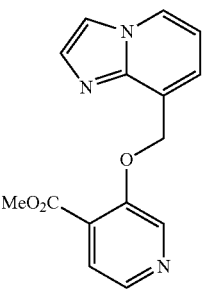

To a DMF (15 mL) solution of the chloride (300 mg, 1.5 mmol, 1.0 eq) and phenol (230 mg, 1.5 mmol, 1.0 eq) was added K$_2$CO$_3$ (621 mg, 4.5 mmol, 3.0 eq) and the reaction mixture was heated at 80-90° C. for 5 h. Solvent was removed and the residue was purified by column chromatography (EtOAc/MeOH) to give the alkylation product. MS: exact mass calculated for C$_{15}$H$_{13}$N$_3$O$_3$, 283.10; m/z found, 284 [M+H]$^+$.

Step 2:

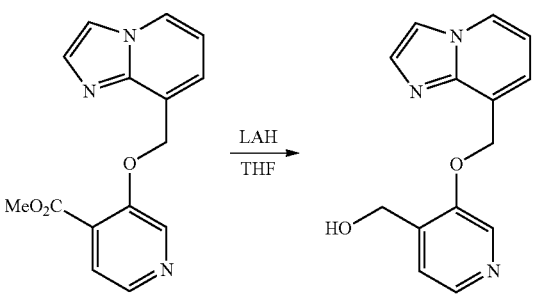 [SMILES: COC(=O)c1ccncc1OCc1cccn2ccnc12 ; "LAH" ; OCc1ccncc1OCc1cccn2ccnc12 ; "THF"]

To a cooled solution of the ester (1.5 mmol, 1.0 eq) in THF (15 mL) was slowly added LAH in THF (1.5 mL, 2.0 M solution in THF, 2.0 eq) and the reaction mixture was stirred at this temperature for 30 min. Excess ethyl acetate was added very slowly followed by water (1.0 mL), 15% NaOH (1.0 mL) and water (3.0 mL) and the mixture was stirred at rt for 30 min. The solution was filtered and the solid was washed with ethyl acetate (3×). Combined organic layers were dried and evaporated to provide the alcohol, which was used in the next step without further purification. MS: exact mass calculated for C$_{14}$H$_{13}$N$_3$O$_2$, 255.10; m/z found, 256 [M+H]$^+$.

Step 3:

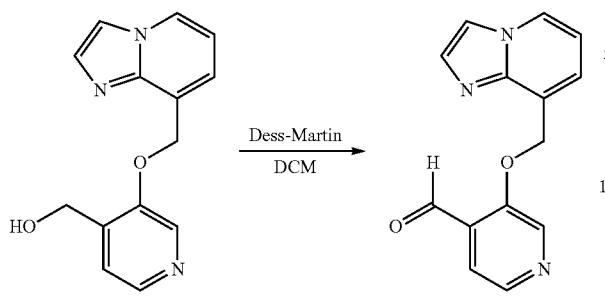

To a solution of the above alcohol (1.5 mmol, 1.0 eq) in DCM (15 mL) was added Dess-Martin reagent (2.25 mmol, 954 mg, 1.5 eq) and the reaction mixture was stirred at rt for 1 h. The reaction was then diluted with 25 ml. DCM and then a 1:1 mixture of sat. NaHCO$_3$ and sat. Na$_2$S$_2$O$_3$ was added and stirred for 30 min to get two clear layers. The aqueous layer was separated and washed with DCM (3×). The organic layer was dried and evaporated to give a crude product which was purified by column chromatography (EtOAc/MeOH). MS: exact mass calculated for C$_{14}$H$_{11}$N$_3$O$_2$, 253.09; m/z found, 254 [M+H]$^+$.

Example 3. Preparation of 3-(imidazo[1,5-a]pyridin-8-ylmethoxy)isonicotinaldehyde

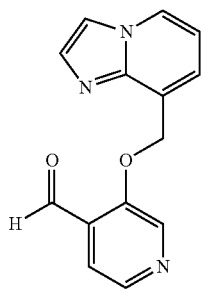 [SMILES: O=Cc1ccncc1OCc1cccn2ccnc12]

Step 1:

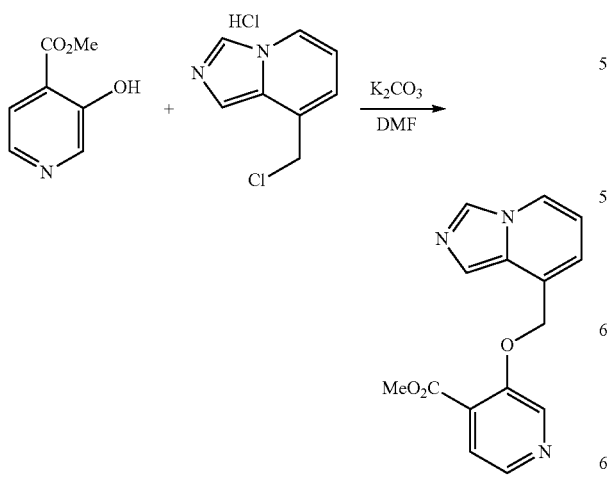

To a solution of chloride (200 mg, 1.0 mmol, 1.0 eq), and phenol (153 mg, 1.0 mmol, 1.0 eq) in DMF (15 mL) was added K$_2$CO$_3$ (414 mg, 3.0 mmol, 3.0 eq) and the reaction mixture was heated at 80-90° C. for 5 h. Solvent was removed and the residue was purified by column chromatography (EtOAc/MeOH) to give the alkylation product. MS: exact mass calculated for C$_{15}$H$_{13}$N$_3$O$_3$, 283.10; m/z found, 284 [M+H]$^+$.

Step 2:

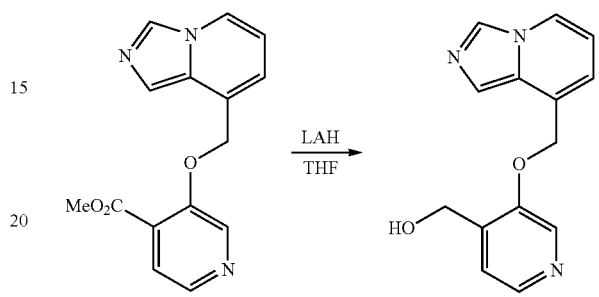

To a cooled solution of the ester (1.0 mmol, 1.0 eq) in THF (15 mL) was slowly added LAH in THF (4 mmol, 2.0 mL, 2.0 M solution in THF, 4.0 eq) and the reaction mixture was stirred at this temperature for 30 min. Excess ethyl acetate was added very slowly followed by water (1.0 mL), 15% NaOH (1.0 mL) and water (3.0 mL) and the mixture was stirred at rt for 30 min. Filtered and the solid was washed with ethyl acetate (3×). Combined organic layers were dried and evaporated to provide the alcohol, which was used in the next step without further purification. MS: exact mass calculated for C$_{14}$H$_{13}$N$_2$O$_2$, 255.10; m/z found, 286 [M+H]$^+$.

Step 3:

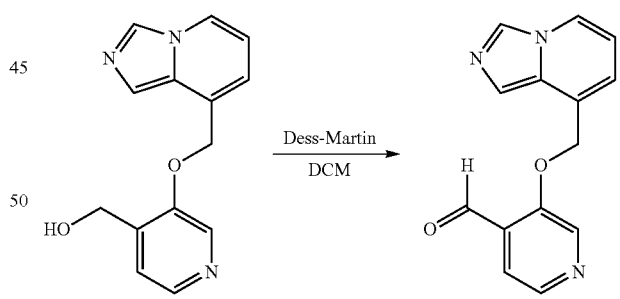

To a cooled solution of the ester (1.0 mmol, 1.0 eq) in THF (15 mL) was slowly added LAH in THF (4 mmol, 2.0 mL, 2.0 M solution in THF, 4.0 eq) and the reaction mixture was stirred at this temperature for 30 min. Excess ethyl acetate was added very slowly followed by water (1.0 mL), 15% NaOH (1.0 mL) and water (3.0 mL) and the mixture was stirred at rt for 30 min. Reaction was filtered and the solid was washed with ethyl acetate (3×). Combined organic layers were dried and evaporated to provide the alcohol, which was used in the next step without further purification. MS: exact mass calculated for C$_{14}$H$_{13}$N$_3$O$_2$, 255.10; m/z found, 286 [M+H]$^+$.

Example 4. Preparation of 4-(pyridin-3-ylmethoxy)nicotinaldehyde

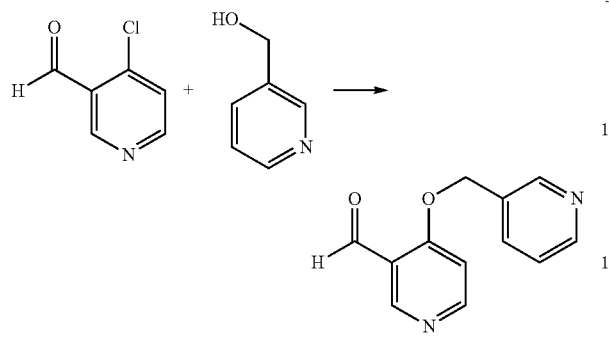

4-chloro-3-pyridine aldehyde (1.0 g, 7 mmol, 1.0 eq), 3-hydroxymethyl pyridine (5.4 g, 49.45 mmol, 7 eq) and p-toluenesulfonic acid mon hydrate (1.3 g, 7.0 mmol, 1.0 eq) in benzene (30 mL) were heated using a Dean-Stark trap for 24 h. Solvent was removed and purified by column chromatography to provide the alkylation product. MS: exact mass calculated for $C_{12}H_{10}N_2O_2$, 214.22; m/z found, 215 $[M+H]^+$.

Example 5. Preparation of 5-(imidazo[1,2-a]pyridin-8-ylmethoxy)-2-methoxyisonicotinaldehyde (Compound 5)

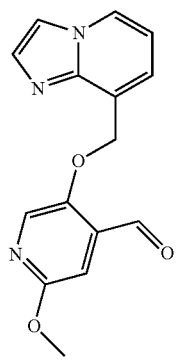

Step 1:

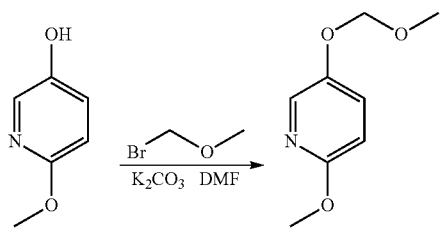

To a mixture of 6-methoxypyridin-3-ol (25 g, 0.2 mol) and $K_2CO_3$ (82.8 g, 0.6 mol) in DMF (250 mL) was added bromomethyl methyl ether (30 g, 0.24 mmol) slowly at rt for a period of 1 h. The reaction mixture was filtered and the filtrate was concentrated. The residue was purified on silica gel with 25% EtOAc/hexanesas eluent to give 2-methoxy-5-(methoxymethoxy)pyridine (20 g, 59%) as a colorless oil. LRMS $(M+H^+)$ m/z 170.1

Step 2:

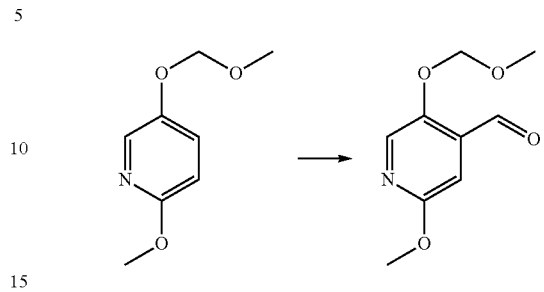

To a solution of 2-methoxy-5-(methoxymethoxy)pyridine (20 g, 0.12 mol) in THF was added diisopropylamine (0.24 g, 2.4 mmol). The solution was cooled to −40° C. followed by addition of MeLi (3M/THF, 72 mL, 0.216 mol) slowly. The resulting mixture was warmed to 0° C., stirred at 0° C. for 3 h, cooled back down to −40° C. and added N-formylpiperidine (24 mL, 0.216 mol). After stirring at −40° C. for 2 h, the mixture was quenched with a mixed solution of HCl (37%, 120 mL) and THF (250 mL). The temperature was then raised to rt and diluted with water (200 mL) and EtOAc (200 mL). The pH of the mixture was adjusted to 8-9 with solid $K_2CO_3$ and extracted with EtOAc (300 mL) twice. The organic layer was combined, dried over $Na_2SO_4$, and concentrated. The residue was purified on silica gel with 25% EtOAc/hexanes as eluent to give 2-methoxy-5-(methoxymethoxy)isonicotinaldehyde (10 g, 42%) as a pale yellow oil. $^1$H NMR (400 MHz; $CD_3OD$) 7.90 (s, 1H), 6.92 (s, 1H), 5.64 (s, 1H), 5.20 (s, 2H), 3.84 (s, 3H), 3.48 (s, 3H).

Step 3:

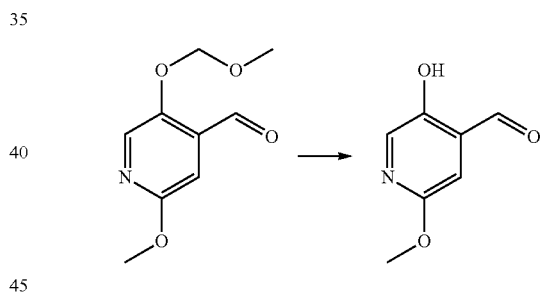

To a solution of 2-methoxy-5-(methoxymethoxy)isonicotinaldehyde (10 g, 0.05 mol) in THF (100 mL) was added 3 N HCl (150 mL). The reaction was stirred at 50° C. for 30 min, cooled to rt, and diluted with water (100 mL). The mixture was neutralized to pH 7-8 and extracted with EtOAc (200 mL) three times. The organic layer was dried over $Na_2SO_4$ and concentrated to give 5-hydroxy-2-methoxyisonicotinaldehyde (4.2 g, 55%) as a yellow solid. $^1$H NMR (400 MHz; DMSO) δ=10.31 (s, 1H), 8.03 (s, 1H), 6.89 (s, 1H), 3.80 (s, 3H).

Step 4:

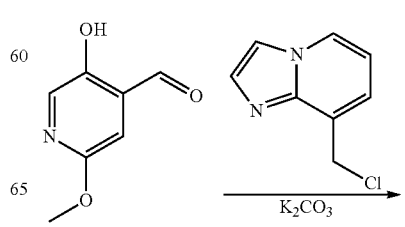

-continued

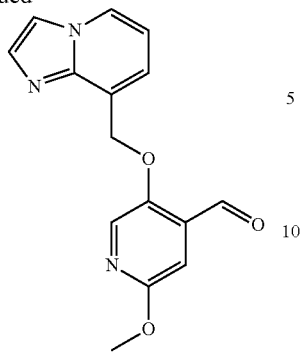

A mixture of 5-hydroxy-2-methoxyisonicotinaldehyde (723.6 mg, 4.7 mmol), 8-(chloromethyl)-imidazol[1,2-a]pyridine (785 mg, 4.7 mmol), and $K_2CO_3$ (1.9 g, 14.1 mmol) in DMF (20 mL) was heated at microwave reactor at 125° C. for 15 min. The mixture was filtered and concentrated. The residue was purified on silica gel (50-100% EtOAc in hexanes) to give 5-(imidazo[1,2-a]pyridin-8-ylmethoxy)-2-methoxyisonicotinaldehyde (500 mg, 38%) as an off-white solid. $^1$H NMR (400 MHz; DMSO) δ=10.37 (s, 1H), 8.58 (d, 1H), 8.39 (s, 1H), 8.02 (s, 1H), 7.61 (s, 1H), 7.44 (d, 1H), 6.98 (s, 1H), 6.93 (t, 1H), 5.61 (a, 2H), 3.84 (s, 3H). LRMS (M+H$^+$) m/z 284.0.

Examples 6-13 were synthesized according to Example 5.

Example 6. Preparation of 2-methoxy-5-((5-methyl-pyridin-3-yl)methoxy)isonicotinaldehyde (Compound 43)

$^1$H NMR (400 MHz, CDCl3) δ 10.43 (s, 1H), 8.69 (s, 1H), 8.56 (s, 1H), 8.09 (s, 1H), 7.94 (s, 1H), 7.15-7.09 (m, 1H), 5.29 (s, 2H), 3.94 (s, 3H), 2.51 (s, 3H), 1H NMR (400 MHz, CDCl3) δ 10.43 (s, 1H), 8.69 (s, 1H), 8.56 (s, 1H), 8.09 (s, 1H), 7.94 (s, 1H), 7.15-7.09 (m, 1H), 5.29 (s, 2H), 3.94 (s, 3H), 2.51 (s, 3H).

Example 7. Preparation of 5-(isoquinolin-1-yl-methoxy)-2-methoxyisonicotinaldehyde (Compound 44)

$^1$HNMR (400 MHz, CDCl3) δ 10.40 (s, 1H), 8.54 (d, J=5.7 Hz, 1H), 8.30 (s, 1H), 8.31 (d, J=8.6 Hz, 1H), 7.90 (d, J=8.4 Hz, 1H), 7.78-7.63 (m, 3H), 7.07 (d, J=0.5 Hz, 1H), 5.82 (s, 2H), 3.91 (s, 3H).

Example 8. Preparation of 2-methoxy-5-(quinolin-2-ylmethoxy)isonicotinaldehyde (Compound 45)

$^1$H NMR (400 MHz, CDCl3) δ 10.61 (s, 1H), 8.26 (d, J=8.5 Hz, 1H), 8.12 (s, 1H), 8.10 (d, J=8.5 Hz, 1H), 7.87 (dd, J=8.2, 1.1 Hz, 1H), 7.78 (ddd, J=8.4, 6.9, 1.4 Hz, 1H), 7.67 (d, J=8.5 Hz, 1H), 7.60 (ddd, J=8.1, 7.0, 1.1 Hz, 1H), 7.13 (s, 1H), 5.52 (s, 2H), 3.91 (s, 3H).

Example 9. Preparation of 2-methoxy-5-(pyridin-4-ylmethoxy)isonicotinaldehyde (Compound 46)

$^1$H NMR (400 MHz, CDCl3) δ 10.44 (s, 1H), 8.59 (d, J=6.0 Hz, 2H), 7.92 (8, 1H), 7.30 (d, J=6.0 Hz, 2H), 7.06 (s, 1H), 5.16 (s, 2H), 3.84 (s, 3H).

Example 10. 3-(imidazo[1,2-a]pyridin-8-yl-methoxy)-6-methylpicolinaldehyde (Compound 49)

$^1$H NMR (400 MHz, DMSO) δ 10.22 (s, 1H), 8.56 (d, J=6.7 Hz, 1H), 8.02 (s, 1H), 7.82 (d, J=8.7 Hz, 1H), 7.60 (s, 1H), 7.53 (d, J=8.7 Hz, 1H), 7.47 (d, J=6.7 Hz, 1H), 6.96 (t, J=6.9 Hz, 1H), 5.59 (s, 2H), 2.49 (8, 3H).

Example 11. Preparation of Methyl 2-((4-formyl-6-methoxypyridin-3-yloxy)methyl)imidazo[1,2-a]pyridine-8-carboxylate (Compound 53)

$^1$H NMR (400 MHz, CDCl3) δ 10.52 (s, 1H), 8.32 (dd, J=6.7, 1.3 Hz, 1H), 8.17 (s, 1H), 8.03 (dd, J=7.2, 1.3 Hz, 1H), 7.76 (s, 1H), 7.11 (s, 1H), 6.94 (t, J=7.0 Hz, 1H), 5.53 (s, 2H), 4.06 (s, 3H), 3.93 (s, 3H).

Example 12. Preparation of 2-methoxy-S-((3-methyl-[1,2,4]triazolo[4,3-a]pyridin-8-yl)methoxy)isonicotinaldehyde (Compound 58)

$^1$H NMR (400 MHz, CDCl3) δ 10.53 (s, 1H), 8.14 (s, 1H), 7.89 (d, J=6.9 Hz, 1H), 7.44 (dd, J=6.8, 1.1 Hz, 1H), 7.11 (s, 1H), 6.94 (t, J=6.9 Hz, 1H), 5.67 (s, 2H), 3.92 (s, 3H), 2.80 (s, 3H).

Example 13. Preparation of 5-((2-(1H-pyrazol-1-yl)pyridin-3-yl)methoxy)-2-methoxyisonicotinaldehyde (Compound 134)

$^1$H NMR (400 MHz, CDCl3) δ 10.47 (s, 1H), 8.53 (d, J=2.1 Hz, 1H), 8.48 (d, J=4.7 Hz, 1H), 8.19 (d, J=7.8 Hz, 1H), 8.10 (s, 1H), 7.75 (s, 1H), 7.35 (dd, J=7.7, 4.7 Hz, 1H), 7.12 (s, 1H), 6.51 (dd, J=2.5, 1.8 Hz, 1H), 5.75 (s, 2H), 3.93 (s, 3H).

Example 14. Preparation of 5-((2-(1H-pyrazol-5-yl)pyridin-3-yl)methoxy)-2-methoxyisonicotinaldehyde (Compound 65)

Step 1:

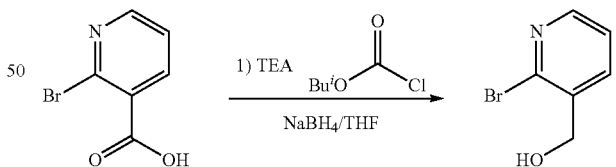

To a solution of 2-bromonicotinic acid (4.0 g, 20 mmol) and triethylamine (3.34 mL, 24 mmol, 1.2 eq.) in THF (100 mL) was added i-butyl chloroformate (3.12 mL, 24 mmol, 1.2 eq.) at 0° C. The mixture was stirred at 0° C. for 10 min and filtered. To this filtrate was added a suspension of NaBH$_4$ (1.52 g, 40 mmol, 2 eq.) in water (1.0 mL) at 0° C. The mixture was stirred for 30 min, added water (3 mL), continued to stir for 2 h, and concentrated to dryness. The crude was purified on silica gel using a mixture of ethylacetate and hexanes as eluent to give (2-bromopyridin-3-yl)methanol (3.4 g, 90%) as a white solid. LRMS (M+H$^+$) m/z 188.0.

Step 2:

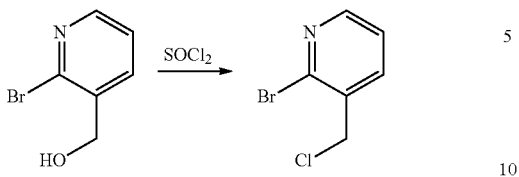

To (2-bromopyridin-3-yl)methanol (380 mg, 2 mmol) in DCM (5 mL) was added SOCl₂ (1 mL) at rt. The reaction mixture was stirred at rt for 4 h and concentrated to dryness. The crude solid was suspended in toluene and concentrated to dryness. The process was repeated three times and dried under vacuum to give an off-white solid (480 mg), which was used for next step without further purification.

Step 3:

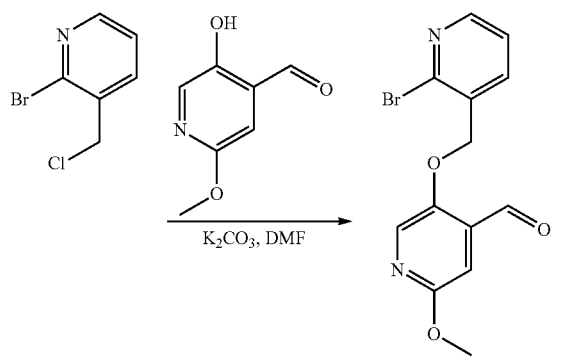

A mixture of 5-hydroxy-2-methoxyisonicotinaldehyde (306 mg, 2 mmol, 1 eq.), 2-bromo-3-(chloromethyl)pyridine (crude above, 2 mmol), and $K_2CO_3$ (828 mg, 6 mmol, 3 eq.) in DMF (1.0 mL) was heated at 50° C. for 2 h. The mixture was cooled and added to water (50 mL) dropwise. The precipitate was filtered, washed with water, dried under high vacuo to give 5-((2-bromopyridin-3-yl)methoxy)-2-methoxyisonicotinaldehyde (350 mg, 85%) as an yellow solid. ¹H NMR (400 MHz; CDCl₃) δ=10.51 (s, 1H), 8.42 (dd, t H), 8.09 (s, 1H) 7.91 (d, 1H), 7.40 (dd, 1H), 7.15 (s, 1H), 5.27 (s, 2H), 3.95 (s, 3H). LRMS (M+H⁺) m/z 323.0.

Step 4:

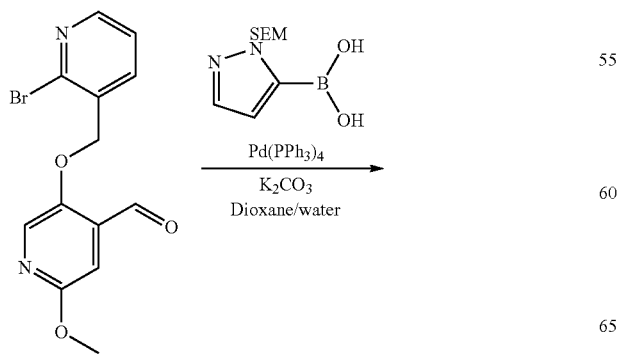

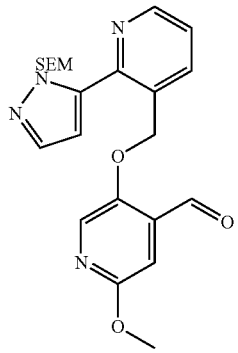

5-((2-bromopyridin-3-yl)methoxy)-2-methoxyisonicotin- aldehyde (258 mg, 0.8 mmol, 1 equiv), 1-((2-(trimethylsilyl) ethoxy)methyl)-1H-pyrazol-5-ylboronic acid (233 mg, 0.96 mmol, 1.2 equiv), Pd(PPh₃)₄ (92 mg, 0.08 mmol, 0.1 equiv), $K_2CO_3$ (331 mg, 2.4 mmol, 3 equiv) in a round bottom flask were added dioxane (8 mL) and water (2 mL). The mixture was heated 2 h at 90° C., cooled, filtered, and concentrated. The crude was purified on silica gel using a mixture of EtOAc and hexanes as eluent to give 2-methoxy-5-((2-(1- ((2-trimethylsilyl)ethoxy)methyl)-1H-pyrazol-5-yl)pyridin- 3-yl)methoxy)isonicotinaldehyde (208 mg, 79%) as a white solid. ¹H NMR (400 MHz; CDCl₃) δ=10.54 (s, 1H), 8.85 (d, 1H), 8.18 (d, 1H) 8.03 (s, 1H), 7.73 (d, 1H), 7.56 (dd, 1H), 7.21 (s, 1H), 6.60 (d, 1H), 5.79 (s, 2H), 5.27 (s, 2H), 4.01 (s, 3H), 3.65 (t, 2H), 0.88 (t, 2H), 0.05 (s, 9H). LRMS (M+H⁺) m/z 441.2.

Step 5:

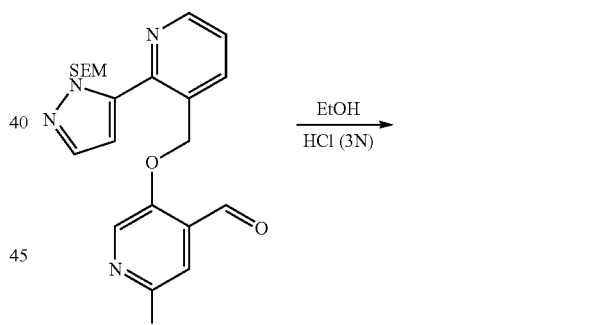

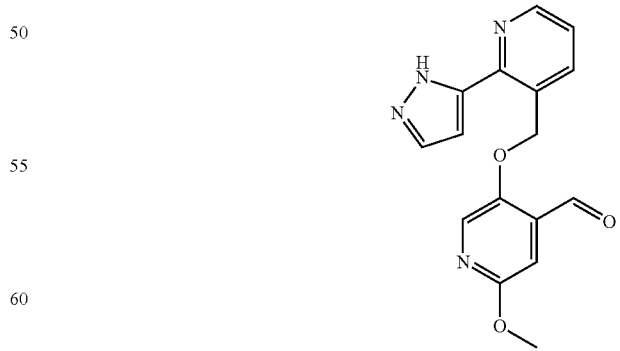

To 2-methoxy-S-((2-(1-((2-(trimethylsilyl)ethoxy) methyl)-1H-pyrazol-5-yl)pyridin-3-yl)methoxy)isonicotin- aldehyde (120 mg, 0.27 mmol, 1 equiv) suspended in EtOH (1 mL) was added HCl (1.0 mL, 3 N). The solution turned homogeneous and the mixture was stirred at rt overnight. The EtOH was partially removed by blowing in $N_2$ gas and the precipitate was collected. The solid was washed with acetonitrile and EtOAc and dried under high vacuo to give 5-((2-(1H-pyrazol-5-yl)pyridin-3-yl)methoxy)-2-methoxy-isonicotinaldehyde dihydrochloride (100 mg, 96%) as a white solid. $^1$H NMR (400 MHz; DMSO, 80° C.) δ=10.27 (s, 1H), 8.68 (br, 1H), 8.32 (br, 1H), 8.22 (s, 1H), 7.82 (br, 1H), 7.57 (br, 1H), 7.00 (br, 2H), 5.75 (s, 2H), 3.89 (s, 3H). LRMS (M+H$^+$) m/z 311.1.

Examples 15-22 were synthesized according to Example 14.

Example 15. Preparation of 5-((2-bromopyridin-3-yl)methoxy)-2-methoxyisonicotinaldehyde (Compound 63)

$^1$H NMR (400 MHz, CDCl3) δ 10.51 (s, 1H), 8.41 (dd, J=4.7, 1.8 Hz, 1H), 8.09 (s, 1H), 7.91 (dd, J=7.6, 1.6 Hz, 1H), 7.39 (dd, J=7.6, 4.8 Hz, 1H), 7.15 (s, 1H), 5.27 (s, 2H), 3.95 (s, 3H).

Example 16. Preparation of 5-((5-bromopyridin-3-yl)methoxy)-2-methoxyisonicotinaldehyde (Compound 66)

$^1$H NMR (400 MHz, CDCl3) δ 10.47 (s, 1H), 8.73 (s, 1H), 8.65 (s, 1H), 8.07 (s, 1H), 7.99 (s, 1H), 7.15 (s, 1H), 5.22 (s, 2H), 3.95 (d, J=0.8 Hz, 3H).

Example 17. Preparation of 2-methoxy-S-((5-(1-methyl-1H-pyrazol-5-yl)pyridin-3-yl)methoxy)isonicotinaldehyde (Compound 74)

$^1$H NMR (400 MHz, CDCl3) δ 10.44 (s, 1H), 8.75 (dd, J=9.0, 2.1 Hz, 2H), 8.11 (s, 1H), 7.88 (t, J=2.1 Hz, 1H), 7.58 (d, J=1.9 Hz, 1H), 7.13 (s, 1H), 6.43 (d, J=1.9 Hz, 1H), 5.30 (s, 2H), 3.95 (s, 3H), 3.94 (s, 3H).

Example 18. Preparation of 5-((2-(1,5-dimethyl-1H-pyrazol-4-yl)pyridin-3-yl)methoxy)-2-methoxyisonicotinaldehyde (Compound 143)

$^1$H NMR (400 MHz, CDCl$_3$) δ 10.40 (s, 1H), 8.69 (dd, J=4.8, 1.7 Hz, 1H), 7.94 (s, 1H), 7.92 (dd, J=7.8, 1.7 Hz, 1H), 7.57 (s, 1H), 7.29 (dd, J=7.8, 4.8 Hz, 2H), 7.10 (s, 1H), 5.24 (s, 2H), 3.92 (s, 3H), 3.88 (s, 3H), 2.42 (s, 3H).

Example 19. Preparation of 5-((2-(1-ethyl-1H-pyrazol-5-yl)pyridin-3-yl)methoxy)-2-methoxyisonicotinaldehyde (Compound 149)

$^1$H NMR (400 MHz, CDCl3) δ 10.32 (s, 1H), 8.68 (dd, J=4.8, 1.6 Hz, 1H), 7.95 (dd, J=7.9, 1.6 Hz, 1H), 7.84 (s, 1H), 7.50 (d, J=1.9 Hz, 1H), 7.36 (dd, J=7.9, 4.8 Hz, 1H), 7.03 (s, 1H), 6.32 (d, J=1.9 Hz, 1H), 5.09 (s, 2H), 4.21 (q, J=7.2 Hz, 2H), 3.83 (s, 3H), 1.32 (t, J=7.2 Hz, 3H).

Example 20. Preparation of 2-methoxy-5-((2-phenylpyridin-3-yl)methoxy)isonicotinaldehyde (Compound 159)

$^1$H NMR (400 MHz, CDCl3) δ 10.26 (s, 1H), 8.63 (dd, J=4.8, 1.6 Hz, 1H), 7.88 (dd, J=7.8, 1.6 Hz, 1H), 7.78 (s, 1H), 7.48-7.44 (m, 2H), 7.41-7.34 (m, 3H), 7.28 (dd, J=7.8, 4.8 Hz, 1H), 6.99 (s, 1H), 5.12 (s, 2H), 3.80 (s, 3H).

Example 21. Preparation of 2-methoxy-5-((2-(o-tolyl)pyridin-3-yl)methoxy)isonicotinaldehyde (Compound 162)

$^1$H NMR (400 MHz, CDCl3) δ 10.36 (s, 1H), 8.71 (dd, J=4.8, 1.6 Hz, 1H), 7.99 (dd, J=7.8, 1.6 Hz, 1H), 7.80 (s, 1H), 7.40 (dd, J=7.8, 4.8 Hz, 1H), 7.36-7.29 (m, 2H), 7.28-7.23 (m, 1H), 7.23-7.18 (m, 1H), 7.06 (s, 1H), 4.98 (s, 2H), 3.89 (s, 3H), 2.13 (s, 3H).

Example 22. Preparation of 2-methoxy-5-((2'-methoxy-[2,3'-bipyridin]-3-yl)methoxy)isonicotinaldehyde (Compound 163)

$^1$H NMR (400 MHz, CDCl3) δ 10.31 (s, 1H), 8.71 (dd, J=4.8, 1.4 Hz, 1H), 8.28 (dd, J=5.0, 1.9 Hz, 1H), 7.96 (dd, J=7.8, 0.9 Hz, 1H), 7.82 (s, 1H), 7.74 (dd, J=7.3, 1.9 Hz, 1H), 7.41 (dd, J=7.8, 4.8 Hz, 1H), 7.09-7.03 (m, 2H), 5.14 (s, 2H), 3.96 (s, 3H), 3.89 (s, 3H).

Example 23. Preparation of 2-methoxy-S-((2-(1-((2-(trimethylsilyl)ethoxy)methyl)-1H-pyrazol-5-yl)pyridin-3-yl)methoxy)isonicotinaldehyde (Compound 193)

$^1$H NMR (400 MHz, CDCl3) δ 10.54 (s, 1H), 8.84 (dd, J=4.8, 1.6 Hz, 1H), 8.14 (dd, J≤7.9, 1.6 Hz, 1H), 8.03 (s, 1H), 7.72 (d, J=1.7 Hz, 1H), 7.55 (dd, J=7.9, 4.8 Hz, 1H), 7.21 (s, 1H), 6.60 (d, J=1.8 Hz, 1H), 5.79 (s, 2H), 5.27 (s, 2H), 4.01 (s, 3H), 3.66-3.59 (m, 2H), 0.92-0.80 (m, 2H), 0.00 (s, 9H).

Example 24. Preparation of 2-methoxy-5-(quinolin-3-ylmethoxy)isonicotinaldehyde (Compound 80)

$^1$H NMR (400 MHz, CDCl3) δ 10.50 (s, 1H), 9.03 (d, J=2.2 Hz, 1H), 8.27 (d, J=13 Hz, 1H), 8.17 (d, J=8.5 Hz, 1H), 8.15 (s, 1H), 7.89 (d, J=8.1 Hz, 1H), 7.79 (ddd, J=8.4, 6.9, 1.4 Hz, 1H), 7.63 (ddd, J=8.1, 7.0, 1.2 Hz, 1H), 7.14 (s, 1H), 5.42 (s, 2H), 3.94 (s, 3H).

Example 25. Preparation of 5-((4-formyl-6-methoxypyridin-3-yloxy)methyl)nicotinic Acid (Compound 79)

Step 1

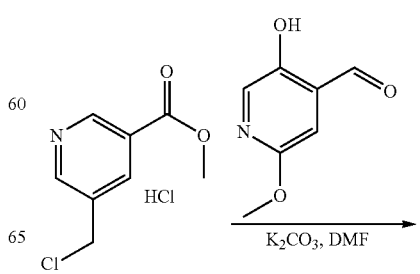

-continued

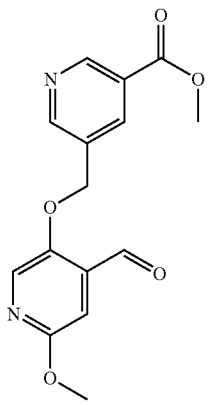

A mixture of 5-hydroxy-2-methoxyisonicotinaldehyde (352 mg, 2.29 mmol, 1 eq.), methyl 5-(chloromethyl)nicotinate hydrochloride (506 mg, 2.29 mmol, 1 eq.), and K$_2$CO$_3$ (1.26 g, 9.16 mmol, 4 eq.) in DMF (8.0 mL) was heated at 60° C. for 3 h. The mixture was cooled and added into water (50 mL) dropwise. The precipitate was filtered, washed with water, and dried to give methyl 5-((4-formyl-6-methoxypyridin-3-yloxy)methyl)nicotinate (350 mg, 85%) as a yellow solid. $^1$H NMR (400 MHz, CDCl$_3$) δ 10.47 (s, 1H), 9.26 (d, 2.0 Hz, 1H), 8.90 (d, J=2.2 Hz, 1H), 8.42 (t, J=2.1 Hz, 1H), 8.09 (s, 1H), 7.15 (s, 1H), 5.29 (s, 2H), 4.01 (s, 3H), 3.95 (s, 3H). LRMS (M+H$^+$) m/z 303.1.

Step 2

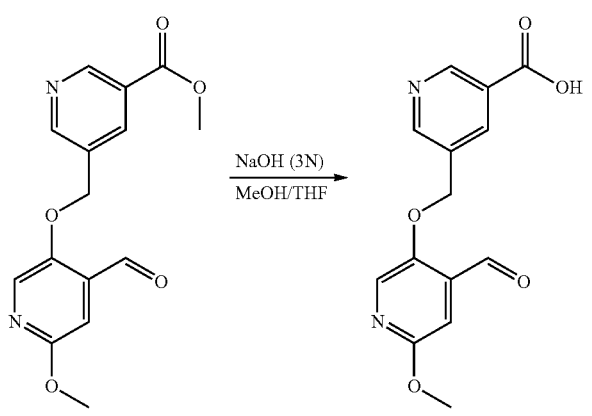 [SMILES: COC(=O)c1cncc(COc2cnc(OC)cc2C=O)c1 ; COc1cc(C=O)c(OCc2cncc(C(=O)O)c2)cn1]

To 5-((4-formyl-6-methoxypyridin-3-yloxy)methyl)nicotinate (96 mg, 0.32 mmol, 1 eq.) in a mixture of MeOH/THF (1/3, 8.0 mL) was added NaOH (3 N, 1.7 mL, 5.1 mmol, 16 eq.). The mixture was stirred at rt for 2 h, acidified to pH 3, extracted with EtOAc (3×20 mL). The combined organic layers were dried over Na$_2$SO$_4$ and concentrated to give 5-((4-formyl-6-methoxypyridin-3-yloxy)methyl)nicotinic acid (86 mg, 93%) as a white solid. $^1$H NMR (400 MHz, DMSO) δ 13.55 (s, 1H), 10.34 (s, 1H), 9.06 (d, J=1.9 Hz, 1H), 8.96 (d, J=2.0 Hz, 1H), 8.42 (t, J=2.0 Hz, 1H), 8.34 (s, 1H), 7.02 (s, 1H), 5.44 (s, 2H), 3.86 (s, 3H). LRMS (M+H$^+$) m/z 289.1.

Examples 26-35 were synthesized according to the procedure in Example 25.

Example 26. Preparation of Methyl 4-(((3-formylpyridin-3-yl)oxy)methyl)benzoate (Compound 64)

$^1$H NMR (400 MHz, CDCl3) δ 10.44 (s, 1H), 8.46 (dd, J=4.3, 0.6 Hz, 1H), 8.11 (d, J=8.1 Hz, 2H), 7.58 (d, J=8.0 Hz, 2H), 7.50-7.40 (m, 2H), 5.33 (s, 2H), 3.95 (s, 3H).

Example 27. Preparation of 4-(((2-formyl-6-methylpyridin-3-yl)oxy)methyl)benzoic Acid (Compound 165)

$^1$H NMR (400 MHz, CDCl$_3$) δ 10.42 (s, 1H), 8.16 (d, J=8.2 Hz, 2H), 7.61 (d, J=8.1 Hz, 2H), 7.33 (d, J=1.8 Hz, 2H), 5.32 (s, 2H), 2.61 (s, 3H).

Example 28. Preparation of 4-(((2formylpyridin-3-yl)oxy)methyl)benzoic Acid (Compound 166)

$^1$H NMR (400 MHz, CDCl$_3$) δ 10.35 (s, 1H), 8.38 (dd, J=4.3, 1.2 Hz, 1H), 8.08 (d, J=8.3 Hz, 2H), 7.54 (d, J=8.2 Hz, 2H), 7.42-7.32 (m, 2H), 5.26 (s, 2H).

Example 29. Preparation of Methyl 3-(((4-formylpyridin-3-yl)oxy)methyl)benzoate (Compound 167)

$^1$H NMR (400 MHz, CDCl$_3$) δ 10.60 (s, 1H), 8.64 (s, 1H), 8.46 (d, J=4.7 Hz, 1H), 8.16 (s, 1H), 8.08 (d, J=7.8 Hz, 1H), 7.71-7.61 (m, 2H), 7.54 (t, J=7.7 Hz, 1H), 5.38 (s, 2H), 3.96 (s, 3H).

Example 30. Preparation of Methyl 3-(((2-formyl-6-methylpyridin-3-yl)oxy)methyl)benzoate (Compound 168)

$^1$H NMR (400 MHz, CDCl$_3$) δ 10.40 (s, 1H), 8.11 (s, 1H), 8.02 (d, J=7.8 Hz, 1H), 7.70 (d, J=7.8 Hz, 1H), 7.50 (t, J=7.7 Hz, 1H), 7.35 (d, J=8.7 Hz, 1H), 7.29 (d, J=8.7 Hz, 1H), 5.26 (s, 2H), 3.93 (s, 3H).

Example 31. Preparation of 3-(((4-formylpyridin-3-yl)oxy)methyl)benzoic Acid (Compound 169)

$^1$H NMR (400 MHz, DMSO) δ 13.21-12.87 (br, 1H), 10.45 (s, 1H), 8.82 (s, 1H), 8.43 (d, J=4.8 Hz, 1H), 8.11 (s, 1H), 7.94 (d, J=7.6 Hz, 1H), 7.81 (d, J=7.1 Hz, 1H), 7.63-7.46 (m, 2H), 5.52 (s, 2H).

Example 32. Preparation of 3-(((2-formyl-6-methylpyridin-3-yl)oxy)methyl)benzoic Acid (Compound 170)

$^1$H NMR (400 MHz, DMSO) δ 12.83 (s, 1H), 9.99 (s, 1H), 7.87 (s, 1H), 7.71 (d, J=7.8 Hz, 1H), 7.60-7.50 (m 2H), 7.38-7.30 (m, 2H), 5.16 (s, 2H).

Example 33. Preparation of 3-(((2-formylpyridin-3-yl)oxy)methyl)benzoic Acid (Compound 171)

$^1$H NMR (400 MHz, DMSO) δ 13.04 (s, 1H), 10.23 (s, 1H), 8.40 (d, J=4.4 Hz, 1H), 8.10 (s, 1H), 7.93 (d, 7-7.7 Hz, 1H), 7.84 (d, J=8.5 Hz, 1H), 7.80 (d, J=7.7 Hz, 1H), 7.68 (dd, J=8.6, 4.4 Hz, 1H), 7.57 (t, J=7.7 Hz, 1H), 5.41 (s, 2H).

Example 34. Preparation of 3-(((4-formyl-6-methoxypyridin-3-yl)oxy)methyl)benzoic Acid (Compound 203)

$^1$H NMR (400 MHz, CDCl3) δ 10.27 (s, 1H), 7.97 (s, 1H), 7.89 (d, J=7.8 Hz, 1H), 7.85 (s, 1H), 7.48 (d, J=7.7 Hz, 1H), 7.32 (t, J=7.7 Hz, 1H), 6.89 (s, 1H), 5.05 (s, 2H), 3.69 (s, 3H).

Example 35. Preparation of Tert-butyl 4-((2-formyl-6-methylpyridin-3-yloxy)methyl)-1H-indazole-1-carboxylate (Compound 86)

The title compound was prepared as for Example 34 above.

$^1$H NMR (400 MHz, CDCl3) δ 10.35 (s, 1H), 8.40 (s, 1H), 8.23 (d, J=8.6 Hz, 1H), 7.57 (dd, J=8.4, 7.3 Hz, 1H), 7.43 (d, J=7.2 Hz, 1H), 7.37 (d, J=8.6 Hz, 1H), 7.30 (d, J=8.6 Hz, 1H), 5.58 (s, 2H), 2.58 (s, 3H), 1.75 (s, 9H).

Example 36. Preparation of 5-methoxy-2-((1-methyl-1H-indazol-4-yl)methoxy)isonicotinaldehyde (Compound 115)

Step 1

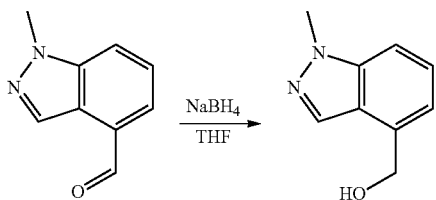

To a mixture of 1-methyl-1H-indazole-4-carbaldehyde (180 mg, 1.12 mol) in THF (10 mL) was added NaBH$_4$ (85 mg, 2.24 mmol) al r.t. The reaction mixture was stirred at r.t. for 1 h, acidified to pH 3, and extracted with EtOAc. The combined organic layer was washed with saturated sodium bicarbonate solution and brine, dried over Na$_2$SO$_4$, filtered, and concentrated to give a crude solid (191 mg), which was used for next step without further purification.

Step 2

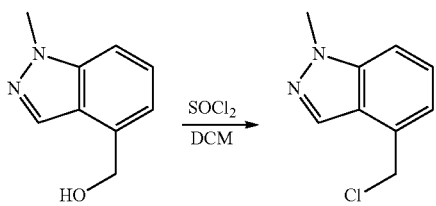

To (1-methyl-1H-indazol-4-yl)methanol (191 mg) in DCM (5 mL) was added SOCl$_2$ (2 mL) at rt. The reaction mixture was stirred at rt for 4 h and concentrated to dryness. The crude solid was suspended in toluene and concentrated to dryness. The process was repeated three times and dried under vacuum to give an off-white solid (210 mg), which was used for next step without further purification.

Step 3

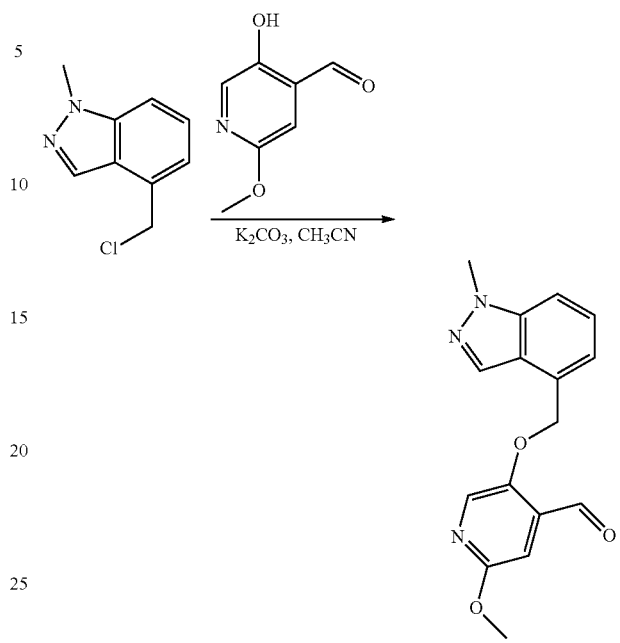

A mixture of 2-hydroxy-5-methoxyisonicatinaldehyde (170 mg, 1.12 mmol), 4-(chloromethyl)-1-methyl-1H-indazole (1.12 mmol), and K$_2$CO$_3$ (618 mg, 4.48 mmol) is refluxed in CH$_3$CN (20 mL) for 2 h. The mixture is filtered and the solid is washed with DCM. The filtrate is concentrated and purified on silica gel using a mixture of EtOAc and MeOH as eluent to give 5-methoxy-2-((1-methyl-1H-indazol-4-yl)methoxy)isonicotinaldehyde as a while solid.

Examples 37-45 were prepared according to Example 36.

Example 37. Preparation of 2-methoxy-5-((1-methyl-1H-indazol-4-yl)methoxy)isonicotinaldehyde (Compound 84)

$^1$H NMR (400 MHz, CDCl3) δ 10.46 (s, 1H), 8.13 (s, 1H), 8.09 (s, 1H), 7.48-7.38 (m, 2H), 7.22 (dd, J=6.0.0.8 Hz, 1H), 7.10 (s, 1H), 5.55 (s, 2H), 4.13 (s, 3H), 3.91 (s, 3H).

Example 38. Preparation of 6-methyl-3-((1-methyl-1H-indazol-6-yl)methoxy)picolinaldehyde (Compound 91)

$^1$H NMR (400 MHz. CDCl3) δ 10.43 (s, 1H), 7.98 (d, J=0.9 Hz, 1H), 7.75 (dd, J=8.3, 0.8 Hz, 1H), 7.60 (d, J=0.8 Hz, 1H), 7.39 (d, J=8.9 Hz, 1H), 7.30 (d, J=9.0 Hz, 1H), 7.18 (dd, J=8.3, 1.3 Hz, 1H), 5.37 (a, 2H), 4.10 (s, 3H), 2.58 (s, 3H).

Example 39. Preparation of 6-methyl-3-((1-methyl-1H-indazol-7-yl)methoxy)picolinaldehyde (Compound 92)

$^1$H NMR (400 MHz, CDCl3) δ 10.28 (s, 1H), 8.02 (s, 1H), 7.77 (dd, J=8.1, 1.0 Hz, 1H), 7.49 (d, J=8.6 Hz, 1H), 7.38 (dd, J=7.0, 1.0 Hz, 1H), 7.34 (d, J=8.6 Hz, 1H), 7.12 (dd, J=8.1, 7.0 Hz, 1H), 5.56 (s, 2H), 4.35 (s, 3H), 2.60 (s, 3H).

Example 40. Preparation of 3-(isoquinolin-1-yl-methoxy)-6-methylpicolinaldehyde (Compound 93)

$^1$H NMR (400 MHz, CDCl3) δ 10.36 (s, 1H), 8.52 (d, J=5.7 Hz, 1H), 8.48 (d, J=9.2 Hz, 1H), 7.88 (d, J=7.5 Hz, 1H), 7.77-7.66 (m, 4H), 7.27 (d, J=8.9 Hz, 1H), 5.86 (s, 2H), 2.55 (s, 3H).

Example 41. Preparation of 5-(benzo[d]oxazol-4-ylmethoxy)-2-methoxyisonicotinaldehyde (Compound 103)

$^1$H NMR (400 MHz, CDCl3) δ 10.51 (s, 1H), 8.18 (d, J=7.3 Hz, 2H), 7.63 (dd, J=8.1, 1.0 Hz, 1H), 7.52 (d, J=7.1 Hz, 1H), 7.46 (t, J=7.8 Hz, 1H), 7.11 (d, J=0.5 Hz, 1H), 5.65 (s, 2H), 3.92 (s, 3H).

Example 42. Preparation of 3-((1,5-naphthyridin-4-yl)methoxy)-6-methylpicolinaldehyde (Compound 106)

$^1$H NMR (400 MHz, CDCl3) δ 10.41 (s, 1H), 9.15 (d, J=2.1 Hz, HO, 9.05 (dd, J=4.2, 1.6 Hz, 1H), 8.52 (d, J=1.1 Hz, 1H), 8.47 (d, J=8.5 Hz, 1H), 7.71 (dd, J=8.5, 4.2 Hz, 1H), 7.44 (d, J=8.6 Hz, 1H), 7.35 (d, J=8.6 Hz, 1H), 5.50 (s, 2H), 2.62 (s, 3H).

Example 43. Preparation of 6-methyl-3-((1-methyl-1H-indazol-5-yl)methoxy)picolinaldehyde (Compound 108)

$^1$H NMR (400 MHz, CDCl3) δ 10.43 (s, 1H), 8.01 (s, 1H), 7.81 (s, 1H), 7.50 (d, J=8.7 Hz, 1H), 7.45 (d, J=8.7 Hz, 1H), 7.42 (d, J=8.6 Hz, 1H), 7.30 (d, J=8.6 Hz, 1H), 5.34 (s, 2H), 4.11 (d, J=0.5 Hz, 3H), 2.59 (s, 3H).

Example 44. Preparation of 6-methyl-3-(quinolin-5-ylmethoxy)picolinaldehyde (Compound 119)

$^1$H NMR (400 MHz, DMSO) δ 10.13 (s, 1H), 8.96 (dd, J=4.2, 1.6 Hz, 1H), 8.64 (d, J=8.4 Hz, 1H), 8.04 (d, J=8.4 Hz, 1H), 7.97 (d, J=8.7 Hz, 1H), 7.91 (d, J=7.2 Hz, 1H), 7.80 (dd, J=8.4, 7.1 Hz, 1H), 7.61 (dd, J=8.6, 4.2 Hz, 1H), 7.58 (d, J=8.8 Hz, 1H), 5.78 (s, 2H), 2.49 (s, 3H).

Example 45. Preparation of 2-methoxy-5-(quinolin-5-ylmethoxy)isonicotinaldehyde (Compound 120)

$^1$H NMR (400 MHz, CDCl3) δ 10.23 (s, 1H), 8.94 (dd, J=4.3, 1.5 Hz, 1H), 8.43 (d, J=8.5 Hz, 1H), 8.16 (d, J=14.1 Hz, 1H), 8.13 (s, 2H), 7.68 (dd, J=8.3, 7.2 Hz, 1H), 7.61 (d, J=6.7 Hz, 1H), 7.47 (dd, J=8.6, 4.3 Hz, 1H), 7.02 (s, 1H), 5.56 (s, 2H), 3.84 (s, 3H).

Example 46. Preparation of 2-methoxy-5-((2-(1-methyl-1H-pyrazol-5-yl)pyridin-3-yl)methoxy)isonicotinaldehyde (Compound 129)

Step 1

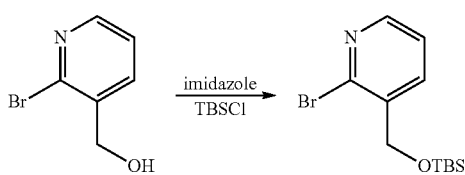

To a mixture of (2-bromopyridin-3-yl)methanol (20.0 g, 106.4 mmol, 1 eq.; refer to example 14) and imidazole (14.5 g, 212.8 mmol, 2 eq.) in DMF (50.0 mL) was added TBSCl (19.2 g, 150.7 mmol, 1.2 eq.) at rt. The mixture was stirred at rt for 1 h and diluted with a mixture of water (100 mL) and EtOAc (300 mL). The organic layer was washed with solution and brine, dried over Na$_2$SO$_4$, concentrated, and purified on silica gel using 10% EtOAc/hexanes as eluent to give 2-bromo-3-((tert-butyldimethylsilyloxy)methyl)pyridine (30.1 g, 94%) as a colorless oil. LRMS (M+H$^+$) m/z 302.0.

Step 2

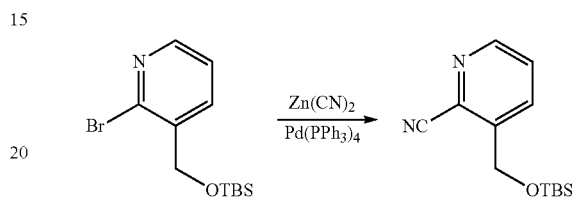

A mixture of 2-bromo-3-((tert-butyldimethylsilyloxy)methyl)pyridine (30.1 g, 100.0 mmol, 1 eq.) and Zn(CN)$_2$ (23.5 g, 200.0 mmol, 2.0 eq.) in DMF (100.0 mL) was purged with N$_2$ for 5 min and added Pd(PPh$_3$)$_4$ (5.78 g, 5.0 mmol, 0.05 eq.). The mixture was heated at 120° C. for 2 h under N$_2$, cooled, filtered, concentrated, and purified on silica gel using a mixture of EtOAc and hexanes as eluent to give 3-((tert-butyldimethylsilyloxy)methyl)picolinonitrile (20.4 g, 82%) as a colorless oil. LRMS (M+H$^+$) m/z 249.1.

Step 3:

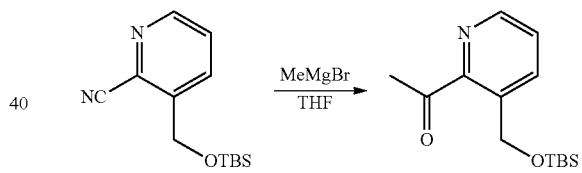

Methyl magnesium bromide (3M/ether, 41.0 mL, 123.4 mmol) was added to a stirred solution of 3-((tert-butyldimethylsilyloxy)methyl)picolinonitrile (20.4 g, 82.25 mmol) in THF (100.0 mL) at −78° C. The reaction mixture was warm to rt, quenched with aqueous citric acid solution, and extracted with EtOAc (50 mL) twice. The combined organic layers were washed with NaHCO$_{3(sat)}$ solution and brine, dried over Na$_2$SO$_4$, concentrated, and purified on silica gel using a mixture of EtOAc/hexanes as eluent to give 1-(3-((tert-butyldimethylsilyloxy)methyl)pyridin-2-yl)ethanone (12.9 g, 59%) as a colorless oil. LRMS (M+H$^+$) m/z 266.2.

Step 4:

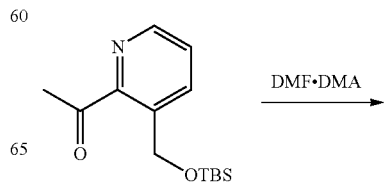

-continued

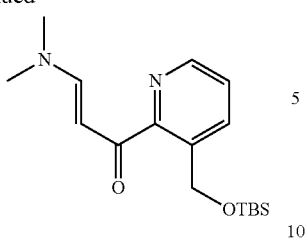

1-(3-((tert-butyldimethylsilyloxy)methyl)pyridin-2-yl) ethanone (10.8 g, 40.75 mmol) in dimethoxy-N,N-dimethylmethanamine (15.0 mL) was heated to reflux for 3 days. The mixture was concentrated and used for next step without further purification. LRMS (M+H⁺) m/z 321.1.

Step 5

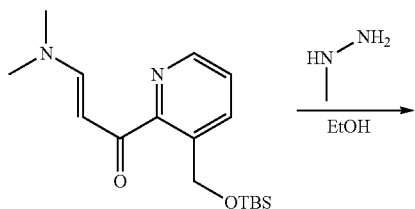

To (E)-1-(3-((tert-butyldimethylsilyloxy)methyl)pyridin-2-yl)-3-(dimethylamino)prop-2-en-1-one (crude above, 966.4 mg, 3.02 mmol, 1 eq.) in EtOH (10 mL) was added methylhydrazine (1.0 mL) at rt. The mixture was heated at 80° C. for 2 h, concentrated, and purified on silica gel using a mixture of EtOAc and hexanes as eluent to give a mixture of regio-isomers (420 mg; 46% for 2 steps). LRMS (M+H⁺) m/z 304.2.

Step 6

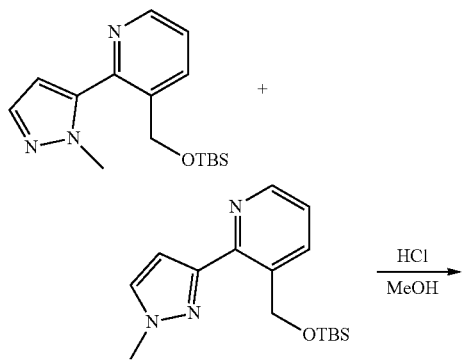

-continued

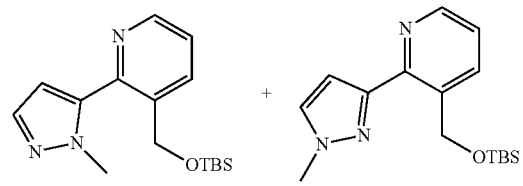

To a mixture of 3-((tert-butyldimethylsilyloxy)methyl)-2-(1-methyl-1H-pyrazol-5-yl)pyridine and 3-((tert-butyldimethylsilyloxy)methyl)-2-(1-methyl-1H-pyrazol-3-yl)pyridine (420 mg, 1.38 mmol) in MeOH (20 mL) was added HCl (4 N, 2.0 mL). The mixture was stirred at rt for 1 h, concentrated, and diluted with EtOAc (50 mL) and NaHCO₃ (sat) solution (10 mL). The layers were separated and aqueous layer was extracted with EtOAc three times. The combined organic layers were dried over Na₂SO₄, concentrated, and purified on silica gel using EtOAc as eluent to give (2-(1-methyl-1H-pyrazol-5-yl)pyridin-3-yl) methanol (187 mg, 72%) and (2-(1-methyl-1H-pyrazol-3-yl)pyridin-5-yl)methanol (55 mg, 21%) as white solids. Data for 2-(1-methyl-1H-pyrazol-5-yl)pyridin-3-yl)methanol: ¹H NMR (400 MHz; CDCl₃) 8.58 (d, 1H), 7.91 (d, 1H), 7.46 (s, 1H), 7.30 (dd, 1H), 6.36 (s, 1H), 4.62 (d, 2H), 3.83 (s, 3H), 2.1 (t, 1H). LRMS (M+H⁺) m/z 190.1; data for (2-(1-methyl-1H-pyrazol-3-yl)pyridin-5-yl)methanol: ¹H NMR (400 MHz; CDCl₃) 8.60 (d, 1H), 7.70 (d, 1H), 7.47 (s, 1H), 7.22 (dd, 1H), 6.99 (s, 1H), 5.91 (t, 1H), 4.68 (d, 2H), 4.01 (s, 3H). LRMS (M+H⁺) m/z 190.1

Step 7

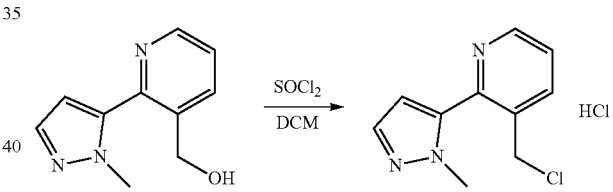

To (2-(1-methyl-1H-pyrazol-5-yl)pyridin-3-yl)methanol (182 mg, 0.96 mmol) in DCM (5 mL) was added SOCl₂ (1.5 mL) at rt. The reaction mixture was stirred at rt for 4 h and concentrated to dryness. The crude solid was suspended in toluene and concentrated to dryness. The process was repeated three times and dried under vacuum to give 3-(chloromethyl)-2-(1-methyl-1H-pyrazol-5-yl)pyridine (236 mg) as an off-white solid, which was used for next step without further purification.

Step 8

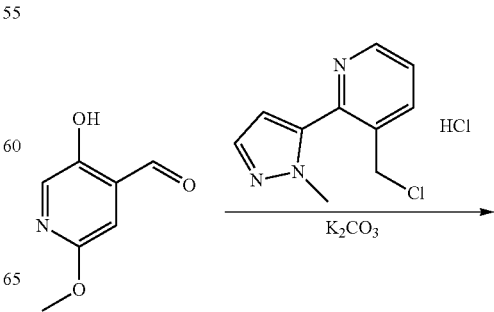

-continued

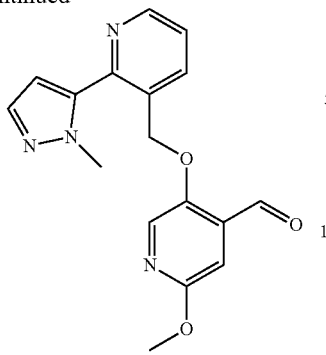

A mixture of 5-hydroxy-2-methoxyisonicotinaldehyde (147 mg, 0.96 mmol, 1 eq.), 3-(chloromethyl)-2-(1-methyl-1H-pyrazol-5-yl)pyridine hydrochloride (236 mg, 0.96 mmol, 1 eq.), and K$_2$CO$_3$ (532 mg, 3.85 mmol, 3 eq.) in DMF (3.0 mL) was heated at 70° C. for 2 h. The mixture was cooled, filtered, concentrated, and purified on silica gel using a mixture of EtOAc and hexanes as eluent to give 2-methoxy-5-((2-(1-methyl-1H-pyrazol-5-yl)pyridin-3-yl)methoxy)isonicotinaldehyde (232.5 mg, 75%) as an off-white solid. $^1$H NMR (400 MHz, CDCl$_3$) δ 10.40 (s, 1H), 8.77 (dd, J=4.7, 1.7 Hz, 1H), 8.03 (dd, J=7.9, 1.7 Hz, 1H), 7.93 (s, 1H), 7.55 (d, J=1.9 Hz, 1H), 7.44 (dd, J=7.9, 4.8 Hz, 1H), 7.11 (d, J=0.4 Hz, 1H), 6.43 (d, J=1.9 Hz, 1H), 5.20 (s, 2H), 3.97 (s, 3H), 3.92 (s, 3H). LRMS (M+H$^+$) m/z 325.1.

1H NMR (400 MHz, CDCl3) δ 10.40 (s, 1H), 8.77 (dd, J=4.7, 1.7 Hz, 1H), 8.03 (dd, J=7.9, 1.7 Hz, 1H), 7.93 (s, 1H), 7.55 (d, J=1.9 Hz, 1H), 7.44 (dd, J=7.9, 4.8 Hz, 1H), 7.11 (d, J=0.4 Hz, 1H), 6.43 (d, J=1.9 Hz, 1H), 5.20 (s, 2H), 3.97 (s, 3H), 3.92 (s, 3H).

Example 47. Preparation of 2-methoxy-5-((2-(1-methyl-1H-pyrazol-3-yl)pyridin-3-yl)methoxy)isonicotinaldehyde (Compound 130)

The title compound was prepared according to the procedure in Example 46.
$^1$H NMR (400 MHz, CDCl3) δ 10.49 (s, 1H), 8.66 (dd, J=4.7, 1.3 Hz, 1H), 8.11 (s, 1H), 8.03 (dd, J=7.8, 1.0 Hz, 1H), 7.45 (d, J=2.3 Hz, 1H), 7.31 (dd, J=7.9, 4.8 Hz, 1H), 7.13 (s, 1H), 6.97 (d, J=2.0 Hz, 1H), 5.73 (s, 2H), 3.95 (s, 3H), 3.93 (s, 3H).

Example 48. Preparation of 5-((2-(2H-tetrazol-5-yl)pyridin-3-yl)methoxy)-2-methoxyisonicotinaldehyde (Compound 131)

Step 1:

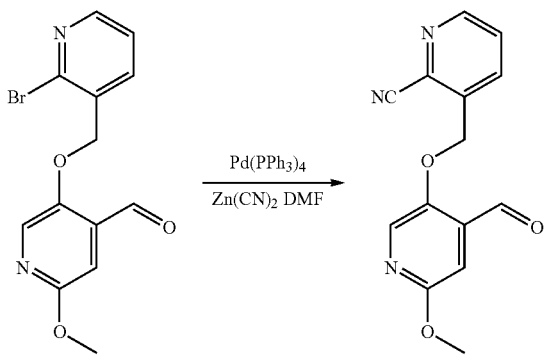 [SMILES: COc1cc(C=O)c(OCc2cccnc2Br)cn1 ; "Zn(CN)2 DMF" ; COc1cc(C=O)c(OCc2cccnc2C#N)cn1 ; "Pd(PPh3)4"]

To a mixture of 5-((2-bromopyridin-3-yl)methoxy)-2-methoxyisonicotinaldehyde (100 mg, 0.31 mmol, 1 equiv), Zn (CN)$_2$ (71 mg, 0.62 mmol, 2.0 equiv), Pd(PPh$_3$)$_4$ (72 mg, 0.06 mmol, 0.2 equiv) in a 5 mL microwave tube was added DMF (2 mL). The mixture was heated 15 min at 125° C. in a microwave reactor. The solid was filtered off and the filtrate was concentrated to dryness. The crude was purified on silica gel using a mixture of EtOAc and hexanes as eluent to give 3-((4-formyl-6-methoxypyridin-3-yloxy)methyl)picolinonitrile (71 mg, 84%) as a white solid. $^1$H NMR (400 MHz; CDCl$_3$) δ=10.54 (s, 1H), 8.86 (d, 1H), 8.22 (s, 1H), 8.20 (d, 1H), 7.74 (dd, 1H), 6.37 (s, 1H) 5.52 (s, 2H), 4.04 (s, 3H). LRMS (M+H$^+$) m/z 270.1.

Step 2:

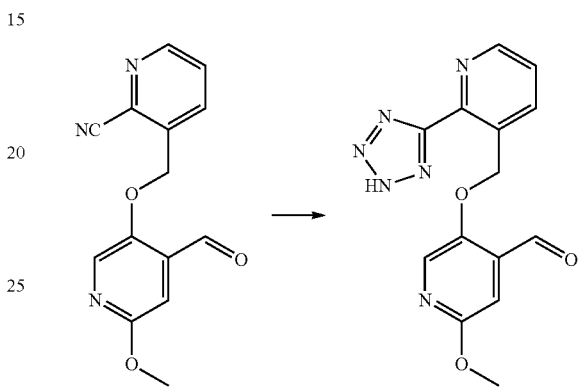

To TEA hydrochloride salt (123 mg, 0.89 mmol, 4 equiv.) and 3-((4-formyl-6-methoxypyridin-3-yloxy)methyl)picolinonitrile (70 mg, 0.26 mmol, 1 equiv.) in chlorobenzene (5.0 mL) was added NaN$_3$ (48 mg, 0.89 mmol, 4 equiv.) at rt. The mixture was heated to 110° C. for 2 h, cooled tort, and added water (5.0 mL). The precipitate was filtered and washed with EtOAc and water and dried under high vacuo to give 5-((2-(2H-tetrazol-5-yl)pyridin-3-yl)methoxy)-2-methoxyisonicotinaldehyde as a white solid. $^1$H NMR (400 MHz; DMSO) δ=10.23 (s, 1H), 8.61 (d, 1H), 8.16 (a, 1H), 8.10 (d, 1H), 7.38 (dd, 1H), 6.96 (s, 1H) 5.73 (s, 2H), 3.83 (s, 3H). LRMS (M+H$^+$) m/z 313.0.

Example 49. Preparation of 2-methoxy-5-((2-(4-methyl-1H-pyrazol-5-yl)pyridin-3-yl)methoxy)isonicotinaldehyde (Compound 132)

Step 1;

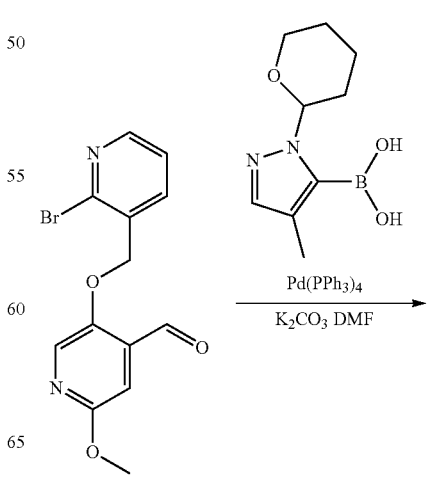

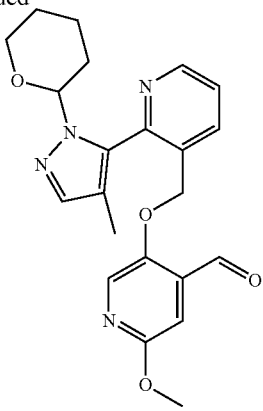

To a mixture of 5-((2-bromopyridin-3-yl)methoxy)-2-methoxyisonicotinaldehyde (100 mg, 0.31 mmol, 1 equiv), 4-methyl-1-(tetrahydro-2H-pyran-2-yl)-1H-pyrazol-5-ylboronic acid (98 mg, 0.47 mmol, 1.5 equiv), Pd(PPh$_3$)$_4$ (70 mg, 0.06 mmol, 0.2 equiv), K$_2$CO$_3$ (171 mg, 1.24 mmol, 4 equiv) in a 5 mL microwave tube was added DMF (2 mL). The mixture was heated 30 min at 125° C. in a microwave reactor. The solid was filtered off and the filtrate was concentrated to dryness. The crude was purified on silica gel using a mixture of EtOAc and hexanes as eluent to give 2-methoxy-5-((2-(4-methyl-1-(tetrahydro-2H-pyridin-2-yl)-1H-pyrazol-5-yl)pyridin-3-yl)methoxy)isonicotinaldehyde (110 mg, 87%) as a colorless oil. LRMS (M+H$^+$) m/z 409.2.

Step 2:

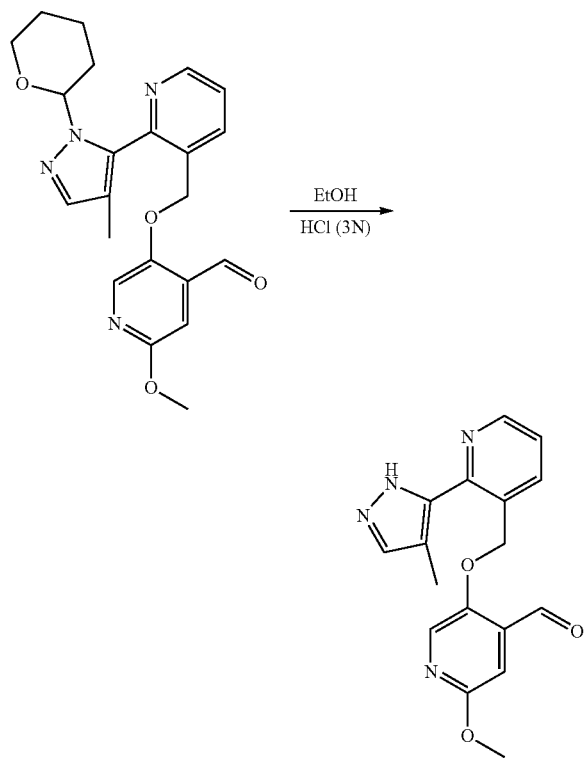

To 2-methoxy-5-((2-(4-methyl-1-(tetrahydro-2H-pyran-2-yl)-1H-pyrazol-5-yl)pyridin-3-yl)methoxy)isonicotinaldehyde (110 mg, 0.27 mmol, 1 equiv) suspended in EtOH (1 mL) was added HCl (1.0 mL, 3 N). The solution turned homogeneous and the mixture was stirred at rt overnight. The EtOH was partially removed by blowing in N$_2$ gas and basified to pH 9. The aqueous solution was extracted with EtOAc three times. The organic layer was dried over Na$_2$SO$_4$ and concentrated. The crude was purified on silica gel using a mixture of MeOH and DCM as eluent to give 2-methoxy-5-((2-(4-methyl-1H-pyrazol-5-yl)pyridin-3-yl)methoxy)isonicotinaldehyde (40 mg, 46%) as a white solid. $^1$H NMR (400 MHz; CDCl$_3$) δ=10.45 (s, 1H), 8.76 (d, 1H), 8.07 (br, 1H), 8.05 (s, 1H), 7.53 (s, 1H), 7.40 (dd, 1H), 7.13 (s, 1H), 5.52 (br, 2H), 3.98 (s, 3H). LRMS (M+H$^+$) m/z 325.1.

Example 50. Preparation of 5-((3-(1H-pyrazol-5-yl)isoquinolin-4-yl)methoxy)-2-methoxyisonicotinaldehyde (Compound 133)

Step 1:

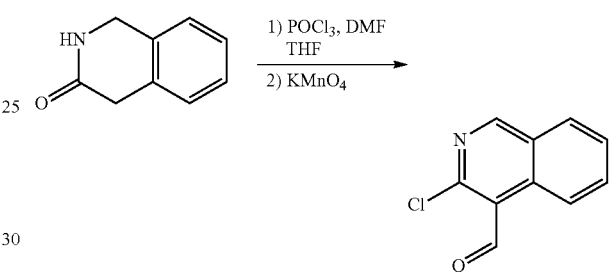

To a mixture of POCl$_3$ (0.73 mL, 7.85 mmol, 3.8 eqiv.) and DMF (0.6 g, 8.16 mmol, 4.0 equiv.) in THF was added 1,2-dihydroisoquinolin-3(4H)-one at 0° C. in portions for 5 min. The mixture was continued to stir at 0° C. for 1 h and poured into a mixture of 2 N NaOH (20 mL), ice (20 g), and toluene (20 mL). The organic phase was separated and the aqueous layer was extracted with toluene one more time. The combined organic layer was washed with water, dried over Na$_2$SO$_4$, and concentrated to half of its volume at low temperature in vacuo. To this mixture was added 2 N H$_2$SO$_4$ (20 mL) under vigorous stirring followed by ground KMnO$_4$ in portions. The mixture was continued to stir for another 4 h. The organic phase was separated, dried over Na$_2$SO$_4$, and concentrated to give 3-chloroisoquinoline-4-carbaldehyde (220 mg, 50% pure) as a oil, which was used for next step without further purification. LRMS (M+H$^+$) m/z 192.0.

Step 2:

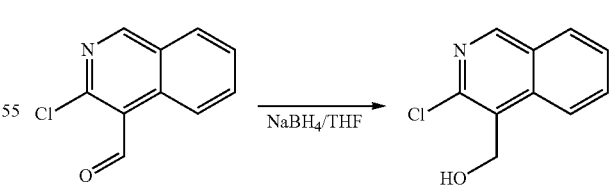

To 3-chloroisoquinoline-4-carbaldehyde (220 mg, crude) in THF (10 mL) was added NaBH$_4$ (155 mg, 4.08 mmol) at 0° C. The reaction mixture was stirred at 0° C. for 1 h, acidified to pH 3, and extracted with EtOAc. The combined organic layers were washed with saturated sodium bicarbonate solution and brine, dried over Na$_2$SO$_4$, filtered, and concentrated to give a crude solid. The crude was purified on silica gel using a mixture of EtOAc and hexanes as eluent to give (3-chloroisoquinolin-4-yl)methanol (92 mg, 24% for three steps). LRMS (M+H⁺) m/z 194.0.

Step 3:

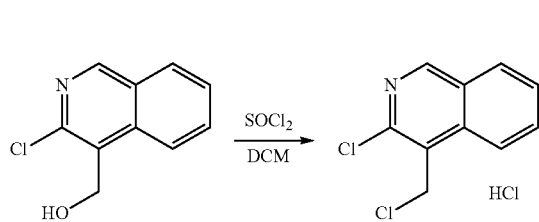

To (3-chloroisoquinolin-4-yl)methanol (92 mg, 0.48 mmol) in DCM (5 mL) was added SOCl₂ (mL) at rt The reaction mixture was stirred at rt for 4 h and concentrated to dryness. The crude solid was suspended in toluene and concentrated to dryness. The process was repeated three times and dried under vacuum to give an off-white solid (120 mg), which was used for next step without further purification.

Step 4:

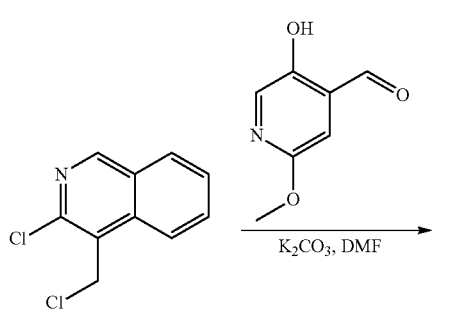

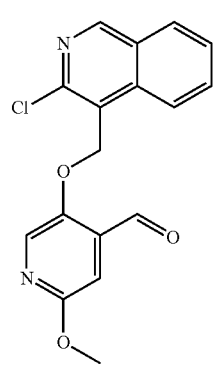

A mixture of 5-hydroxy-2-methoxyisonicotinaldehyde (73 mg, 0.48 mmol, 1 eq.), 3-chloro-4-(chloromethyl)isoquinoline (crude above, 0.48 mmol), and K₂CO₃ (265 mg, 1.92 mmol, 4 eq.) in DMF (2.0 mL) was heated at 60° C. for 1 h. The mixture was cooled, filtered, concentrated to dryness. The crude was purified on silica gel using a mixture of EtOAc and hexanes to give 5-((3-chloroisoquinolin-4-yl)methoxy)-2-methoxyisonicotinaldehyde (22 mg, 14%) as an yellow solid. ¹H NMR (400 MHz; CDCl₃) δ=10.19 (s, 1H), 9.05 (s, 1H), 8.23 (s, 1H) 8.06 (d, 1H), 7.98 (d, 1H), 7.76 (t, 1H), 7.63 (t, 1H), 7.01 (s, 1H), 5.72 (s, 2H), 3.87 (s, 3H). LRMS (M+H⁺) m/z 329.1.

Step 5:

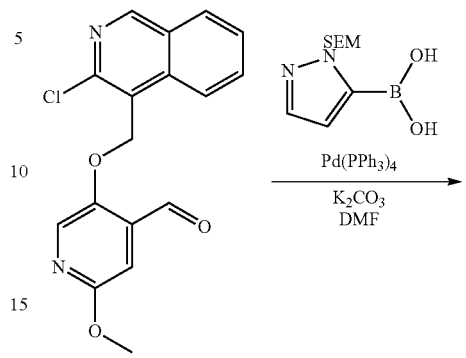

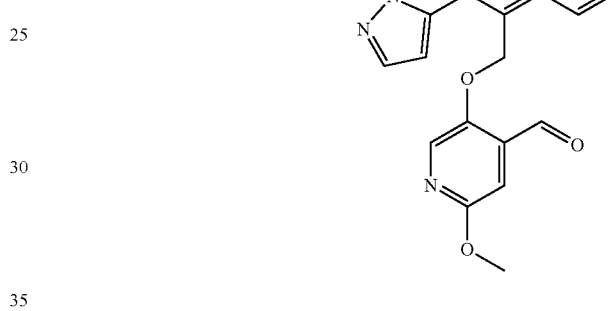

To a mixture of 5-((3-chloroisoquinolin-4-yl)methoxy)-2-methoxyisonicotinaldehyde (18 mg, 0.05 mmol, 1 equiv), 1-((2*(trimethylsilyl)ethoxy)methyl)-1H-pyrazol-5-ylboronic acid (20 mg, 0.08 mmol, 1.5 equiv), Pd(PPh₃)₄ (12 mg, 0.01 mmol, 0.2 equiv), K₂CO₃ (30 mg, 0.22 mmol, 4 equiv) in a 5 mL microwave tube were added DMF (2 mL). The mixture was heated 30 min at 125° C. in a microwave reactor. The solid was filtered off and the filtrate was concentrated to dryness. The crude was purified on silica gel using a mixture of EtOAc and hexanes as eluent to give 2-methoxy-5-((3-(1-((2-(trimethylsilyl)ethoxy)methyl)-1H-pyrazol-5-yl)isoquinolin-4-yl)methoxy)isonicotinaldehyde (10 mg, 38%) as a white solid. LRMS (M+H⁺) m/z 491.1.

Step 6: 1

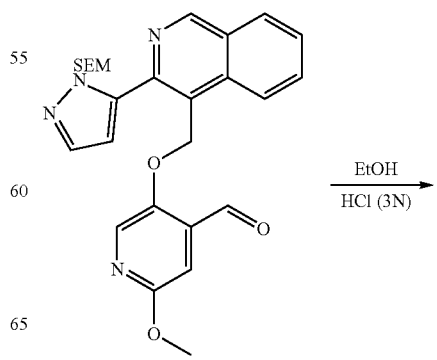

-continued

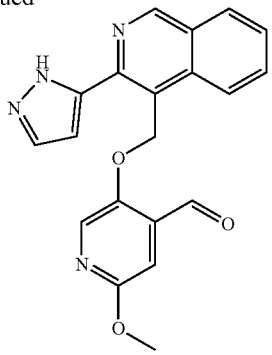

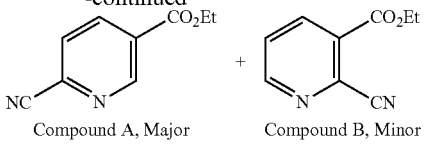

Compound A, Major     Compound B, Minor

To 2-methoxy-5-((3-(1-((2-(trimethylsilyl)ethoxy)methyl)-1H-pyrazol-5-yl)isoquinolin-4-yl)methoxy)isonicotinaldehyde (10 mg, 0.02 mmol, 1 equiv) suspended in EtOH (1 mL) was added HCl (0.1 mL, 3 N). The solution turned homogeneous and the mixture was stirred at rt overnight. The EtOH was partially removed by blowing in $N_2$ gas and basified to pH 9. The aqueous solution was extracted with EtOAc three times. The organic layer was dried over $Na_2SO_4$ and concentrated. The crude was purified on silica gel using MeOH and DCM as eluent to give 5-((3-(1H-pyrazol-5-yl)isoquinolin-4-yl)methoxy)-2-methoxyisonicotinaldehyde (6.0 mg, 83%) as a white solid. $^1$H NMR (400 MHz; CDCl$_3$) δ=10.17 (s, 1H), 9.25 (s, 1H), 8.18 (s, 1H), 8.05 (d, 1H), 7.99 (d, 1H), 7.73 (t, 1H), 7.60-7.68 (m, 2H), 7.03 (s, 1H), 6.70 (d, 1H), 5.85 (s, 2H), 3.85 (s, 3H). LRMS (M+H$^+$) m/z 361.1.

Example 51. Preparation of 2-(imidazo[1,5-a]pyridin-8-ylmethoxy)-5-methoxyisonicotinaldehyde Step 1:

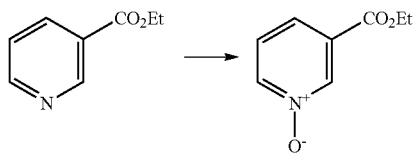 [SMILES: CCOC(=O)c1cccnc1 ; CCOC(=O)c1ccc[n+]([O-])c1]

To a cold solution of 3-ethoxycarbonylpyridine (25 g, 165.4 mmol, 1 eq) in DCM was slowly added mCPBA (70% wt, 198.5 mmol) and the reaction mixture was stirred at rt overnight. Reaction was cooled and diluted with DCM and then neutralized with slow addition of sat. NaHCO$_3$. Aqueous layer was washed with DCM (3×) and the combined organic layer was dried and evaporated to give a residue, which was purified by column chromatography (EtOAc/MeOH) to give 3-ethoxycarbonylpyridine N-oxide (13.6 g). MS: exact mass calculated for $C_8H_9NO_3$, 167.06; m/z found. 168 [M+H]$^+$.

Step 2:

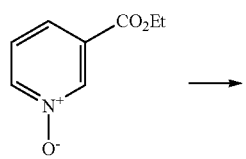

To a solution of 3-ethoxycarbonylpyridine N-oxide in 330 mL of DCM were added trimethylsilyl cyanide (TMSCN) (11.0 g, 65.9 mmol, 1.0 eq) and dimethylcarbamoyl chloride (7.1 g, 65.9 mmol, 1.0 eq) and the reaction mixture was stirred at rt for 2 days. Then 10% $K_2CO_3$ was slowly added to make the reaction mixture basic. Organic layer was separated, dried and evaporated to provide the crude, which was purified by column chromatography to provide compounds A (5.7 g) and B (3.5 g).

Steps 3 and 4:

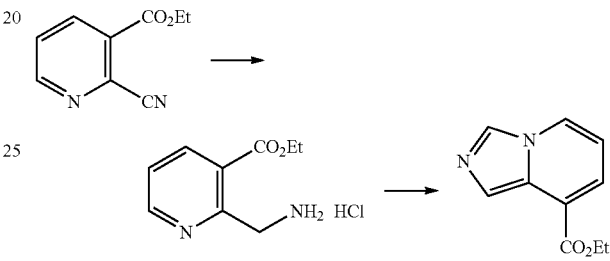

To a solution of ethyl 2-cyano-3-pyridinecarboxylate (2.5 g) and conc. HCl (5 mL) in 150 mL ethanol was added 10% Pd/C (wet, 250 mg) and the reaction mixture was hydrogenated using a hydrogen balloon and stirred for 12 h. The reaction was filtered through celite and ethanol was evaporated to give ethyl 2-(aminomethyl)-3-pyridinecarboxylate HCl as a white solid which was used in the next step without further purification.

A mixture of 44.8 mL of acetic anhydride and 19.2 mL of formic acid was heated in a 50-60° C. oil bath temperature for 3 h and then cooled to rt to give formic-acetic anhydride, which was then slowly added to the solid ethyl 2-(aminomethyl)-3-pyridinecarboxylate HCl and then stirred at rt for 8 h. Excess reagent was evaporated to give a residue, which was neutralized by very stow addition of sat. NaHCO$_3$ solution. Solution was extracted with DCM, dried and evaporated to provide ethyl imidazo[1,5-a]pyridine-8-carboxylate as a yellow solid (crude weight 2.7 g). MS: exact mass calculated for $C_{10}H_{10}N_2O_2$, 190.07; m/z found, 191 [M+H]$^+$.

Steps 5 and 6:

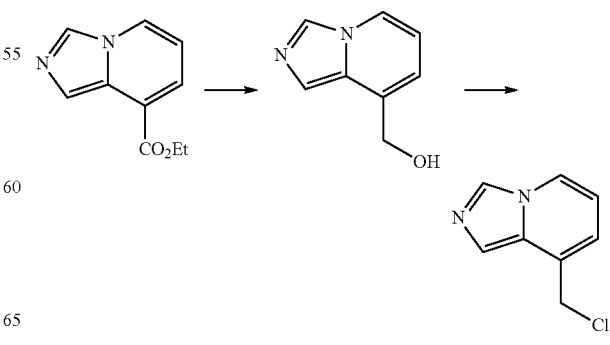

To a cold solution of lithium aluminum hydride (1.62 g, 42.4 mmol, 4.0 eq) in THF (50 mL) was added the crude ethyl imidazo[1,5-a]pyridine-8-carboxylate (2.7 g, 14.2 mmol, 1.0 eq) and the reaction mixture was heated at reflux for 2 h. The reaction was cooled and water (1.7 mL), 15% NaOH (1.7 mL) and water (5.1 mL) were slowly added. Solution was diluted with excess EtOAc and stirred at rt for 30 min. The solution was filtered and the solid was washed with ethyl acetate. Organic layers were combined, dried and solvent was removed to give crude imidazo[1,5-a]pyridine-8-methanol, which was purified by column chromatography (EtOAc/Hexane). MS: exact mass calculated for $C_8H_8N_2O$, 148.06; m/z found, 149 $[M+H]^+$.

To a solution of imidazo[1,5-a]pyridine-8-methanol (800 mg) in chloroform (50 mL) was slowly added thionyl chloride (10 mL) and the reaction mixture was stirred at rt for 8 h. Chloroform was removed and the residue was then taken in toluene and toluene was evaporated (3×) to give a solid, which was used in the next step without further purification. MS: exact mass calculated for $C_8H_7?ClN_2$, 166.03; m/z found, 167 $[M+H]^+$.

Step 7:

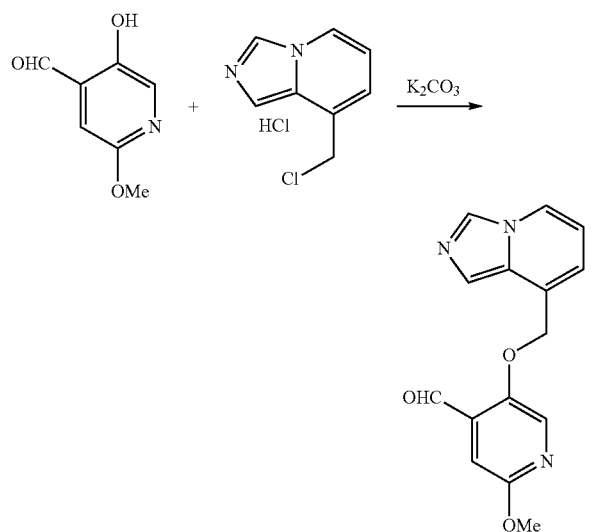

To a solution of chloride (1.25 mmol, 1.0 eq), and hydroxynicotinaldehyde (1.25 mmol, 1.0 eq) in DMF (10 mL) is added $K_2CO_2$ (3.0 eq) and the reaction mixture was heated at 80-90° C. for 5 h. Solvent is removed and the residue is purified by column chromatography (EtOAc/MeOH).

Example 52. Preparation of 5-(imidazo[1,5-a]pyridin-8-ylmethoxy)-2-methoxyisonicotinaldehyde (Compound 140)

The title compound was prepared according to the procedure in Example 51.

$^1$H NMR (400 MHz, CDCl3) δ 10.47 (s, 1H), 8.21 (s, 1H), 8.11 (s, 1H), 7.97 (d, J=7.0 Hz, 1H), 7.52 (s, 1H), 7.12 (s, 1H), 6.87 (t, J=8.1 Hz, 1H), 6.62 (t, J=6.8 Hz, 1H), 537 (s, 2H), 3.92 (s, 3H).

Example 53. Preparation of 2-(5-(imidazo[1,2-a]pyridin-8-ylmethoxy)-2-methoxypyridin-4-yl)thiazolidine (Compound 155)

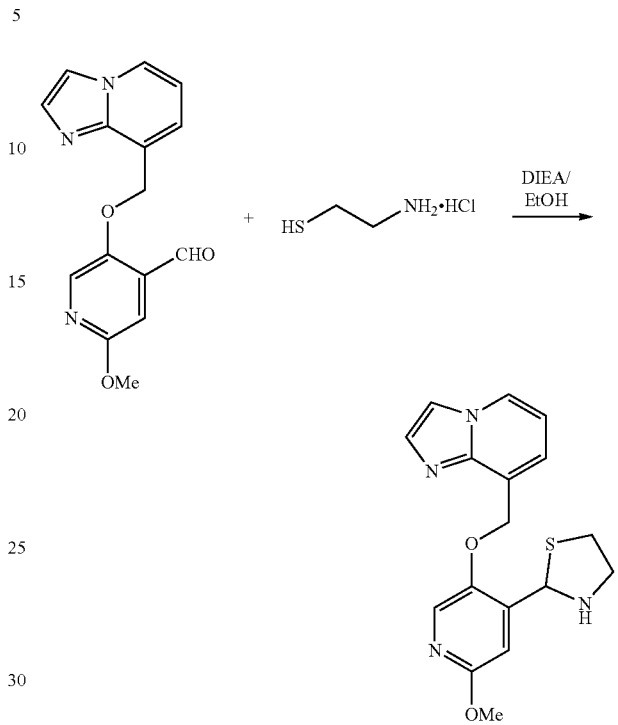

To a solution of aldehyde (0.326 g, 1.15 mmol, 1 eq) and DIEA (0.15 g 1.15 mmol, 1.0 eq) in EtOH (4 mL) was added cysteamine.HCl (135 mg, 1.15 mmol, 1.0 eq) and the reaction mixture was stirred at rt for 24 h. The reaction mixture was diluted with water and the solid was filtered, washed (water) and dried. The crude was purified by column chromatography (DCM/MeOH) to give the pure material. MS: exact mass calculated for $C_{17}H_{18}N_4O_2S$, 342.12; m/z found, 343 $[M+H]^+$.

Example 54. Preparation of 1-(2-(5-(imidazo[1,2-a]pyridin-8-ylmethoxy)-2-methoxypyridin-4-yl)thiazolidin-5-yl)ethanone (Compound 156)

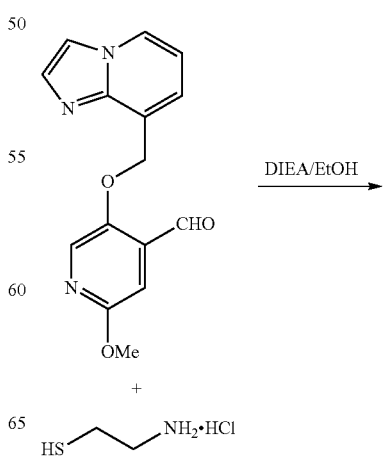

-continued

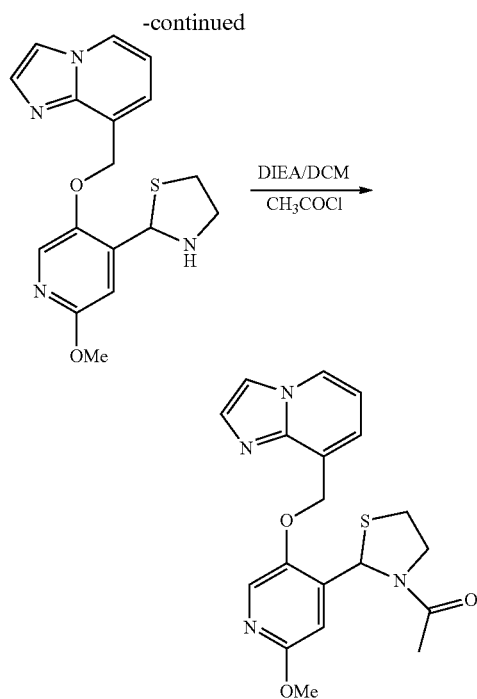

To a solution of aldehyde (0.900 g, 3.18 mmol, 1 eq) and DIEA)(0.45 g, 3.5 mmol, 1.1 eq) in EtOH (11 mL) was added cysteamine.HCl (0.398 g, 3.5 mmol, 1.1 eq) and the reaction mixture was stirred at rt for 24 h. Solvent was removed and the crude was directly used in the next step. To a solution of crude thiazoline (3.18 mmol) and DIEA (1.5 eq) in DCM (25 mL) at 0° C. was added acetyl chloride (1.2 eq) drop wise and the reaction mixture was stirred at room temperature for 24 h. The reaction mix was diluted with DCM and washed with saturated aq. NaHCO3. The organic layer was dried and solvent was removed to give the crude amide, which was purified by column chromatography (EtOAc/MeOH) to give the amide. MS: exact mass calculated for C19H20N4O3S, 384.13; m/z found, 385 [M+H]+.

Example 55. Preparation of 5-hydroxy-2-methoxyisonicotinaldehyde

Step 1

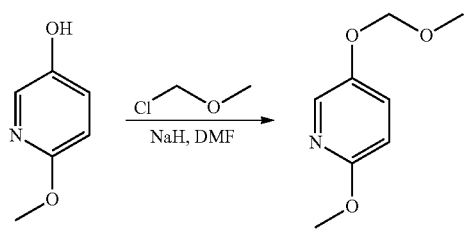

To a solution of 6-methoxypyridin-3-ol (20 g, 0.16 mol, 1 eq.) in DMF (200 mL) was added NaH (60% in mineral oil; 9.6 g, 0.24 mol, 1.5 eq.) at 0-5° C. portion-wise. Upon the completion of addition, the mixture was continued to stir at 0-5° C. for 15 min, added chloromethyl methyl ether (15.5 g, 0.19 mol, 1.2 eq.), stirred at 0-5° C. for another 20 min, and quenched with NH4Cl$_{(sat.)}$ solution. The aqueous layer was extracted with EtOAc (3×100 mL) and the combined organic layers were washed with water and brine, dried over Na2SO4, concentrated, and purified on silica gel using 25% EtOAc/hexanes as eluent to give 2-methoxy-5-(methoxymethoxy)pyridine (24.1 g, 89.3%) as a colorless oil. $^1$H NMR (400 MHz; CDCl$_3$) 7.97 (d, 1H), 7.35 (dd, 1H), 6.70 (d, 1H), 5.12 (s, 2H), 3.91 (s, 3H), 3.51 (s, 3H), LRMS (M+H+) m/z 170.1

Step 2

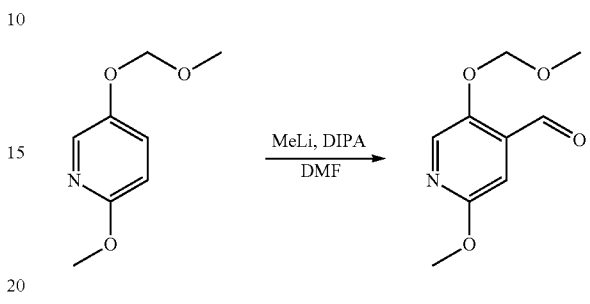

To a mixture of 2-methoxy-5-(methoxymethoxy)pyridine (30 g, 0.178 mol, 1 eq.) and diisopropylamine (507 uL, 3.6 mmol, 0.02 eq.) in THF (500 mL) was added methyl lithium (1.6 M/THF, 200 mL, 0.32 mol, 1.8 eq.) at −40° C. Upon the completion of addition, the mixture was warmed to 0° C., continued to stir at 0° C. for 3 h, cooled back down to −40° C. and added DMF (24.7 mL, 0.32 mol, 1.8 eq.) slowly. The mixture was then stirred at −40° C. for 1 h, quenched with a mixture of HCl (12 N, 120 mL) and THF (280 mL), warmed to rt, and added water (200 mL). The pH of the mixture was adjusted to pH 8-9 with solid K2CO3. The aqueous layer was extracted with EtOAc (300 mL) twice. The combined organic layers were dried over Na2SO4 and concentrated to give 2-methoxy-5-(methoxymethoxy)isonicotinaldehyde (33.5 g, 95.7%) as a brown solid, which was used for next step without further purification. $^1$H NMR (400 MHz; CD$_3$OD) 7.90 (s, 1H), 6.92 (s, 1H), 5.64 (s, 1H), 5.20 (s, 2H), 3.84 (s, 3H), 3.48 (s, 3H). LRMS (M+H+) m/z 198.1

Step 3

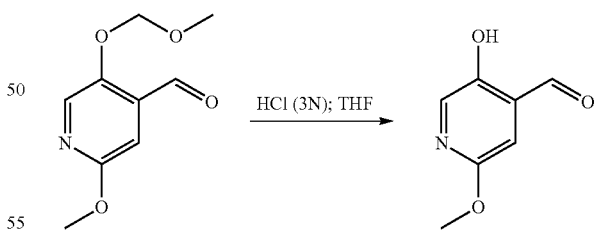

To a solution of 2-methoxy-5-(methoxymethoxy)isonicotinaldehyde (33.5 g, 0.17 mol, 1 eq.) in THF (150 mL) was added HCl (3 N, 250 ml., 4.4 eq.). The reaction was stirred at 50° C. for 1 h, cooled to rt, and diluted with water (500 mL). The mixture was neutralized to pH 7-8 with solid K2CO3. The pale yellow solid was collected, washed with water, and dried to give 5-hydroxy-2-methoxyisonicotinaldehyde (17.9 g, 74.6%) as a pale yellow solid. $^1$H NMR (400 MHz; DMSO) δ=10.31 (s, 1H), 8.03 (s, 1H), 6.89 (s, 1H), 3.80 (s, 3H). LRMS (M+H+) m/z 154.0.

Example 56. Preparation of 5-((2-(1-isopropyl-1H-pyrazol-5-yl)pyridin-3-yl)methoxy)-2-methoxyisonicotinaldehyde (Compound 150)

Step 1:

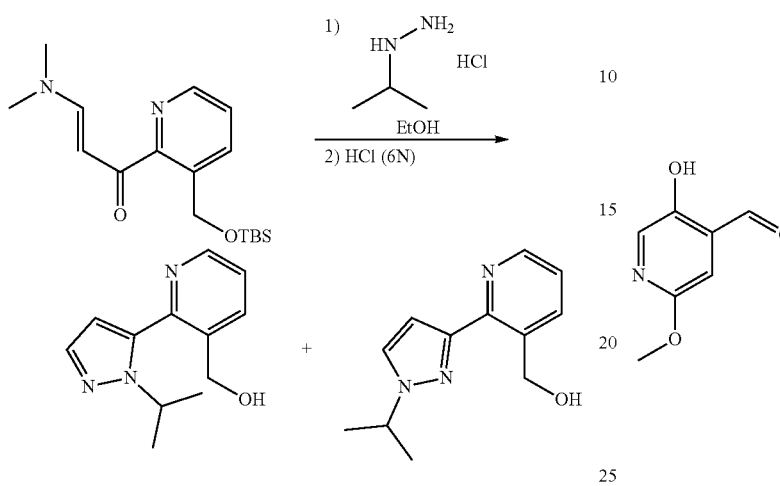

To (E)-1-(3-((tert-butyldimethylsilyloxy)methyl)pyridin-2-yl)-3-(dimethylamino)prop-2-en-1-one (crude, 1.03 g, 3.22 mmol, 1 eq.; refer to Example 46) in EtOH (10 mL) was added isopropylhydrazine hydrochloride (430 mg, 3.86 mmol, 1.2 eq.). The mixture was heated at 80° C. for 2 h, cooled, added HCl (6 N, 0.5 mL), and stirred O/N. The mixture was concentrated and diluted with EtOAc (80 mL) and NaHCO$_{3(sat)}$ (10 mL) solution. The layers were separated and the aqueous layer was extracted with EtOAc three times. The combined organic layers were dried over Na$_2$SO$_4$, concentrated, and purified on silica gel using EtOAc as eluent to give (2-(1-isopropyl-1H-pyrazol-5-yl)pyridin-3-yl)methanol (500 mg, 71%) and (2-(1-isopropyl-1H-pyrazol-3-yl)pyridin-5-yl)methanol (55 mg, 25%) as pale yellow oils. Data for 2-(1-isopropyl-1H-pyrazol-5-yl)pyridin-3-yl)methanol: $^1$H NMR (400 MHz, CDCl$_3$) δ 8.67 (dd, J=4.7, 1.5 Hz, 1H), 8.0 (d, J=7.8 Hz, 1H), 7.61 (d, J=1.8 Hz, 1H), 7.39 (dd, J=7.8, 4.8 Hz, 1H), 6.37 (d, J=1.8 Hz, 1H), 4.67 (s, 2H), 4.55 (sep, J=6.6 Hz 1H), 1.98-2.05 (br, 1H), 1.47 (d, J=6.6 Hz, 6H). LRMS (M+H$^+$) m/z 218.1 Data for (2-(1-isopropyl-1H-pyrazol-3-yl)pyridin-5-yl)methanol: $^1$H NMR (400 MHz, CDCl$_3$) δ 8.62 (dd, J=4.8, 1.6 Hz, 1H), 7.72 (d, J=7.6 Hz, 1H), 7.55 (d, J=2.4 Hz, 1H), 7.23 (dd, J=7.6.4.8 Hz, 1H), 6.99 (dd, J=8.0, 6.5 Hz, 1H), 6.07 (t, J=7.6 Hz, 1H), 4.67 (d, J=7.6 Hz, 2H), 4.58 (sep, J=6.7 Hz, 1H), 1.60 (d, J=6.7 Hz, 1H). LRMS (M+H$^+$) m/z 218.1

Step 2:

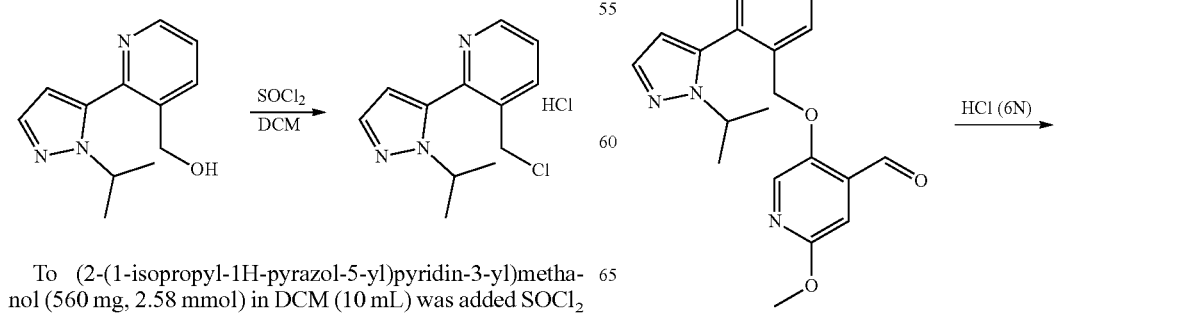

To (2-(1-isopropyl-1H-pyrazol-5-yl)pyridin-3-yl)methanol (560 mg, 2.58 mmol) in DCM (10 mL) was added SOCl$_2$ (3.0 mL) at rt The reaction mixture was stirred at rt for 4 h and concentrated to dryness. The crude solid was suspended in toluene and concentrated to dryness. The process was repeated three times and dried under vacuum to give 3-(chloromethyl)-2-(1-isopropyl-1H-pyrazol-5-yl)pyridine hydrochloride (700 mg) as an off-white solid, which was used for next step without further purification.

Step 3:

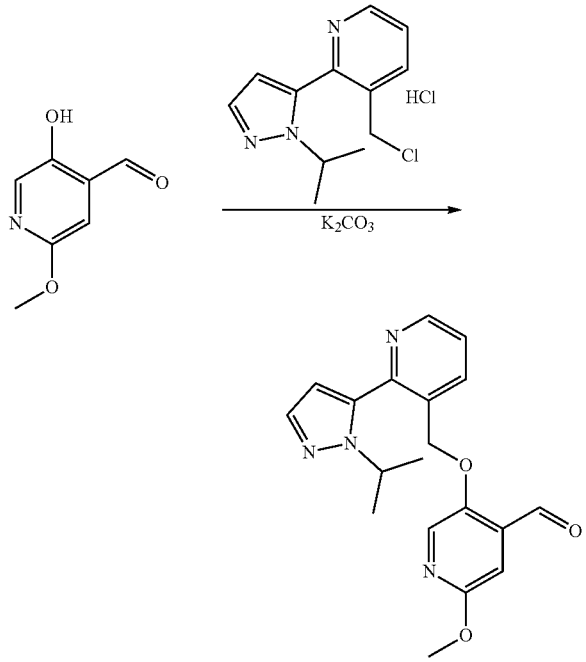

A mixture of 5-hydroxy-2-methoxyisonicotinaldehyde (395 mg, 2.58 mmol, 1 eq.), 3-(chloromethyl)-2-(1-isopropyl-1H-pyrazol-5-yl)pyridine hydrochloride (700 mg, 2.58 mmol, 1 eq.), and K$_2$CO$_3$ (1.4 g, 10.32 mmol, 4 eq.) in DMF (10.0 mL) was heated at 70° C. for 2 h. The mixture was cooled, filtered, concentrated, and purified on silica gel using a mixture of EtOAc and hexanes as eluent to give 5-((2-(1-isopropyl-1H-pyrazol-5-yl)pyridin-3-yl)methoxy)-2-methoxyisonicotinaldehyde (590 mg, 65%) as an off-white solid. $^1$H NMR (400 MHz. CDCl$_3$) δ 10.41 (s, 1H), 8.76 (dd, J=4.7, 1.6 Hz, 1H), 8.04 (dd, J=7.9, 1.6 Hz, 1H), 7.90 (s, 1H), 7.61 (d, J=1.8 Hz, 1H), 7.44 (dd, J=7.9, 4.8 Hz, 1H), 7.10 (s, 1H), 6.37 (d, J=1.8 Hz, 1H), 5.14 (s, 2H), 4.65 (sep, 6.6 Hz, 1H), 3.91 (s, 3H), 1.49 (d, J=6.6 Hz, 6H). LRMS (M+H$^+$) m/z 353.1.

Step 4:

-continued

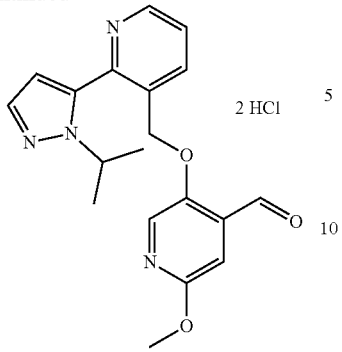

5-((2-(1-isopropyl-1H-pyrazol-5-yl)pyridin-3-yl) methoxy)-2-methoxyisonicotinaldehyde (980 mg, 2.78 mmol, 1 eq.) in HCl (6 N, 92 mL, 20 eq.) solution was freeze at −78° C. The mixture was lyophilized O/N to give 5-((2-(1-isopropyl-1H-pyrazol-5-yl)pyridin-3-yl)methoxy)-2-methoxyisonicotinaldehyde bis-hydrochloride as a yellow solid. $^1$H NMR (400 MHz, D$_2$O) δ 8.85 (dd, J=5.7, 1.3 Hz, 1H), 8.78 (d, J=8.2 Hz, 1H), 8.12 (dd, J=8.1, 5.7 Hz, 1H), 7.76 (s, 1H), 7.72 (d, J=2.0 Hz, 1H), 7.46 (s, 1H), 6.65 (d, J=2.1 Hz, 1H), 6.09 (s, 1H), 5.09 (s, 2H), 4.24 (sep, J=6.6 Hz, 1H), 4.04 (s, 3H), 1.26 (d, J=6.6 Hz, 7H). LRMS (M+H$^+$) m/z 353.1.

$^1$H NMR (400 MHz, CDCl$_3$) δ 10.41 (s, 1H), 8.76 (dd, J=4.7, 1.6 Hz, 1H), 8.04 (dd, J=7.9, 1.6 Hz, 1H), 7.90 (s, 1H), 7.61 (d, J=1.8 Hz, 1H), 7.44 (dd, J=7.9, 4.8 Hz, 1H), 7.10 (s, 1H), 6.37 (d, 1.8 Hz, 1H), 5.14 (s, 2H), 4.65 (hept, J=6.6 Hz, 1H), 3.91 (s, 3H), 1.49 (d, J=6.6 Hz, 6H).

Examples 57-62 were prepared according to the procedure in Example 55.

Example 57. Preparation of 2-methoxy-5-((2-(1-(2-methoxyethyl)-1H-pyrazol-5-yl)pyridin-3-yl)methoxy)isonicotinaldehyde (Compound 172)

$^1$H NMR (400 MHz, DMSO) δ 13.04 (s, 1H), 10.23 (s, 1H), 8.40 (d, J=4.4 Hz, 1H), 8.10 (s, 1H), 7.93 (d, J=7.7 Hz, 1H), 7.84 (d, J=8.5 Hz, 1H), 7.80 (d, J=7.7 Hz, 1H), 7.68 (dd, J=8.6, 4.4 Hz, 1H), 7.57 (t, J=7.7 Hz, 1H), 5.41 (s, 2H).

Example 58. Preparation of 2-methoxy-5-((2-(1-propyl-1H-pyrazol-5-yl)pyridin-3-yl)methoxy)isonicotinaldehyde (Compound 173)

$^1$H NMR (400 MHz, CDCl3) δ 10.41 (s, 1H), 8.76 (dd, J=4.7, 1.6 Hz, 1H), 8.04 (dd, J=7.9, 1.3 Hz, 1H), 7.93 (s, 1H), 7.57 (d, J=1.8 Hz, 1H), 7.44 (dd, J=7.9, 4.8 Hz, 1H), 7.11 (s, 1H), 6.41 (d, J=1.9 Hz, 1H), 5.17 (s, 2H), 4.23 (t, J=7.4 Hz, 2H), 3.92 (s, 3H), 1.80 (sex, J=7.4 Hz, 2H), 0.81 (t, J=7.4 Hz, 3H).

Example 59. Preparation of 2-methoxy-5-((2-(1-(2,2,2-trifluoroethyl)-1H-pyrazol-5-yl)pyridin-3-yl)methoxy)isonicotinaldehyde (Compound 174)

$^1$H NMR (400 MHz, CDCl3) δ 10.33 (s, 1H), 8.67 (dd, J=4.8, 1.6 Hz, 1H), 7.97 (dd, J=7.9, 1.4 Hz, 1H), 7.91 (s, 1H), 7.59 (d, J=1.9 Hz, 1H), 7.38 (dd, J=7.9, 4.8 Hz, 1H), 7.05 (s, 1H), 6.47 (d, J=1.9 Hz, 1H), 5.17 (q, J=8.6 Hz, 2H), 5.11 (s, 2H), 3.85 (s, 3H).

Example 60. Preparation of 5-((2-(1-(2,2-difluoroethyl)-1H-pyrazol-5-yl)pyridin-3-yl)methoxy)-2-methoxyisonicotinaldehyde (Compound 175)

$^1$H NMR (400 MHz, CDCl$_3$) δ 10.31 (s, 1H), 8.66 (dd, J=4.8, 1.6 Hz, 1H), 7.96 (dd, J=7.9, 1.4 Hz, 1H), 7.87 (s, 1H), 7.55 (d, J=0.9 Hz, 1H), 7.36 (dd, J=7.9, 4.8 Hz, 1H), 7.02 (s, 1H), 6.42 (d, J=1.9 Hz, 1H), 6.11 (tt, J=56.0, 4.4 Hz, 1H), 5.11 (s, 2H), 4.67 (td, J=13.4, 4.4 Hz, 2H), 3.83 (s, 3H).

Example 61. Preparation of 3-((2-(1-isopropyl-1H-pyrazol-5-yl)pyridin-3-yl)methoxy)picolinaldehyde (Compound 176)

$^1$H NMR (400 MHz, CDCl$_3$) δ 10.34 (s, 1H), 8.76 (dd, J=4.7, 1.6 Hz, 1H), 8.47 (dd, J=4.4, 1.0 Hz, 1H), 8.32 (dd, J=7.9, 1.5 Hz, 1H), 7.64 (d, J=1.8 Hz, 1H), 7.49 (td, J=8.3, 4.6 Hz, 2H), 7.31 (d, J=8.5 Hz, 1H), 6.39 (d, J=1.8 Hz, 1H), 5.15 (s, 2H), 4.65 (sep, J=6.6 Hz, 1H), 1.49 (d, J=6.6 Hz, 6H).

Example 62. Preparation of 3-((2-(1-isopropyl-1H-pyrazol-5-yl)pyridin 3-yl)methoxy)-6-methylpicolinaldehyde (Compound 177)

$^1$H NMR (400 MHz, CDCl$_3$) δ 10.31 (s, 1H), 8.75 (dd, J=4.7, 1.3 Hz, 1H), 8.29 (d, J=7.9 Hz, 1H), 7.64 (d, J=1.7 Hz, 1H), 7.48 (dd, J=7.9, 4.8 Hz, 1H), 7.31 (d, J=8.6 Hz, 1H), 7.20 (d, J=8.6 Hz, 1H), 6.38 (d, J=1.7 Hz, 1H), 5.11 (s, 2H), 4.64 (sep, J=6.6 Hz, 1H), 2.61 (s, 3H), 1.49 (d, J=6.6 Hz, 6H).

Example 63. Preparation of 5-((2-(1-cyclobutyl-1H-pyrazol-5-yl)pyridin-3-yl)methoxy)-2-methoxyisonicotinaldehyde (Compound 195)

$^1$H NMR (400 MHz, CDCl3) δ 10.31 (s, 1H), 8.68 (dd, J=4.8, 1.6 Hz, 1H), 7.94 (dd, J=7.9, 1.6 Hz, 1H), 7.79 (s, 1H), 7.54 (d, J=1.8 Hz, 1H), 7.36 (dd, J=7.9, 4.8 Hz, 1H), 7.01 (s, 1H), 6.30 (d, J=1.8 Hz, 1H), 5.05 (s, 2H), 4.77 (quin, J=8.4 Hz, 1H), 3.82 (s, 3H), 2.74-2.56 (m, 2H), 2.32-2.15 (m, 2H), 1.87-1.73 (m, 1H), 1.72-1.59 (m, 1H).

Example 64. Preparation of 5-((2-(1-cyclohexyl-1H-pyrazol-5-yl)pyridin-3-yl)methoxy)-2-methoxyisonicotinaldehyde (Compound 196)

$^1$H NMR (400 MHz, CDCl3) δ 10.33 (s, 110, 8.68 (dd, J=4.7, 1.5 Hz, 1H), 7.96 (dd, J=7.9, 1.2 Hz, 1H), 7.81 (s, 1H), 7.51 (d, J=1.8 Hz, 1H), 7.36 (dd, J=7.9, 4.8 Hz, 1H), 7.02 (s, 1H), 6.28 (d, J=1.8 Hz, 1H), 5.05 (s, 2H), 4.10 (quin, J=7.6 Hz, 1H), 3.83 (s, 3H), 1.96-1.83 (m, J=2.9 Hz, 4H), 1.83-1.68 (m, 2H), 1.68-1.45 (m, 2H), 1.33-1.06 (m, 2H).

Example 65. Preparation of 5-((2-(1-(cyclohexylmethyl)-1H-pyrazol-5-yl)pyridin-3-yl)methoxy)-2-methoxyisonicotinaldehyde (Compound 197)

$^1$H NMR (400 MHz, CDCl3) δ 10.43 (s, 1H), 8.76 (dd, J=4.7, 1.4 Hz, 1H), 8.04 (dd, J=7.9, 1.0 Hz, 1H), 7.93 (s, 1H), 7.58 (d, J=1.7 Hz, 1H), 7.45 (dd, J=7.9, 4.8 Hz, 1H), 7.11 (s, 1H), 6.40 (d, J=1.8 Hz, 1H), 5.16 (s, 2H), 4.13 (d, J=7.3 Hz, 2H), 3.92 (s, 3H), 1.92-1.74 (m, 1H), 1.60 (dd, J=8.2, 4.5 Hz, 3H), 1.47 (d, J=11.4 Hz, 2H), 1.21-0.98 (m, 3H), 0.91-0.71 (m, 2H).

Example 66. Preparation of 5-((2-(1-cyclopentyl-1H-pyrazol-5-yl)pyridin-3-yl)methoxy)-2-methoxy-isonicotinaldehyde (Compound 198)

¹H NMR (400 MHz, CDCl3) δ 10.42 (s, 1H), 8.77 (dd, J=4.7, 1.5 Hz, 1H), 8.04 (dd, J=7.9, 1.2 Hz, 1H), 7.90 (s, 1H), 7.60 (d, J=1.8 Hz, 1H), 7.45 (dd, J=7.9, 4.8 Hz, 1H), 7.11 (s, 1H), 6.38 (d, J=1.9 Hz, 1H), 5.15 (s, 2H), 4.74 (quin, J=7.5 Hz, 1H), 3.92 (s, 3H), 2.23-1.85 (m, 6H), 1.63-1.51 (m, 2H).

Example 67. Preparation of 2-(difluoromethoxy)-5-(imidazo[1,2-a]pyridin-8-ylmethoxy)isonicotinaldehyde (Compound 158)

Step 1:

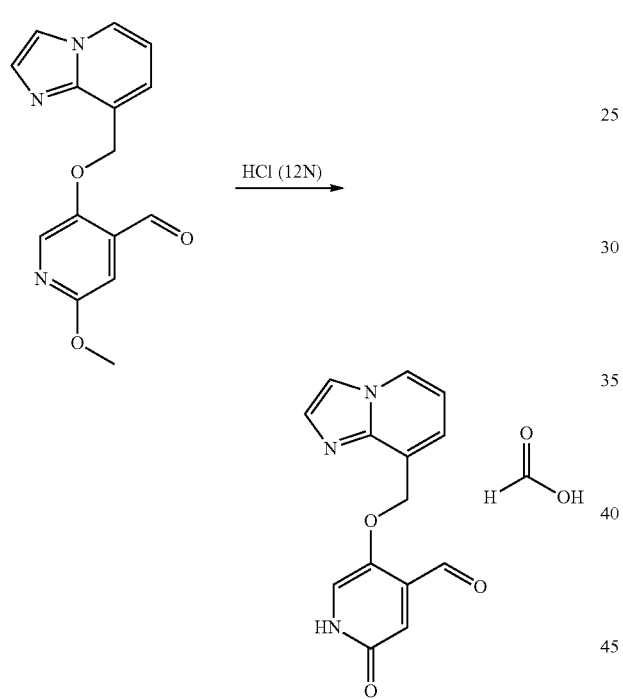

To 5-(imidazo[1,2-a]pyridin-8-ylmethoxy)-2-methoxy-isonicotinaldehyde (300 mg, 0.84 mmol, 1 equiv) in a vial was added HCl (6 N, 1 mL, 6 mmol). The mixture was concentrated, dried under vaccum at 60° C. O/N, cooled to rt, and dissolved in NaOH (3 N, 5 mL), filtered, and washed with with EtOAc twice. The pH of the aqueous layer was adjust to pH 6-7, filtered, and purified by RP-HPLC (Gemini 21.2×150 mm) with a mixture of CH₃CN and water (0.1% HCOOH) as eluent to give 5-(imidazo[1,2-a]pyridin-8-ylmethoxy)-2-oxo-1,2-dihydropyridine-4-carbaldehyde formate (82.5 mg, 31%) as an yellow solid, ¹H NMR (400 MHz, D₂O) δ 8.56 (d, J=7.1 Hz, 1H), 8.32 (s, 1H), 8.01 (d, J=2.1 Hz, 1H), 7.83 (d, J=7.2 Hz, 1H), 7.81 (t, J=2.1 Hz, 1H), 7.31 (t, J=7.2 Hz, 1H), 7.27 (s, 1H), 6.68 (s, 1H), 5.94 (s, 1H), 5.32 (s, 2H). LRMS (M+H⁺) m/z 270.1.

Step 2:

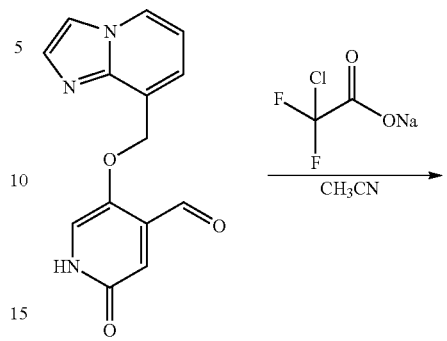

To 5-(imidazo[1,2-a]pyridin-8-ylmethoxy)-2-oxo-1,2-dihydropyridine-4-carbaldehyde (100 mg, 0.37 mmol, 1 equiv) in CH₃CN (10 mL) was added sodium 2-chloro-2,2-difluoroacetate (84.5 mg, 0.56 mmol, 1.5 eq.). The mixture was stirred at rt O/N and concentrated. The crude was purified on silica gel using 10% MeOH/DCM as eluent to give 2-(difluoromethoxy)-5-(imidazo[1,2-a]pyridin-8-ylmethoxy)isonicotinaldehyde (6.0 mg, 5%) as a yellow solid, ¹H NMR (400 MHz, CDCl₃) δ 10.46 (s, 1H), 8.14 (s, 1H), 8.10 (d, J=7.0 Hz, 1H), 7.61 (s, 2H), 0.7.44 (t, J=60.0 Hz, 1H), 7.24-7.27 (m, 2H), 6.79 (t, J=7.0 Hz, 1H), 5.63 (a, 2H). LRMS (M+H⁺) m/z 320.0.

Example 68. Preparation of 2-(difluoromethoxy)-5-((2-(1-isopropyl-1H-pyrazol-5-yl)pyridin-3-yl)methoxy)isonicotinaldehyde (Compound 178)

The title compound was prepared according to the procedure in Example 67.

¹H NMR (400 MHz, CDCl₃) δ 10.44 (s, 1H), 8.80 (d, J=3.7 Hz, 1H), 8.03 (d, J=8.0 Hz, 1H), 7.95 (s, 1H), 7.63 (d, 1.6 Hz, 1H), 7.47 (dd, J=7.9, 4.8 Hz, 1H), 7.33 (t, J=72.8 Hz, 1H), 6.37 (d, J=1.7 Hz, 1H), 5.21 (s, 2H), 4.67 (sep, 6.6 Hz, 1H), 1.50 (d, J=6.6 Hz, 6H).

Example 69 Preparation of 5-((3-(1-isopropyl-1H-pyrazol-5-yl)pyridin-4-yl)methoxy)-2-methoxyisonicotinaldehyde (Compound 160)

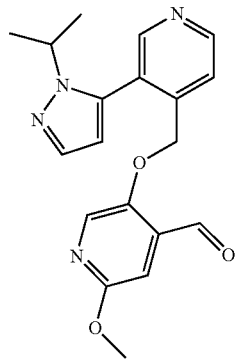 [SMILES: COc1cc(C=O)c(OCc2ccncc2-c2ccnn2C(C)C)cn1]

Step 1:

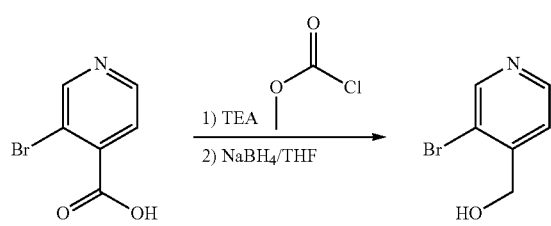

To a mixture of 3-bromoisonicotinic acid (2.5 g, 12.37 mmol, 1 eq.) and TEA (3.44 mL, 24.75 mmol, 2.0 eq.) in THF (100 mL) was added methyl chloroformate (1.2 mL, 14.85 mmol, 12 eq.) at 0° C. The mixture was stirred at 0° C. for 10 min and filtered. To this filtrate was added a suspension of NaBH$_4$ (0.95 g, 24.75 mmol, 2 eq.) in water (1.0 mL) at 0° C. The mixture was stirred at 0° C. for 1 h, quenched with NH$_4$Cl$_{(aq)}$ solution, extracted with EtOAc twice. The combined organic layers were dried over Na$_2$SO$_4$, concentrated, and purified on silica gel using a mixture of EtOAc and hexanes as eluent to give (3-bromopyridin-4-yl)methanol (1.2 g, 52%) as a white solid. $^1$H NMR (400 MHz, CDCl$_3$) δ 8.48 (s, 1H), 8.37 (d, J=4.9 Hz, 1H), 7.37 (d, J=4.9 Hz, 1H), 4.61 (d, J=5.5 Hz, 2H), 2.3 (t, J=5.5 Hz, 1H). LRMS (M+H$^+$) m/z 188.0.

Step 2:

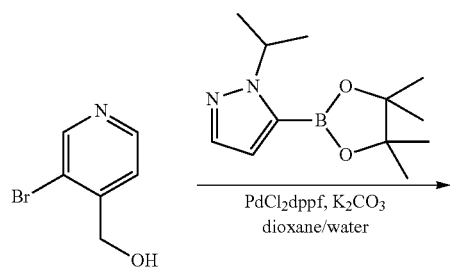

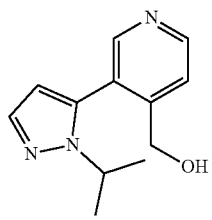

To a mixture of (3-bromopyridin-4-yl)methanol (150 mg, 0.8 mmol, 1 eq.), 1-isopropyl-5-(4,4,5,5-tetramethyl-1,3,2-dioxaborolan-2-yl)-1H-pyrazole (226 mg, 0.96 mmol, 1.2 eq.), Pd(dppf)Cl$_2$ (58 mg, 0.08 mmol, 0.1 eq.), and K$_2$CO$_3$ (331 mg, 3.0 mmol, 3 eq.) in a RB flask were added dioxane (6 mL) and water (2 mL). The mixture was heated at 100° C. for 2 h, cooled, filtered, and concentrated. The crude was purified on silica gel using a mixture of EtOAc and hexanes as eluent to give (3-(1-isopropyl-1H-pyrazol-5-yl)pyridin-4-yl)methanol (75 mg, 43%) as a yellow oil. LRMS (M+H$^+$) m/z 218.1.

Step 3:

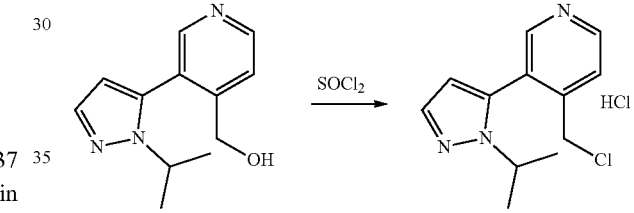

(3-(1-isopropyl-1H-pyrazol-5-yl)pyridin-4-yl)methanol (75 mg, 0.35 mmol) in SOCl$_2$ (5 mL) was heated at 60° C. for 30 min and concentrated. The crude solid was suspended in toluene and concentrated to dryness. The process was repeated three times and dried under vacuum to give a brown solid (95 mg), which was used for next step without further purification.

Step 4:

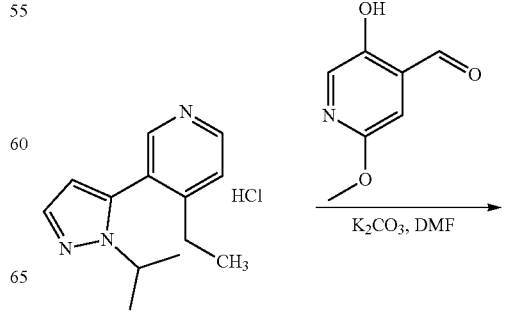

-continued

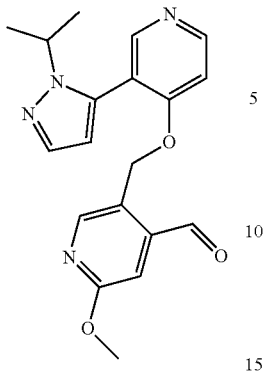

A mixture of 5-hydroxy-2-methoxyisonicotinaldehyde (79 mg, 0.52 mmol, 1.5 eq.), 4-(chloromethyl)-3-(1-isopropyl-1H-pyrazol-5-yl)pyridine hydrochloride (crude above, 0.35 mmol), and K$_2$CO$_3$ (145 mg, 1.05 mmol, 3 eq.) in DMF (10.0 mL) was heated at 100° C. for 2 h. The mixture was cooled, filtered, concentrated, and purified on RP-HPLC (Gemini 21.2×150 mm) twice using a mixture of CH$_3$CN/water (0.1% HCOOH) as eluent to give 5-((3-(1-isopropyl-1H-pyrazol-5-yl)pyridin-4-yl)methoxy)-2-methoxyisonicotinaldehyde (6.0 mg, 5%) as an off-white solid. $^1$H NMR (400 MHz, CDCl$_3$) δ 10.29 (s, 1H), 8.63 (s, 1H), 8.42 (s, 1H), 7.67 (s, 1H), 7.54 (s, 1H), 7.52 (d, J=1.7 Hz, 1H), 6.96 (s, 1H), 6.15 (d, J=1.8 Hz, 1H), 4.87 (s, 2H), 4.06 (sep, J=6.6 Hz, 1H), 3.75 (s, 3H), 1.31 (d, J=6.6 Hz, 6H). LRMS (M+H$^+$) m/z 353.1.

Example 70. Preparation of 5-([2,3'-bipyridin]-3-ylmethoxy)-2-methoxyisonicotinaldehyde (Compound 161)

The title compound was prepared according to the procedure in Example 69.
$^1$H NMR (400 MHz. CDCl3) δ 10.36 (s, 1H), 8.85 (d, J=1.7 Hz, 1H), 8.78 (dd, J=4.8, 1.6 Hz, 1H), 8.71 (dd, J=4.8, 1.5 Hz, 1H), 8.02 (dd, J=7.8, 1.5 Hz, 1H), 7.96 (dt, J=7.9.1.9 Hz, 1H), 7.90 (s, 1H), 7.49-7.42 (m, 2H), 7.10 (s, 1H), 5.21 (s, 2H), 3.91 (s, 3H).

Example 71. Preparation of 5-(imidazo[1,2-a]pyridin-8-ylmethoxy)-2-(2-methoxyethoxy)isonicotinaldehyde (Compound 179)

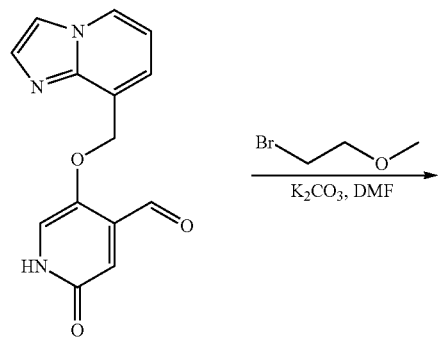

-continued

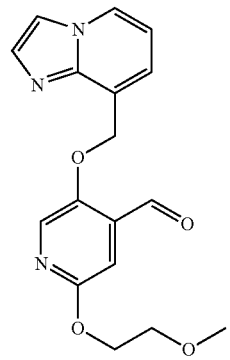

To u mixture of 5-(imidazo[1,2-a]pyridin-8-ylmethoxy)-2-oxo-1,2-dihydropyridine-4-carbaldehyde (100 mg, 0.37 mmol, 1 equiv) and K$_2$CO$_3$ (153.2 mg, 1.11, 3.0 eq.) in DMF (5 mL) was added 1-bromo-2-methoxyethane (154.3 mg, 1.11 mmol, 3.0 eq.). The mixture was stirred at rt O/N, filtered, concentrated, and purified on silica gel using 10% MeOH/DCM as eluent to give 5-(imidazo[1,2-a]pyridin-8-ylmethoxy)-2-(2-methoxyethoxy)isonicotinaldehyde (6.0 mg, 5%) as an yellow solid. $^1$H NMR (400 MHz, CDCl$_3$) δ 10.45 (a, 1H), 8.08 (d, J=6.8 Hz, 1H), 8.06 (s, 1H), 7.60 (dd, J=6.8, 1.2 Hz, 2H), 7.27 (dd, J=6.9, 1.0 Hz, 1H), 7.09 (s, 1H), 6.78 (t, J=6.9 Hz, 1H), 5.58 (s, 2H), 4.35 (dd, J=5.4, 3.9 Hz, 2H), 3.66 (dd, 5.4, 3.9 Hz, 2H), 3.36 (s, 3H). LRMS (M+H$^+$) m/z 328.1.

Example 72. Preparation of 3-((2-(1-isopropyl-1H-pyrazol-5-yl)pyridin-3-yl)methoxy)-2-(2-methoxyethoxy)isonicotinaldehyde (Compound 180)

The title compound was prepared according to the procedure in Example 71.
$^1$H NMR (400 MHz, CDCl$_3$) δ 10.40 (s, 1H), 8.76 (dd, J=4.7, 1.5 Hz, 1H), 8.04 (dd, J=7.9, 1.2 Hz, 1H), 7.87 (s, 1H), 7.61 (d, J=1.8 Hz, 1H), 7.44 (dd, J=7.9, 4.8 Hz, 1H), 7.16 (s, 1H), 6.37 (d, J=1.8 Hz, 1H), 5.14 (s, 2H), 4.65 (sep, J=6.6 Hz, 1H), 4.42 (t, J=4.8 Hz, 2H), 3.74 (t, J=4.8 Hz, 2H), 3.44 (s, 3H), 1.49 (d, j=6.6 Hz, 6H).

Example 73. Preparation of 3-((3-(1-isopropyl-1H-pyrazol-5-yl)pyrazin-2-yl)methoxy)-2-methoxyisonicotinaldehyde (Compound 181)

Step 1:

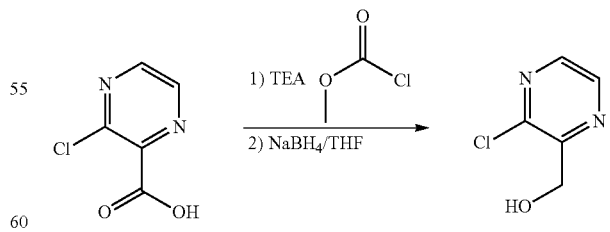

To a solution of 3-chloropyrazine-2-carboxylic acid (2.0 g, 12.70 mmol, 1.0 eq.) and TEA (3.50 mL, 25.40 mmol, 2.0 eq.) in THF (50 mL) was added methyl chloroformate (1.2 mL, 15.20 mmol, 1.2 eq.) at 0° C. The mixture was stirred at 0° C. for 10 min and filtered. To this filtrate was added a suspension of NaBH$_2$ (0.97 g, 25.40 mmol, 2 eq.) in water (1.0 mL) at 0° C. The mixture was stirred at 0° C. for 1 h, quenched with NH$_4$Cl$_{(aq)}$ solution, and extracted with EtOAc twice. The combined organic layers were dried over Na$_2$SO$_4$, concentrated, and purified on silica gel using a mixture of EtOAc and hexanes as eluent to give (3-chloropyrazin-2-yl)methanol (400 mg, 22%) as a white solid. $^1$H NMR (400 MHz, MeOD) δ 8.58 (d, 2.5 Hz, 1H), 8.38 (d, J=2.5 Hz, 1H), 4.84 (s, 2H). LRMS (M+H$^+$) m/z 145.1.

Step 2:

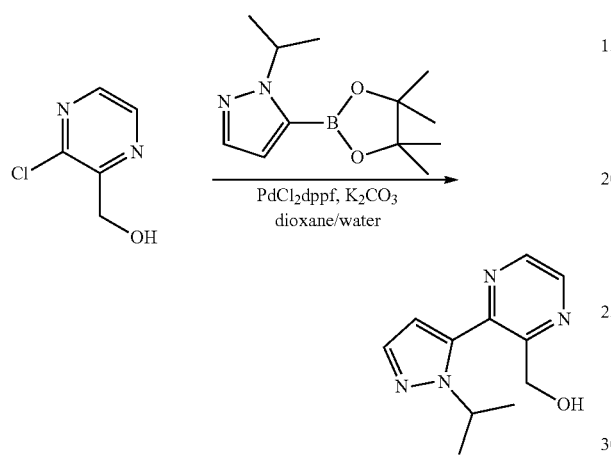

To a mixture of (3-chloropyrazin-2-yl)methanol (200 mg, 1.4 mmol, 1 eq.), 1-isopropyl-5-(4,4,5,5-tetramethyl-1,3,2-dioxaborolan-2-yl)-1H-pyrazole (393 mg, 1.67 mmol, 1.2 eq.), Pd(dppf)Cl$_2$ (102 mg, 0.14 mmol, 0.1 eq.), and K$_2$CO$_3$ (580 mg, 4.2 mmol, 3 eq.) in a RB flask were added dioxane (6 mL) and water (2 mL). The mixture was heated at 100° C. for 1 h, cooled to rt, filtered, concentrated, and purified on silica gel using a mixture of EtOAc and hexanes as eluent to give (3-(1-isopropyl-1H-pyrazol-5-yl)pyrazin-2-yl)methanol (110 mg, 36%) as a yellow oil. LRMS (M+H$^+$) m/z 219.1.

Step 3:

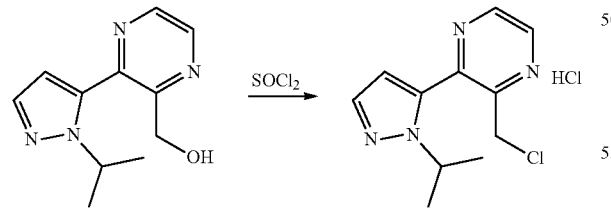

3-(1-isopropyl-1H-pyrazol-5-yl)pyrazin-2-yl)methanol (75 mg, 0.35 mmol) in SOCl$_2$ (5 mL) was heated at 60° C. for 30 min and concentrated. The crude solid was suspended in toluene and concentrated to dryness. The process was repeated three times and dried under vacuum to give a brown solid (95 mg), which was used for next step without further purification.

Step 4:

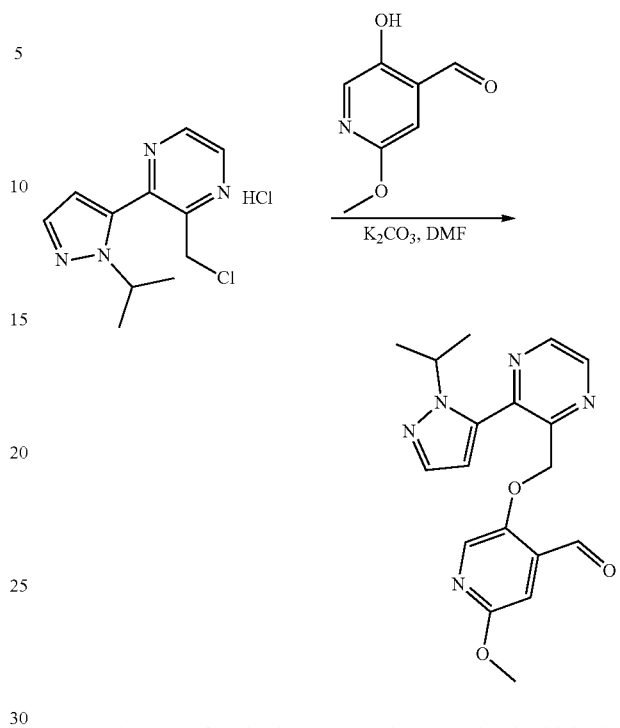

A mixture of 5-hydroxy-2-methoxyisonicotinaldehyde (110 mg, 0.60 mmol, 1.2 eq.), 2-(chloromethyl)-3-(1-isopropyl-1H-pyrazol-5-yl)pyrazine hydrochloride (crude above, 0.5 mmol, 1 eq.), and K$_2$CO$_3$ (207 mg, 1.50 mmol, 3 eq.) in DMF (15.0 mL) was heated at 100° C. for 30 min. The mixture was cooled, filtered, concentrated, and purified on silica gel using a mixture of EtOAc and hexanes as eluent to give 5-((3-(1-isopropyl-1H-pyrazol-5-yl)pyrazin-2-yl)methoxy)-2-methoxyisonicotinaldehyde (12.0 mg, 68%) as an off-white solid. NMR (400 MHz, CDCl$_3$) δ 10.31 (s, 1H), 8.73 (d, J=2.4 Hz, 1H), 8.65 (d, J=2.4 Hz, 1H), 8.05 (s, 1H), 7.61 (d, J=1.9 Hz, 1H), 7.06 (s, 1H), 6.49 (d, J=1.9 Hz, 1H), 5.32 (s, 2H), 4.68 (sep, 6.6 Hz, 1H), 3.89 (s, 2H), 1.48 (d, J=6.6 Hz, 6H). LRMS (M+H$^+$) m/z, 354.1.

Example 74. Preparation of Methyl 3-((4-formyl-6-methoxypyridin-3-yloxy)methyl)picolinate (Compound 182)

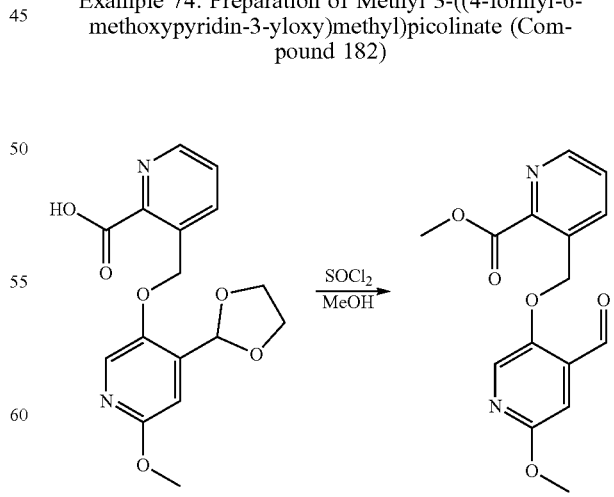

To 3-((4-(1,3-dioxolan-2-yl)-6-methoxypyridin-3-yloxy)methyl)picolinic acid (55 mg, 0.17 mmol, 1 equiv) in MeOH (15 mL) was added SOCl$_2$ (5.0 mL). The mixture was healed to reflux O/N, concentrated, and neutralized to pH 8-9 with NaHCO$_{3(sat)}$ solution. The aqueous layer was extracted with EtOAc three times. The combined organic layers were dried over Na$_2$SO$_4$, concentrated, and purified on silica gel using a mixture of EtOAc and hexanes as eluent to give methyl 3-((4-formyl-6-methoxypyridin-3-yloxy)methyl)picolinate (51.5 mg, quantitative yield) as a white solid. $^1$H NMR (400 MHz, CDCl$_3$) δ 10.44 (s, 1H), 8.67 (dd, J=4.6, 1.5 Hz, 1H), 8.14 (dd, J=8.0, 1.5 Hz, 1H), 8.03 (s, 1H), 7.51 (dd, J=8.0, 4.6 Hz, 1H), 7.06 (s, 1H), 5.60 (s, 2H), 3.95 (s, 3H), 3.85 (s, 3H). LRMS (M+H$^+$) m/z 303.1.

Example 75. Preparation of 5-((2-(2-hydroxypropan-2-yl)pyridin-3-yl)methoxy)-2-methoxyisonicotinaldehyde (Compound 183)

Step 1:

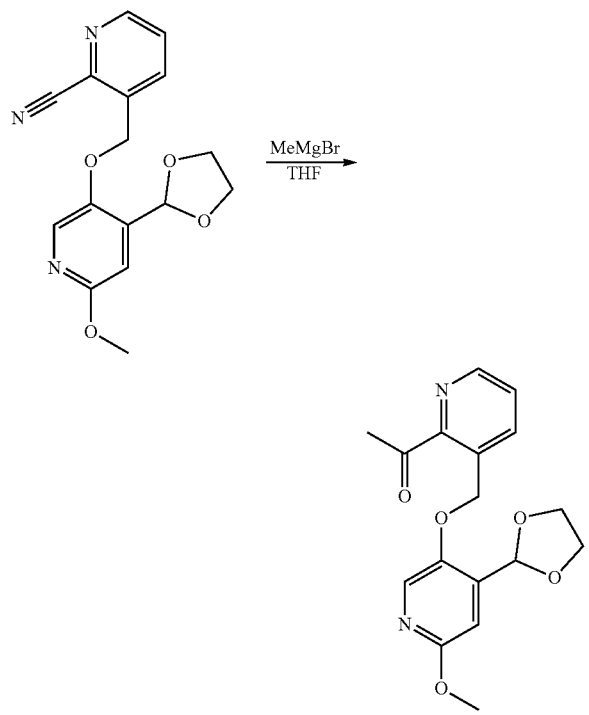

Methylmagnesium bromide (3M/ether, 2.0 mL, 5.65 mmol, 1.5 eq.) was added to a stirred solution of 3-((4-(1,3-dioxolan-2-yl)-6-methoxypyridin-3-yloxy)methyl)picolinonitrile (1180 mg, 3.76 mmol, 1 eq.) in THF (10.0 mL) at −78° C. After addition, the reaction mixture was allowed to warm to rt and quenched with aqueous citric acid solution. The aqueous layer was extracted with EtOAc (30 mL) twice. The combined organic layers were washed with NaHCO$_3$ $_{(sat)}$ solution and brine, dried over Na$_2$SO$_4$, concentrated, and purified on silica gel using a mixture of EtOAc and hexanes as eluent to give 1-(3-((4-(1,3-dioxolan-2-yl)-6-methoxypyridin-3-yloxy)methyl)pyridin-2-yl)ethanone (776 mg, 63%) as a colorless oil. $^1$H NMR (400 MHz, CDCl$_3$) δ 8.66 (d, J=4.0 Hz, 1H), 8.26 (d, J=7.9 Hz, 1H), 7.82 (s, 1H), 7.54 (dd, J=8.0, 4.0 Hz, 1H), 6.95 (s, 1H), 6.23 (s, 1H), 5.59 (s, 2H), 4.22-4.04 (m, 4H), 3.90 (s, 3H), 2.79 (s, 3H). LRMS (M+H$^+$) m/z 331.1.

Step 2:

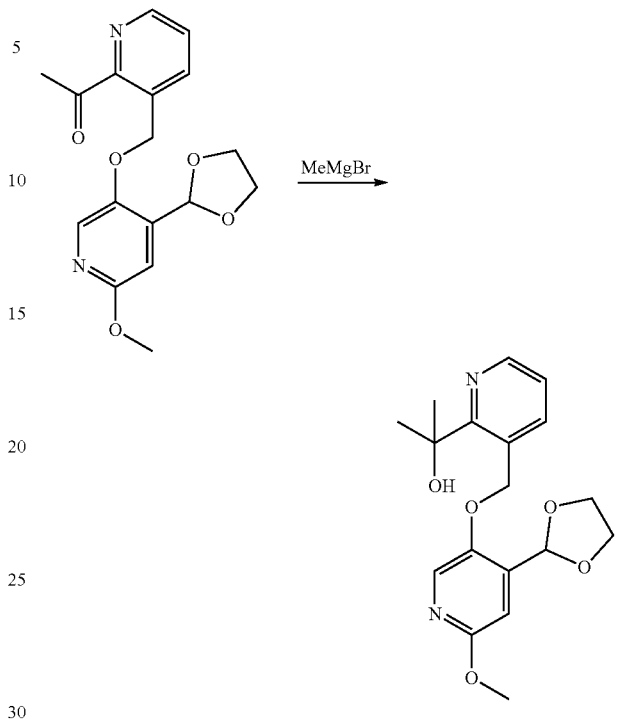

Methylmagnesium bromide (3M/ether, 0.25 mL, 0.75 mmol, 3.0 eq.) was added to a stirred solution of 1-(3-((4-(1,3-dioxolan-2-yl)-6-methoxypyridin-3-yloxy)methyl) pyridin-2-yl)propan-1-one (82 mg, 0.25 mmol, 1 eq.) in THF (5.0 mL) at −78° C. After addition, the reaction mixture was warm to rt and quenched with aqueous citric acid solution. The aqueous layer was extracted with EtOAc (20 mL) twice. The combined organic layers were washed with NaHCO$_{3(sat)}$ solution and brine, dried over Na$_2$SO$_4$, concentrated, and purified on silica gel using a mixture of EtOAc and hexanes as eluent to give 2-(3-((4-(1,3-dioxolan-2-yl)-6-methoxypyridin-3-yloxy)methyl)pyridin-2-yl)propan-2-ol (38 mg, 44%) as a colorless oil. $^1$H NMR (400 MHz, CDCl$_3$) δ 8.43 (dd, 7.7, 1.6 Hz, 1H), 7.84 (dd, J=7.7, 1.5 Hz, 1H), 7.74 (s, 1H), 7.18 (dd, J=7.7, 4.7 Hz, 1H), 6.84 (s, 1H), 6.01 (s, 1H), 5.27 (s, 2H), 4.07-3.88 (m, 4H), 3.82 (s, 3H), 1.55 (s, 6H). LRMS (M+H$^+$) m/z 347.1.

Step 3:

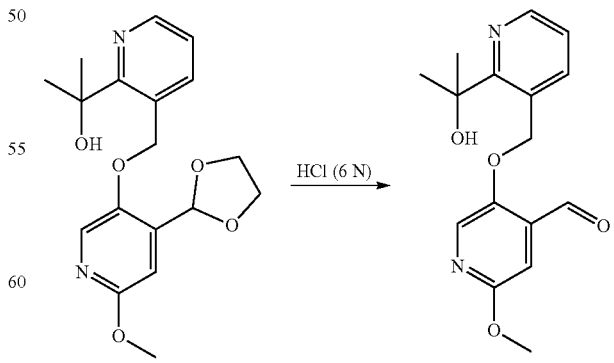

To 2-(3-((4-(1,3-dioxolan-2-yl)-6-methoxypyridin-3-yloxy)methyl)pyridin-2-yl)propan-2-ol (30 mg, 0.087 mmol, 1 eq.) in a RB flask was added HCl (6 N, 3.0 mL).

The mixture was warmed to 40° C. O/N, cooled to rt, neutralized to pH 7-8 with NaHCO$_{3(sat)}$ solution, and extracted with EtOAc twice. The combined organic layers were washed with brine, dried over Na$_2$SO$_4$, concentrated, and purified on silica gel using a mixture of EtOAc and hexanes as eluent to give 5-((2-(2-hydroxypropan-2-yl)pyridin-3-yl)methoxy)-2-methoxyisonicotinaldehyde (10.2 mg, 99%) as a pale-yellow oil. $^1$H NMR (400 MHz, CDCl$_3$) δ 10.36 (s, 1H), 8.46 (dd, J=4.7, 1.6 Hz, 1H), 7.99 (s, 1H), 7.86 (dd, J=7.8, 1.5 Hz, 1H), 7.24 (dd, 7.8, 4.7 Hz, 1H), 7.05 (s, 1H), 5.37 (s, 2H), 3.85 (s, 3H), 1.57 (s, 6H). LRMS (M+H$^+$) m/z 303.1.

Example 76. Preparation of 5-hydroxy-2-(2-methoxyethoxy)isonicotinaldehyde and 5-hydroxy-2-(2-methoxyethoxy)nicotinaldehyde Step 1 j

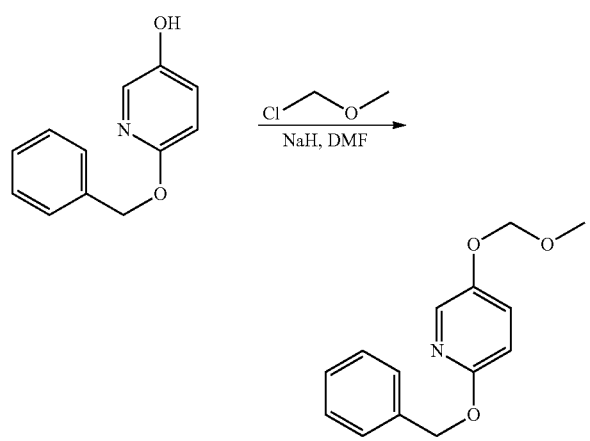

To a solution of 6-(benzyloxy)pyridin-3-ol (2.0 g, 10 mmol, 1 eq.) in DMF (20 mL) was added NaH (60% in mineral oil; 0.6 g, 15 mmol, 1.5 eq.) at 0-5° C. portion-wise. Upon the completion of addition, the mixture was continued to stir at 0-5° C. for 15 min, added chloromethyl methyl ether (0.88 g, 11 mmol, 1.1 eq.), stirred at 0-5° C. for another 20 min, and quenched with NH$_4$Cl$_{(sat.)}$ solution. The aqueous layer was extracted with EtOAc (3×20 mL) and the combined organic layers were washed with water and brine, dried over Na$_2$SO$_4$, concentrated, and purified on silica gel using 25% EtOAc/hexanes as eluent to give 2-(benzyloxy)-5-(methoxymethoxy)pyridine (2.1 g, 87%) to a colorless oil. LRMS (M+H$^+$) m/z 246.1

Step 2

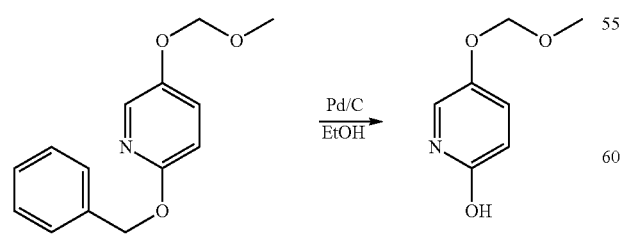

To 2-(benzyloxy)-5-(methoxymethoxy)pyridine (1.8 g, 8.71 mol) in EtOH was added Pd/C (1.0 g). The mixture was charged with H$_2$ (15 psi), stirred at rt for 45 min, filtered, and concentrated to give 5-(methoxymethoxy)pyridin-2-ol (1.35 g, quantitative yield) as a pale yellow solid. LRMS (M+H$^+$) m/z 156.1

Step 3

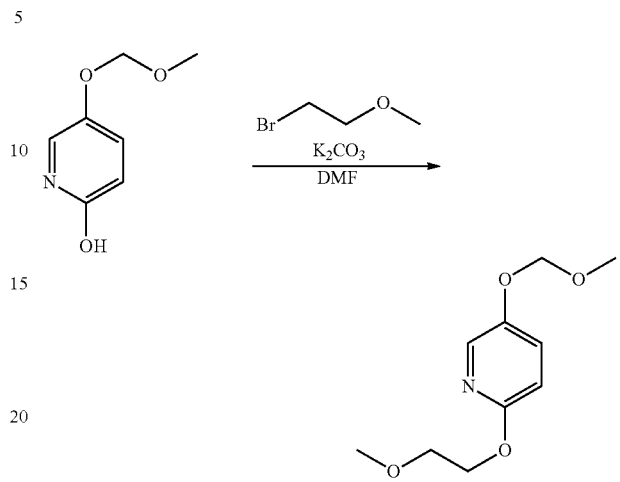

To a mixture of 5-(methoxymethoxy)pyridin-2-ol (1.35 g, 8.71 mmol, 1 eq.) and K$_2$CO$_3$ (6.01 g, 43.6 mmol, 5.0 eq.) in DMF (30.0 mL) was added 1-bromo-2-methoxyethane (3.61 g, 26.1 mmol, 3 eq.). The mixture was heated at 60° C. for 2 h, cooled, filtered, concentrated, and purified on silica gel using a mixture of EtOAc and hexanes as eluent to give 2-(2-methoxyethoxy)-5-(methoxymethoxy)pyridine (500 mg, 27%) as a colorless oil. $^1$H NMR (400 MHz, CDCl$_3$) δ 7.94 (d, J=3.0 Hz, 1H), 7.35 (ddd, J=8.9, 3.0, 1.0 Hz, 1H), 6.76 (dd, J=8.9, 1.0 Hz, 1H), 5.11 (s, 2H), 4.48-4.40 (m, 2H), 3.79-3.71 (m, 2H), 3.50 (s, 3H), 3.45 (s, 3H). LRMS (M+H$^+$) m/z 214.1.

Step 4

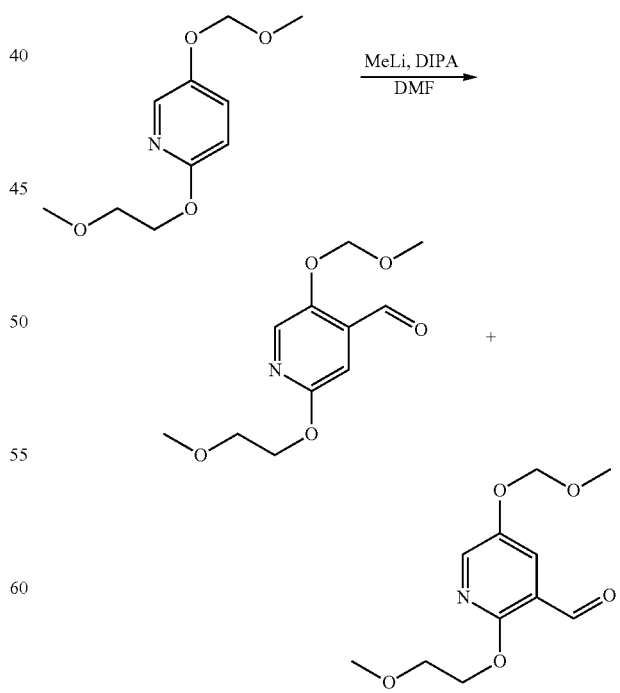

To a mixture of 2-(2-methoxyethoxy)-5-(methoxymethoxy)pyridine (1.34 g, 6.3 mol, 1 eq.) and diisopropylamine (17.5 uL, 0.13 mmol, 0.02 eq.) in THF (50 mL) was added methyl lithium (1.6 M/THF, 7 mL, 11.3 mol, 1.8 eq.) at −40° C. Upon the completion of addition, the mixture was warmed to 0° C., continued to stir at 0° C. for 3 h, cooled back down to −40° C., and added DMF (0.83 mL, 11.3 mol, 1.8 eq.) slowly. The mixture was then stirred at −40° C. for 1 h, quenched with a mixture of HCl (12 N, 12 mL) and THF (28 mL), warmed to rt, and added water (20 mL). The pH of the mixture was adjusted to pH 8-9 with solid $K_2CO_3$. The aqueous layer was extracted with EtOAc (30 mL) twice. The combined organic layers were dried over $Na_2SO_4$, concentrated, and purified on silica gel using a mixture of EtOAc and hexanes as eluent to give a mixture of 2-(2-methoxyethoxy)-5-(methoxymethoxy)isonicotinaldehyde and 2-(2-methoxyethoxy)-5-(methoxymethoxy)nicotinaldehyde (5/1, 1.27 g, 83.6%) as a pale yellow oil. $^1$H NMR (400 MHz, CDCl$_3$) δ 10.45 (s, 1H), 8.23 (s, 1H), 7.16 (s, 1H), 5.27 (s, 2H), 4.46 (dd, J=5.4, 3.9 Hz, 2H), 4.14 (q, 7.1 Hz, 1H), 3.77-3.71 (m, 2H), 3.56 (s, 3H), 3.46 (s, 3H) and $^1$H NMR (400 MHz, CDCl$_3$) δ 10.41 (s, 1H), 8.18 (d, J=3.2 Hz, 1H), 7.85 (d, J=3.1 Hz, 1H), 5.16 (s, 2H), 4.64-4.57 (m, 2H), 3.85-3.79 (m, J=5.4, 4.0 Hz, 2H), 3.50 (s, 3H), 3.46 (s, 3H); LRMS (M+H$^+$) m/z 242.1.1 trated, and purified on silica gel using a mixture of EtOAc and hexanes to give 5-hydroxy-2-(2-methoxyethoxy)isonicotinaldehyde (630 mg, 60%) and 5-hydroxy-2-(2-methoxyethoxy)nicotinaldehyde (120 mg, 11%). Data for 5-hydroxy-2-(2-methoxyethoxy)isonicotinaldehyde: $^1$H NMR (400 MHz, CDCl$_3$) δ 9.98 (s, 1H), 9.50 (s, 1H), 8.07 (s, 1H), 7.02 (s, 1H), 4.51-4.39 (m, 2H), 3.81-3.72 (m, 2H), 3.47 (a, 3H). LRMS (M+H$^+$) m/z 198.1. Data for and 5-hydroxy-2-(2-methoxyethoxy)nicotinaldehyde: $^1$H NMR (400 MHz, CDCl$_3$) δ 10.3 (s, 1H), 7.99 (d, J=3.2 Hz, 1H), 7.58 (d, J=3.2 Hz, 1H), 7.18-7.07 (br, 1H), 4.54 (dd, J=5.4, 3.7 Hz, 2H), 3.84 (dd, J=5.4, 3.7 Hz, 2H), 3.49 (s, 3H). LRMS (M+H$^+$) m/z 198.1

Example 77. Preparation of 2-(2-methoxyethoxy)-5-((2-(1-methyl-1H-pyrazol-5-yl)pyridin-3-yl)methoxy)isonicotinaldehyde (Compound 184)

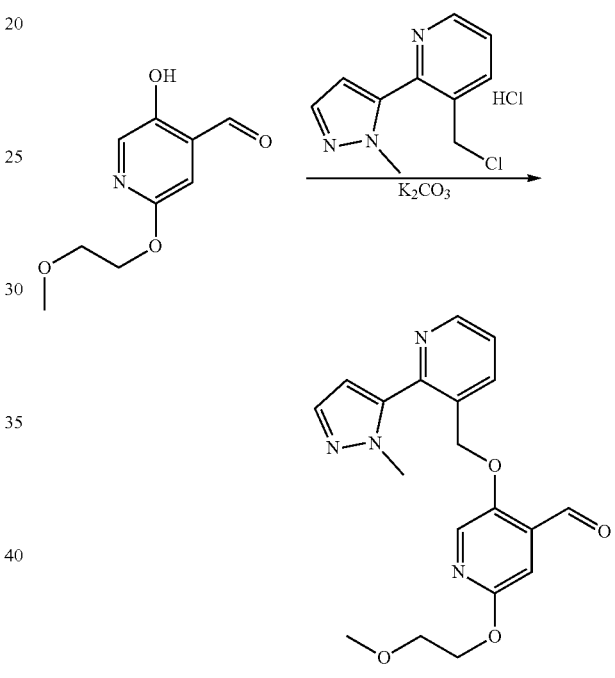

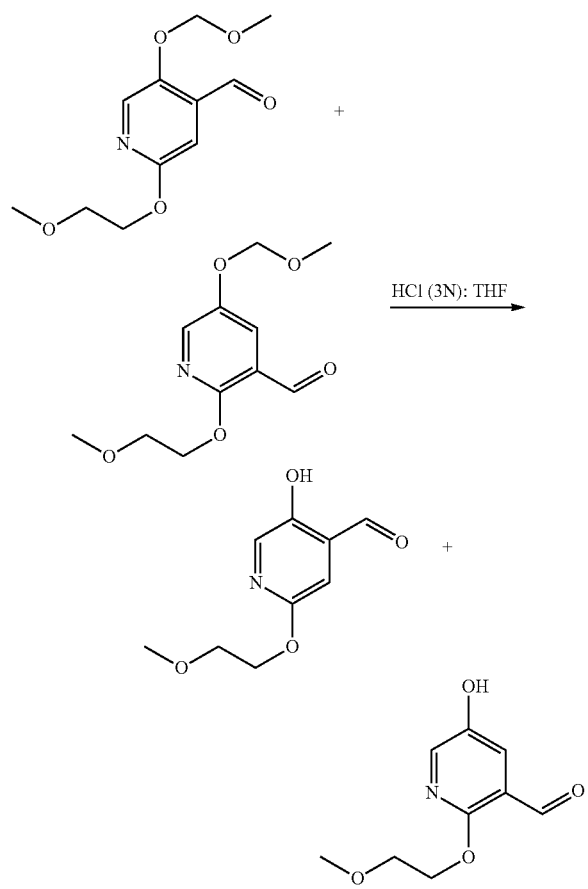

A mixture of 5-hydroxy-2-(2-methoxyethoxy)isonicotinaldehyde (125 mg, 0.63 mmol, 1 eq.), 3-(chloromethyl)-2-(1-methyl-1H-pyrazol-5-yl)pyridine hydrochloride salt (120 mg, 0.63 mmol, 1 eq.), and $CS_2CO_3$ (410 mg, 1.26 mmol, 2 eq.) in DMF (3.0 mL) was heated at 60° C. for 2 h. Tire mixture was cooled, filtered, concentrated, and purified on silica gel using a mixture of EtOAc and hexanes as eluent to give 2-(2-methoxyethoxy)-5-((2-(1-methyl-1H-pyrazol-5-yl)pyridin-3-yl)methoxy)isonicotinaldehyde (59 mg, 25%) as a yellow oil. $^1$H NMR (400 MHz, CDCl$_3$) δ 10.22 (s, 1H), 8.59 (dd, J=4.7, 1.6 Hz, 1H), 7.87 (dd, J=7.9, 1.3 Hz, 1H), 7.73 (s, 1H), 7.38 (d, 1.9 Hz, 1H), 7.27 (dd, J=7.9, 4.8 Hz, 1H), 7.00 (s, 1H), 6.25 (d, J=1.9 Hz, 1H), 5.02 (s, 2H), 4.26 (dd, J=5.4, 3.9 Hz, 2H), 3.80 (s, 3H), 3.57 (dd, J=5.4, 3.9 Hz, 2H), 3.28 (a, 3H). LRMS (M+H$^+$) m/z 387.1.

Example 78. Preparation of 2-(2-methoxyethoxy)-5-((2-(1-methyl-1H-pyrazol-5-yl)pyridin-3-yl)methoxy)nicotinaldehyde (Compound 185)

The title compound was prepared according to the procedure in Example 77.

To a solution of 2-methoxy-5-(methoxymethoxy)isonicotinaldehyde (1.27 g, 5.29 mol) in THF (5 mL) was added HCl (3 N, 4 mL). The reaction was stirred at 50° C. for 1 h, cooled to rt, and diluted with water (5 mL). The mixture was neutralized to pH 7-8 with solid $K_2CO_3$ and the aqueous layer was extracted with EtOAc (100 mL) twice. The combined organic layers were dried over $Na_2SO_4$, concen- $^1$H NMR (400 MHz, CDCl3) δ 10.38 (s, 1H), 8.74 (dd, J=4.7, 1.5 Hz, 1H), 8.07 (d, J=3.3 Hz, 1H), 7.98 (dd, J=7.9, 1.2 Hz, 1H), 7.64 (d, J=3.3 Hz, 1H), 7.53 (d, J=0.9 Hz, 1H), 7.41 (dd, J=7.9.4.8 Hz, 1H), 6.41 (d, J=1.9 Hz, 1H), 5.04 (s, 2H), 4.62-4.51 (m, 2H), 3.96 (s, 3H), 3.82-3.76 (m, 2H), 3.45 (s, 3H).

Example 79. Preparation of 3-hydroxy-5-((2-(1-isopropyl-1H-pyrazol-5-yl)pyridin-3-yl)methoxy)isonicotinaldehyde (Compound 186)

Step 1:

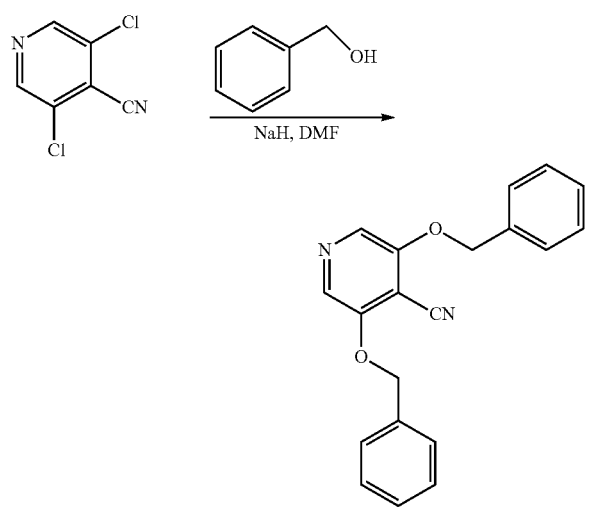

To a mixture of NaH (60% in mineral oil) (2.77 g, 69.25 mmol, 2.5 eq.) in DMF (40.0 mL) was added benzyl alcohol (6.6 g, 61.0 mmol, 2.2 eq.) at 0° C. The mixture was stirred at 0° C. for 10 min, added 3,5-dichloroisonicotinonitrile (4.8 g, 27.7 mmol, 1 eq.), continued to stir at 0° C. for 30 min, gradually warm to rt, stirred at it O/N, and quenched with NH$_4$Cl$_{(sat.)}$ solution. The aqueous layer was extracted with EtOAc three times. The combined organic layers were washed with brine, dried over Na$_2$SO$_4$, concentrated, and purified on silica gel using a mixture of EtOAc and hexanes as eluent to give 3,5-bis(benzyloxy)isonicotinonitrile (4.94 g, 56%) as an off-white solid. $^1$H NMR (400 MHz, CDCl$_3$) δ 8.14 (s, 2H), 7.58-7.30 (m, 10H), 5.33 (s, 4H). LRMS (M+H$^+$) m/z 317.1

Step 2:

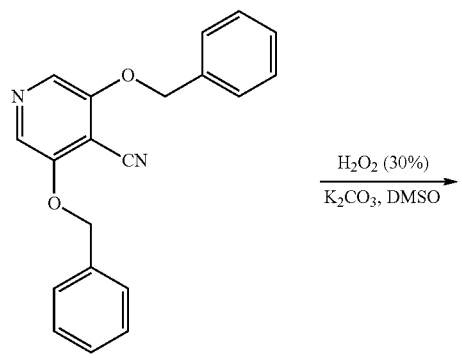

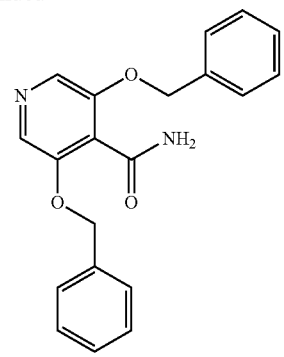

To a mixture of 3,5-bis(benzyloxy)isonicotinonitrile (2.5 g, 7.9 mmol, 1 eq.) and K$_2$CO$_3$ (4.37 g, 31.6 mmol, 4 eq.) in DMSO (10 mL) was added H$_2$O$_2$ (30% in water, 2.0 mL) at rt. The mixture was stirred at rt O/N and added water (50 mL). The solid was collected and dried to give 3,5-bis(benzyloxy)isonicotinamide (2.2 g, 83%) as a white solid. $^1$H NMR (400 MHz, CDCl$_3$) δ 8.13 (s, 2H), 7.59-7.33 (m, 10H), 5.83 (s, 2H), 5.25 (s, 4H), 4.81 (s, 2H). LRMS (M+H$^+$) m/z 335.1

Step 3:

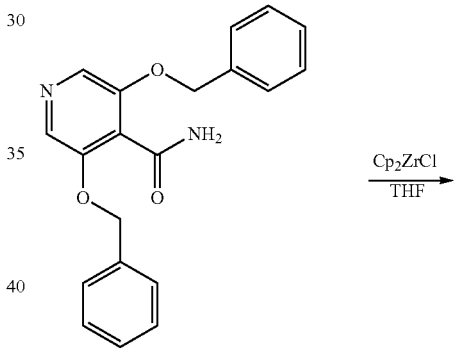

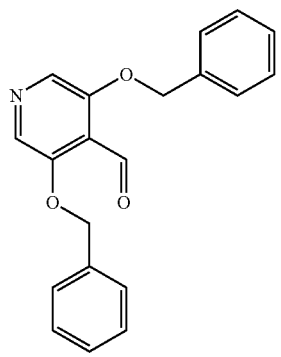 +

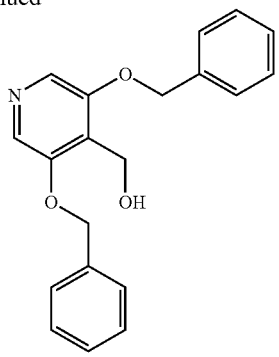

To 3,5-bis(benzyloxy)isonicotinamide (1.6 g, 4.79 mmol) in THF (30 mL) was added Cp2ZrCl (3.7 g, 14.4 mmol, 3 eq.) at rt. The mixture was stirred at rt for 2 h, concentrated, and purified on silica gel using a mixture of EtOAc and hexanes as eluent to give 3,5-bis(benzyloxy)isonicotinaldehyde (580 mg, 38%) and (3,5-bis(benzyloxy)pyridin-4-yl)methanol (710 mg, 46%) as white solids. Data for aldehyde $^1$H NMR (400 MHz, CDCl$_3$) δ 10.53 (s, 1H), 8.13 (s, 2H), 7.51-7.22 (m, 10H), 5.21 (s, 4H); LRMS (M+H$^+$) m/z 320.1. Data for alcohol $^1$H NMR (400 MHz, CDCl$_3$) δ 8.12 (s, 2H), 7.58-7.34 (m, 10H), 5.22 (s, 4H), 4.87 (s, 1H).; LRMS (M+H) m/z 322.1.

Step 4:

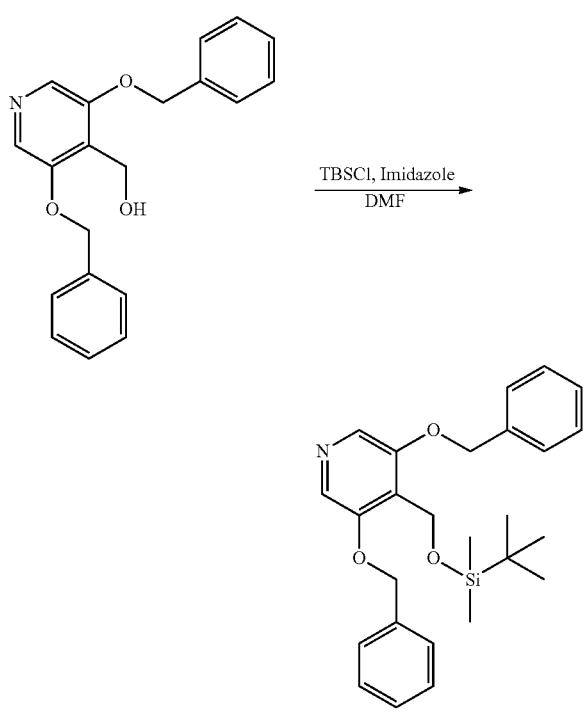

To a solution of (3,5-bis(benzyloxy)pyridin-4-yl)methanol (910 mg, 2.83 mmol) and imidazole (385 mg, 5.66 mmol) in DMF (10.0 mL) was added TBSCl (513 mg, 3.4 mmol) at rt. The mixture was stirred at rt for 1 h and diluted with a mixture of water (10 mL) and EtOAc (40 mL). The organic layer was washed with NH$_4$Cl$_{(sat.)}$ solution and brine, dried over Na$_2$SO$_4$, concentrated, and purified on silica gel using 10% EtOAc/hexanes as eluent to give 3,5-bis(benzyloxy)-4-((tert-butyldimethylsilyloxy)methyl)pyridine (728 mg, 59%) as an off-white solid. LRMS (M+H$^+$) m/z 436.3.

Step 5:

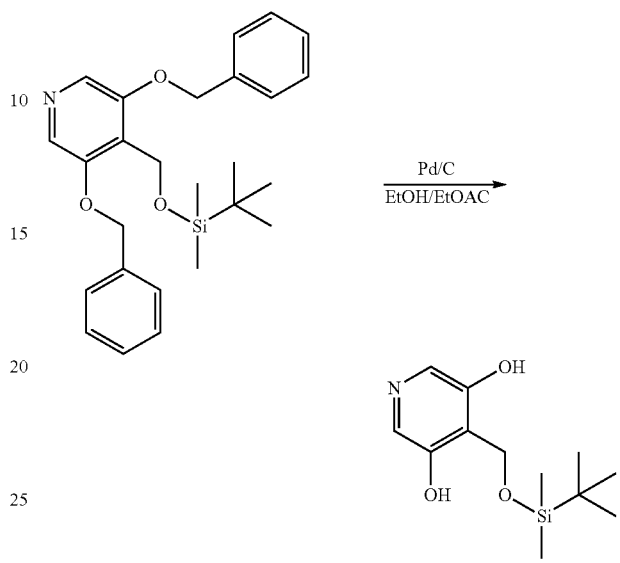

To 3,5-bis(benzyloxy)-4-((tert-butyldimethylsilyloxy) methyl)pyridine (720 mg, 1.66 mmol, 1 eq.) in a mixture of EtOAc/EtOH (5/2.28 mL) was added Pd/C (400.0 mg). The mixture was charged with H$_2$ (60 psi), stirred at rt for 2 h, filtered, and concentrated to give 4-((tert-butyldimethylsilyloxy)methyl)pyridine-3,5-diol as a yellow solid. $^1$H NMR (400 MHz, CDCl$_3$) δ 7.54 (s, 2H), 4.91 (s, 2H), 0.73 (s, 9H), −0.00 (s, 6H). LRMS (M+H) m/z 256.1.

Step 6:

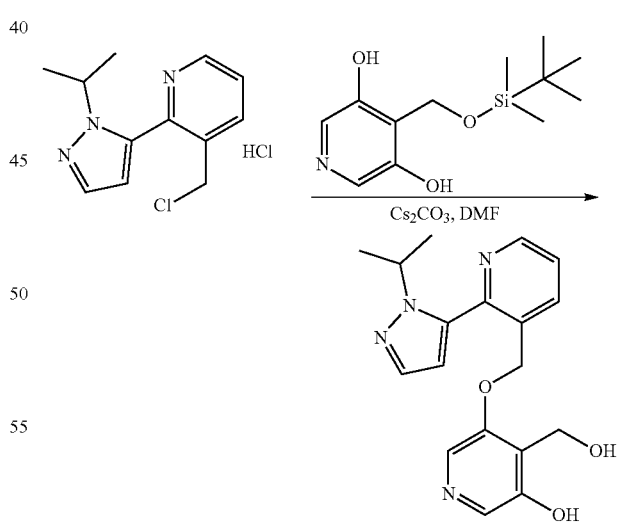

A mixture of 4-((tert-butyldimethylsilyloxy)methyl)pyridine-3,5-diol (100 mg, 0.39 mmol, 2 eq.) and CS$_2$CO$_3$ (381 mg, 1.17 mmol, 3 eq.) in DMF (15 mL) was stirred at rt for 30 min. To this mixture was added 3-(chloromethyl)-2-(1-isopropyl-1H-pyrazol-5-yl)pyridine hydrochloride (53 mg, 0.39 mmol, 1 eq.) at rt. The mixture was continued to stir at rt O/N, filtered, concentrated, and purified on silica gel using a mixture of EtOAc and hexanes as eluent to give 4-(hydroxymethyl)-5-((2-(1-isopropyl-1H-pyrazol-5-yl)pyridin-3-yl)methoxy)pyridin-3-ol (36 mg, 27%) as a pale yellow oil. ¹H NMR (400 MHz, CDCl₃) δ 8.51 (dt, J=33.0, 16.5 Hz, 1H), 7.72 (d, J=1.6 Hz, 1H), 7.69 (s, 1H), 7.47 (s, 1H), 7.33 (s, 1H), 7.21 (dd, J=7.8, 4.8 Hz, 1H), 6.10 (d, J=1.8 Hz, 1H), 4.84 (s, 2H), 4.68 (s, 1H), 4.44 (sep, 6.6 Hz, 1H), 1.24 (d, J=6.6 Hz, 6H). LRMS (M+H⁺) m/z 341.1

Step 7:

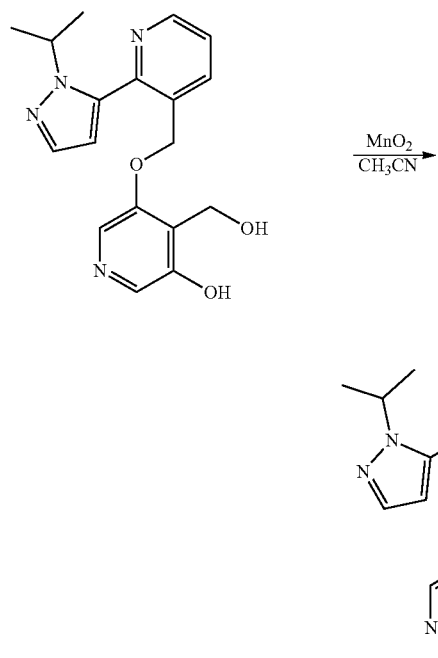

To 4-(hydroxymethyl)-5-((2-(1-isopropyl-1H-pyrazol-5-yl)pyridin-3-yl)methoxy)pyridin-3-ol (26 mg, 0.076 mmol, 1 eq.) in CH₃CN (10 mL) was added MnCO₂ (66 mg, 0.76 mmol, 10 eq.). The mixture was heated to 46° C. with stirring O/N, cooled to rt, filtered, and concentrated to give 3-hydroxy-5-((2-(1-isopropyl-1H-pyrazol-5-yl)pyridin-3-yl)methoxy)isonicotinaldehyde as a pale yellow oil. ¹H NMR (400 MHz, CDCl₃) δ 11.06 (s, 1H), 10.35 (s, 1H), 8.70 (dd, J=4.7, 1.5 Hz, 1H), 8.11 (s, 1H), 7.89 (dd, J=7.9, 1.1 Hz, 1H), 7.80 (s, 1H), 7.53 (d, 1.8 Hz, 1H), 7.36 (dd, J=7.9, 4.8 Hz, 1H), 6.27 (d, J=1.8 Hz, 1H), 5.14 (s, 2H), 4.61 (sep, J=6.6 Hz, 1H), 1.41 (d, J=6.6 Hz, 6H). LRMS (M+H⁺) m/z 339.1

Example 80. Preparation of 3-(benzyloxy)-5-hydroxyisonicotinaldehyde (Compound 187)

The title compound was prepared according to the procedure in Example 79.

¹H NMR (400 MHz, CDCl₃) δ 11.08 (s, 1H), 10.41 (s, 1H), 8.08 (s, 1H), 7.99 (s, 1H), 7.39-7.28 (m, 5H), 5.18 (s, 2H).

Example 81. Preparation of 3-((2-(1-isopropyl-1H-pyrazol-5-yl)pyridin-3-yl)methoxy)-5-methoxyisonicotinaldehyde (Compound 188)

Step 1:

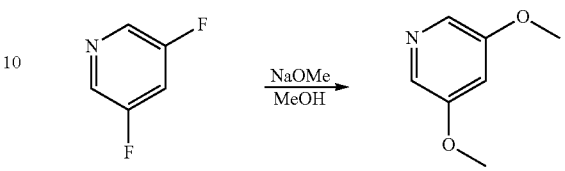

To a solution of 3,5-difluoropyridine (5.4 g, 46.8 mmol, 1 eq.) in MeOH (45 mL) was added NaOMe (7.5 g, 140.4 mmol). The mixture was divided into three microwave tubes and individually heated at 135° C. for 1 h in a microwave reactor. The three tubes were combined, concentrated, and diluted with a mixture EtOAc (100 mL) and brine (30 mL). The organic layer was dried over Na₂SO₄ and concentrated. The erode was re-dissolved in MeOH (45 mL) and added NaOMe (7.5 g, 140.4 mmol). The mixture was again divided into three microwave tubes and individually heated at 135° C. for 1 h in a microwave reactor. The three tubes were combined and concentrated. The crude was dissolved in a mixture of EtOAc (200 mL) and brine (30 mL). The organic layer was dried over Na₂SO₄, concentrated, and purified on silica gel using a mixture of EtOAc and hexanes as eluent to give 3,5-dimethoxypyridine (3.73 g, 57%) as an off-white solid. ¹H NMR (400 MHz, CDCl₃) δ 7.98 (d, J=2.4 Hz, 2H), 6.76 (t, J=2.4 Hz, 1H), 3.88 (s, 6H). LRMS (M+H⁺) m/z 140.1.

Step 2:

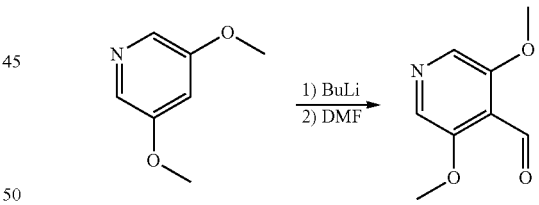

To a solution of 3,5-dimethoxypyridine (3.6 g, 25.90 mmol, 1 eq.) in THF (80 mL) was added BuLi (3M/hexanes, 13.0 ml, 38.85 mmol, 1.5 eq.) at −20° C. The mixture was warmed to 0° C., stirred at 0° C. for 30 min, cooled back down to −78° C., and added DMF (3.8 g, 51.8 mmol, 2 eq.). The mixture was gradually warmed to 0° C., quenched with NH₄Cl₍ₛₐₜ.₎ solution, and diluted with EtOAc. The aqueous layer was extracted with EtOAc twice. The combined organic layers were washed with brine, dried over Na₂SO₄, concentrated, and purified on silica gel using a mixture of EtOAc and hexanes as eluent to give 3,5-dimethoxyisonicotinaldehyde (2.7 g, 62%) as a yellow solid. LRMS (M+H⁺) m/z 168.1.

Step 3:

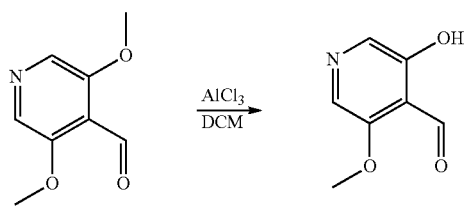

To a solution of 3,5-dimethoxyisonicotinaldehyde (2.7 g, 16.16 mmol, 1 eq.) in DCM (100 mL) was added AlCl$_3$ (4.31 g, 32.32 mmol, 2.0 eq.) at rt. The mixture was reflux O/N, cooled to rt, and added into ice (200 g). The aqueous layer was extracted with DCM three times. The combined organic layers were dried over Na$_2$SO$_4$, concentrated, and purified on silica gel using a mixture of EtOAc and hexanes as eluent to give 3-hydroxy-5-methoxyisonicotinaldehyde (420 mg, 17%) as an off-white solid, $^1$H NMR (400 MHz, CDCl$_3$) δ 10.96 (s, 1H), 10.26 (a, 1H), 7.96 (s, 1H), 7.80 (s, 1H), 3.84 (s, 3H). LRMS (M+H$^+$) m/z 154.1.

Step 4:

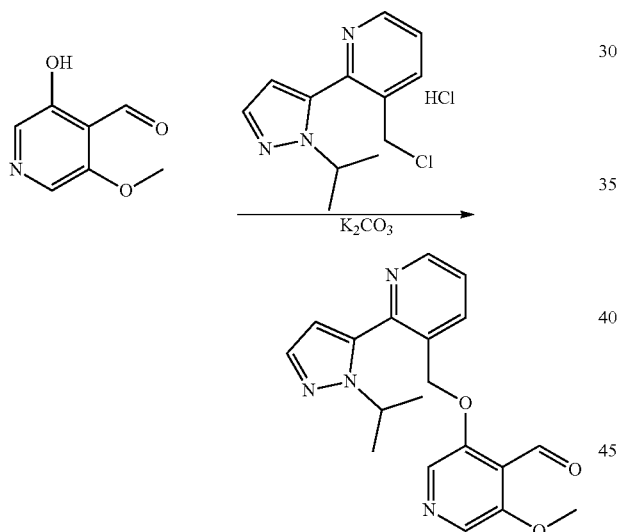

A mixture of 3-hydroxy-5-methoxyisonicotinaldehyde (30 mg, 0.20 mmol, 1 eq.), 3-(chloromethyl)-2-(1-isopropyl-1H-pyrazol-5-yl)pyridine hydrochloride (54 mg, 0.20 mmol, 1 eq.), and K$_2$CO$_3$ (110 mg, 0.80 mmol, 4 eq.) in DMF (2.0 mL) was heated at 70° C. for 2 h. The mixture was cooled, filtered, concentrated, and purified on silica gel using a mixture of EtOAc and hexanes to give 3-((2-(1-isopropyl-1H-pyrazol-5-yl)pyridin-3-yl)methoxy)-5-methoxyisonicotinaldehyde (30 mg, 43%) as an off-white solid. $^1$H NMR (400 MHz, CDCl$_3$) δ 10.46 (s, 1H), 8.65 (dd, J=4.7, 1.1 Hz, 1H), 8.13 (s, 1H), 8.11 (dd, J=7.9, 1.1 Hz, 1H), 7.96 (s, 1H), 7.54 (d, J=1.7 Hz, 1H), 7.37 (dd, J=7.9, 4.8 Hz, 1H), 6.29 (d, J=1.7 Hz, 1H), 5.11 (s, 2H), 4.55 (sep, J=6.6 Hz, 1H), 3.95 (s, 3H), 1.40 (d, J=6.6 Hz, 6H). LRMS (M+H$^+$) m/z 353.1.

Example 82. Preparation of 5-((2-(2-isopropyl-2H-1,2,4-triazol-3-yl)pyridin-3-yl)methoxy)-2-methoxy-isonicotinaldehyde (Compound 189)

Step 1:

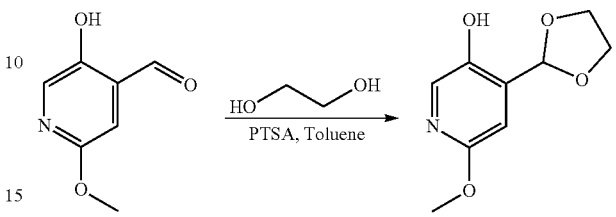

To 5-hydroxy-2-methoxyisonicotinaldehyde (1.0 g, 6.54 mmol, 1.0 eq.) in toluene (50.0 mL) were added ethane-1,2-diol (10.0 mL) and PTSA (248 mg, 1.31 mmol, 0.2 eq.). The mixture was heated to reflux O/N, cooled to rt, neutralized to pH 8, and extracted with EtOAc three times. The combined organic layers were washed with brine, dried over Na$_2$SO$_4$, and concentrated to give 4-(1,3-dioxolan-2-yl)-6-methoxypyridin-3-ol (980 mg, 76%) as an off-white solid. LRMS (M+H$^+$) m/z 198.1.

Step 2:

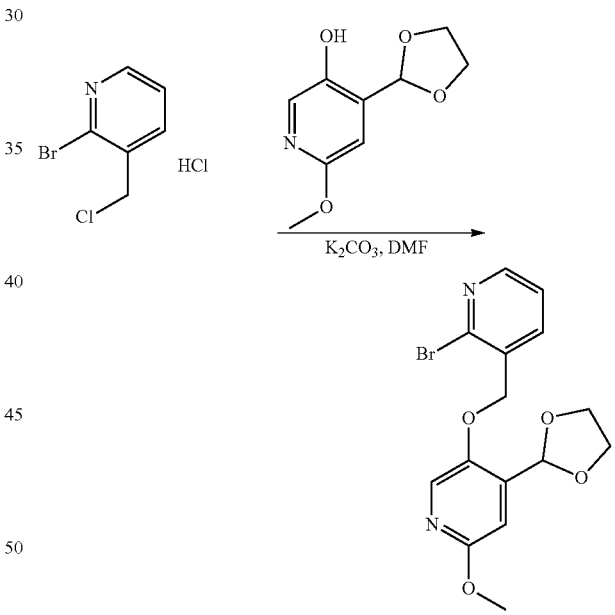

A mixture of 4-(1,3-dioxolan-2-yl)-6-methoxypyridin-3-ol (980 mg, 4.97 mmol, 1 eq.), 2-bromo-3-(chloromethyl)pyridine hydrochloride (1.2 g, 4.93 mmol, 1 eq.) and K$_2$CO$_3$ (2.7 g, 19.88 mmol, 4 eq.) in DMF (10.0 mL) was heated at 70° C. for 2 h. The mixture was cooled, filtered, concentrated, and purified on silica gel using a mixture of EtOAc and hexanes as eluent to give 5-((2-bromopyridin-3-yl)methoxy)-4-(1,3-dioxolan-2-yl)-2-methoxypyridine (1.21 g, 66%) as a white solid, $^1$H NMR (400 MHz, CDCl$_3$) δ 8.26 (dd, J=4.7, 1.9 Hz, 1H), 7.83 (dd, J=7.6, 1.9 Hz, 1H), 7.74 (s, 1H), 7.25 (dd, J=7.6, 4.8 Hz, 1H), 6.86 (s, 1H), 6.10 (s, 1H), 5.09 (s, 2H), 4.07-3.93 (m, 4H), 3.82 (s, 3H). LRMS (M+H$^+$) m/z 367.0.

Step 3:

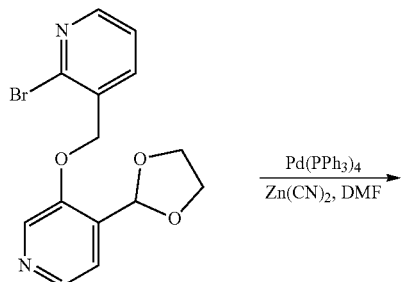

Pd(PPh₃)₄
Zn(CN)₂, DMF
→

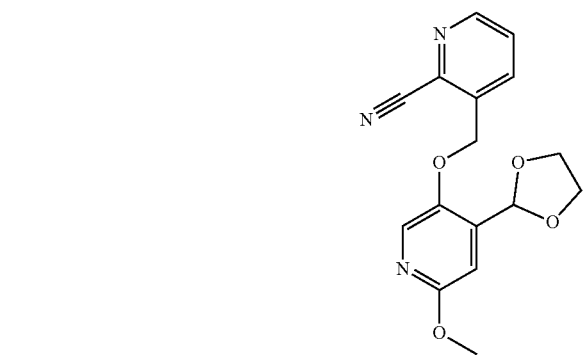

A mixture of 5-((2-bromopyridin-3-yl)methoxy)-4-(1,3-dioxolan-2-yl)-2-methoxypyridine (1.1 g, 3.0 mmol, 1 eq.), Zn (CN)₂ (704 mg, 6.0 mmol, 2.0 eq.), and Pd(PPh₃)₄ (346 mg, 0.3 mmol, 0.2 eq.) in DMF (10 mL) was heated at 125° C. for 2 h under N₂. The mixture was cooled, filtered, concentrated, and purified on silica gel using a mixture of EtOAc and hexanes as eluent to give 3-((4-(1,3-dioxolan-2-yl)-6-methoxypyridin-3-yloxy)methyl)picolinonitrile (820 mg, 84%) as a white solid, ¹H NMR (400 MHz, CDCl₃) δ 8.71 (d, J=4.6 Hz, 1H), 8.12 (dd, J=8.0, 0.7 Hz, 1H), 7.88 (s, 1H), 7.60 (dd, J=8.0, 4.7 Hz, 1H), 6.95 (s, 1H), 6.16 (a, 1H), 5.37 (s, 2H), 4.18-4.00 (m, 4H), 3.92 (s, 3H). LRMS (M+H⁺) m/z 314.1.

Step 4:

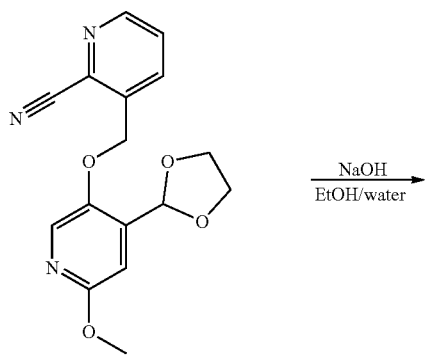

NaOH
EtOH/water
→

-continued

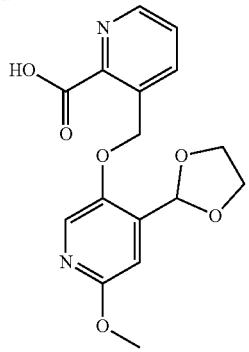

To 3-((4-(1,3-dioxolan-2-yl)-6-methoxypyridin-3-yloxy)methyl)picolinonitrile (150 mg, 0.48 mmol, 1 eq.) in a mixture of EtOH/water (5/1.12 mL) was added NaOH (192 mg, 4.8 mmol, 10 eq.). The mixture was heated to reflux O/N, partially concentrated, added ice, and acidified to pH 3 with HCl(conc.). The solid was collected and dried to give 3-((4-(1,3-dioxolan-2-yl)-6-methoxypyridin-3-yloxy)methyl)picolinic acid (145 mg, 91%) as a white solid. ¹H NMR (400 MHz, MeOD) δ 8.38-8.48 (br, 1H), 8.28-8.35 (br, 1H), 7.76 (s, 1H), 7.50-7.70 (br, 1H), 6.81 (s, 1H), 6.04 (s, 1H), 5.50-5.64 (br, 2H), 4.03-3.87 (m, 3H), 3.75 (s, 3H). LRMS (M+H⁺) m/z 333.0.

Step 5:

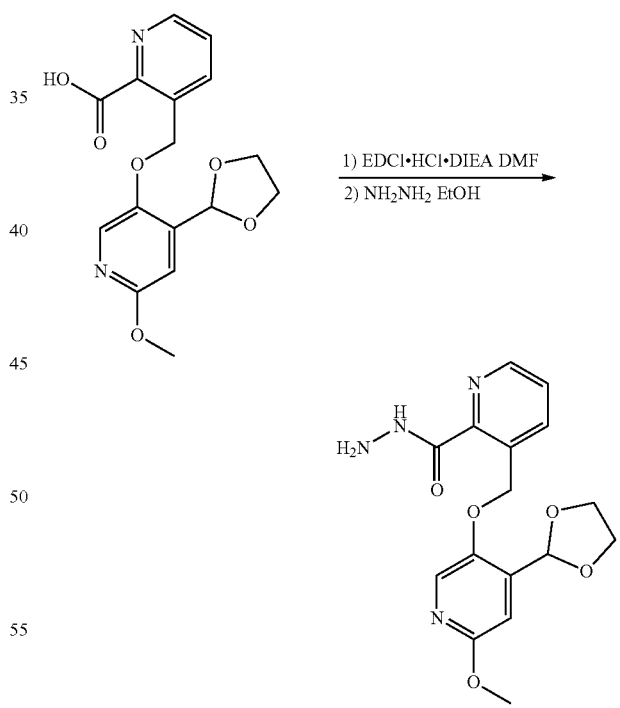

1) EDCl·HCl·DIEA DMF
2) NH₂NH₂ EtOH
→

To a mixture of 3-((4-(1,3-dioxolan-2-yl)-6-methoxypyridin-3-yloxy)methyl)picolinic acid (145 mg, 0.44 mmol, 1 eq.) and EDCl. HCl (169 mg, 0.88 mmol, 2 eq.) in DMF (3.0 mL) was added DIEA (146 uL, 0.88 mmol, 2 eq.). The mixture was stirred at rt for 1 h and purified by RP-HPLC (Gemini 21.2×150 mm) using a mixture of CH₃CN and water to isolate the urea intermediate. The fractions were concentrated and dissolved in EtOH (5.0 mL). To this mixture was added hydrazine (0.5 mL) at rt. The mixture was stirred at rt for 1 h, partially concentrated, and diluted with water (10 mL). The solid was collected, washed with water, and dried to give 3-((4-(1,3-dioxolan-2-yl)-6-methoxypyridin-3-yloxy)methyl)picolinohydrazide (97 mg, 64% for two steps) as a white solid. $^1$H NMR (400 MHz, CDCl$_3$) 9.13 (s, 1H), 8.51 (d, J=4.6 Hz, 1H), 8.24 (d, J=7.9 Hz, 1H), 7.85 (s, 1H), 7.51 (dd, J=8.0, 4.6 Hz, 1H), 6.95 (s, 1H), 6.24 (s, 1H), 5.80 (s, 2H), 4.20-4.06 (m, 4H), 3.90 (s, 3H). LRMS (M+H$^+$) m/z 347.1.

Step 6:

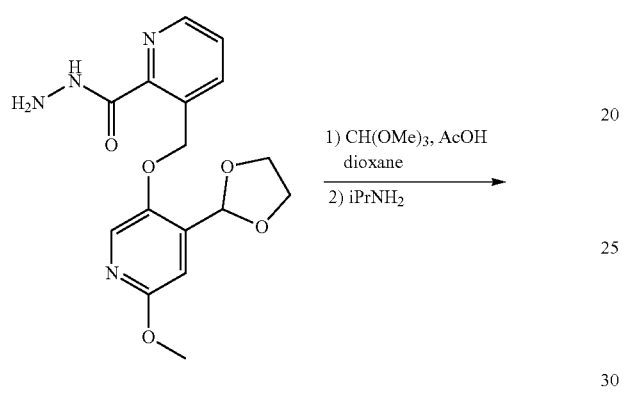

To a mixture of 3-((4-(1,3-dioxolan-2-yl)-6-methoxypyridin-3-yloxy)methyl)picolinohydrazide (90 mg, 0.26 mmol, 1 eq.) and AcOH (0.4 mL) in dioxane (2.0 mL) was added CH(OMe)$_3$ (0.4 mL). The mixture was sealed and heated at 110° C. for 1 h, cooled to rt, and added isopropyl amine (0.4 mL). The mixture was re-sealed, heated at 110° C. O/N, concentrated, and purified on RP-HPLC (Gemini 21.2×150 mm) using a mixture of CH$_3$CN and water as eluent to give 4-(1,3-dioxolan-2-yl)-5-((2-(2-isopropyl-2H-1,2,4-triazol-3-yl)pyridin-3-yl)methoxy)-2-methoxypyridine (68 mg, 66%) as a white solid. $^1$H NMR (400 MHz, CDCl$_3$) δ 8.66 (dd, J=4.7, 1.2 HZ, 1H), 8.41 (s, 1H), 8.24 (dd, J=8.0, 1.2 Hz, 1H), 7.76 (s, 1H), 7.45 (dd, J=8.0, 4.7 Hz, 1H), 6.90 (s, 1H), 6.17 (s, 1H), 5.61 (s, 2H), 5.30 (sep, J=6.7 Hz, 1H), 4.17-4.02 (m, 4H), 3.88 (s, 3H), 1.55 (d, J=6.7 Hz, 6H). LRMS (M+H$^+$) m/z 398.2.

Step 7:

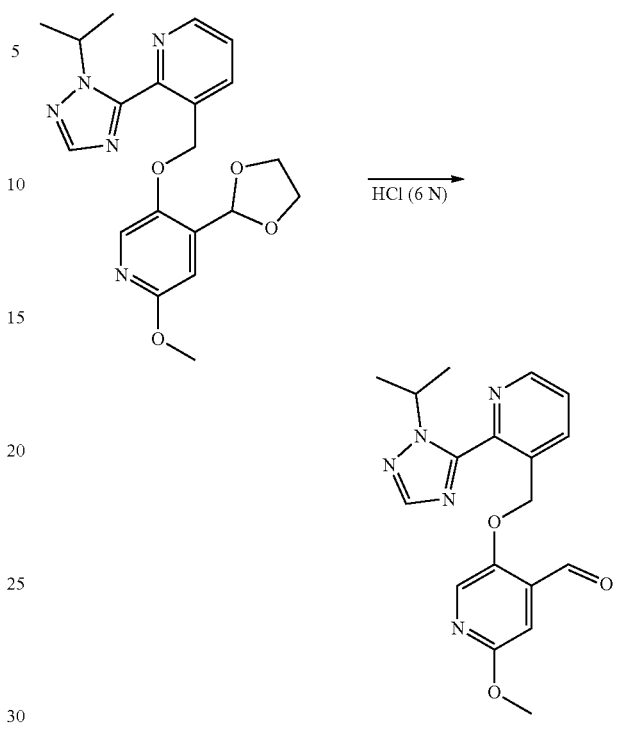

To 4-(1,3-dioxolan-2-yl-5-((2-(2-isopropyl-2H-1,2,4-triazol-3-yl)pyridin-3-yl)methoxy)-2-methoxypyridine (60 mg, 0.15 mmol, 1 eq.) in a RB flask was added HCl (6 N, 2.0 mL). The mixture was warmed to 40° C. O/N, cooled to rt, neutralized to pH 7-8 with NaHCO$_{3(sat)}$ solution, and extracted with EtOAc three times. The combined organic layers were washed with brine, dried over Na$_2$SO$_4$, and concentrated to give 5-((2-(2-isopropyl-2H-1,2,4-triazol-3-yl)pyridin-3-yl)methoxy)-2-methoxyisonicotinaldehyde (52.2 mg, 99%) as a yellow solid. $^1$H NMR (400 MHz, CDCl$_3$) δ 10.35 (a, 1H), 8.62 (dd, J=4.6, 1.2 Hz, 1H), 8.33 (s, 1H), 8.11 (dd, J=8.0, 1.2 Hz, 1H), 7.98 (s, 1H), 7.40 (dd, J=8.0, 4.7 Hz, 1H), 6.99 (s, 1H), 5.62 (s, 2H), 5.28 (sep, 0.7-6.7 Hz, 1H), 3.82 (s, 3H), 1.46 (d, J=6.7 Hz, 6H). LRMS (M+H$^+$) m/z 354.1.

Example 83. Preparation of 5-((2-(1-isopropyl-4-methyl-1H-pyrazol-5-yl)pyridin-3-yl)methoxy)-2-methoxyisonicotinaldehyde (Compound 190)

Step 1:

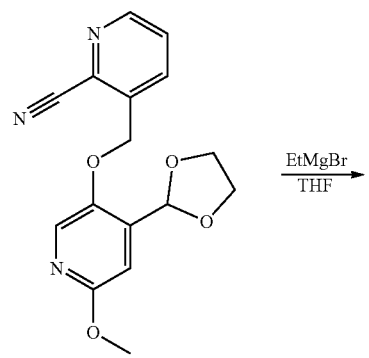

-continued

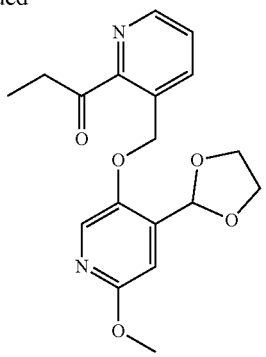

Ethyl magnesium bromide (3M/ether, 1.53 mL, 4.60 mmol, 1.5 eq.) was added to a stirred solution of 3-((4-(1,3-dioxolan-2-yl)-6-methoxypyridin-3-yloxy)methyl)picolinonitrile (960 mg, 3.07 mmol, 1 eq.) in THF (15.0 mL) at −78° C. After addition, the reaction mixture was allowed to warm to rt and quenched with aqueous citric acid solution. The aqueous layer was extracted with EtOAc (2×30 mL). The combined organic layers were washed with NaHCO$_3$ $_{(sat)}$ solution and brine, dried over Na$_2$SO$_4$, concentrated, and purified on silica gel using a mixture of EtOAc and hexanes as eluent to give 1-(3-((4-(1,3-dioxolan-2-yl)-6-methoxypyridin-3-yloxy)methyl)pyridin-2-yl)propan-1-one (611 mg, 58%) as a colorless oil. LRMS (M+H$^+$) m/z 345.1.

Step 2:

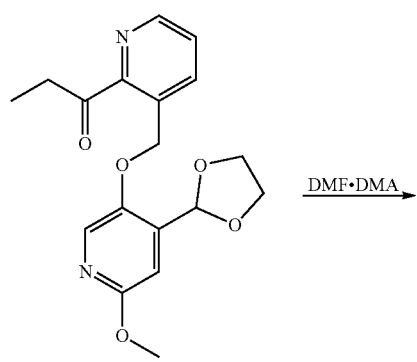

1-(3-((4-(1,3-dioxolan-2-yl)-6-methoxypyridin-3-yloxy)methyl)pyridin-2-yl)propan-1-one (600 mg, 1.74 mmol) in dimethoxy-N,N-dimethylmethanamine (10.0 mL) was heated to reflux O/N. The mixture was concentrated to give (E)-1-(3-((4-(1,3-dioxolan-2-yl)-6-methoxypyridin-3-yloxy)methyl)pyridin-2-yl)-3-(dimethylamino)-2-methyl-prop-2-en-1-one, which was used for next step without further purification. LRMS (M+H$^+$) m/z 400.2.

Step 3:

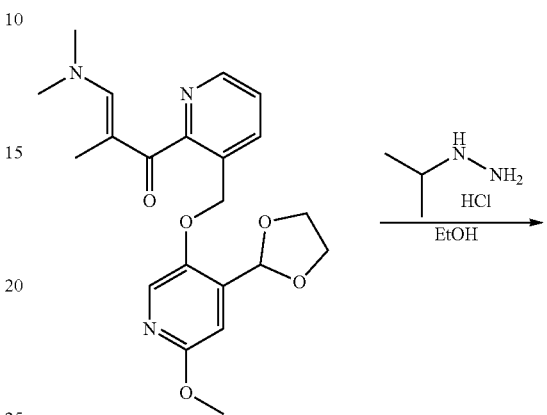

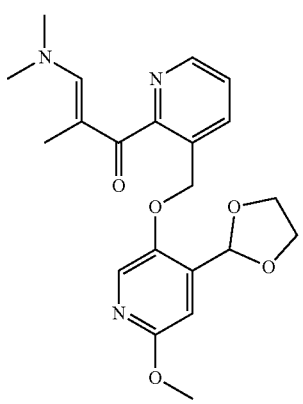

To (E)-1-(3-((4-(1,3-dioxolan-2-yl)-6-methoxypyridin-3-yloxy)methyl)pyridin-2-yl)-3-(dimethylamino)-2-methyl-prop-2-en-1-one (crude, 230 mg, 0.58 mmol, 1 eq.) in EtOH (5 mL) was added isopropylhydrazine hydrochloride (128 mg, 1.16 mmol, 2 eq.) at rt. The mixture was heated at 80° C. for 2 h, cooled to rt, concentrated, and diluted with a mixture of EtOAc (50 mL) and NaHCO$_{3(sat)}$ (10.0 mL) solution. The layers were separated and aqueous layer was extracted with EtOAc three times. The combined organic layers were dried over Na$_2$SO$_4$, concentrated, and purified on silica gel using a mixture of EtOAc and hexanes as eluent to give 4-(1,3-dioxolan-2-yl)-5-((2-(1-isopropyl-4-methyl-1H-pyrazol-5-yl)pyridin-3-yl)methoxy)-2-methoxypyridine (48 mg, 20% for two steps). $^1$H NMR (400 MHz, CDCl$_3$) δ 8.75 (dd, J=4.7, 1.4 Hz, 1H), 8.12 (d, J=8.1 Hz, 1H), 7.62 (s, 1H), 7.49-7.44 (m, 2H), 6.91 (s, 1H), 6.11 (s, 1H), 4.85-5.01 (m, 2H), 4.30-3.98 (m, 5H), 3.88 (s, 3H), 1.94 (s, 3H), 1.50 (d, J=6.7 Hz, 3H), 1.39 (d, J=6.7 Hz, 3H). LRMS (M+H$^+$) m/z 411.2.

Step 4:

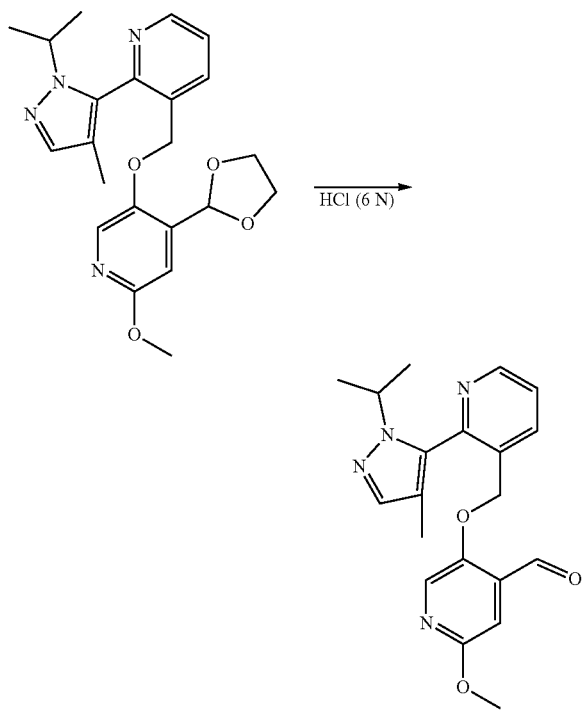

To 4-(1,3-dioxolan-2-yl)-5-((2-(1-isopropyl-4-methyl-1H-pyrazol-5-yl)pyridin-3-yl)methoxy)-2-methoxypyridine (41 mg, 0.1 mmol, 1 eq.) in a RB flask was added HCl (6 N, 2.0 mL). The mixture was warmed to 40° C. O/N, cooled to rt, neutralized to pH 7-8 with NaHCO$_{3(sat)}$ solution, and extracted with EtOAc three times. The combined organic layers were washed with brine, dried over Na$_2$SO$_4$, concentrated, and purified on silica gel using a mixture of EtOAc and hexanes as eluent to give 5-((2-(1-isopropyl-4-methyl-1H-pyrazol-5-yl)pyridin-3-yl)methoxy)-2-methoxyisonicotinaldehyde (33.3 mg, 99%) as an pale-yellow oil. $^1$H NMR (400 MHz, CDCl$_3$) δ 10.32 (s, 1H), 8.71 (dd, J=4.7, 1.6 Hz, 1H), 7.99 (dd, J=7.9, 1.5 Hz, 1H), 7.76 (s, 1H), 7.40 (dd, J=7.1, 4.7 Hz, 1H), 7.39 (s, 1H), 7.01 (s, 1H), 4.86-4.99 (m, 2H), 4.12 (sep, J=6.7, 1H), 3.82 (s, 3H), 1.86 (s, 3H), 1.40 (d, J=767 Hz, 3H), 1.29 (d, J=6.7 Hz, 3H). LRMS (M+H$^+$) m/z 367.1.

Example 84. Preparation of 5-((2-(1-(2-hydroxyethyl)-1H-pyrazol-5-yl)pyridin-3-yl)methoxy)-2-methoxyisonicotinaldehyde (Compound 191)

The title compound was prepared according to the procedure in Example 83.

$^1$H NMR (400 MHz, CDCl$_3$) δ 10.18 (s, 1H), 8.50 (dd, J=4.8, 1.6 Hz, 1H), 7.89 (dd, J=7.9, 1.5 Hz, 1H), 7.72 (s, 1H), 7.42 (d, J=1.9 Hz, 1H), 7.27 (dd, J=7.9, 4.9 Hz, 1H), 6.90 (s, 1H), 6.26 (d, J1.9 Hz, 1H), 5.34 (s, 1H), 5.04 (s, 2H), 4.24-4.16 (m, 2H), 3.94-3.85 (m, 2H), 3.70 (8, 3H).

Example 85. Synthesis of 2,2,2-trifluoroacetic Acid: 6 (((4-formylpyridin-3-yl)oxy)methyl)picolinic Acid (1:1) (Compound 192)

Step 1:

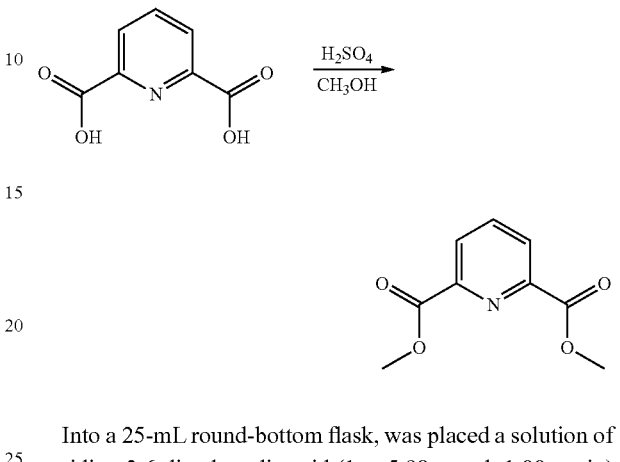

Into a 25-mL round-bottom flask, was placed a solution of pyridine-2,6-dicarboxylic acid (1 g, 5.98 mmol, 1.00 equiv) in methanol (12.5 mL). Sulfuric acid (2.5 mL) was added to the reaction mixture. The resulting solution was stirred overnight at 70° C., and then it was quenched by the addition of 10 mL of water. The pH value of the solution was adjusted to 7 with sodium carbonate. The resulting solution was extracted with 2×25 mL of dichloromethane, and the combined organic layers were dried over anhydrous sodium sulfate and concentrated under vacuum. This resulted in 0.95 g (81%) of 2,6-dimethyl pyridine-2,6-dicarboxylate as a white solid Step 2:

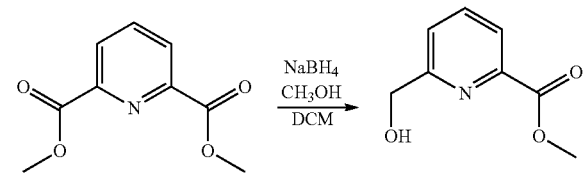

Into a 100-mL round-bottom flask, was placed a solution of 2,6-dimethyl pyridine-2,6-dicarboxylate (950 mg, 4.87 mmol, 1.00 equiv) in a solvent mixture of methanol (33.2 mL) and dichloromethane (14.2 mL). NaBH$_4$ (185 mg, 5.02 mmol, 1.00 equiv) was added to the reaction mixture in several batches at 0° C. The resulting solution was stirred overnight at room temperature, and then it was quenched by the addition of 50 mL of NH$_4$Cl (aq.). The resulting solution was extracted with 2×50 mL of dichloromethane and the combined organic layers were dried over anhydrous sodium sulfate and concentrated under vacuum. The residue was applied onto a silica gel column with ethyl acetate/petroleum ether (1:1-2:1) as eluent to yield 750 mg (92%) of methyl 6-(hydroxymethyl)pyridine-2-carboxylate as a white solid.

Step 3:

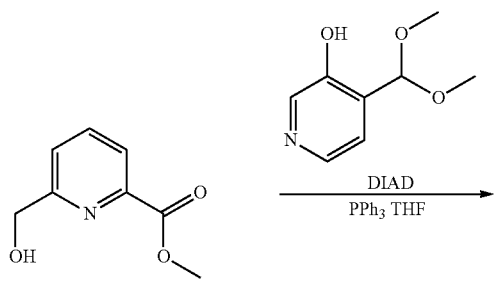

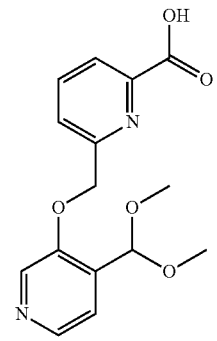

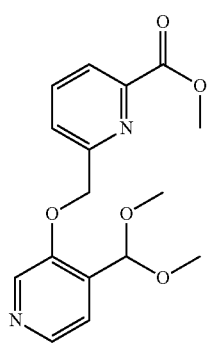

Into a 50-mL round-bottom flask, which was purged and maintained with an inert atmosphere of nitrogen, was placed a solution of methyl 6-(hydroxymethyl)pyridine-2-carboxylate (300 mg, 1.79 mmol, 1.00 equiv) in tetrahydrofuran (15 mL). 4-(Dimethoxymethyl)pyridin-3-ol (304.2 mg, 1.80 mmol, 1.00 equiv), and triphenylphosphane (615 mg, 2.34 mmol, 1.30 equiv) was added to the reaction mixture. This was followed by the addition of DIAD (473.1 mg, 2.34 mmol, 1.30 equiv) dropwise at 0° C. The resulting solution was stirred overnight at room temperature, and then it was quenched by the addition of 10 mL of water. The resulting solution was extracted with 2×50 mL of ethyl acetate and the combined organic layers were dried over anhydrous sodium sulfate and concentrated under vacuum. The residue was applied onto a silica gel column with ethyl acetate/petroleum ether (1:5-1:1) as eluent to yield 340 mg (60%) of methyl 6-([[4-(dimethoxymethyl)pyridin-3-yl]oxy]methyl)pyridine-2-carboxylate as a white solid.

Step 4:

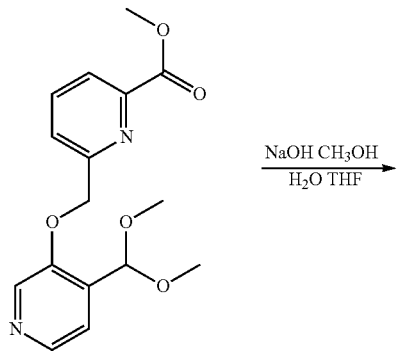

Into a 100-mL round-bottom flask, was placed methyl 6-([[4-(dimethoxymethyl)pyridin-3-yl]oxy]methyl)pyridine-2-carboxylate (310 mg, 0.97 mmol, 1.00 equiv) and sodium hydroxide (117 mg, 2.93 mmol, 3.00 equiv) in a solvent mixture of methanol (10 mL), water (10 mL) and tetrahydrofuran (10 mL). The resulting solution was stirred overnight at room temperature. The pH value of the solution was adjusted to 4-5 with hydrogen chloride (1 mol/L). The resulting solution was extracted with 3×20 mL of isopropal/DCM(1/3) and the organic layers combined and dried over anhydrous sodium sulfate and concentrated under vacuum. This resulted in 230 mg (78%) of 6-([[4-(dimethoxymethyl)pyridin-3-yl]oxy]methyl)pyridine-2-carboxylic acid as a white solid.

Step 5:

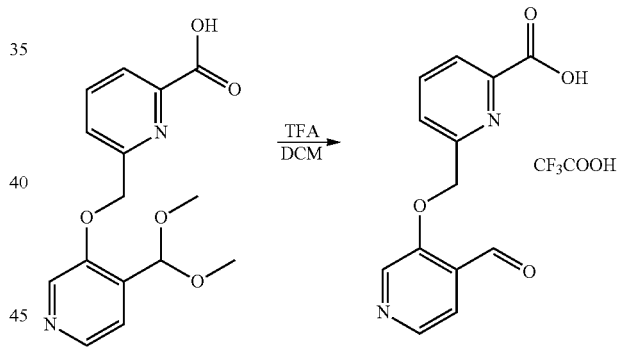

Into an 8-mL sealed tube, was placed a solution of 6-([[4-(dimethoxymethyl)pyridin-3-yl]oxy]methyl)pyridine-2-carboxylic acid (150 mg, 0.49 mmol, 1.00 equiv) in dichloromethane (4 mL) and trifluoroacetic acid (2 mL). The resulting solution was stirred for 3.5 h at 45° C. m an oil bath. The resulting mixture was concentrated under vacuum. The crude product (100 mg) was purified by Prep-HPLC with the following conditions (2#-AnalyseHPLC-SHIMADZU(HPLC-10)): Column, SunFire Prep CIS OBD Column, 5 um, 19*150 mm; mobile phase, water with 0.05% TFA and MeCN (10% MeCN up to 35% in 4 min, up to 100% in 1 min, down to 10% in 1 min); Detector, Waters2545 UvDector 254&220 nm. This resulted in 49 mg (38%) of 6-[[(4-formylpyridin-3-yl)oxy]methyl]pyridine-2-carboxylic acid as a light yellow solid. LC-MS-PH-GBT-ZL-HS-19-0 (ES, m/z): 259 [M+1]$^+$ H-NMR-PH-GBT-ZL-HS-19-0 (300 MHz, DMSO, ppm): 10.52 (s, 1H), 8.92 (s, 1H), 8.52 (d, J=4.8 Hz, 1H), 8.09 (m, 2H), 7.95 (m, 1H), 7.76 (d. J=4.8 Hz, 1H), 5.61 (s, 2H).

Example 86. Preparation of 5((2-(4-methyl-1H-pyrazol-5-yl)pyridin-3-yl)methoxy)-2-oxo-1,2-dihydropyridine-4-carbaldehyde (Compound 194)

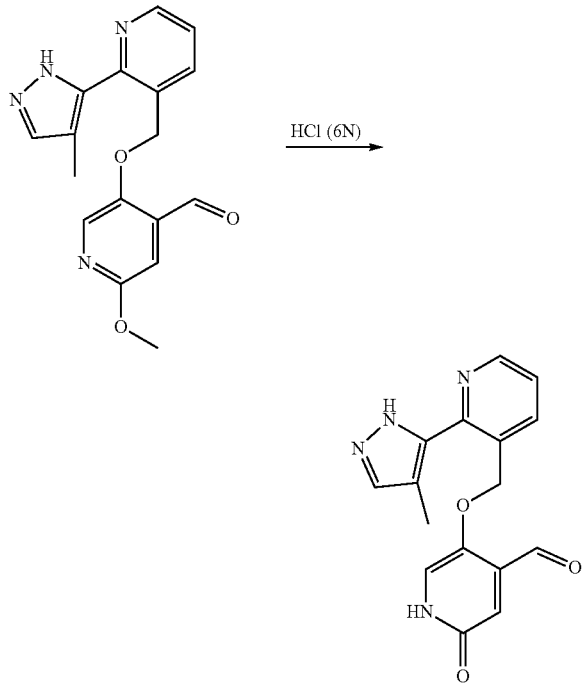

To 2-methoxy-5-((2-(4-methyl-1H-pyrazol-5-yl)pyridin-3-yl)methoxy)isonicotinaldehyde (862 mg, 2.66 mmol, 1 equiv) suspened in water (5.0 mL) was added HCl (6 N, 4.43 mL, 26.6 mmol, 10 eq.). Once the mixture turned into a homogeneous solution, it was frezee at −78° C. to an solid and pomp under high vaccum O/N. The yellow solid was continued to pump at 45° C. for 20 h, dissolved in water (2.0 mL), and basified to pH 11 with NaOH (2 N). The aqueous layer was washed with DCM three times and the pH of the mixture was adjusted to pH 6-7. The solid was collected and dried to give 5-((2-(4-methyl-1H-pyrazol-5-yl)pyridin-3-yl)methoxy)-2-oxo-1,2-dihydropyridine-4-carbaldehyde (180 mg, 44% based on 50% recovered of SM) as a white solid. $^1$H NMR (400 MHz, DMSO at 90° C.) δ 10.14 (s, 1H), 8.63 (s, 1H), 8.09-8.03 (br, 1H), 7.56-7.50 (br, 2H), 7.42-7.35 (br, 1H), 6.70 (s, 1H), 5.39 (s, 2H), 2.18 (s, 3H). LRMS (M+H$^+$) m/z 311.1.

Example 87. Preparation of 2-(5-(3-((4-formyl-6-methoxypyridin-3-yloxy)methyl)pyridin-2-yl)-1H-pyrazol-1-yl)acetic Acid (Compound 199)

Step 1

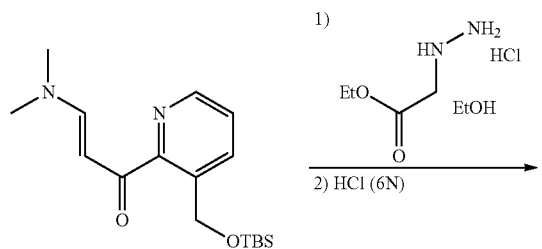

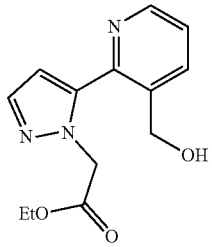

To (E)-1-(3-((tert-butyldimethylsilyloxy)methyl)pyridin-2-yl)-3-(dimethylamino)prop-2-en-1-one (crude, 350 mg, 1.09 mmol, 1 eq.) in EtOH (10 mL) was added ethyl 2-hydrazinylacetate hydrochloride (338 mg, 2.18 mmol, 2.0 eq.). The mixture was heated at 80° C. for 2 h, cooled to rt, added HCl (6 N, 0.5 mL), and stirred O/N. The mixture was concentrated, and diluted with a mixture of EtOAc (50 mL) and NaHCO$_{3(sat)}$ (10 mL). The layers were separated and the aqueous layer was extracted with EtOAc three times. The combined organic layers were dried over Na$_2$SO$_4$, concentrated, and purified on silica gel using EtOAc as eluent to give ethyl 2-(5-(3-(hydroxymethyl)pyridin-2-yl)-1H-pyrazol-1-yl)acetate (212 mg, 74%) as a colorless oil. $^1$H NMR (400 MHz, CDCl$_3$) δ 8.61 (dd, J=4.7, 1.6 Hz, 1H), 7.97 (dd, J=7.8, 1.4 Hz, 1H), 7.64 (d, J=1.9 Hz, 1H), 7.36 (dd, J=7.8, 4.8 Hz, 1H), 6.56 (d, J=1.9 Hz, 1H), 5.21 (s, 2H), 4.79 (d, J=5.8 Hz, 2H), 4.09 (q, J=7.1 Hz, 2H), 2.54 (t, J=6.0 Hz, 1H), 1.18 (t, J=7.1 Hz, 3H). LRMS (M+H$^+$) m/z 262.1

Step 2

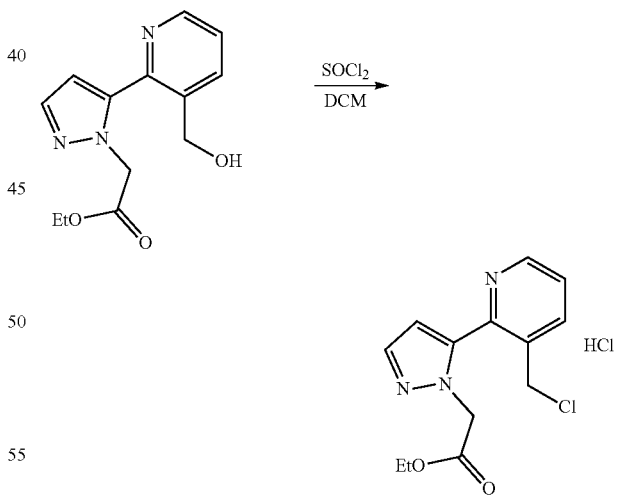

To ethyl 2-(5-(3-(hydroxymethyl)pyridin-2-yl)-1H-pyrazol-1-yl)acetate (182 mg, 0.70 mmol) in DCM (10 mL) was added SOCl$_2$ (3.0 mL) at it. The reaction mixture was stirred at rt for 4 h and concentrated to dryness. The crude solid was suspended in toluene and concentrated to dryness. The process was repeated three times and dried under vacuum to give ethyl 2-(5-(3-(chloromethyl)pyridin-2-yl)-1H-pyrazol-1-yl)acetate hydrochloride (220 mg) as an off-white solid, which was used for next step without further purification.

Step 3

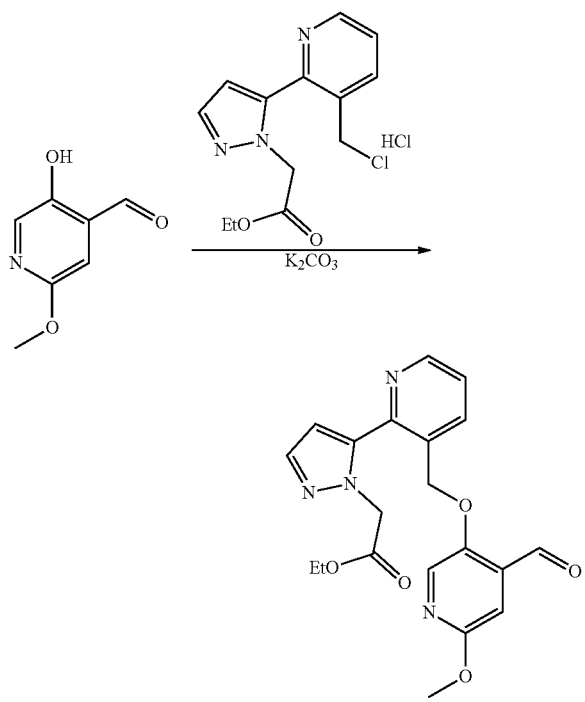

A mixture of 5-hydroxy-2-methoxyisonicotinaldehyde (107 mg, 0.70 mmol, 1 eq.), ethyl 2-(5-(3-(chloromethyl)pyridin-2-yl)-1H-pyrazol-1-yl)acetate hydrochloride (220 mg, 0.70 mmol, 1 eq.), and K₂CO₃ (386 mg, 2.8 mmol, 4 eq.) in DMF (6.0 mL) was heated at 70° C. for 2 h. The mixture was cooled, filtered, concentrated, and purified on silica gel using a mixture of EtOAc and hexanes as eluent to give ethyl 2-(5-(3-((4-formyl-6-methoxypyridin-3-yloxy)methyl)pyridin-2-yl)-1H-pyrazol-1-yl)acetate (261 mg, 94%) as a white solid. ¹H NMR (400 MHz, CDCl₃) δ 10.45 (s, 1H), 8.69 (d, J=3.8 Hz, 1H), 8.02 (s, 1H), 8.01 (d, J=7.5 Hz, 1H), 7.63 (d, J=1.6 Hz, 1H), 7.40 (dd, J=7.6, 4.0 Hz, 1H), 7.13 (s, 1H), 6.53 (d, J=1.6 Hz, 1H), 5.30 (s, 2H), 5.28 (s, 2H), 4.12 (q, J=7.1 Hz, 2H), 3.93 (s, 3H), 1.18 (t, J=7.1 Hz, 3H). LRMS (M+H⁺) m/z 397.1.

Step 4

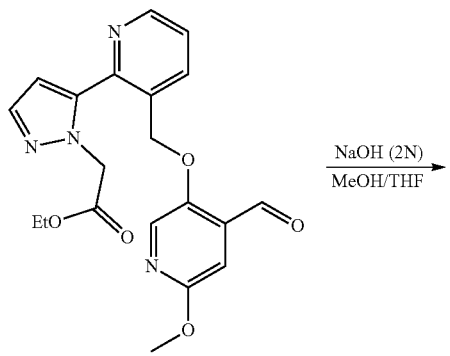

-continued

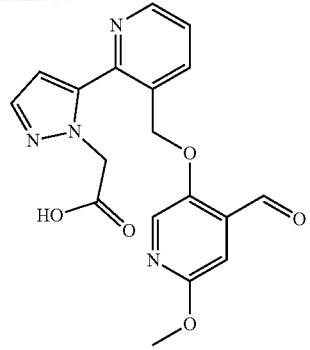

To ethyl 2-(5-(3-((4-formyl-6-methoxypyridin-3-yloxy)methyl)pyridin-2-yl)-1H-pyrazol-1-yl)acetate (182 mg, 0.46 mmol, 1 eq.) in a mixture of MeOH/THF (1/5, 12.0 mL) was added NaOH (2N, 2.3 mL, 4.6 mmol, 10 eq.). The mixture was stirred at rt for 2 h, acidified to pH 3, and extracted with EtOAc (3×20 mL). The combined organic layers were dried over Na₂SO₄ and concentrated to give 2-(5-(3-((4-formyl-6-methoxypyridin-3-yloxy)methyl)pyridin-2-yl)-1H-pyrazol-1-yl)acetic acid (135.1 mg, 80%) as a white solid. ¹H NMR (400 MHz, CDCl₃) δ 10.42 (s, 1H), 8.71 (d, 4.7 Hz, 1H), 8.13 (d, J=7.8 Hz, 1H), 7.97 (s, 1H), 7.66 (d, J=1.6 Hz, 1H), 7.52 (dd, J=7.9, 4.9 Hz, 1H), 7.13 (s, 1H), 6.56 (d, J=1.7 Hz, 1H), 5.31 (s, 2H), 5.14 (s, 2H), 3.91 (s, 3H). LRMS (M+H⁺) m/z 369.1.

Examples 88 and 89 were prepared according to example 87 above.

Example 88, Preparation of Methyl 3-(5-(3-(((4-formyl)-6-methoxypyridin-3-yl)oxy)methyl)pyridin-2-yl)-1H-pyrazol-1-yl)propanoate (Compound 200)

¹H NMR (400 MHz. CDCl3) δ 10.44 (s, 1H), 8.75 (dd, J=4.8, 1.6 Hz, 1H), 8.05 (dd, J=7.9, 1.4 Hz, 1H), 7.99 (s, 1H), 7.58 (d, J=1.9 Hz, 1H), 7.44 (dd, J=7.9.4.8 Hz, 1H), 7.12 (s, 1H), 6.41 (d, J=1.9 Hz, 1H), 5.21 (s, 2H), 4.55 (t, J=7.1 Hz, 2H), 3.92 (s, 3H), 3.62 (s, 3H), 3.00 (t, J=7.1 Hz, 2H).

Example 89. Preparation of 3-(5-(3-(((4-formyl-6-methoxypyridin-3-yl)oxy)methyl)pyridin-2-yl)-1H-pyrazol-1-yl)propanoic Acid (Compound 202)

¹H NMR (400 MHz, CDCl3) δ 10.33 (s, 1H), 8.66 (dd, J=4.8, 1.6 Hz, 1H), 7.96 (dd, J=7.9, 1.5 Hz, 1H), 7.83 (s, 1H), 7.53 (d, J=1.9 Hz, 1H), 7.37 (dd, J=7.9, 4.8 Hz, 1H), 7.02 (s, 1H), 6.33 (d, J=1.9 Hz, 1H), 5.13 (s, 2H), 4.49 (t, J=6.5 Hz, 2H), 3.81 (s, 3H), 2.94 (t, J=6.5 Hz, 2H).

Example 90. Preparation of 3-(3-(3-((4-formyl-6-methoxypyridin-3-yloxy)methyl)pyridin-2-yl)-1H-pyrazol-1-yl)propanoic Acid (Compound 201)

Step 1

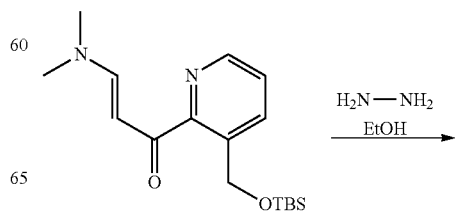

-continued

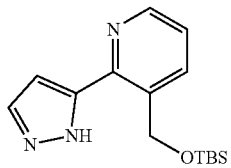

To (E)-1-(3-((tert-butyldimethylsilyloxy)methyl)pyridin-2-yl)-3-(dimethylamino)prop-2-en-1-one (crude, 350 mg, 1.09 mmol, 1 eq.) in EtOH (5 mL) was added hydrazine (140 mg, 4.36 mmol, 4 eq.). The mixture was heated at 80° C. for 2 h, cooled, concentrated, and purified on silica gel using EtOAc as eluent to give 3-((tert-butyldimethylsilyloxy)methyl)-2-(1H-pyrazol-5-yl)pyridine (282 mg, 90%) as a while solid. LRMS (M+H+) m/z 290.1
Step 2

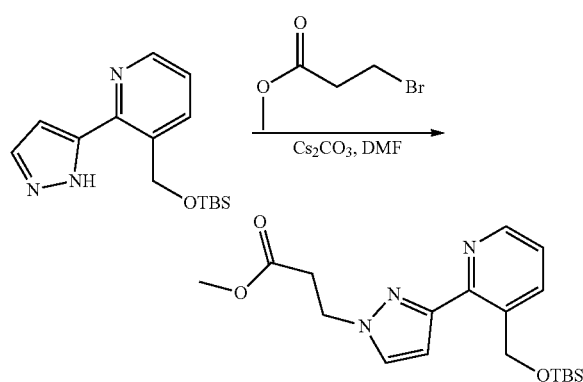

To a mixture of 3-((tert-butyldimethylsilyloxy)methyl)-2-(1H-pyrazol-5-yl)pyridine (140 mg, 0.48 mmol, 1 eq.) and Cs₂CO₃ (312 mg, 0.96 mmol, 2 eq.) in DMF (3 mL) was added methyl 3-bromopropanoate (122 mg, 0.73 mmol, 1.5 eq.). The mixture was stirred at rt for 6 h, filtered, concentrated, and purified on silica gel using a mixture of EtOAc and hexanes as eluent to give methyl 3-(3-(3-((tert-butyldimethylsilyloxy)methyl)pyridin-2-yl)-1H-pyrazol-1-yl)propanoate (110 mg, 61%). LRMS (M+H+) m/z 376.1.
Step 3

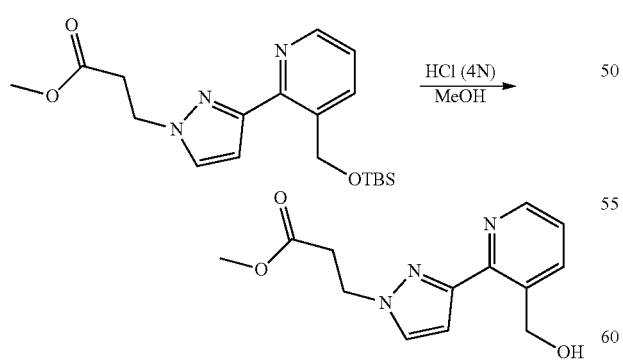

To methyl 3-(3-(3-((tert-butyldimethylsilyloxy)methyl)pyridin-2-yl)-1H-pyrazol-1-yl)propanoate in MeOH (10 mL) was added HCl (2 N, 1.2 mL, 10 eq.). The mixture was stirred at rt for 4 h, concentrated, neutralized to pH 7-8 with NaHCO₃(sat) solution, and extracted with EtOAc three times. The combined organic layers were washed with brine, dried over Na₂SO₄, concentrated, and purified on silica gel using EtOAc as eluent to give methyl 3-(3-(3-(hydroxymethyl)pyridin-2-yl)-1H-pyrazol-1-yl)propanoate (51 mg, 67%) as an oil. LRMS (M+H+) m/z 262.1.
Step 4

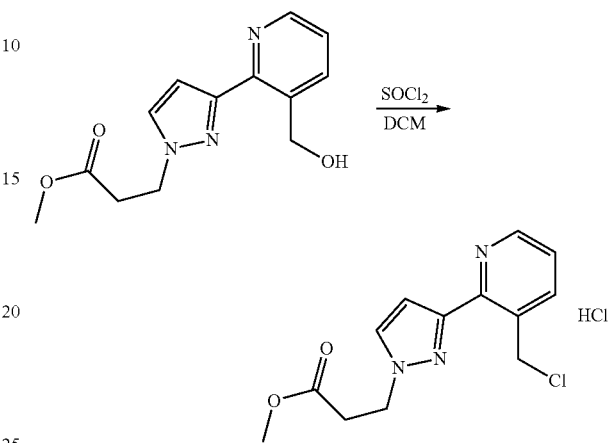

To methyl 3-(3-(3-(hydroxymethyl)pyridin-2-yl)-1H-pyrazol-1-yl)propanoate (51 mg, 0.20 mmol) in DCM (5 mL) was added SOCl₂ (1.0 mL) at rt. The reaction mixture was stirred at rt for 4 h and concentrated to dryness. The crude solid was suspended in toluene and concentrated to dryness. The process was repeated three times and dried under vacuum to give methyl 3-(3-(3-(chloromethyl)pyridin-2-yl)-1H-pyrazol-1-yl)propanoate hydrochloride (63 mg) as an off-white solid, which was used for next step without further purification.
Step 5

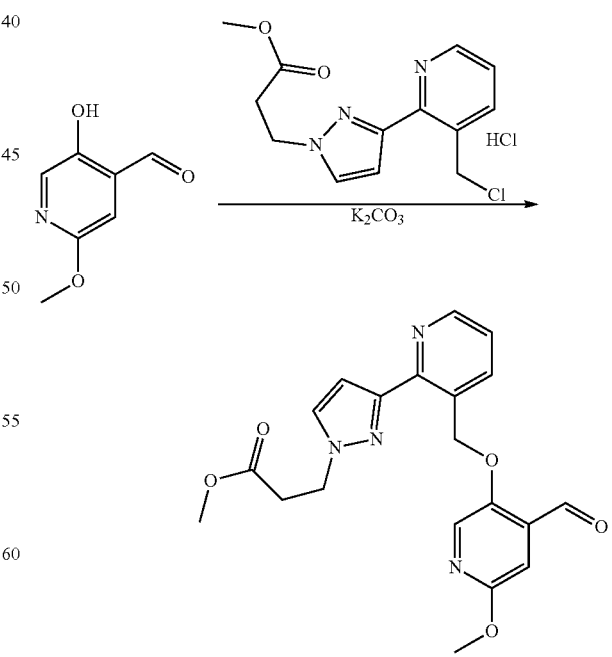

A mixture of 5-hydroxy-2-methoxyisonicotinaldehyde (30 mg, 0.20 mmol, 1 eq.), methyl 3-(3-(3-(chloromethyl)

pyridin-2-yl)-1H-pyrazol-1-yl)propanoate hydrochloride (63 mg, 0.20 mmol, 1 eq.), and K₂CO₃ (100 mg, 10.32 mmol, 4 eq.) in DMF (5.0 mL) was heated at 70° C. for 2 h. The mixture was cooled, filtered, concentrated, and purified on silica gel using a mixture of EtOAc and hexanes as eluent to give methyl 3-(3-(3-((4-formyl-6-methoxypyridin-3-yloxy)methyl)pyridin-2-yl)-1H-pyrazol-1-yl)propanoate (88 mg, quantitative yield) as a white solid. ¹H NMR (400 MHz, CDCl₃) δ 10.50 (s, 1H), 8.65 (dd, J=4.7, 0.9 Hz, 1H), 8.09 (s, 1H), 8.02 (dd, 7.8, 0.8 Hz, 1H), 7.53 (d, J=2.3 Hz, 1H), 7.31 (dd, J=7.9, 4.8 Hz, 1H), 7.12 (s, 1H), 6.96 (d, J=2.3 Hz, 1H), 5.71 (s, 2H), 4.46 (t, J=6.6 Hz, 2H), 3.93 (s, 3H), 3.69 (s, 3H), 2.91 (t, J=6.6 Hz, 2H). LRMS (M+H⁺) m/z 397.1.

Step 6

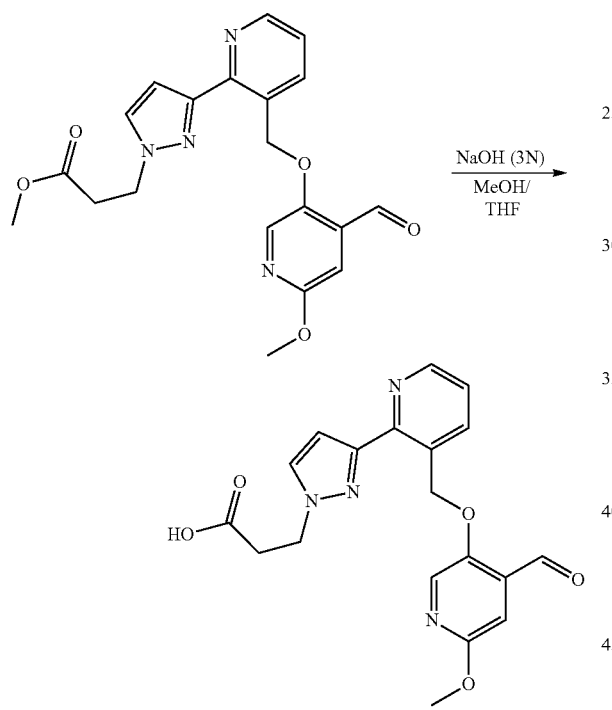

To methyl 3-(3-(3-((4-formyl-6-methoxypyridin-3-yloxy) methyl)pyridin-2-yl)-1H-pyrazol-1-yl)propanoate (72 mg, 0.18 mmol, 1 eq.) in a mixture of MeOH/THF (1/6, 6.0 mL) was added NaOH (3 N, 0.6 mL, 1.8 mmol, 10 eq.). The mixture was stirred at rt for 2 h, acidified to pH 3, extracted with EtOAc (3×20 mL). The combined organic layers were dried over Na₂SO₄ and concentrated to give 3-(3-(3-((4-formyl-6-methoxypyridin-3-yloxy)methyl)pyridin-2-yl)-1H-pyrazol-1-yl)propanoic acid (53.4 mg, 78%) as a white solid, ¹H NMR (400 MHz, CDCl₃) δ 10.42 (s, 1H), 8.57 (d, J=4.6 Hz, 1H), 8.08 (s, 1H), 7.95 (d, J=7.8 Hz, 1H), 7.46 (d, J=2.3 Hz, 1H), 7.23 (dd, J=7.9, 4.6 Hz, 1H), 7.03 (s, 1H), 6.85 (d, J=2.3 Hz, 1H), 5.64 (s, 2H), 4.42 (t, J=6.1 Hz, 2H), 3.83 (s, 3H), 2.86 (t, J=6.1 Hz, 2H). LRMS (M+H⁺) m/z 383.1.

Example 91. Preparation of 6-(((4-formylpyridin-3-yl)oxy)methyl)nicotinonitrile 2,2,2-trifluoroacetate (Compound 204)

Step 1:

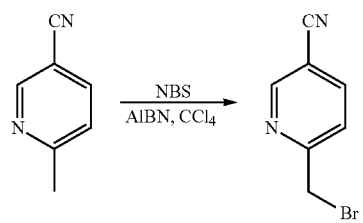

Into a 250-mL round-bottom flask, was placed a solution of 6-methylpyridine-3-carbonitrile (8 g, 67.72 mmol, 1.00 equiv) in CCl4 (125 mL). N-Bromosuccinimide (13.4 g, 75.29 mmol, 1.10 equiv), and AIBN (480 mg, 2.92 mmol, 0.04 equiv) were added to the reaction solution. The resulting solution was stirred for 5 h at 85° C. The resulting mixture was concentrated under vacuum. The residue was applied onto a silica gel column with ethyl acetate/petroleum ether (1:5) as eluent to yield 5 g (37%) of 6-(bromomethyl)pyridine-3-carbonitrile as a beige solid.

Step 2:

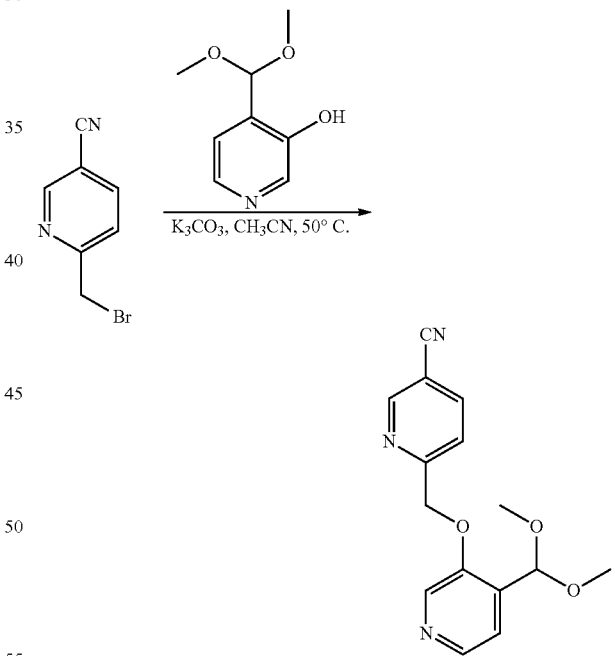

Into a 250-mL round-bottom flask, was placed a solution of 6-(bromomethyl)pyridine-3-carbonitrile (3 g, 15.23 mmol, 1.00 equiv) in CH3CN (100 mL). Potassium carbonate (4.24 g, 30.68 mmol, 2.00 equiv) and 4-(dimethoxymethyl)pyridin-3-ol (2.83 g, 16.73 mmol, 1.10 equiv) were added to the reaction mixture. The resulting solution was stirred for 2 h at 50° C., and then it was concentrated under vacuum. The residue was applied onto a silica gel column with ethyl acetate/petroleum ether (1:3) as eluent to furnish 1.4 g (32%) of 6-([[4-(dimethoxymethyl)pyridin-3-yl]oxy]methyl)pyridine-3-carbonitrile as a red solid.

Step 2:

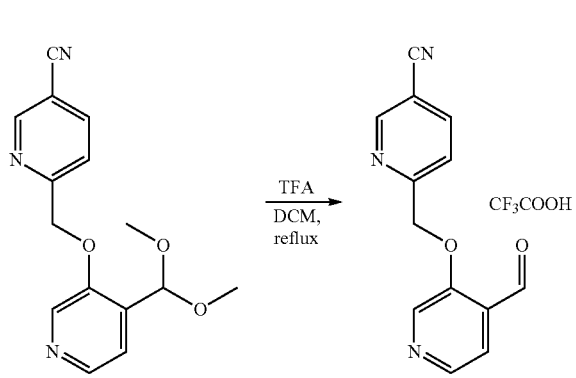

Into an 8-mL vial, was placed a solution of 6-([[4-(dimethoxymethyl)pyridin-3-yl]oxy]methyl)pyridine-3-carbonitrile (100 mg, 0.35 mmol, 1.00 equiv) in a mixture of dichloromethane (2 mL) and trifluoroacetic acid (1 mL). The resulting solution was stirred for 5 h at 45° C., and then it was concentrated under vacuum. The crude product (50 mg) was purified by Prep-HPLC with the following conditions (Prep-HPLC-010): Column, SunFire Prep C18 ODD Column, 5 um, 19*150 mm; mobile phase, Water and MeCN (10.0% MeCN up to 40.0% in 3 min, up to 100.0% in 2 min, down to 10.0% in 1 min); Detector, Waters2S45 UvDector 254&220 nm. This resulted in 8 mg (10%) of 6-[[(4-formylpyridin-3-yl)oxy]methyl]pyridine-3. carbonitrile as a white solid. LC-MS-PH-GBT-ZL-HS-13-0: (ES, m/z):258 [M+1+18]$^+$. H-NMR-PH-GBT-ZL-HS-13-0: (300 MHz, DMSO, ppm): 10.48 (s, 1H), 9.06 (s, 1H), 8.80 (s, 1H), 8.47 (m, 2H), 7.94 (d, J=8.1 Hz, 1H), 7.65 (d, J=5.1 Hz, 1H), 5.69 (s, 2H).

Example 92. Preparation of 6-(((4-formylpyridin-3-yl)oxy)methyl)nicotinic acid hydrochloride (Compound 205)

Step 1:

Into a 100-mL round-bottom flask, was placed a solution of 6-([[4-(dimethoxymethyl)pyridin-3-yl]oxy]methyl)pyridine-3-carbonitrile (1 g, 3.51 mmol, 1.00 equiv) in water (30 mL). Sodium hydroxide (1.4 g, 35.00 mmol, 10.00 equiv) was added to the reaction. The resulting solution was stirred for 4 h at 90° C. The pH value of the solution was adjusted to 4-5 with hydrogen chloride (aq. 3 mol/L). The resulting solution was extracted with 3×200 ml of ethyl acetate. The aqueous layer was extracted again with 3×200 ml of tetrahydrofuran. The combined organic layers were concentrated under vacuum. This resulted in 1 g (94%) of 6-([[4-(dimethoxymethyl)pyridin-3-yl]oxy]methyl)pyridine-3-carboxylic acid as a yellow solid.

Step 2:

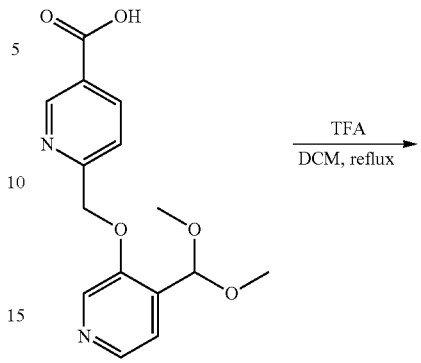

Into on 8-mL vial, was placed a solution of 6-([[4-(dimethoxymethyl)pyridin-3-yl]oxy]methyl)pyridine-3-carboxylic acid (100 mg, 0.33 mmol, 1.00 equiv) in a solvent mixture of dichloromethane (2 mL) and trifluoroacetic acid (1 mL). The resulting solution was stirred for 3 h at 40° C., and then it was concentrated under vacuum. The crude product (70 mg) was purified by Prep-HPLC with the following conditions (Prep-HPLC-010): Column, SunFire Prep C18 OBD Column, 5 um, 19*150 mm; mobile phase, water (0.05% HCl) and MeCN (10.0% MeCN up to 40.0% in 3 min, up to 100.0% in 2 min, down to 10.0% in 1 min); Detector, Waters2545 UvDector 254&220 nm. This resulted in 30 mg (31%) of 6-[[(4-formylpyridin-3-yl)oxy]methyl] pyridine-3-carboxylic acid hydrochloride as a white solid. The compound exhibited a melting point of 192-194° C. LC-MS-PH-GBT-ZL-HS-14-0: (ES, m/z):259 [M+1]+/211 [M+1+18]$^+$. H-NMR-PH-GBT-ZL-HS-14-0: (300 MHz, DMSO, ppm): 13.42 (s, 1H), 10.48 (s, 1H), 9.03 (s, 1H), 8.74 (s, 1H), 8.40 (d, J=4.8 Hz, 1H), 8.30 (dd, J=8.1 Hz, 1H), 7.80 (d, J=8.7 HZ, 1H), 7.57 (d, J=4.8 Hz, 1H), 5.55 (s, 2H).

Example 93. Preparation of 2,2,2-trifluoroacetic Acid: 6-(((4-formylpyridin-3-yl)oxy)methyl)-N-(methylsulfonyl)nicotinamide (2:1) (Compound 206)

Step 1:

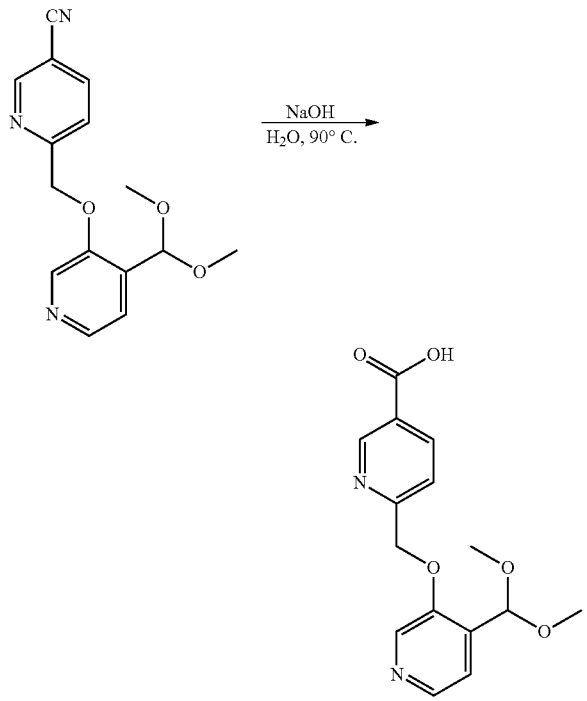

Into a 100-mL round-bottom flask, was placed a solution of 6-([[4-(dimethoxymethyl)pyridin-3-yl]oxy]methyl)pyridine-3-carbonitrile (1 g, 3.51 mmol, 1.00 equiv) and sodium hydroxide (1.4 g, 35.00 mmol, 10.00 equiv) in water (30 mL). The resulting solution was stirred for 4 h at 90° C. The pH value of the solution was adjusted to 4-5 with hydrogen chloride (3 mol/L). The resulting solution was extracted with 3×200 mL of ethyl acetate and 3×200 ml of tetrahydrofuran. The combined organic layers were concentrated under vacuum. This resulted in 1 g (94%) of 6-([[4-(dimethoxymethyl)pyridin-3-yl]oxy]methyl)pyridine-3-carboxylic acid as a yellow solid.

Step 2.

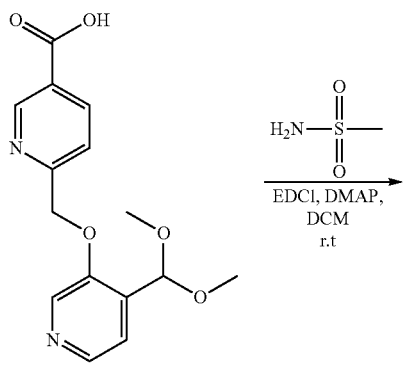 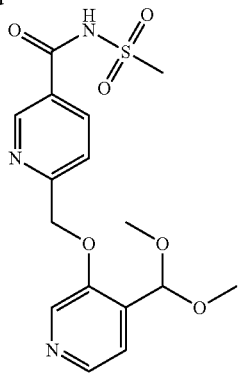

Into a 100-mL round-bottom flask, was placed a solution of 6-([[4-(dimethoxymethyl)pyridin-3-yl]oxy]methyl)pyridine-3-carboxylic acid (200 mg, 0.66 mmol, 1.00 equiv) in dichloromethane (30 mL). EDCl (190 mg, 0.99 mmol, 1.50 equiv), 4-dimethylaminopyridine (120 mg, 0.98 mmol, 1.50 equiv), and methanesulfonamide (80 mg, 0.84 mmol, 1.20 equiv) were added to the reaction mixture. The resulting solution was stirred for 3 h at room temperature. The resulting mixture was concentrated under vacuum. The residue was applied onto a silica gel column with McOH:DCM (1:10) as eluent. This resulted in 200 mg (80%) of 6-([[4-(dimethoxymethyl)pyridin-3-yl]oxy]methyl)-N-methanesulfonylpyridine-3-carboxamide as a yellow solid.

Step 3:

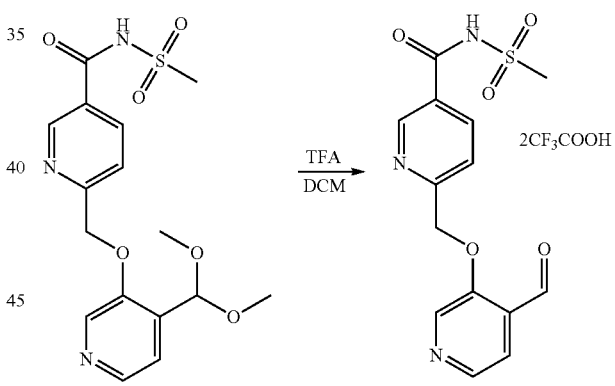

Into a 50-mL round-bottom flask, which was purged and maintained with an inert atmosphere of nitrogen, was placed a solution of 6-([[4-(dimethoxymethyl)pyridin-3-yl]oxy]methyl)-N-methanesulfonylpyridine-3-carboxamide (80 mg, 0.21 mmol, 1.00 equiv) in dichloromethane (5 mL), and trifluoroacetic acid (2 mL). The resulting solution was stirred for 3 h at 40° C. in an oil bath, and then it was concentrated under vacuum. The crude product (60 mg) was purified by Flash-Prep-HPLC with the following conditions (CombiFlash-1): Column, C18 silica gel; mobile phase, $CH_3CN/H_2O=1/99$ increasing to $CH_3CN/H_2O=40/60$ within 20 min; Detector, UV 254 nm. This resulted in 20 mg (17%) of 6-[[4-formylpyridin-3-yl)oxy]methyl]-N-methanesulfonylpyridine-3-carboxamide; bis(trifluoroacetic acid) as a white solid. The compound exhibited a melting point of 102-104° C. LC-MS: (ES, m/z):336 [M+1]+/354 [M+1+18]+. H-NMR (300 MHz, DMSO, ppm): 10.53 (s, 1H), 9.07

(s, 1H), 8.78 (s, 1H), 8.43 (d, J=4.5 Hz, 1H), 8.36 (dd, J=8.1 Hz, 1H), 7.84 (d, J=8.4 Hz, 1H), 7.62 (d, J=4.5 Hz, 1H), 5.60 (s, 2H), 3.37 (s, 3H).

Example 94. Preparation of Substituted Isonicotinaldehydes

Compounds 207-217 were prepared according to the methods described above.

2-(2-methoxyethoxy)-5-((2-(1-(2,2,2-trifluoroethyl)-1H-pyrazol-5-yl)pyridin-3-yl)methoxy)isonicotinaldehyde (Compound 207). $^1$H NMR (400 MHz, CDCl$_3$) δ 10.32 (s, 1H), 8.67 (dd, J=4.8, 1.6 Hz, 1H), 7.97 (dd, J=7.9, 1.5 Hz, 1H), 7.87 (s, 1H), 7.59 (d, J=1.9 Hz, 1H), 7.38 (dd, J=7.9, 4.8 Hz, 1H), 7.11 (s, 1H), 6.47 (d, J=1.9 Hz, 1H), 5.17 (q, 8.6 Hz, 2H), 5.10 (s, 2H), 4.39-4.32 (m, 2H), 3.70-3.63 (m, 2H), 3.37 (s, 3H).

2-methoxy-5-((2-(1-(3,3,3-trifluoropropyl)-1H-pyrazol-5-yl)pyridin-3-yl)methoxyl)isonicotinaldehyde (Compound 208). $^1$H NMR (400 MHz, CDCl$_3$) δ 10.41 (s, 1H), 8.77 (dd, J=4.7.1.6 Hz, 1H), 8.06 (dd, J=7.9, 1.6 Hz, 1H), 7.97 (s, 1H), 7.61 (d, J=1.9 Hz, 1H), 7.46 (dd, J=7.9, 4.8 Hz, 1H), 7.13 (s, 1H), 6.46 (d, J=1.9 Hz, 1H), 5.21 (s, 2H), 4.61-4.49 (m, 2H), 3.93 (s, 3H), 2.95-2.79 (m, 2H).

2-(2-methoxyethoxy)-5-((2-(1-(3,3,3-trifluoropropyl)-1H-pyrazol-5-yl)pyridin-3-yl)methoxy)isonicotinaldehyde (Compound 209). $^1$H NMR (400 MHz, CDCl$_3$) δ 10.40 (s, 1H), 8.76 (dd, J=4.7, 1.6 Hz, 1H), 8.06 (dd, J=7.9, 1.6 Hz, 1H), 7.93 (s, 1H), 7.61 (d, J=1.9 Hz, 1H), 7.45 (dd, J=7.9, 4.8 Hz, 1H), 7.19 (s, 1H), 6.45 (d, J=1.9 Hz, 1H), 5.20 (s, 2H), 4.63-4.48 (m, 2H), 4.48-4.36 (m, 2H), 3.75 (dd, J=5.4, 3.9 Hz, 2H), 3.45 (s, 3H), 3.01-2.69 (m, 2H).

2-methyl-5-((2-(1-(2,2,2-trifluoroethyl)-1H-pyrazol-5-yl)pyridin-3-yl)methoxy)isonicotinaldehyde (Compound 210). $^1$H NMR (400 MHz, CDCl$_3$) δ 10.23 (s, 1H), 8.64 (dd, J=4.7, 1.6 Hz, 1H), 8.16 (dd, J=7.9, 1.5 Hz, 1H), 7.61 (d, J=1.9 Hz, 1H), 7.38 (dd, J=7.9, 4.8 Hz, 1H), 7.21 (d, J=8.6 Hz, 1H), 7.10 (d, 8.6 Hz, 1H), 6.47 (d, J=1.9 Hz, 1H), 5.19 (q, J=8.6 Hz, 2H), 5.12 (d, J=6.1 Hz, 2H), 2.51 (s, 3H).

2-methyl-5-((2-(1-(3,3,3-trifluoropropyl)-1H-pyrazol-5-yl)pyridin-3-yl)methoxy)isonicotinaldehyde (Compound 211). $^1$H NMR (400 MHz, CDCl$_3$) δ 10.31 (s, 1H), 8.75 (dd, J=4.7, 1.7 Hz, 1H), 8.27 (dd, J=7.9, 1.6 Hz, 1H), 7.62 (d, J=1.9 Hz, 1H), 7.49 (dd, J=7.9, 4.8 Hz, 1H), 7.33 (d, J=8.6 Hz, 1H), 7.24 (d, J=8.6 Hz, 1H), 6.46 (d, J=1.9 Hz, 1H), 5.18 (s, 2H), 4.61-4.44 (m, 2H), 2.96-2.75 (m, 2H), 2.62 (s, 3H).

3-((2-(1-(2,2,2-trifluoroethyl)-1H-pyrazol-5-yl)pyridin-3-yl)methoxy)isonicotinaldehyde (Compound 212). $^1$H NMR (400 MHz, CDCl$_3$) δ 10.26 (s, 1H), 8.65 (dd, J=4.7, 1.5 Hz, 1H), 8.38 (dd, J=4.4, 1.0 Hz, 1H), 8.19 (dd, J=7.9, 1.0 Hz, 1H), 7.61 (d, J=1.9 Hz, 1H), 7.43-7.33 (m, 2H), 7.21 (d, J=8.6 Hz, 1H), 6.48 (d, J=1.9 Hz, 1H), 5.19 (q, J=8.6 Hz, 2H), 5.15 (s, 2H).

3-((2-(1-(3,3,3-trifluoropropyl)-1H-pyrazol-5-yl)pyridin-3-yl)methoxy)isonicotinaldehyde (Compound 213). $^1$H NMR (400 MHz, CDCl$_3$) δ 10.24 (s, 1H), 8.66 (dd, J=4.7, 1.6 Hz, 1H), 8.39 (dd, 4.5, 1.1 Hz, 1H), 8.21 (dd, J=7.9, 1.6 Hz, 1H), 7.53 (d, J=1.9 Hz, 1H), 7.44-7.37 (m, 2H), 7.26 (d, J=8.5 Hz, 1H), 6.37 (d, J=1.9 Hz, 1H), 5.13 (s, 2H), 4.49-4.40 (m, 2H), 2.87-2.64 (m, 2H).

3-chloro-5-((2-(1-isopropyl-1H-pyrazol-5-yl)pyridin-3-yl)methoxy)isonicotinaldehyde (Compound 214). $^1$H NMR (400 MHz, CDCl$_3$) δ 10.51 (s, 1H), 8.77 (dd, J=4.7, 1.6 Hz, 1H), 8.41 (s, 1H), 8.28 (s, 1H), 8.13 (dd, J=7.9, 1.5 Hz, 1H), 7.63 (d, J=1.8 Hz, 1H), 7.47 (dd, J=7.9, 4.8 Hz, 1H), 6.37 (d, J=1.8 Hz, 1H), 5.23 (s, 2H), 4.66 (sep, J™ 6.6 Hz, 1H), 1.49 (d, J=6.6 Hz, 6H).

3-((2-(1-isopropyl-1H-pyrazol-5-yl)pyridin-3-yl)methoxy)-5-methylisonicotinaldehyde (Compound 215). $^1$H NMR (400 MHz, CDCl$_3$) δ 10.58 (s, 1H), 8.69 (dd, J=4.7, 1.5 Hz, 1H), 8.18 (d, J=3.7 Hz, 2H), 7.92 (dd, J=7.9, 1.2 Hz, 1H), 7.53 (d, J=1.8 Hz, 1H), 7.36 (dd, J=7.9, 4.8 Hz, 1H), 7.19 (s, 1H), 6.29 (d, J=1.8 Hz, 1H), 5.14 (s, 2H), 4.59 (sep, J=6.6 Hz, 1H), 1.41 (d, J=6.6 Hz, 6H).

3-chloro-5-((2-(1-(3,3,3-trifluoropropyl)-1H-pyrazol-5-yl)pyridin-3-yl)methoxy)isonicotinaldehyde (Compound 216). $^1$H NMR (400 MHz, CDCl$_3$) δ 10.43 (s, 1H), 8.67 (dd, J=4.7, 1.5 Hz, 1H), 8.35 (s, 1H), 8.26 (s, 1H), 8.06 (dd, J=7.9, 1.3 Hz, 1H), 7.61 (d, J=1.9 Hz, 1H), 7.40 (dd, 7.9, 4.8 Hz, 1H), 6.47 (d, J=1.9 Hz, 1H), 5.21-5.10 (m, 4H).

3-methyl-5-((2-(1-(2,2,2-trifluoroethyl)-1H-pyrazol-5-yl)pyridin-3-yl)methoxy)isonicotinaldehyde (Compound 217). $^1$H NMR (400 MHz, CDCl$_3$) δ 10.68 (s, 1H), 8.77 (dd, J=4.7, 1.3 Hz, 1H), 8.35 (s, 1H), 8.30 (s, 1H), 8.04 (d, J=7.9 Hz, 1H), 7.69 (d, J=1.9 Hz, 1H), 7.47 (dd, J=7.9, 4.8 Hz, 1H), 6.55 (d, J=1.9 Hz, 1H), 5.34-5.22 (m, 4H), 2.57 (s, 3H).

In Vitro Testing

Example 95. Modulation of Hemoglobin Oxygen Affinity by Heteroaryl Aldehydes-Assay Procedure Oxygen equilibrium curves (OEC) in purified Hemoglobin S (HbS) were measured by the change in p50, the partial pressure of oxygen at which the heme binding sites m the HbS sample are 50% saturated with oxygen. HbS was purified by a modified procedure (Antonini and Brunori, 1971; Heomoglobin and Myoglobin in their Reactions with Ligands; North Holland Publishing Company; Amsterdam, London) from blood obtained from homozygous sickle cell patients though the Hemoglobinopathy Center at Children's Hospital Oakland Research Institute (CHORD with Institutional Review Board approval. Oxygen equilibrium curves were carried out with a HEMOX analyzer, (TCS Scientific, New Hope, Pa.). Five hundred μL of 250 μM purified HbS were diluted into 4.5 mL of HEMOX buffer (30 mM TES, 130 mM NaCl, 5 mM KCl, pH=7.4) resulting in a final hemoglobin concentration of 25 μM. The compounds were added at the final desired concentrations. The mixture was incubated for 45 min at 37° C. and then transferred to the Hemox sample chamber. The samples were saturated with oxygen by flushing with compressed air for 10 minutes. The samples were then flushed with pure nitrogen and the absorbance of deoxy-Hb was recorded as a function of the solution pO$_2$. The oxygen equilibrium data was then fit to the Hill Model to obtain values for p50. The deoxygenation curves for both HbS alone (control) and HbS in the presence of compound were collected with the TCS software. The p50 for purified Hbs was typically 13.8±1.6. Delta p50 values were obtained from the p50 value for control minus the p50 value for HbS treated with compound divided by the p50 value for the control. A positive delta p50 value corresponds to a left shifted curve and a lower p50 value relative to control, indicating that the compound acts to modulate HbS to increase its affinity for oxygen.

Example 96 Modulation of Hemoglobin Oxygen Affinity by Heteroaryl Aldehyde—Assay Results The compounds of Table 1 that were where tested in the assay above were all found to have positive delta p50 values. Delta p50% is calculated from [[p50(HbS)−p50(HbS treated with compound)]/p50(HbS)]×100. Table 2 below lists the delta p50% values where + indicates a delta p50% of between 0 and 29, ++ indicates a delta p50% of between 30 and 50, and +++ indicates a delta p50% of 50 or greater. Unless noted otherwise, the compounds in Table 2 were tested at 30 μM.

TABLE 2 delta p50%

| Compound | delta p50 |
|---|---|
| 1 | + |
| 2 | ++ (100 μM) |
| 3 | + |
| 4 | + |
| 5 | ++ |
| 6 | + |
| 7 | + |
| 12 | + (100 μM) |
| 38 | + |
| 39 | + |
| 40 | + (100 μM) |
| 41 | + |
| 42 | + |
| 43 | ++ |
| 44 | +++ |
| 45 | +++ |
| 46 | ++ |
| 47 | + |
| 48 | ++ (100 μM) |
| 49 | ++ |
| 50 | + |
| 51 | + |
| 52 | + (100 μM) |
| 53 | ++ |
| 54 | ++ (100 μM) |
| 55 | + (100 μM) |
| 56 | + (100 μM) |
| 57 | ++ (100 μM) |
| 58 | ++ |
| 59 | + |
| 61 | + |
| 62 | + |
| 63 | +++ |
| 64 | + |
| 65 | ++ |
| 66 | ++ |
| 68 | + |
| 69 | + |
| 70 | + |
| 71 | + |
| 72 | + |
| 73 | + |
| 74 | ++ |
| 75 | + |
| 76 | + |
| 77 | + |
| 78 | + |
| 79 | ++ |
| 80 | ++ |
| 81 | + |
| 82 | + |
| 83 | + |
| 84 | ++ |
| 85 | + |
| 86 | ++ |
| 87 | + |
| 88 | + |
| 89 | + |
| 90 | + |
| 91 | ++ |
| 92 | ++ |
| 93 | ++ |

TABLE 2-continued delta p50%

| Compound | delta p50 |
|---|---|
| 94 | + |
| 95 | + |
| 96 | + |
| 97 | + |
| 98 | + |
| 99 | + |
| 100 | + |
| 101 | + |
| 102 | + |
| 103 | ++ |
| 104 | + |
| 105 | + |
| 106 | ++ |
| 107 | + |
| 108 | ++ |
| 109 | + |
| 110 | + |
| 111 | + |
| 112 | + |
| 113 | + |
| 114 | + |
| 115 | + |
| 116 | + |
| 117 | + |
| 118 | + |
| 119 | ++ |
| 120 | ++ |
| 121 | + |
| 122 | + |
| 123 | + |
| 124 | + |
| 125 | + |
| 126 | + |
| 127 | + |
| 128 | + |
| 129 | ++ |
| 130 | ++ |
| 131 | ++ |
| 132 | +++ |
| 133 | ++ |
| 134 | ++ |
| 135 | + |
| 136 | + |
| 137 | + |
| 138 | + |
| 139 | + |
| 140 | ++ |
| 141 | + |
| 142 | + |
| 143 | ++ |
| 149 | +++ |
| 150 | +++ |
| 158 | ++ |
| 159 | +++ |
| 160 | +++ |
| 161 | ++ |
| 162 | +++ |
| 163 | +++ |
| 164 | ++ |
| 165 | ++ |
| 169 | ++ |
| 172 | ++ |
| 173 | +++ |
| 174 | +++ |
| 175 | +++ |
| 176 | +++ |
| 177 | +++ |
| 178 | ++ |
| 179 | ++ |
| 180 | +++ |
| 181 | +++ |
| 183 | +++ |
| 184 | ++ |
| 186 | +++ |
| 187 | ++ |
| 188 | +++ |

TABLE 2-continued

| delta p50% | |
|---|---|
| Compound | delta p50 |
| 189 | ++ |
| 190 | +++ |
| 191 | +++ |
| 193 | ++ |
| 194 | ++ |
| 195 | +++ |
| 196 | +++ |
| 197 | ++ |
| 198 | +++ |
| 199 | +++ |
| 200 | ++ |
| 201 | ++ |
| 202 | +++ |
| 203 | +++ |

Example 97. Polymerization Assay

Polymerization assays are carried out in vitro using purified HBS exchanged into 1.8 M potassium phosphate buffer at pH 7.4. Using a slightly modified protocol (Antonini and Brunori, 1971), HbS is purified by the CRO VIRUS YS, from blood obtained from homozygous sickle cell patients through the Hemoglobinopathy Center at Children's Hospital Oakland Research Institute (CHORI) with Institutional Review Board approval. Compounds are prepared in 100% DMSO and a desired amount is added to 50 µM of purified HBS at a final DMSO concentration of 0.3%. Final potassium phosphate concentration is adjusted to 1.8 M using a combination of 2.5 M potassium phosphate stock solution and water at pH 7.4. The reaction mixture is incubated for an hour at 37° C. and then transferred into a 24-well plate for deoxygenation in a glove box containing 99.5% nitrogen and 0.5% oxygen. The 24-well plate is not covered and incubated at 4° C. on a plate cooler inside the glove box for one and a half hours. Fifty µL of the reaction mixture is transferred into a 96-well plate and the absorbance at 700 nm is measured every minute for one hour at 37° C. in a plate reader located inside the glove box. A plot of the absorbance against time is fitted using a Boltzman sigmoidal fit and the delay time (from zero to time at half Vmax) is measured. To compare and rank compounds, delay times are expressed as percent delay (% DT), which is defined as the difference in delay times for HBS/compound and HBS alone multiplied by 100 and divided by the delay time for HBS alone.

Compounds listed below have been tested in the polymerization assay. Activity ranges are defined by the number of dagger (†) symbols indicated, † denotes activity ≥40% but ≤80%; †† denotes activity >80% but ≤120%; ††† denotes activity >120% but ≤140%; †††\ denotes activity >160%.

TABLE 3

| % delta Delay | |
|---|---|
| Compound | % delta Delay |
| 5 | † |
| 108 | |
| 130 | † |
| 132 | |
| 91 | |
| 149 | † |
| 150 | ††† |
| 158 | † |

TABLE 3-continued

| % delta Delay | |
|---|---|
| Compound | % delta Delay |
| 179 | |
| 159 | †† |
| 160 | †† |
| 161 | |
| 162 | †† |
| 173 | † |
| 174 | †† |
| 195 | ††† |
| 197 | † |
| 198 | † |
| 175 | †† |
| 162 | †† |
| 203 | †† |
| 163 | †† |
| 181 | ††† |
| 206 | ††† |
| 178 | † |
| 180 | † |
| 199 | ††† |
| 176 | † |
| 177 | † |
| 202 | ††† |
| 187 | †† |
| 164 | ††† |
| 165 | ††† |
| 169 | ††† |
| 186 | †††† |
| 188 | ††† |
| 189 | ††† |
| 190 | ††† |

Example 98. R/T Assay

A relaxed-to-tense transition assay ("R/T assay") was used to determine the ability of substituted benzaldehyde compounds to maintain the high-oxygen affinity relaxed (R) stale of hemoglobin under deoxygenated conditions. This ability can be expressed as a "delta R" value (i.e., the change in the time-period of the R state after hemoglobin is treated with a compound, as compared to the period without treatment with the compound). Delta R is the % R to remaining after the compounds treatment compared with no treatment (e.g. if R % without treatment is 8% while with treatment with a target compound is 48% Rat 30 µM, then % R is 40% for that compound.

A mixture of HbS/A was purified from blood obtained from homozygous sickle cell patients though the Hemoglobinopathy Center at Children's Hospital Oakland Research Institute (CHORI) with Institutional Review Board approval. HbS/A (at a final concentration of 3 µM) was incubated for 1 hr at 37° C. in presence or absence of compounds in 50 µM potassium phosphate buffer, pH-7.4 and 30 µM 2,3 diphosphoglycerate (DPG) in 96 well plates in a final volume of 160 µl. Compounds were added at different concentrations (3 µM to 100 µM final concentrations). Plates were covered with a Mylar film. After incubation was completed the Mylar cover was removed and the plates were placed in a Spectrostar Nano plate reader previously heated at 37° C. Five minutes later, $N_2$ (flow rate=20 L/min) was flowed through the spectrophotometer. Spectroscopic measurements (300 nm to 700 nm) were taken every 5 mm for 2 hours. Data analysis was performed by using linear regression from the data retrieved for all wavelengths.

Table 4 below lists the delta R values where + indicates a delta R of between 0 and 30, ++ indicates a delta R of between 30 and 50, and +++ indicates a delta R of 50 or greater. Unless noted otherwise, the compounds in Table 2 were tested at 30 μM.

TABLE 4

| Compound | delta R |
|---|---|
| 5 | ++ |
| 43 | + (9 μM) |
| 45 | ++ (9 μM) |
| 46 | + (9 μM) |
| 53 | + (9 μM) |
| 58 | + (9 μM) |
| 63 | ++ (9 μM) |
| 193 | + (9 μM) |
| 65 | + (9 μM) |
| 66 | ++ (9 μM) |
| 79 | ++ (9 μM) |
| 80 | +++ (9 μM) |
| 84 | ++ (9 μM) |
| 86 | + (9 μM) |
| 91 | +++ (9 μM) |
| 92 | + (9 μM) |
| 93 | + (9 μM) |
| 103 | ++ (9 μM) |
| 108 | +++ (9 μM) |
| 119 | ++ (9 μM) |
| 120 | ++ (9 μM) |
| 129 | ++ (9 μM) |
| 130 | + (9 μM) |
| 131 | + (9 μM) |
| 132 | ++ |
| 133 | ++ (9 μM) |
| 134 | + (9 μM) |
| 140 | + (9 μM) |
| 143 | + (9 μM) |
| 149 | + (9 μM) |
| 150 | +++ |
| 194 | + (9 μM) |
| 158 | + (9 μM) |
| 179 | + (9 μM) |
| 159 | ++ |
| 160 | + |
| 161 | + (9 μM) |
| 172) | + (9 μM) |

TABLE 4-continued

| Compound | delta R |
|---|---|
| 191 | + (9 μM) |
| 173 | +++ |
| 195 | +++ |
| 174 | ++ |
| 196 | ++ |
| 197 | + (9 μM) |
| 198 | ++ |
| 175 | ++ |
| 162 | +++ |
| 203 | + (9 μM) |
| 163 | ++ |
| 181 | + (9 μM) |
| 206 | + (9 μM) |
| 178 | + (9 μM) |
| 180 | ++ |
| 199 | + (9 μM) |
| 176 | + (9 μM) |
| 177 | + (3 μM) |
| 183 | ++ |
| 184 | ++ |
| 200 | + (9 μM) |
| 201 | + (9 μM) |
| 202 | + (9 μM) |
| 187 | +++ (9 μM) |
| 164 | ++ (9 μM) |
| 165 | + (9 μM) |
| 169 | ++ (9 μM) |
| 186 | +++ |

Example 99. Whole Blood Assay

Oxygen Equilibrium Curves (OEC) of whole blood before and after treatment with different concentrations of substituted benzaldehyde compounds were performed as follows using a HEMOX analyzer (TCS Scientific, New Hope, Pa.). Blood samples from homozygous sickle cell patients were obtained though the Hemoglobinopathy Center at Children's Hospital Oakland Research Institute (CHORI) with Institutional Review Board approval. The hematocrit was adjusted to 20% using autologous plasma and the blood samples were incubated for 1 hour at 37° C. in absence or presence of compounds. 100 μl of these samples were added to 5 mL of Hemox buffer (30 mM TES, 130 mM NaCl, 5 mM KCl, pH=7.4) at 37° C. and then transferred to the Hemox sample chamber. The samples were saturated with oxygen by flushing with compressed air for 10 minutes. The samples were then flushed with pure nitrogen and the respective absorbances of oxy- and deoxy-Hb are recorded as a function of the solution pO2. The oxygen equilibrium data were then fitted to the Hill Model to obtain values for p50. The deoxygenation curves for both whole blood alone (control) and whole blood in the presence of the compound were collected with the TCS software.

Table 5 below lists the delta p50% values where + indicates a delta p50% of between 0 and 29, ++ indicates a delta p50% of between 30 and 50, and +++ indicates a delta p50% of 50 or greater. Unless noted otherwise, the compounds in Table 2 were tested at 1000 μM. A positive delta p50 value corresponds to a left shifted curve and a lower p50 value relative to control, indicating that the compound acts to modulate HbS to increase its affinity for oxygen.

TABLE 5 delta p50% Values for Whole Blood Assay

| Compound | delta p50% |
|---|---|
| 5 | + |
| 44 | + |
| 58 | + |
| 65 | + |
| 74 | ++ |
| 79 | + |
| 80 | + |
| 92 | + |
| 93 | + |
| 103 | + |
| 106 | + |
| 108 | + |
| 120 | + |
| 129 | ++ |
| 130 | ++ |
| 131 | + |
| 132 | ++ |
| 133 | + |
| 140 | + |
| 143 | + |
| 149 | +++ |
| 150 | +++ |
| 194 | + |
| 158 | + |
| 179 | ++ |
| 159 | +++ |
| 160 | +++ |
| 191 | +++ |
| 173 | +++ |
| 174 | +++ |
| 195 | +++ |
| 196 | ++ |
| 197 | +++ |
| 198 | +++ |
| 175 | +++ |
| 162 | +++ |
| 209 | + |
| 163 | +++ |
| 181 | +++ |
| 206 | +++ |
| 178 | ++ |
| 180 | +++ |
| 199 | + |
| 176 | +++ |
| 177 | +++ |
| 183 | +++ |
| 184 | +++ |
| 200 | +++ |
| 201 | + |
| 202 | + |
| 187 | + |
| 164 | ++ |
| 165 | + |
| 169 | ++ |
| 186 | +++ |
| 188 | +++ |
| 189 | +++ |
| 190 | +++ |

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A method for preparing a compound of formula (A):

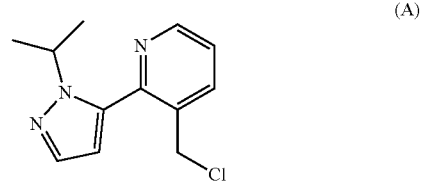

(A)

or a salt thereof, comprising contacting a compound of formula (B):

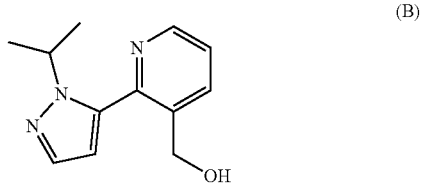 [SMILES: CC(C)n1nccc1-c1ncccc1CCl]

(B)

with SOCl$_2$ under conditions sufficient to form a compound of formula (A) or a salt thereof.

2. The method of claim 1, wherein the conditions sufficient to form a compound of formula (A) or a salt thereof comprise dichloromethane.

3. The method of claim 1, further comprising preparing a compound of formula (B), wherein preparing a compound of formula (B) comprises contacting a compound of formula (C):

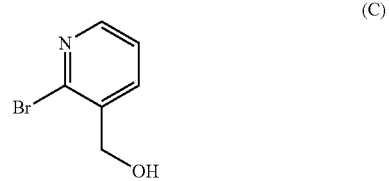

(C)

with a compound of formula (D):

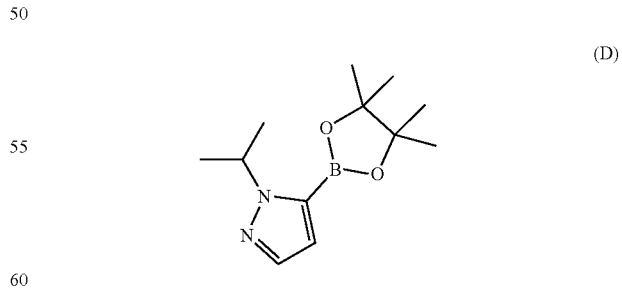

(D)

under conditions sufficient to form a compound of formula (B).

4. The method of claim 3, wherein the conditions sufficient to form a compound of formula (B) comprise Pd(dppf)Cl$_2$.

* * * * *